(12) United States Patent
Leung et al.

(10) Patent No.: US 12,018,029 B2
(45) Date of Patent: Jun. 25, 2024

(54) HEXAHYDROPYRROLO[3,4-C]PYRROLE DERIVATIVES USEFUL AS LOX INHIBITORS

(71) Applicant: THE INSTITUTE OF CANCER RESEARCH: ROYAL CANCER HOSPITAL, London (GB)

(72) Inventors: Leo Leung, Macclesfield (GB); Kiri North, Abingdon (GB); Deborah Smithen, Macclesfield (GB); Mohammed Aljarah, Macclesfield (GB); Michael Brown, Macclesfield (GB); Ben Ayers, Singapore (SG); Dan Niculescu-Duvaz, Macclesfield (GB); Caroline Springer, Macclesfield (GB)

(73) Assignee: The Institute of Cancer Research: Royal Cancer Hospital, London (GB)

( * ) Notice: Subject to any disclaimer, the term of this patent is extended or adjusted under 35 U.S.C. 154(b) by 352 days.

(21) Appl. No.: 16/972,335

(22) PCT Filed: Jun. 5, 2019

(86) PCT No.: PCT/GB2019/051552
§ 371 (c)(1),
(2) Date: Dec. 4, 2020

(87) PCT Pub. No.: WO2019/234418
PCT Pub. Date: Dec. 12, 2019

(65) Prior Publication Data
US 2021/0238179 A1  Aug. 5, 2021

(30) Foreign Application Priority Data
Jun. 6, 2018 (GB) .................... 1809295

(51) Int. Cl.
*A61P 35/00* (2006.01)
*C07D 487/04* (2006.01)

(52) U.S. Cl.
CPC ............ *C07D 487/04* (2013.01); *A61P 35/00* (2018.01)

(58) Field of Classification Search
CPC ............................... C07D 487/04; A61P 35/00
See application file for complete search history.

(56) References Cited

U.S. PATENT DOCUMENTS

| | | | |
|---|---|---|---|
| 5,302,720 A | 4/1994 | Gopalan | |
| 2011/0076285 A1 | 3/2011 | Stalmans et al. | |
| 2012/0010186 A1* | 1/2012 | Lachance ............ | C07D 471/10 514/363 |
| 2013/0237502 A1 | 9/2013 | Curtis et al. | |
| 2017/0334927 A1* | 11/2017 | Zhao .................... | C07D 519/00 |

FOREIGN PATENT DOCUMENTS

| | | |
|---|---|---|
| DE | 10216144 | 11/2003 |
| DE | 102004056226 | 5/2006 |
| EP | 0330218 | 8/1989 |
| JP | 2006527756 A | 12/2006 |
| JP | 2017537133 A | 12/2017 |
| WO | 2001/044243 | 6/2001 |
| WO | 2001/081347 | 11/2001 |
| WO | 2004/110996 | 12/2004 |
| WO | 2004110996 A1 | 12/2004 |
| WO | 2006/043090 | 4/2006 |
| WO | 2007/005737 | 1/2007 |
| WO | 2007/008338 | 1/2007 |
| WO | 2007/011702 | 1/2007 |
| WO | 2007/027734 | 3/2007 |
| WO | 2008/125633 | 10/2008 |
| WO | 2009/010974 | 1/2009 |
| WO | 2009/077766 | 6/2009 |
| WO | 2009/091889 | 7/2009 |
| WO | 2009/137308 | 11/2009 |
| WO | 2009/155388 | 12/2009 |
| WO | 2010/026029 | 3/2010 |
| WO | 2010/080769 | 7/2010 |
| WO | 2010/091279 | 8/2010 |

(Continued)

OTHER PUBLICATIONS

Smith, M. B. Organic Synthesis, McGraw-Hill, Inc. 1994, Chapter 1 (Year: 1994).*
International Search Report and Written Opinion issued for Application No. PCT/GB2019/051552, dated Aug. 14, 2019.
Search Report issued for Application No. GB1809295, dated Jan. 14, 2019.
Abourbih, D. A., et al. (2010). "Lysyl oxidase expression and inhibition in uveal melanoma." Melanoma research 20(2): 97-106.
Adam, O., et al. (2011). "Increased lysyl oxidase expression and collagen cross-linking during atrial fibrillation." J. Mol. Cell. Cardiol. 50(4): 678-685.
Akiri, G., et al. (2003). "Lysyl oxidase-related protein-1 promotes tumor fibrosis and tumor progression in vivo." Cancer research 63(7): 1657-1666.
Albinger-Hegyi, A., et al. (2010). "Lysyl oxidase expression is an independent marker of prognosis and a predictor of lymph node metastasis in oral and oropharyngeal squamous cell carcinoma (OSCC)." International journal of cancer Journal international du cancer 126(11): 2653-2662.

(Continued)

*Primary Examiner* — Erich A Leeser
(74) *Attorney, Agent, or Firm* — Meunier Carlin & Curfman LLC

(57) ABSTRACT

The disclosure relates to compounds of Formula (I), or pharmaceutically acceptable salts thereof, wherein $X^1$ and $X^5$ is each selected from $CR^1$ or N; $X^2$, $X^3$ and $X^4$ is each selected from $CR^1$, $CR^2$ or N, provided at least one of $X^2$, $X^3$ and $X^4$ is $CR^2$ and provided only one of $X^1$, $X^2$, $X^3$, $X^4$ and $X^5$ can be N. $R^1$, $R^2$, $R^3$, $R^4$, $R^5$, $L^1$, $L^2$ and $L^3$ are as defined herein. Compounds according to Formula (I) are pharmacologically effective as lysyl oxidase (LOX) inhibitors and are believed to be useful in the treatment of, for instance, cancer.

19 Claims, No Drawings
Specification includes a Sequence Listing.

(56) References Cited

FOREIGN PATENT DOCUMENTS

| WO | 2011/022670 | 2/2011 | | |
|---|---|---|---|---|
| WO | 2011/022710 | 2/2011 | | |
| WO | 2011/050198 | 4/2011 | | |
| WO | 2011/092469 | 8/2011 | | |
| WO | 2012/139045 | 10/2012 | | |
| WO | 2012/145581 | 10/2012 | | |
| WO | 2013/111013 | 8/2013 | | |
| WO | 2014/145751 | 9/2014 | | |
| WO | 2014/152122 | 9/2014 | | |
| WO | 2015/038755 | 3/2015 | | |
| WO | 2015/051230 | 4/2015 | | |
| WO | 2015/075483 | 5/2015 | | |
| WO | 2016/086200 | 6/2016 | | |
| WO | 2016/144702 | 9/2016 | | |
| WO | 2016/144703 | 9/2016 | | |
| WO | 2017/003862 | 1/2017 | | |
| WO | 2017/015221 | 1/2017 | | |
| WO | 2017/141049 | 8/2017 | | |
| WO | 2018/048928 | 3/2018 | | |
| WO | 2018/175188 | 9/2018 | | |
| WO | 2018/175190 | 9/2018 | | |
| WO | WO 2018/175190 | * | 9/2018 | ........... A61K 31/397 |
| WO | 2019/073251 | 4/2019 | | |
| WO | 2019/217890 A | 11/2019 | | |

OTHER PUBLICATIONS

Anderson, C., et al. (2007). "Chemical genetics suggests a critical role for lysyl oxidase in zebrafish notochord morphogenesis." Mol Biosyst 3(1): 51-59.

Aslam, T., et al. (2015). "Optical molecular imaging of lysyl oxidase activity-detection of active fibrogenesis in human lung tissue." Chemical Science 6(8): 4946-4953.

Baker, A.-M., et al. (2011). "The role of lysyl oxidase in SRC-dependent proliferation and metastasis of colorectal cancer." Journal of the National Cancer Institute 103(5): 407-424.

Baker, A.-M., et al. (2013). "Lysyl oxidase plays a critical role in endothelial cell stimulation to drive tumor angiogenesis." Cancer research 73(2): 583-594.

Barker, H. E., et al. (2011). "LOXL2-mediated matrix remodeling in metastasis and mammary gland involution." Cancer research 71(5): 1561-1572.

Barker, H. E., et al. (2012). "The rationale for targeting the LOX family in cancer." Nature reviews Cancer 12(8): 540-552.

Barker, H. E., et al. (2013). "Tumor-Secreted LOXL2 Activates Fibroblasts through FAK Signaling." Molecular Cancer Research 11(11): 1425-1436.

Barry-Hamilton, V., et al. (2010). "Allosteric inhibition of lysyl oxidase-like-2 impedes the development of a pathologic microenvironment." Nat Med 16(9): 1009-1017.

Beerlage, C., et al. (2013). "Hypoxia-inducible factor 1-regulated lysyl oxidase is involved in Staphylococcus aureus abscess formation." Infect. Immun. 81(7): 2562-2573.

Bianco, R., et al. (2007). "Rational bases for the development of EGFR inhibitors for cancer treatment." The International Journal of Biochemistry & Cell Biology 39(7-8): 1416-1431.

Bondareva, A., et al. (2009). "The lysyl oxidase inhibitor, beta-aminopropionitrile, diminishes the metastatic colonization potential of circulating breast cancer cells." PLoS One 4(5): e5620.

Boufraqech, M., et al. (2015). "miR30a Inhibits LOX Expression and Anaplastic Thyroid Cancer Progression." Cancer research 75(2): 367-377.

Brasselet, C., et al. (2005). "Collagen and elastin cross-linking: A mechanism of constrictive remodeling after arterial injury." Am. J. Physiol. 289(5, Pt. 2): H2228-H2233.

Bunnelle, William H., et al. "Octahydropyrrolo [3, 4-c] pyrrole: a diamine scaffold for construction of either α4β2 or α7-selective nicotinic acetylcholine receptor (nAChR) ligands. Substitutions that switch subtype selectivity." Journal of medicinal chemistry 52.15 (2009): 4126-4141.

Burke A. A., et al.(2017) Comparing hydrazine-derived reactive groups as inhibitors of quinone-dependent amine oxidases, Journal of Enzyme Inhibition and Medicinal Chemistry, 32:1, 496-503.

Carrington, M. J., et al. (1984). "The inhibition of lysyl oxidase in vivo by isoniazid and its reversal by pyridoxal. Effect on collagen cross-linking in the chick embryo." Biochem J 221(3): 837-843.

Chang, J., et al.(2017) "Pre-clinical evaluation of small molecule LOXL2 inhibitors in breast cancer." Oncotarget, 8(16):26066-26078.

Chanoki, M., et al. (1995). "Increased expression of lysyl oxidase in skin with scleroderma." Br J Dermatol 133(5): 710-715.

Chen, RT et al. (2017) "Blocking Surgically Induced Lysyl Oxidase Activity Reduces the Risk of Lung Metastases". Cell Reports 19(4), 774-784.

Chen, W.-C., et al. (2015). "Matrix-Stiffness-Regulated Inverse Expression of Krüppel-Like Factor 5 and Krüppel-Like Factor 4 in the Pathogenesis of Renal Fibrosis." The American Journal of Pathology 185(9): 2468-2481.

Chien, J. W., et al. (2014). "Serum lysyl oxidase-like 2 levels and idiopathic pulmonary fibrosis disease progression." European Respiratory Journal 43(5): 1430- 1438.

Cox, T. R., et al. (2013). "LOX-Mediated Collagen Crosslinking Is Responsible for Fibrosis-Enhanced Metastasis." Cancer research 73(6): 1721-1732.

Cox, T. R., et al. (2015). "The hypoxic cancer secretome induces pre-metastatic bone lesions through lysyl oxidase." Nature 522(7554): 106-110.

Crowley, V. et al. (2016). "Development of Glucose Regulated Protein 94-Selective Inhibitors Based on the BnIm and Radamide Scaffold." J Med. Chem. 59, 3471-3488.

Da Silva, R., et al. (2015). "LOX Expression and Functional Analysis in Astrocytomas and Impact of IDH1 Mutation." PLoS One 10(3): e0119781.

Decitre, M., et al. (1998). "Lysyl oxidase-like protein localizes to sites of de novo fibrinogenesis in fibrosis and in the early stromal reaction of ductal breast carcinomas." Lab. Invest. 78(2): 143-151.

Dentillo, D. B., et al. (2010). "Deregulation of LOXL1 and HTRA1 Gene Expression in Endometriosis." Reproductive Sciences 17(11): 1016-1023.

Di Donato, A., et al. (1997). "Lysyl oxidase expression and collagen cross-linking during chronic adriamycin nephropathy." Nephron 76(2): 192-200.

Dong, K., et al. (2014). "Effects of lox gene expression on proliferation, invasion and radiosensitivity of laryngeal cancer hep-2 cells." Tianjin Yiyao 42(5): 417-420. English Abstract.

Erler, J. T., et al. (2006). "Lysyl oxidase is essential for hypoxia-induced metastasis." Nature 440(7088): 1222-1226.

Erler, J. T., et al. (2009). "Hypoxia-induced lysyl oxidase is a critical mediator of bone marrow cell recruitment to form the premetastatic niche." Cancer Cell 15(1): 35-44.

Fong, S. F., et al. (2007). "Lysyl oxidase-like 2 expression is increased in colon and esophageal tumors and associated with less differentiated colon tumors." Genes Chromosomes Cancer 46(7): 644-655.

Gao, Y., et al. (2010). "LKB1 inhibits lung cancer progression through lysyl oxidase and extracellular matrix remodeling." Proceedings of the National Academy of Sciences 107(44): 18892-18897.

Georges, P. C., et al. (2007). "Increased stiffness of the rat liver precedes matrix deposition: implications for fibrosis." Am. J. Physiol. 293(6, Pt. 1): G1147-G1154.

Giboda, M., et al. (1992). "Experimental schistosomiasis mansoni: modulation of granulomas by inhibition of collagen cross-link formation. Preliminary report." Ann Trop Med Parasitol 86(6): 631-636.

Gilad, G. M. and V. H. Gilad (2001). "β-Aminopropionitrile treatment can accelerate recovery of mice after spinal cord injury." Eur. J. Pharmacol. 430(1): 69-72.

Gilad, G. M., et al. (2001). "Lysyl oxidase, the extracellular matrix-forming enzyme, in rat brain injury sites." Neurosci. Lett. 310(1): 45-48.

(56) References Cited

OTHER PUBLICATIONS

Gilad, G. M., et al. (2005). "Evidence for increased lysyl oxidase, the extracellular matrix-forming enzyme, in Alzheimer's disease brain." Neurosci Lett 376(3): 210- 214.

Gonzalez, G. E., et al. (2014). "N-acetyl-seryl-aspartyl-lysyl-proline reduces cardiac collagen cross-linking and inflammation in angiotensin II-induced hypertensive rats." Clin. Sci. 126(1): 85-94.

Gonzalez-Santamaria, J., et al., (2016) "Matrix cross-linking lysyl oxidases are induced in response to myocardial infarction and promote cardiac dysfunction". Cardiovascular Research 109, (1), 67-78.

Gorogh, T., et al. (2007). "Selective upregulation and amplification of the lysyl oxidase like-4 (LOXL4) gene in head and neck squamous cell carcinoma." J Pathol 212(1): 74-82.

Haase, V. H. (2009). "Pathophysiological Consequences of HIF Activation." Annals of the New York Academy of Sciences 1177(1): 57-65.

Halberg, N., et al. (2009). "Hypoxia-inducible factor 1a induces fibrosis and insulin resistance in white adipose tissue." Mol. Cell. Biol. 29(16): 4467-4483.

Hase, H., et al. (2014). "LOXL2 Status Correlates with Tumor Stage and Regulates Integrin Levels to Promote Tumor Progression in ccRCC." Molecular Cancer Research 12(12): 1807-1817.

Herranz, N., et al. (2012). "Lysyl Oxidase-like 2 Deaminates Lysine 4 in Histone H3." Molecular Cell 46(3): 369-376.

Hornstra, I. K., et al. (2003). "Lysyl oxidase is required for vascular and diaphragmatic development in mice." J Biol Chem 278(16): 14387-14393.

Huang, C.-S., et al. (2013). "Long-term ethanol exposure-induced hepatocellular carcinoma cell migration and invasion through lysyl oxidase activation are attenuated by combined treatment with pterostilbene and curcumin analogues." Journal of Agricultural and Food Chemistry 61(18): 4326-4335.

Jiang, W.-P., et al. (2014). "Identification of the involvement of LOXL4 in generation of keratocystic odontogenic tumors by RNA-Seq analysis." In J Oral Sci 6(1): 31-38.

Jourdan-Le Saux, C., et al. (1994). "Lysyl oxidase cDNA of myofibroblast from mouse fibrotic liver." Biochem Biophys Res Commun 199(2): 587-592.

Kagan, H. M. (1994). "Lysyl oxidase: mechanism, regulation and relationship to liver fibrosis." Pathol Res Pract 190(9-10): 910-919.

Kagan, H. M., et al. (1981). "Changes in aortic lysyl oxidase activity in diet-induced atherosclerosis in the rabbit." Arteriosclerosis 1(4): 287-291.

Kagan, Herbert M., and Kathleen A. Sullivan. "[35] Lysyl oxidase: Preparation and role in elastin biosynthesis." Methods in enzymology. vol. 82. Academic Press, 1982. 637-650.

Kamath, Lakshmi, et al. "Signaling from protease-activated receptor-1 inhibits migration and invasion of breast cancer cells." Cancer research 61.15 (2001): 5933-5940.

Karagiannis, G. S., et al. (2012). "Cancer-Associated Fibroblasts Drive the Progression of Metastasis through both Paracrine and Mechanical Pressure on Cancer Tissue." Molecular Cancer Research 10(11): 1403-1418.

Kasashima, H., et al. (2014). "Lysyl oxidase-like 2 (LOXL2) from stromal fibroblasts stimulates the progression of gastric cancer." Cancer Letters 354(2): 438-446.

Kasashima, H., et al. (2016). "Lysyl oxidase is associated with the epithelial-mesenchymal transition of gastric cancer cells in hypoxia." Gastric Cancer, 19:431-442.

Kim, Y., et al. (1999). "Coexpression of the lysyl oxidase-like gene (LOXL) and the gene encoding type III procollagen in induced liver fibrosis." Journal of cellular biochemistry 72(2): 181-188.

Kim, Y.-M., et al. (2011). "The human lysyl oxidase-like 2 protein functions as an amine oxidase toward collagen and elastin." Mol. Biol. Rep. 38(1): 145-149.

Kirschmann, D. A., et al. (2002). "A molecular role for lysyl oxidase in breast cancer invasion." Cancer research 62(15): 4478-4483.

Kumarasamy, A., et al. (2009). "Lysyl oxidase activity is dysregulated during impaired alveolarization of mouse and human lungs." Am. J. Respir. Crit. Care Med. 180(12): 1239-1252.

Lachance, Nicolas, et al. "Discovery of potent and liver-targeted stearoyl-CoA desaturase (SCD) inhibitors in a bispyrrolidine series." Bioorganic & medicinal chemistry letters 22.2 (2012): 980-984.

Lee, G.-H., et al. (2011). "Lysyl oxidase-like-1 enhances lung metastasis when lactate accumulation and monocarboxylate transporter expression are involved." Oncology Letters 2(5): 831-838.

Levene, C. I., et al. (1992). "Inhibition of chick embryo lysyl oxidase by various lathyrogens and the antagonistic effect of pyridoxal." Int J Exp Pathol 73(5): 613-624.

Levental, K. R., et al. (2009). "Matrix crosslinking forces tumor progression by enhancing integrin signaling." Cell 139(5): 891-906.

Li, R.-k., et al. (2015). "Lysyl oxidase-like 4 (LOXL4) promotes proliferation and metastasis of gastric cancer via FAK/Src pathway." Journal of Cancer Research and Clinical Oncology 141(2): 269-281.

Li, W., et al. (2003). "Lysyl oxidase oxidizes basic fibroblast growth factor and inactivates its mitogenic potential." Journal of cellular biochemistry 88(1): 152-164.

Liu, G., et al. (1997). "Irreversible inhibition of lysyl oxidase by homocysteine thiolactone and its selenium and oxygen analogues. Implications for homocystinuria." J Biol Chem 272(51): 32370-32377.

Liu, J., et al. (2014). "Correlations of lysyl oxidase with MMP2/MMP9 expression and its prognostic value in non-small cell lung cancer." Int J Clin Exp Pathol 7(9): 6040-6047.

Lopez, B., et al. (2010). "Role of lysyl oxidase in myocardial fibrosis: from basic science to clinical aspects." Am. J. Physiol. 299(1, Pt. 2): H1-H9.

Lopez, B., et al. (2012). "Collagen Cross-Linking But Not Collagen Amount Associates With Elevated Filling Pressures in Hypertensive Patients With Stage C Heart Failure: Potential Role of Lysyl Oxidase." Hypertension 60(3): 677-683.

Lopez, B., et al. (2013). "Osteopontin-mediated myocardial fibrosis in heart failure: a role for lysyl oxidase?" Cardiovasc. Res. 99(1): 111-120.

Lucero, H. A., et al. (2008). "Lysyl oxidase oxidizes cell membrane proteins and enhances the chemotactic response of vascular smooth muscle cells." J Biol Chem 283(35): 24103-24117.

Maki, J. M., et al. (2002). "Inactivation of the lysyl oxidase gene Lox leads to aortic aneurysms, cardiovascular dysfunction, and perinatal death in mice." Circulation 106(19): 2503-2509.

Mambetsariev, I., et al. (2014). "Stiffness-activated GEF-H1 expression exacerbates LPS-induced lung inflammation." PLoS One 9(4): e92670/92671-e92670/92612, 92612 pp.

Mammoto, A., et al. (2013). "Control of lung vascular permeability and endotoxin-induced pulmonary oedema by changes in extracellular matrix mechanics." Nature communications 4: 1759.

Mammoto, T., et al. (2013). "Role of Collagen Matrix in Tumor Angiogenesis and Glioblastoma Multiforme Progression." The American Journal of Pathology 183(4): 1293-1305.

Martinez-Martinez, E., et al. (2016). "The lysyl oxidase inhibitor (β-aminopropionitrile) reduces leptin profibrotic effects and ameliorates cardiovascular remodeling in diet-induced obesity in rats. Journal of Molecular and Cellular." Cardiology, 92, 96-104.

Miana, M., et al. (2015). "The lysyl oxidase inhibitor β-aminopropionitrile reduces body weight gain and improves the metabolic profile in diet-induced obesity in rats." Dis. Models Mech. 8(6): 543-551.

Millanes-Romero, A., et al. (2013). "Regulation of Heterochromatin Transcription by Snail1/LOXL2 during Epithelial-to-Mesenchymal Transition." Molecular Cell 52(5): 746-757.

Miller, B. W., et al. (2015). "Targeting the LOX/hypoxia axis reverses many of the features that make pancreatic cancer deadly: inhibition of LOX abrogates metastasis and enhances drug efficacy." EMBO Mol Med 7(8): 1063-1076.

Moreno-Bueno, G., et al. (2011). "Lysyl oxidase-like 2 (LOXL2), a new regulator of cell polarity required for metastatic dissemination of basal-like breast carcinomas." EMBO Mol Med 3(9): 528-544.

(56) References Cited

OTHER PUBLICATIONS

Murawaki, Y., et al. (1991). "Serum lysyl oxidase activity in chronic liver disease in comparison with serum levels of prolyl hydroxylase and laminin." Hepatology 14(6): 1167-1173.
Nave, A. H., et al. (2014). "Lysyl Oxidases Play a Causal Role in Vascular Remodeling in Clinical and Experimental Pulmonary Arterial Hypertension." Arterioscler., Thromb., Vasc. Biol. 34(7): 1446-1458.
Nicholson, R. I., et al. (2001). "EGFR and cancer prognosis." European Journal of Cancer 37, Supplement 4: 9-15.
Nishikawa, R., et al. (2015). "Tumour-suppressive microRNA-29s directly regulate LOXL2 expression and inhibit cancer cell migration and invasion in renal cell carcinoma." FEBS letters 589(16): 2136-2145.
Nuthakki, V. K., et al. (2004). "Lysyl oxidase expression in a rat model of arterial balloon injury." J Vasc Surg 40(1): 123-129.
Offenberg, H., et al. (2008). "TIMP-1 expression in human colorectal cancer is associated with TGF-B1, LOXL2, INHBA1, TNF-AIP6 and TIMP-2 transcript profiles." Mol Oncol 2(3): 233-240.
Ohmura, H., et al. (2012). "Cardiomyocyte-specific transgenic expression of lysyl oxidase-like protein-1 induces cardiac hypertrophy in mice." Hypertens. Res. 35(11): 1063-1068.
Osawa, T., et al. (2013). "Lysyl oxidase secreted by tumour endothelial cells promotes angiogenesis and metastasis." Br J Cancer 109(8): 2237-2247.
Papadantonakis, N., et al. (2012). "Megakaryocyte pathology and bone marrow fibrosis: the lysyl oxidase connection." Blood 120(9): 1774-1781.
Park, H.-Y. L., et al. (2014). "Lysyl oxidase-like 2 level and glaucoma surgical outcomes." Invest. Ophthalmol. Visual Sci. 55(5): 3337-3343.
Peinado, H., et al. (2005). "A molecular role for lysyl oxidase-like 2 enzyme in snail regulation and tumor progression." EMBO J 24(19): 3446-3458.
Peinado, H., et al. (2008). "Lysyl Oxidase-Like 2 as a New Poor Prognosis Marker of Squamous Cell Carcinomas." Cancer research 68(12): 4541-4550.
Peng, L., et al. (2009). "Secreted LOXL2 is a novel therapeutic target that promotes gastric cancer metastasis via the Src/FAK pathway." Carcinogenesis 30(10): 1660-1669.
Pickup, M. W., et al. (2013). "Stromally Derived Lysyl Oxidase Promotes Metastasis of Transforming Growth Factor-β-Deficient Mouse Mammary Carcinomas." Cancer Res. 73(17): 5336-5346.
Pinnell, S. R. and G. R. Martin (1968). "The cross-linking of collagen and elastin: enzymatic conversion of lysine in peptide linkage to alpha-aminoadipic-delta-semialdehyde (allysine) by an extract from bone." Proceedings of the National Academy of Sciences 61(2): 708-716.
Priyanka, T. et al. (2016) "Lysyl oxidase (LOX) inhibitors as anti-scarring agents" Abstracts of Papers, 252nd ACS National Meeting & Exposition, Philadelphia, PA, United States, Aug. 21-25, 2016, BIOL-98.
Renault, O. et al. (1997). "A convenient synthesis of new halothienyl β-aminoacids as versatile building block." Org. Prep. Proc. Int. 29(4): 488-494.
Rimar, D., et al. (2014). "Brief report: lysyl oxidase is a potential biomarker of fibrosis in systemic sclerosis." Arthritis Rheumatol 66(3): 726-730.
Roehrig, F. et al. (2017) "VEGF-ablation therapy reduces drug delivery and therapeutic response in ECM-dense tumors" Oncogene 36(1), 1-12.
Rosin, N. L., et al. (2015). "Disruption of Collagen Homeostasis Can Reverse Established Age-Related Myocardial Fibrosis." Am. J. Pathol. 185(3): 631-642.
Ruiz, L. A., et al. (2011). "Single-nucleotide polymorphisms in the lysyl oxidase-like protein 4 and complement component 3 genes are associated with increased risk for endometriosis and endometriosis-associated infertility." Fertil Steril 96(2): 512-515.

Schietke, R., et al. (2010). "The lysyl oxidases LOX and LOXL2 are necessary and sufficient to repress E-cadherin in hypoxia: insights into cellular transformation processes mediated by HIF-1." J Biol Chem 285(9): 6658-6669.
Schlotzer-Schrehardt, U., et al. (2008). "Genotype-correlated expression of lysyl oxidase-like 1 in ocular tissues of patients with pseudoexfoliation syndrome/glaucoma and normal patients." American Journal of Pathology 173(6): 1724-1735.
Schuetze, F., et al. (2015). "Inhibition of Lysyl Oxidases Improves Drug Diffusion and Increases Efficacy of Cytotoxic Treatment in 3D Tumor Models." Sci. Rep. 5: 17576.
Scola, N. and T. Gorogh (2010). "LOXL4 as a selective molecular marker in primary and metastatic head/neck carcinoma." Anticancer Res 30(11): 4567-4571.
Se, Lee, Y et al. (2017) " Expression of Lysyl Oxidase Predictive of Distant Metastasis of Laryngeal Cancer". Otolaryngology—head and neck surgery; 156(3), 489-497.
Shen, C. J., et al. (2014). "Ionizing radiation induces tumor cell lysyl oxidase secretion." BMC Cancer 14: 532/531-532/510.
Shinobu, Matsuura et al. (2016) "Lysyl oxidase is associated with increased thrombosis and platelet reactivity". Blood; 127(11), 1493-1501.
Siegel, R. C., et al. (1978). "Biochemical and immunochemical study of lysyl oxidase in experimental hepatic fibrosis in the rat." Proceedings of the National Academy of Sciences 75(6): 2945-2949.
Stewart, G. D., et al. (2008). "Analysis of hypoxia-associated gene expression in prostate cancer: lysyl oxidase and glucose transporter-1 expression correlate with Gleason score." Oncol Rep 20(6): 1561-1567.
Tadmor, T., et al. (2013). "The expression of lysyl-oxidase gene family members in myeloproliferative neoplasms." American Journal of Hematology 88(5): 355-358.
Tang, H., et al. (2017) "Lysyl oxidase drives tumour progression by trapping EGF receptors at the cell surface." Nat Commun. 8:14909.
Tang, S. S., et al. (1984). "Beta-substituted ethylamine derivatives as suicide inhibitors of lysyl oxidase." J Biol Chem 259(2): 975-979.
Toustrup, K., et al. (2011). "Development of a hypoxia gene expression classifier with predictive impact for hypoxic modification of radiotherapy in head and neck cancer." Cancer research 71(17): 5923-5931.
Vadasz, Z., et al. (2005). "Abnormal deposition of collagen around hepatocytes in Wilson's disease is associated with hepatocyte specific expression of lysyl oxidase and lysyl oxidase like protein-2." J Hepatol 43(3): 499-507.
Van Bergen, T., et al. (2013). "The role of LOX and LOXL2 in scar formation after glaucoma surgery." Invest. Ophthalmol. Visual Sci. 54(8): 5788-5796.
Van Bierbeek, A and Gingras, M. (1998) "Polysulfurated branched molecules containing functionalized m-phenylene sulfides." Tetrahedron Lett, 39(35): 6283-6286.
Van Nimwegen, M. J. and B. van de Water (2007). "Focal adhesion kinase: a potential target in cancer therapy." Biochem Pharmacol 73(5): 597-609.
Vitalba, DiStefano, et al. (2016). "Major Action of Endogenous Lysyl Oxidase in Clear Cell Renal Cell Carcinoma Progression and Collagen Stiffness Revealed by Primary Cell Cultures" Am. J. Pathol.; 186(9), 2473-2485.
Weihua, Z., et al. (2008). "Survival of Cancer Cells Is Maintained by EGFR Independent of Its Kinase Activity." Cancer Cell 13(5): 385-393.
Wiel, C., et al. (2013). "Lysyl oxidase activity regulates oncogenic stress response and tumorigenesis." Cell Death Dis 4: e855.
Wilgus, M.-L., et al. (2011). "Lysyl oxidase: A lung adenocarcinoma biomarker of invasion and survival." Cancer 117(10): 2186-2191.
Wilhelmus, M. M. M., et al. (2013). "Extracellular matrix modulator lysyl oxidase colocalizes with amyloid-beta pathology in Alzheimer's disease and hereditary cerebral hemorrhage with amyloidosis-Dutch type." Exp. Gerontol. 48(2): 109-114.
Williamson, P. R. and H. M. Kagan (1987). "Electronegativity of aromatic amines as a basis for the development of ground state inhibitors of lysyl oxidase." J Biol Chem 262(30): 14520-14524.

(56) References Cited

OTHER PUBLICATIONS

Wilson, et al. "Modulation of LDL receptor mRNA stability by phorbol esters in human liver cell culture models," Lipid Res. 38, 437-446 (1997).

Wong, C. C.-L., et al. (2014). "Lysyl oxidase-like 2 is critical to tumor microenvironment and metastatic niche formation in hepatocellular carcinoma." Hepatology (Hoboken, NJ, U. S.) 60(5): 1645-1658.

Xiao Q and Ge G. (2012) "Lysyl Oxidase, Extracellular Matrix Remodeling and Cancer Metastasis" Cancer Microenviron. 5(3): 261-273.

Xu, J., et al. (2014). "67 laminin receptor promotes the malignant potential of tumour cells up-regulating lysyl oxidase-like 2 expression in cholangiocarcinoma." Digestive and Liver Disease 46(8): 750-757.

Yang, X., et al. (2013). "Inactivation of lysyl oxidase by β-aminopropionitrile inhibits hypoxia-induced invasion and migration of cervical cancer cells." Oncol Rep 29(2): 541-548.

Yang, Z., et al. (2010). "Uric acid increases fibronectin synthesis through upregulation of lysyl oxidase expression in rat renal tubular epithelial cells." Am. J. Physiol. 299(2, Pt. 2): F336-F346.

Zaffryar-Eilot, S., et al. (2013). "Lysyl oxidase-like-2 promotes tumour angiogenesis and is a potential therapeutic target in angiogenic tumours." Carcinogenesis 34(10): 2370-2379.

Zenkel, M., et al. (2011). "Regulation of lysyl oxidase-like 1 (LOXL1) and elastin-related genes by pathogenic factors associated with pseudoexfoliation syndrome." Invest Ophthalmol Vis Sci 52(11): 8488-8495.

Zhi, Chen et al. (2017) "Elevated ischaemia-associated lysyl oxidase activity in delayed graft failure 6-12 months after renal transplantation" Experimental Physiology 102(2), 282-287.

Zhu, J., et al. (2015). "Lysyl Oxidase Is Predictive of Unfavorable Outcomes and Essential for Regulation of Vascular Endothelial Growth Factor in Hepatocellular Carcinoma." Digestive Diseases and Sciences: 1-13.

Zibadi, S., et al. (2010). "T lymphocyte regulation of lysyl oxidase in diet-induced cardiac fibrosis." Cardiovasc Toxicol 10(3): 190-198.

Office Action, dated Jun. 26, 2023, received in connection with corresponding JP Patent Application No. 2020-567240.

CAS Database Registry on STN, pp. 1-16, American Chemical Society (2023).

\* cited by examiner

HEXAHYDROPYRROLO[3,4-C]PYRROLE DERIVATIVES USEFUL AS LOX INHIBITORS

TECHNICAL FIELD

This disclosure relates to compounds useful as lysyl oxidase (LOX) and lysyl oxidase-like (LOXL) family members (LOXL1, LOXL2, LOXL3, LOXL4) inhibitors, to pharmaceutical compositions comprising the compounds, to the compounds for use in the treatment of conditions mediated by LOX and/or LOXL, for example cancer; and to a LOX inhibitor for use in the treatment of a cancer associated with EGFR.

BACKGROUND

LOX (protein-6-lysine-oxidase; EC 1.4.3.13) is an extracellular enzyme that catalyses oxidative deamination of the primary amines of lysine and hydroxylysine in proteins such as collagen and tropoelastin to generate peptidyl-[α]-aminoadipic-[δ]-semialdehyde, an aldehyde that spontaneously condenses to form inter- and intra-chain cross-links (Lucero and Kagan 2006). LOX regulates maturation of proteins in the extracellular matrix (ECM), thereby contributing to ECM tensile strength and function and so playing an important role in connective tissue remodelling. Other proteins have been reported as substrates for oxidation by LOX, such as basic fibroblast growth factor, PDGFR-β and other cationic proteins (Kagan and Li 2003, Li, Nugent et al. 2003, Lucero and Kagan 2006, Lucero, Ravid et al. 2008).

LOX is secreted as a precursor protein that is proteolytically processed by procollagen C-proteinases (bone morphogenetic protein 1—BMP-1) and mammalian tolloid-like protein (mTLL-1)(Uzel, Scott et al. 2001) to generate an 18 kDa pro-peptide and the 32 kDa active LOX enzyme (Lucero and Kagan 2006). The catalytic domain contains copper and a lysine-tyrosylquinone (LTQ) cofactor. LTQ is formed by post-translational oxidation of a catalytic site tyrosine (Tyr349), which then condenses onto a lysine, also within the catalytic site (Lys314), to form a stable covalent modification that is an essential part of the catalytic mechanism (Lucero and Kagan 2006) (Kagan and Li 2003).

LOX is part of a protein family consisting of five paralogues, LOX, LOX-like 1 [LOXL1], LOX-like 2 [LOXL2], LOX-like 3 [LOXL3] and LOX-like 4 [LOXL4]), all containing a conserved catalytic region. LOX enzymes play a crucial role in maintaining ECM stability, by initiating and regulating the crosslinking of collagens and elastin within the extracellular matrix (ECM). The activity of these enzymes is key to maintaining the normal tensile and elastic features of connective tissue of many organ systems within the body. LOX expression decreases during ageing indicating that its activity is especially important during development.

In addition to its role in tissue remodelling, LOX also plays a critical role in primary cancer and metastasis. Studies have shown that LOX plays a fundamental role in the growth of primary tumours in colorectal and lung cancer (Gao, Xiao et al. 2010, Baker, Cox et al. 2011) and glioblastoma (Mammoto, Jiang et al. 2013).

Expression of LOX is elevated in more than 70% of breast cancer patients with Estrogen Receptor negative disease, in 80% of head and neck cancer patients, in 33% of primary colorectal carcinomas (CRC) and 48% of metastatic tissues from patients with CRC (Baker, Cox et al. 2011), and in cirrhotic hepatocellular carcinoma (HCC) patients with a history of alcoholism (Huang, Ho et al. 2013). As discussed in more detail in the description, LOX is also overexpressed in numerous other cancers including lung, prostate and pancreatic cancers.

Elevated LOX expression is also associated with metastasis and decreased patient survival (Baker, Cox et al. 2011, Wilgus, Borczuk et al. 2011)

Other members of the LOX family have been implicated in proliferative diseases such as cancer. LOXL2 is another member of the LOX family that is involved in the cross-linking of extracellular collagens and elastin (Vadasz, Kessler et al. 2005) (Kim, Kim et al. 2010). In addition to conserved C-terminal region, the LOXL2 protein has scavenger receptor cysteine-rich regions that are commonly found in cell surface receptors and adhesion molecules, as well as a cytokine receptor-like domain.

LOXL2 expression has been found upregulated in breast, gastric, colon, esophageal, head and neck, lung and laryngeal carcinomas, as reviewed in Barker et al (Barker, Cox et al. 2012) and in renal cells carcinoma (Hase, Jingushi et al. 2014) (Nishikawa, Chiyomaru et al. 2015).

Studies have suggested that LOX and LOXL2 do not compensate one another, as manipulation of LOX expression did not affect LOXL2 levels in a colorectal cancer model (Baker, Cox et al. 2011). Thus, while LOX and LOXL2 are involved in similar extra-cellular processes, it appears that they have distinct roles.

LOXL1 was found to be overexpressed in metastatic non-small cells lung cancer (NSCLC), and the metastatic phenotype can be reduced by inhibition with LOXL1 siRNA (Lee, Kim et al. 2011).

LOXL3 mRNA was expressed in Hs578T highly invasive breast cancer cells, but not in poorly invasive and non-metastatic breast cancer cells MCF7 and T47D (Kirschmann, Seftor et al. 2002). Overexpression of LOXL3 in MDCK epithelial cells induces an epithelial-mesenchymal transition (EMT) process, which is a key step in the progression of metastasis (Peinado, Del Carmen Iglesias-de la Cruz et al. 2005).

In a study on the mRNA levels of LOXL4 in head and neck squamous cell carcinomas, high expression of LOXL4 gene was detected in 71% of all carcinomas and only in 9% of the healthy mucosa samples, indicating that LOXL4 may serve as a selective molecular marker in primary and metastatic head and neck carcinoma (Scola and Gorogh 2010). Up-regulation of LOXL4 was demonstrated in invasive HNC and revealed a significant correlation between LOXL4 expression and local lymph node metastases and higher tumour stages (Goeroegh, Weise et al. 2007). LOXL4 promotes metastasis in gastric cancer (Li, Zhao et al. 2015). LOXL4 together with LOXL2 has been found to be required for metastatic niche formation in a breast orthotopic mouse model (Wong, Gilkes et al. 2011).

LOX and LOXL are implicated in fibrotic diseases, such as liver fibrosis, lung fibrosis, kidney fibrosis, cardiac fibrosis, myelofibrosis and scleroderma. Both LOX and LOXL are highly expressed in fibrotic areas, in surrounding myofibroblasts and in serum of patients with fibrotic conditions (Kagan 1994) (Kim, Peyrol et al. 1999) (Siegel, Chen et al. 1978) (Jourdan-Le Saux, Gleyzal et al. 1994) (Murawaki, Kusakabe et al. 1991).

LOX is also implicated in cardiovascular disease. As discussed in the detailed description of the invention, LOX inhibition may prove beneficial in the treatment or prevention of cardiovascular conditions, including hypertensive heart disease, heart failure, cardiac hypertrophy and atherosclerosis.

LOX is associated with the amyloid-beta (Aβ) related pathological hallmarks (such as cerebral amyloid angiopathy and senile plaques) of both Alzheimer's disease (AD) and hereditary cerebral hemorrhage with amyloidosis of the Dutch type (HCHWA-D) pathogenesis (Wilhelmus, Bol et al. 2013). LOX activity is increased in the hippocampal samples of Alzheimer's disease and also in non-Alzheimer's dementia (Gilad, Kagan et al. 2005). LOX is increased at the site of brain injury (Gilad, Kagan et al. 2001) and spinal cord injury and its inhibition lead to accelerated functional recovery in an unilateral spinal cord dissection model (Gilad and Gilad 2001).

LOXLs are implicated in pulmonary diseases. LOXL2 and LOXL3 are likely to have a role in Primary Alveolar Proteinosis (PAP) since both are expressed in PAP tissue, but not normal lung tissue (Neufeld and Brekhman 2009).

LOX inhibition may be beneficial in the treatment of various ocular conditions. Inhibition of LOX or LOXL2 prevents neovascularization and fibrosis following laser-induced choroidal neovascularization (CNV). Therefore LOX and LOXL inhibitors can be useful in the treatment of conditions characterized by neovascularization, such as age-related macular degeneration (AMD), diabetic retinopathy and retinopathy of prematurity (Stalmans, Marshall et al. 2010).

LOX is implicated in inflammatory conditions and may be useful in the treatment of conditions including, but not limited to acute respiratory distress syndrome (ARDS) (Mambetsariev, Tian et al. 2014).

LOX is the main isoenzyme expressed in human adipose tissue and that its expression is strongly upregulated in samples from obese patients. β-aminopropionitrile reduces body weight gain and improves the metabolic profile in diet-induced obesity in rats (Miana, Galan et al. 2015) and reduces local adipose tissue inflammation (Halberg, Khan et al. 2009).

LOX is upregulated in endometriosis and may be implicated in the establishment and progression of endometriotic lesions (Ruiz, Dutil et al. 2011) (Dentillo, Meola et al. 2010).

Certain LOX inhibitors are known. These include β-aminopropionitrile (BAPN), haloamines, 1,2-diamines, allyl and propargyl amines, hydrazines, semicarbazide and thiolactones, benzylamines, mercaptopyridine and pyridazinone compounds (Pinnell and Martin 1968) (Tang, Simpson et al. 1984) (Palfreyman, McDonald et al. 1989) (Sayre 2007) (Carrington, Bird et al. 1984) (Levene, Sharman et al. 1992) (Liu, Nellaiappan et al. 1997) (Williamson and Kagan 1987) (Anderson, Bartlett et al. 2007) (Schohe-Loop, Burchardt et al. 2003) (Burchardt 2006, Aslam, Miele et al. 2015). However, in general these compounds are either non-selective, lack potency or are unsuitable for use in patients. It is believed that the only LOX inhibitor which has progressed to clinical trials in humans is BAPN. However, it is believed that this compound has not been used clinically since 1978. More recent LOX and LOXL2 inhibitors have been described: LOX inhibitors containing hydrazine and hydrazide groups (Burke et al, 2017); LOXL2 inhibitors: derivatives of haloallylamine (Chang et al, 2017), pyridines (Rowbottom et al, 2016a; Rowbottom et al, 2016b), pyrimidines (Rowbottom & Hutchinson, 2017a) and chromenones (Rowbottom & Hutchinson, 2017b).

WO 2017/141049 A1 discloses methylamine derivatives as LOX inhibitors.

WO 2004/110996 A1 relates to compounds disclosed to exhibit neurokinin (NK) inhibitory properties and useful for treatment of neurokinin-mediated conditions.

WO 2007/027734 A2 relates to bicyclic and bridged nitrogen heterocycles as which are disclosed to be effective as modulators of one or more chemokine receptors (CCRs) and useful in treating inflammatory and immune disorder conditions and diseases.

WO 2011/050198 A1 and WO 2012/145581 A1 relate to disubstituted octahydropyrrolo[3,4-c]pyrroles disclosed to be orexin receptor modulators and useful for treatment of diseases or conditions mediated by orexin activity, such as insomnia.

WO 2009/137308 A1 relate to disclosed to selective ligands for neuronal nicotinic receptors (NNRs) and useful as for treating a condition or disorder where modulation of α4β2 NNR activity is of therapeutic benefit.

BRIEF SUMMARY OF THE DISCLOSURE

It is an object of the present invention to provide novel compounds that are useful for the treatment of diseases, disorders and/or conditions which is affected and/or mediated by LOX, such as cancer or fibrosis.

In accordance with the present invention, there is provided a compound having the structure of Formula (I):

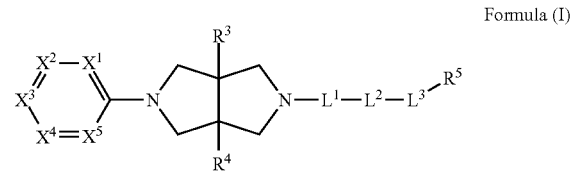

Formula (I)

or a pharmaceutically acceptable salt thereof, wherein
$X^1$ and $X^5$ is each selected from $CR^1$ or N;
$X^2$, $X^3$ and $X^4$ is each selected from $CR^1$, $CR^2$ or N, provided at least one of $X^2$, $X^3$ and $X^4$ is $CR^2$ and provided only one of $X^1$, $X^2$, $X^3$, $X^4$ and $X^5$ can be N;
$R^1$ is at each occurrence independently selected from hydrogen, halo, cyano, hydroxy, $C_1$-$C_6$ alkyl, $C_2$-$C_6$ alkenyl, $C_2$-$C_6$ alkynyl, $C_1$-$C_6$ alkoxy, $C_1$-$C_6$ alkylcarbonyl, $C_1$-$C_6$ alkoxy-carbonyl, —C(O)NR$^7$R$^8$, —SO$_2$R$^7$, or —SO$_2$NR$^7$R$^8$, where
any alkyl, alkenyl, alkynyl or alkoxy in $R^1$ may be optionally substituted by one, two or three substituents independently selected from halo, cyano, oxo, hydroxy, carboxy, $R^7$, —OR$^7$, —C(O)R$^7$ or —C(O)OR$^7$;
$R^2$ is at each occurrence independently selected from —O—Y$^1$—R$^{2a}$, —O—Y$^2$—C(O)—Y$^1$—R$^{2a}$, —O—Y$^2$—C(O)—Y$^1$—NR$^{2b}$R$^{2c}$, —S—Y$^1$—R$^{2a}$, —S—Y$^2$—C(O)—Y$^1$—NR$^{2b}$R$^{2c}$, —SO$_2$—Y$^1$—R$^{2a}$, —NR$^{2b}$R$^{2c}$ or —NR$^{2a}$—Y$^2$—C(O)—Y$^1$—NR$^{2b}$R$^{2c}$;
$Y^1$ is selected from a bond, $C_1$-$C_4$ alkylene, $C_2$-$C_4$ alkenylene or $C_2$-$C_4$ alkynylene, where
any alkylene, alkenylene or alkynylene in $Y^1$ may be optionally substituted by one or two substituents independently selected from halo, cyano, hydroxy, carboxy, $R^6$, —OR$^6$, —C(O)R$^6$ or —C(O)OR$^6$;
$Y^2$ is selected from $C_1$-$C_4$ alkylene, $C_2$-$C_4$ alkenylene or $C_2$-$C_4$ alkynylene, where any alkylene, alkenylene or alkynylene in $Y^2$ may be optionally substituted by one or two substituents independently selected from halo, cyano, hydroxy, carboxy, $R^6$, —OR$^6$, —C(O)R$^6$ or —C(O)OR$^6$;
$R^{2a}$ is selected from $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkenyl, 3- to 6-membered monocyclic heterocyclyl, phenyl, or 5- or 6-membered heteroaryl, where any alkyl, alkenyl, alkynyl, cycloalkyl, cycloalkenyl or heterocyclyl in $R^{2a}$ may be optionally substituted by one, two or three substituents independently selected from halo, cyano, oxo, hydroxy, carboxy, $R^6$, —$OR^6$, —$C(O)R^6$, —$C(O)OR^6$, —$OC(O)R^6$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$;

any phenyl or heteroaryl in $R^{2a}$ may be optionally substituted by one, two or three substituents independently selected from halo, cyano, carboxy, $R^6$, —$OR^6$, —$C(O)R^6$, —$C(O)OR^6$, —$OC(O)R^6$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$; and any heterocyclyl or heteroaryl in $R^{2a}$ includes 1, 2 or 3 heteroatoms selected from N, O or S in the ring;

$R^{2b}$ and $R^{2c}$ is each independently selected from $C_1$-$C_6$ alkyl, $C_3$-$C_6$ alkenyl or $C_3$-$C_6$ alkynyl, where any alkyl, alkenyl or alkynyl in $R^{2b}$ and $R^{2c}$ may be optionally substituted by one, two or three substituents independently selected from halo, cyano, oxo, hydroxy, carboxy, $R^6$, —$OR^6$, —$C(O)R^6$, —$C(O)OR^6$, —$OC(O)R^6$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$; or $R^{2b}$ and $R^{2c}$ together with the nitrogen atom to which they are attached form a 3- to 7-membered heterocycloalkyl, optionally including one or two additional heteroatoms (i.e. in addition to the nitrogen atom of —$NR^{2b}R^{2c}$) selected from O, N or S in the ring, said heterocycloalkyl formed by $R^{2b}$ and $R^{2c}$ may be optionally substituted by one, two or three substituents independently selected from halo, cyano, hydroxy, carboxy, $R^6$, —$OR^6$, —$C(O)R^6$, —$C(O)OR^6$, —$OC(O)R^6$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$;

any S in the ring of said heterocycloalkyl formed by $R^{2b}$ and $R^{2c}$ may be optionally oxidized;

optionally when (i) $CR^1$ and $CR^2$ are adjacent, (ii) $R^1$ is $C_1$-$C_6$ alkyl, (iii) $R^2$ is —O—$Y^1$—$R^{2a}$, —O—$Y^2$—C(O)—$Y^1$—$R^{2a}$, —S—$Y^1$—$R^{2a}$ or —$SO_2$—$Y^1$—$R^{2a}$, and (iv) $R^{2a}$ is $C_1$-$C_6$ alkyl, then $R^1$ and $R^2$ together with the carbon atom to which they are attached may form a 4- to 7-membered heterocycloalkyl including one heteroatom selected from O or S in the ring;

optionally when (i) $CR^2$ and $CR^2$ are adjacent, (ii) each $R^2$ is independently selected from —O—$Y^1$—$R^{2a}$, —O—$Y^2$—C(O)—$Y^1$—$R^{2a}$, —S—$Y^1$—$R^{2a}$ or —$SO_2$—$Y^1$—$R^{2a}$, and (iii) each $R^{2a}$ is $C_1$-$C_6$ alkyl, then the first $R^2$ and the second $R^2$ together with the carbon atom to which they are attached may form a 4- to 7-membered heterocycloalkyl including two heteroatoms selected from O or S in the ring;

$R^3$ and $R^4$ is each independently selected from hydrogen, hydroxy, carboxy, $C_1$-$C_6$ alkyl, $C_1$-$C_6$ alkoxy, $C_1$-$C_6$ alkyl-carbonyl or $C_1$-$C_6$ alkoxy-carbonyl, any alkyl or alkoxy in $R^3$ and $R^4$ may be optionally substituted by one, two or three substituents independently selected from halo, cyano, or hydroxy; or $R^3$ and $R^4$ together with the carbon atom to which they are attached form a 3- to 7-membered cycloalkyl, said cycloalkyl formed by $R^3$ and $R^4$ may be optionally substituted by one, two or three substituents independently selected from halo, cyano, hydroxy, carboxy, $R^6$, —$OR^6$, —$C(O)R^6$ or —$C(O)OR^6$;

$L^1$ and $L^3$ is each independently selected from a bond, $C_1$-$C_4$ alkylene, $C_2$-$C_4$ alkenylene or $C_2$-$C_4$ alkynylene, where any alkylene, alkenylene or alkynylene in $L^3$ and $L^1$ may be optionally substituted by one or two substituents independently selected from halo, cyano, oxo, hydroxy, carboxy, $R^6$, —$OR^6$, —$C(O)R^6$ or —$C(O)OR^6$;

$L^2$ is selected from a bond, —O—, —C(O)—, —C(O)O—, —OC(O)—, —C(O)NR^7—, —NR^7C(O)—, —$NR^7$—, —$SO_2NR^7$—, —$NR^7SO_2$—, —S—, —$SO_2$—, —$SO_2O$—, —$OSO_2$—, —$NR^7SO_2NR^8$—, —$NR^7C(O)NR^8$—, —$C(O)NR^7NR^8$—, —$NR^7NR^8C(O)$—, —$NR^7C(O)O$— or —$OC(O)NR^7$—;

$R^5$ is selected from hydrogen, $C_1$-$C_6$ alkyl, $C_2$-$C_6$ alkenyl, $C_2$-$C_6$ alkynyl, $C_3$-$C_{12}$ cycloalkyl, $C_3$-$C_{12}$ cycloalkenyl, 3- to 12-membered heterocyclyl, phenyl or 5- or 6-membered heteroaryl, where any heterocyclyl or heteroaryl in $R^5$ includes 1, 2 or 3 heteroatoms selected from N, O or S in the ring;

any alkyl, alkenyl or alkynyl in $R^5$ may be optionally substituted by one, two or three substituents independently selected from halo, cyano, oxo, hydroxy, carboxy, nitro, $R^6$, —$OR^6$, —$C(O)R^6$, —$C(O)OR^6$, —$OC(O)R^6$, —$C(O)NR^6R^7$, —$NR^7C(O)R^8$, —$NR^6R^7$, —$SO_2NR^6R^7$, —$NR^7SO_2R^8$, —$SR^7$, —$SO_2R^7$, —$SO_2OR^7$, —$OSO_2R^7$, —$NR^8SO_2NR^6R^7$, —$NR^8C(O)NR^6R^7$, —$NR^7C(O)OR^8$ or —$OC(O)NR^6R^7$;

any cycloalkyl, cycloalkenyl, heterocyclyl, phenyl or heteroaryl in $R^5$ may be optionally substituted by one, two or three substituents independently selected from halo, cyano, oxo, nitro, $R^7$, —$OR^7$, —$C(O)R^7$, —$OC(O)R^7$, —$C(O)OR^7$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$;

$R^6$ is at each occurrence independently selected from $C_1$-$C_4$ alkyl, $C_1$-$C_4$ haloalkyl, $C_1$-$C_4$ hydroxyalkyl, $C_1$-$C_4$ cyanoalkyl;

$R^7$, $R^8$ and $R^9$ is at each occurrence independently selected from hydrogen or $C_1$-$C_4$ alkyl, where any $C_1$-$C_4$ alkyl in $R^7$, $R^8$ and $R^9$ may be optionally substituted by one, two or three substituents independently selected from halo, cyano, oxo, hydroxy, carboxy, $R^6$, —$OR^6$, —$C(O)R^6$ or —$C(O)OR^6$;

provided when $L^2$ is linked to $L^1$ by a nitrogen atom, $L^1$ is not a bond;

provided when $R^5$ is $C_3$-$C_{12}$ cycloalkyl, $C_3$-$C_{12}$ cycloalkenyl, 3- to 12-membered heterocyclyl, phenyl or 5- or 6-membered heteroaryl, at least one of $L^1$, $L^2$ and $L^3$ is not a bond;

provided -$L^1$-$L^2$-$L^3$-$R^5$ is not benzyl, benzyloxycarbonyl or tert-butyloxycarbonyl;

provided when $X^3$ is N and each of $X^5$ and $X^1$ is $CR^1$, then $R^1$ is not cyano;

provided when one of $X^2$ or $X^4$ is N, one of $X^2$ or $X^4$ is $CR^2$ and -$L^1$-$L^2$-$L^3$-$R^5$ is 2-pyridylmethyl or 3-pyridylmethyl, then $R^2$ is not —O-benzyl; and provided when one of $X^2$ or $X^4$ is $CR^2$ and $X^3$ is $CR^1$, then $R^1$ is not chloro.

Also provided is a pharmaceutical composition comprising a compound of the invention, or a pharmaceutically acceptable salt thereof, and a pharmaceutically acceptable excipient.

Also provided is a compound of the invention, or a pharmaceutically acceptable salt thereof, or a pharmaceutical composition of the invention, for use as a medicament. In some embodiments, there is provided a compound of the invention, or a pharmaceutically acceptable salt thereof, for use in the treatment of a disease or a medical condition mediated by LOX.

Also provided is a method of treating a disease or a medical condition mediated by LOX in a subject, the method comprising administering to the subject an effective amount of a compound of the invention or a pharmaceutical composition of the invention.

In some embodiments, a compound of the invention, or a pharmaceutically acceptable salt thereof, or a pharmaceutical composition of the invention, is for use in the treatment of a proliferative disease, particularly cancer.

In some embodiments, a compound of the invention, or a pharmaceutically acceptable salt thereof, or a pharmaceutical composition of the invention, is for use in the treatment or prevention of cancer associated with overexpression of EGFR.

In some embodiments, a compound of the invention, or a pharmaceutically acceptable salt thereof, or a pharmaceutical composition of the invention, is for use in the treatment of fibrotic disease, such as liver fibrosis, lung fibrosis, kidney fibrosis, cardiac fibrosis, myelofibrosis or schleroderma.

DETAILED DESCRIPTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "halo" or "halogen" refers to one of the halogens, group 17 of the periodic table. In particular the term refers to fluorine, chlorine, bromine and iodine. Preferably, the term refers to fluorine or chlorine.

The term $C_{m-n}$ refers to a group with m to n carbon atoms. $C_{m-n}$ is herein also referred to as $C_m$-$C_n$.

The term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. "$C_{1-4}$ alkyl" similarly refers to such groups containing up to 4 carbon atoms. Alkylene groups are divalent alkyl groups and may likewise be linear or branched and have two points of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_1$-$C_4$ alkoxy. Other substituents for the alkyl group may alternatively be used.

The term "$C_{1-6}$ haloalkyl", e.g. "$C_{1-4}$ haloalkyl", refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoroethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" includes a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" includes a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

As used herein, the term "cycloalkyl" represents a saturated monocyclic or polycyclic (e.g. bicyclic) aliphatic ring system containing ring carbon atoms. The term cycloalkyl includes both fused and bridged polycyclic systems.

The term "$C_{3-6}$ cycloalkyl" includes a saturated hydrocarbon ring system containing 3, 4, 5 or 6 carbon atoms. For example, the "$C_3$-$C_6$ cycloalkyl" may be cyclopropyl, cyclobutyl, cyclopentyl, cyclohexyl, bicycle[2.1.1]hexane or bicycle[1.1.1]pentane.

As used herein, "cycloalkenyl" refers to a cycloalkyl group having at least one carbon-carbon double bond in at least one ring.

The term "heterocyclyl", "heterocyclic" or "heterocycle" includes a non-aromatic saturated or partially saturated monocyclic or fused, bridged, or spiro bicyclic heterocyclic ring system(s). Monocyclic heterocyclic rings may contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles may contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles comprising at least one nitrogen in a ring position include, for example, azetidinyl, pyrrolidinyl, piperidinyl, piperazinyl, morpholinyl, thiomorpholinyl, tetrahydrotriazinyl, tetrahydropyrazolyl, tetrahydropyridinyl, homopiperidinyl, homopiperazinyl, 3,8-diaza-bicyclo[3.2.1]octanyl, 8-aza-bicyclo[3.2.1]octanyl, 2,5-Diaza-bicyclo[2.2.1]heptanyl and the like. Typical sulfur containing heterocycles include tetrahydrothienyl, dihydro-1,3-dithiol, tetrahydro-2H-thiopyran, and hexahydrothiepine. Other heterocycles include dihydro oxathiolyl, tetrahydro oxazolyl, tetrahydro-oxadiazolyl, tetrahydrodioxazolyl, tetrahydrooxathiazolyl, hexahydrotriazinyl, tetrahydro oxazinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (═O), for example, 2 oxopyrrolidinyl, 2-oxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. For example, the term "piperidino" or "morpholino" refers to a piperidin-1-yl or morpholin-4-yl ring that is linked via the ring nitrogen.

As used herein, the term "heterocycloalkyl" is a subset of heterocyclyls and represents a saturated monocyclic or polycyclic (e.g. bicyclic) aliphatic ring system containing, for instance, from 3 to 12 ring atoms, at least one being a heteroatom selected from nitrogen, oxygen and sulphur in the ring.

The term "bridged ring systems" includes ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane, and quinuclidine.

The term "spiro bi-cyclic ring systems" includes ring systems in which two ring systems share one common spiro carbon atom, i.e. the heterocyclic ring is linked to a further carbocyclic or heterocyclic ring through a single common spiro carbon atom. Examples of spiro ring systems include 3,8-diaza-bicyclo[3.2.1]octane, 2,5-Diaza-bicyclo[2.2.1]heptane, 6-azaspiro[3.4]octane, 2-oxa-6-azaspiro[3.4]octane, 2-azaspiro[3.3]heptane, 2-oxa-6-azaspiro[3.3]heptane, 6-oxa-2-azaspiro[3.4]octane, 2,7-diaza-spiro[4.4]nonane, 2-azaspiro[3.5]nonane, 2-oxa-7-azaspiro[3.5]nonane and 2-oxa-6-azaspiro[3.5]nonane.

"Heterocyclyl-$C_{m-n}$ alkyl" includes a heterocyclyl group covalently attached to a $C_{m-n}$ alkylene group, both of which are defined herein.

The term "aromatic" when applied to a substituent as a whole includes a single ring or polycyclic ring system with 4n+2 electrons in a conjugated π system within the ring or ring system where all atoms contributing to the conjugated π system are in the same plane.

The term "aryl" includes an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" includes an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated π system where all atoms contributing to the conjugated π system are in the same plane.

Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzoisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl and imidazo[1,2-b][1,2,4]triazinyl. Examples of heteroaryl groups comprising at least one nitrogen in a ring position include pyrrolyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, indolyl, isoindolyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl and pteridinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl-$C_{m-n}$ alkyl-" includes a heteroaryl group covalently attached to a $C_{m-n}$ alkylene group, both of which are defined herein. Examples of heteroaralkyl groups include pyridin-3-ylmethyl and the like.

As used herein, the term "alkoxy" denotes —O-alkyl wherein alkyl is as defined above. $C_1$-$C_6$ alkoxy includes an alkyl having from 1 to 6 carbon atoms. Non-limiting examples of $C_1$-$C_6$ alkoxy are methoxy, ethoxy, n-propyloxy, iso-propyloxy, 2-methyl-1-propyloxy, 2-methyl-2-propyloxy, 2-methyl-1-butyloxy, 3-methyl-1-butyloxy, 2-methyl-3-butyloxy, 2,2-dimethyl-1-propyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2,2-dimethyl-1-butyloxy, 3,3-dimethyl-1-butyloxy, 2-ethyl-1-butyloxy, butyloxy, iso-butyloxy, t-butyloxy, pentyloxy, iso-pentyloxy, neo-pentyloxy, hexyloxy, and the like.

As used herein, the term "alkoxy-carbonyl" refers to —C(O)—O-alkyl.

As used herein, the term "alkyl-carbonyl" refers to —C(O)-alkyl.

As used herein, the term "halo" refers to fluoro, chloro, bromo and iodo.

As used herein, the term "nitro" refers to —$NO_2$.

As used herein, the term "hydroxy" refers to —OH.

As used herein, the term "carboxy" refers to —COOH.

As used herein, the term "nitrile" (sometimes also called "cyano") refers to —CN.

As used herein, the term "oxo" refers to =O.

The term "optionally substituted" includes either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

A bond terminating in a "⌇" represents that the bond is connected to another atom that is not shown in the structure and denotes the point of attachment of a chemical moiety to the remainder of a molecule or chemical formula. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "⌇".

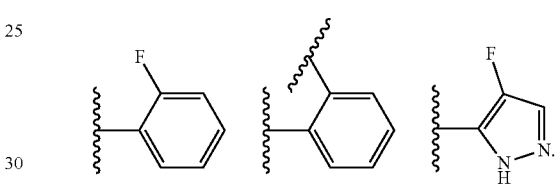

"Meta" substitution is a substitution pattern where two substituents are on carbons one carbon removed from each other, i.e. with a single carbon atom between the substituted carbons. In other words there is a substituent on the second atom away from the atom with another substituent. For example the groups below are meta substituted.

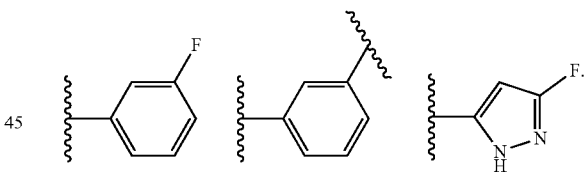

"Para" substitution is a substitution pattern where two substituents are on carbons two carbons removed from each other, i.e. with two carbon atoms between the substituted carbons. In other words there is a substituent on the third atom away from the atom with another substituent. For example the groups below are para substituted.

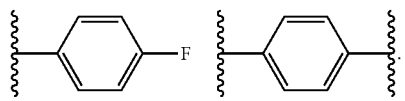

The term "acyl" includes an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, e.g. R is H or $C_{1-3}$ alkyl. In one embodiment acyl is alkyl-carbonyl. Examples of acyl groups include, but are not limited to, formyl, acetyl, propionyl and butyryl. A particular acyl group is acetyl (also represented as Ac).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

The invention contemplates pharmaceutically acceptable salts of the compounds of the invention. These may include the acid addition and base salts of the compounds. These may be acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by for example, one or more of the following methods:
   (i) by reacting the compound of the invention with the desired acid or base;
   (ii) by removing an acid- or base-labile protecting group from a suitable precursor of the compound of the invention or by ring-opening a suitable cyclic precursor, for example, a lactone or lactam, using the desired acid or base; or
   (iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereo centres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%

The compounds of this invention may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess LOX inhibitory activity.

Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^2$H (also written as "D" for deuterium), $^3$H (also written as "T" for tritium), $^{11}$C, $^{13}$C, $^{14}$C, $^{15}$O, $^{17}$O, $^{18}$O, $^{18}$F and the like. The radionuclide that is used will depend on the specific application of that radio-labelled derivative. For example, for in vitro competition assays, $^3$H or $^{14}$C are often useful. For radio-imaging applications, $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^{18}$F.

It is also to be understood that certain compounds of the invention may exist in solvated as well as unsolvated forms such as, for example, hydrated forms. It is to be understood that the invention encompasses all such solvated forms that possess LOX inhibitory activity.

It is also to be understood that certain compounds of the invention may exhibit polymorphism, and that the invention encompasses all such forms that possess LOX inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

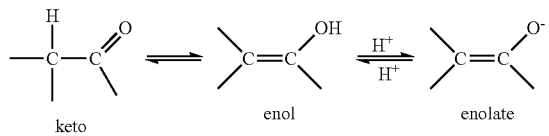

The in vivo effects of a compound of the invention may be exerted in part by one or more metabolites that are formed within the human or animal body after administration of a compound of the invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Further information on the preparation of the compounds of the invention is provided in the Examples section. The general reaction schemes and specific methods described in the Examples form a further aspect of the invention.

The resultant compound of the invention from the processes defined above can be isolated and purified using techniques well known in the art.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

The processes defined herein may further comprise the step of subjecting the compound of the invention to a salt exchange, particularly in situations where the compound of the invention is formed as a mixture of different salt forms. The salt exchange suitably comprises immobilising the compound of the invention on a suitable solid support or resin, and eluting the compounds with an appropriate acid to yield a single salt of the compound of the invention.

In a further aspect of the invention, there is provided a compound of the invention obtainable by any one of the processes defined herein.

Certain of the intermediates described in the reaction schemes above and in the Examples herein are novel. Such novel intermediates, or a salt thereof, particularly a pharmaceutically acceptable salt thereof, form a further aspect of the invention.

Compounds

In particular embodiments of compounds of Formula (I), when each of $L^1$, $L^2$, and $L^3$ is a bond, then $R^5$ is not hydrogen. Thus, in embodiments of compounds of Formula (I), $L^1$-$L^2$-$L^3$-$R^5$ is not hydrogen. In some embodiments, $R^5$ is not hydrogen.

In particular embodiments of compounds of Formula (I), when each of $L^1$, $L^2$, and $L^3$ is a bond, then $R^5$ is not methyl. Thus, in embodiments of compounds of Formula (I), $L^1$-$L^2$-$L^3$-$R^5$ is not methyl.

In particular embodiments of compounds of Formula (I) -L¹-L²-L³-R⁵— is not

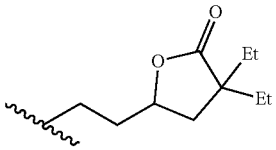 [SMILES: *CCC1CC(CC)(CC)C(=O)O1]

or a stereoisomer thereof.

In particular embodiments of compounds of Formula (I), the compounds of Formula (I) is not compound (i) to (xi) below, or a stereoisomer and/or a salt thereof:
  (i) 2-(5-ethoxy-3-pyridinyl)octahydropyrrolo[3,4-c]pyrrole;
  (ii) 2-[6-(ethylthio)-3-pyridinyl]octahydropyrrolo[3,4-c]pyrrole;
  (iii) 2-[5-(ethylthio)-3-pyridinyl]octahydropyrrolo[3,4-c]pyrrole;
  (iv) 2-[5-methoxy-3-pyridinyl]octahydropyrrolo[3,4-c]pyrrole;
  (v) 2-[5-ethoxy-3-pyridinyl]octahydropyrrolo[3,4-c]pyrrole;
  (vi) 2-[5-propoxy-3-pyridinyl]octahydropyrrolo[3,4-c]pyrrole;
  (vii) 2-[5-(2,2,2-trifluoroethoxy)-3-pyridinyl]octahydropyrrolo[3,4-c]pyrrole;
  (viii) 2-[5-(phenylmethoxy)-3-pyridinyl]octahydropyrrolo[3,4-c]pyrrole;
  (ix) 2-[5-(1-methylethoxy)-3-pyridinyl]octahydropyrrolo[3,4-c]pyrrole;
  (x). 2-methyl-5-[5-(phenylmethoxy)-3-pyridinyl]octahydropyrrolo[3,4-c]pyrrole;
  (xi) 2-[(2-chloro-5-trifluoromethoxy)phenyl]octahydropyrrolo[3,4-c]pyrrole.

In particular embodiments of compounds of Formula (I), when $X^3$ is N, then $R^1$ is not cyano.

In particular embodiments of compounds of Formula (I), when any of $X^1$, $X^2$, $X^3$, $X^4$ and $X^5$ is N, then $R^1$ is not cyano.

In particular embodiments of compounds of Formula (I), when one of $X^2$ or $X^4$ is N and one of $X^2$ or $X^4$ is $CR^2$, then $R^2$ is not —O-benzyl.

In particular embodiments of compounds of Formula (I), when any of $X^1$, $X^2$, $X^3$, $X^4$ and $X^5$ is N, then $R^2$ is not —O-benzyl.

In particular embodiments of compounds of Formula (I), when one of $X^2$ or $X^4$ is $CR^2$, then $R^1$ is not chloro.

In particular embodiments of compounds of Formula (I), when one of $X^2$ or $X^4$ is $CR^2$, then $R^1$ is not halo.

In particular embodiments of compounds of Formula (I), when $L^1$ is a bond and $L^2$ is —C(O)—, then $R^5$ is not a 3- to 12-membered heterocyclyl, phenyl or 5- or 6-membered heteroaryl.

In particular embodiments of compounds of Formula (I), when $L^2$ is —C(O)—, then R 5 is not a 3- to 12-membered heterocyclyl, phenyl or 5- or 6-membered heteroaryl.

In particular embodiments of compounds of Formula (I), when $L^2$ is —C(O)NR⁷—, —NR⁷—, —SO₂NR⁷—, —NR⁷SO₂NR⁸—, —NR⁷C(O)NR⁸—, —C(O)NR⁷NR⁸—, or —OC(O)NR⁷— and $R^5$ is linked to $L^3$ by a nitrogen atom, then $L^3$ is not a bond.

In particular embodiments of compounds of Formula (I), when $R^5$ is linked to $L^3$ by a nitrogen atom and $L^3$ is a bond, then $L^2$ is selected from —C(O)—, —OC(O)—, —NR⁷C(O)—, —NR⁷SO₂—, —SO₂—, —OSO₂— or —NR⁷NR⁸C(O)—, in particular $L^2$ is —C(O)—.

In embodiments, a compound of Formula (I) is a compound according to Formula (I-a):

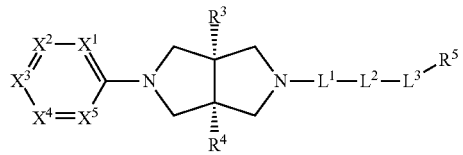

Formula (I-a)

or a pharmaceutically acceptable salt thereof.

In embodiments of compounds of Formula (I) or (I-a), one or two of $X_2$, $X_3$ and $X_4$ is $CR^2$.

In embodiments of compounds of Formula (I) or (I-a), one of $X_2$, $X_3$ and $X_4$ is $CR^2$ and the remaining two groups are selected from $CR^1$ and N.

In embodiments of compounds of Formula (I) or (I-a), $X^3$ is $CR^2$.

In embodiments, a compound of Formula (I) is a compound according to Formula (I-b):

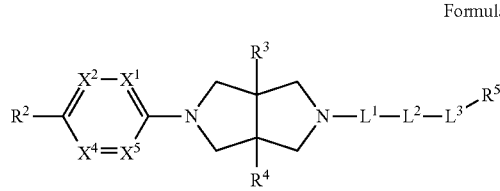

Formula (I-b)

or a pharmaceutically acceptable salt thereof.

In embodiments of compounds of Formula (I-b), each of $X^1$, $X^2$, $X^4$ and $X^5$ is selected from $CR^1$ or N; provided only one of $X^1$, $X^2$, $X^4$ and $X^5$ can be N.

In embodiments of compounds of Formula (I-b), each of $X^1$, $X^2$, $X^4$ and $X^5$ is $CR^1$.

In embodiments, a compound of Formula (I) is a compound according to Formula (II-a) or Formula (II-b):

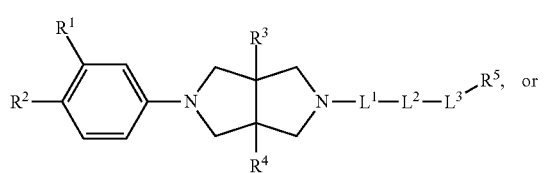

Formula (II-a)

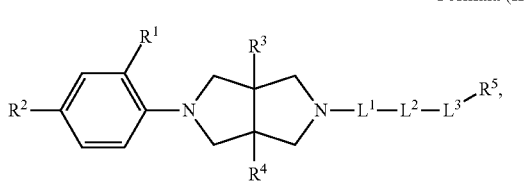

Formula (II-b)

or a pharmaceutically acceptable salt thereof.

In embodiments, a compound of Formula (I) is a compound according to Formula (II-a):

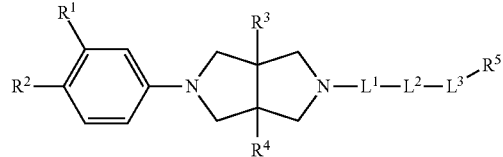

Formula (II-a)

or a pharmaceutically acceptable salt thereof.

In embodiments, a compound of Formula (I) is a compound according to Formula (II-c):

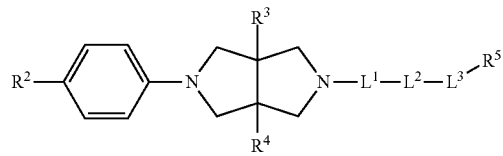

Formula (II-c)

or a pharmaceutically acceptable salt thereof.

In embodiments of compounds of Formula (I), one of $X^2$ and $X^4$ is $CR^2$ and one of $X^2$ and $X^4$ is $CR^1$ or N.

In embodiments, a compound of Formula (I) is a compound according to Formula (I-c):

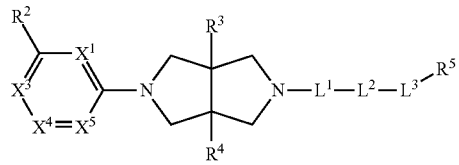

Formula (I-c)

or a pharmaceutically acceptable salt thereof.

In embodiments of compounds of Formula (I-c), each of $X^1$, $X^3$, $X^4$ and $X^5$ is selected from $CR^1$ or N; provided only one of $X^1$, $X^2$, $X^3$, $X^4$ and $X^5$ can be N.

In embodiments of compounds of Formula (I-c), each of $X^1$, $X^3$, $X^4$ and $X^5$ is $CR^1$. Thus, in embodiments of compounds of Formula (I), one of $X^2$ and $X^4$ is $CR^2$, one of $X^2$ and $X^4$ is $CR^1$, and each of $X^1$, $X^3$ and $X^5$ is $CR^1$.

In embodiments, a compound of Formula (I) is a compound according to any one of Formulas (II-d) to (II-g):

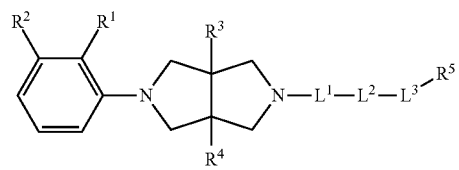

Formula (II-d)

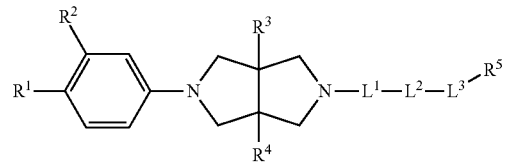

Formula (II-e)

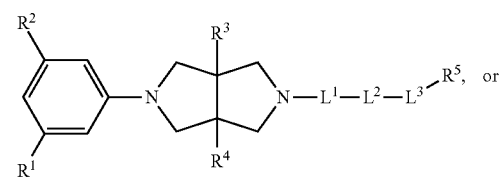

Formula (II-f)

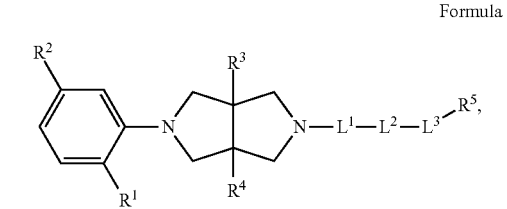

Formula (II-g)

or a pharmaceutically acceptable salt thereof.

In embodiments, a compound of Formula (I) is a compound according to Formula (II-e):

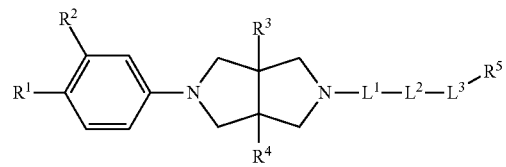

Formula (II-e)

or a pharmaceutically acceptable salt thereof.

In embodiments, a compound of Formula (I) is a compound according to Formula (II-h):

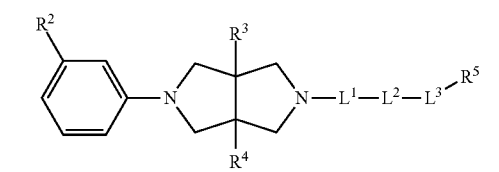

Formula (II-h)

or a pharmaceutically acceptable salt thereof.

In embodiments, a compound of Formula (I) is a compound according to any one of Formula (I-d) to (I-i):

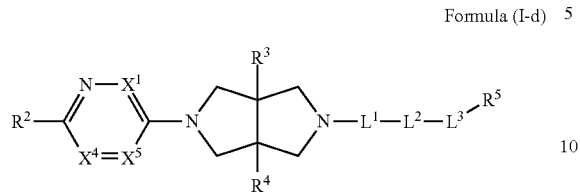
Formula (I-d)

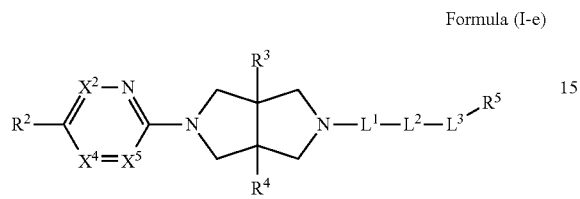
Formula (I-e)

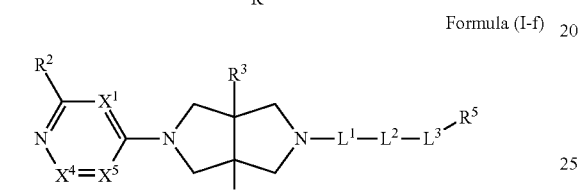
Formula (I-f)

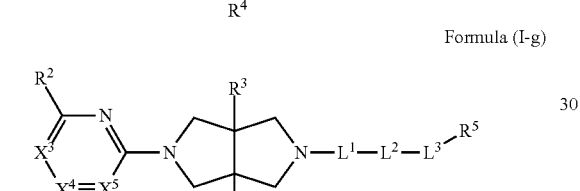
Formula (I-g)

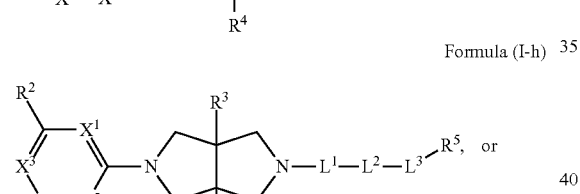
Formula (I-h)

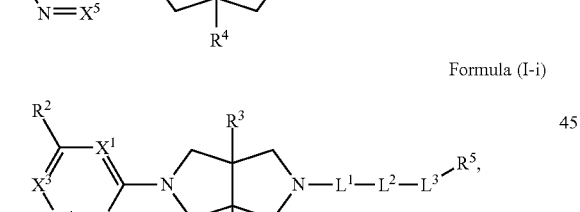
Formula (I-i)

or a pharmaceutically acceptable salt thereof, wherein each of $X^1$, $X^2$, $X^4$ and $X^5$ is $CR^1$.

In embodiments, a compound of Formula (I) is a compound according to any one of Formulas (III-a) to (III-i):

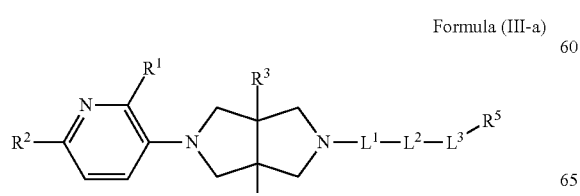
Formula (III-a)

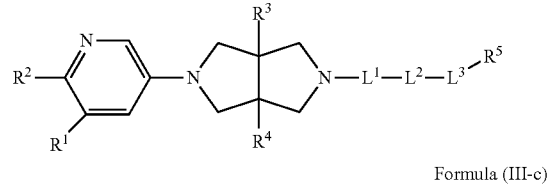
Formula (III-b)

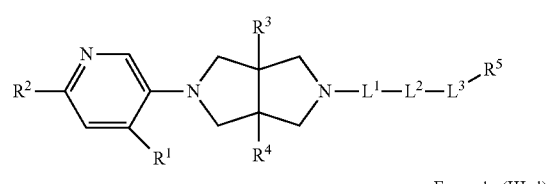
Formula (III-c)

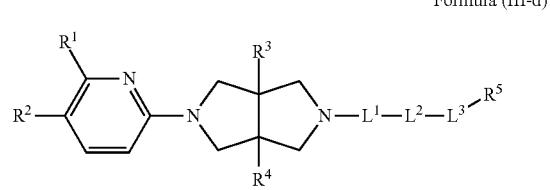
Formula (III-d)

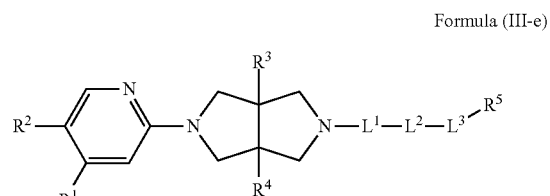
Formula (III-e)

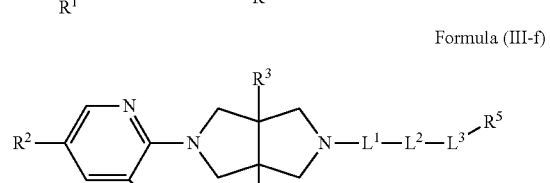
Formula (III-f)

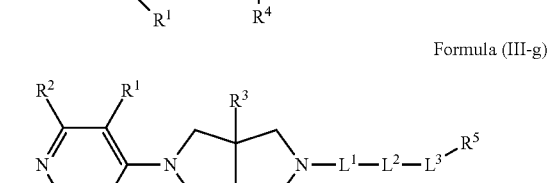
Formula (III-g)

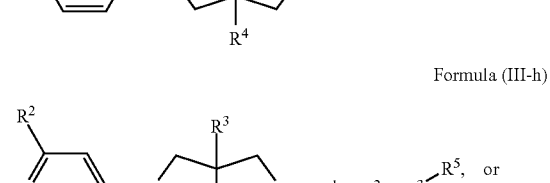
Formula (III-h)

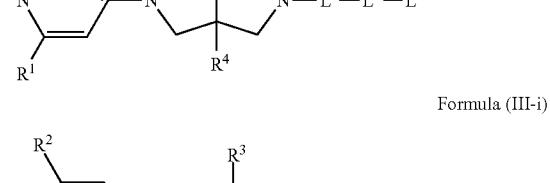
Formula (III-i)

or a pharmaceutically acceptable salt thereof.

In embodiments, a compound of Formula (I) is a compound according to any one of Formulas (III-b), (III-d) or (III-e):

Formula (III-b)

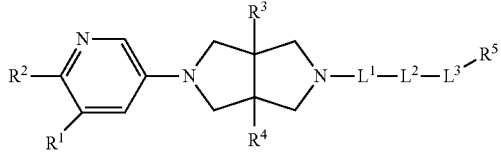

Formula (III-d)

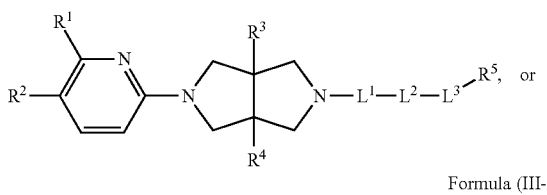

Formula (III-e)

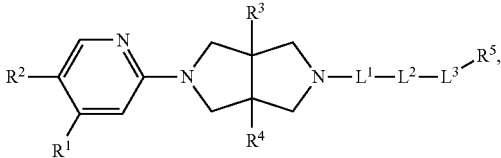

or a pharmaceutically acceptable salt thereof.

In embodiments of compounds as disclosed herein, in particular according to any one of Formulas (III-a) to (III-i), $R^1$ is hydrogen.

In embodiments of compounds as disclosed herein, in particular according to any one of Formulas (I), (I-a) to (I-i), (II-a) to (II-h) or (III-a) to (III-i), $R^1$ is $C_1$-$C_6$ alkyl, $R^{2a}$ is $C_1$-$C_6$ alkyl, and $R^1$ and $R^2$ together with the carbon atom to which they are attached form a 4- to 7-membered heterocycloalkyl including one heteroatom selected from O or S in the ring.

In embodiments of compounds as disclosed herein, in particular according to any one of Formulas (I), (I-a) to (I-i), (II-a) to (II-h) or (III-a) to (III-i), $L^1$ is selected from a bond or unsubstituted $C_1$-$C_4$ alkylene, in particular $L^1$ is a bond.

In embodiments of compounds as disclosed herein, in particular according to any one of Formulas (I), (I-a) to (I-i), (II-a) to (II-h) or (III-a) to (III-i), $L^3$ is selected from a bond or unsubstituted $C_1$-$C_4$ alkylene, in particular $L^3$ is a bond.

In embodiments of compounds as disclosed herein, in particular according to any one of Formulas (I), (I-a) to (I-i), (II-a) to (II-h) or (III-a) to (III-i), $L^1$ is selected from a bond or unsubstituted $C_1$-$C_4$ alkylene and $L^3$ is selected from a bond or unsubstituted $C_1$-$C_4$ alkylene.

In embodiments of compounds as disclosed herein, in particular according to any one of Formulas (I), (I-a) to (I-i), (II-a) to (II-h) or (III-a) to (III-i), $L^1$ a bond and $L^3$ is a bond.

In embodiments, a compound of Formula (I) is a compound according to Formula (IV-a) or (IV-b):

Formula (IV-a)

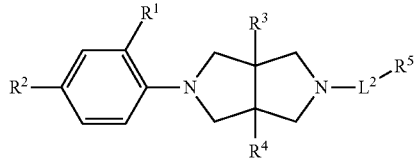

Formula (IV-b)

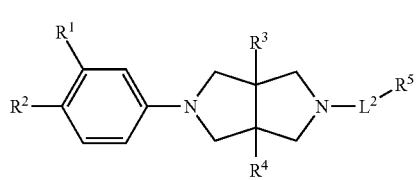

or a pharmaceutically acceptable salt thereof.

In embodiments, a compound of Formula (I) is a compound according to Formula (IV-a):

Formula (IV-a)

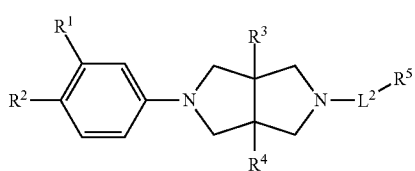

or a pharmaceutically acceptable salt thereof.

In embodiments of compounds as disclosed herein, in particular according to any one of Formulas (I), (I-a) to (I-i), (II-a) to (II-h), (III-a) to (III-i), (IV-a) or (IV-b), $R^1$ is hydrogen.

In embodiments, a compound of Formula (I) is a compound according to Formula (IV-c):

Formula (IV-c)

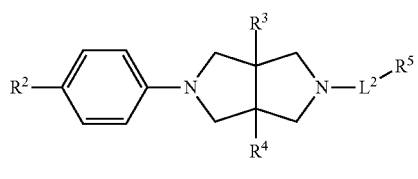

or a pharmaceutically acceptable salt thereof.

In embodiments of compounds as disclosed herein, in particular according to any one of Formulas (I), (I-a) to (I-i), (II-a) to (II-h), (III-a) to (III-i), or (IV-a) to (IV-c), $L^2$ is selected from a bond, —C(O)—, —C(O)O—, —C(O)NR$^7$—, —SO$_2$NR$^7$—, —SO$_2$— or —C(O)NR$^7$NR$^8$—, such as a bond, —C(O)—, —C(O)O—, —C(O)NH—, —C(O)N(CH$_3$)—, —C(O)N(—CH$_2$CH$_3$OH)—, —SO$_2$NH—, —SO$_2$— or —C(O)NHNH.

In embodiments of compounds as disclosed herein, in particular according to any one of Formulas (I), (I-a) to (I-i), (II-a) to (II-h), (III-a) to (III-i), or (IV-a) to (IV-c), $L^2$ is selected from a bond, —C(O)—, —C(O)O— or —C(O)NR$^7$—, in particular $L^2$ is selected from a bond, —C(O)— or —C(O)NR$^7$—.

In embodiments of compounds as disclosed herein, in particular according to any one of Formulas (I), (I-a) to (I-i), (II-a) to (II-h), (III-a) to (III-i), or (IV-a) to (IV-c), $L^2$ is —C(O)NH—.

In embodiments, a compound of Formula (I) is a compound according to Formula (V):

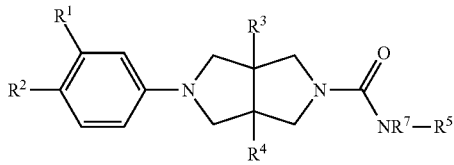

Formula (V)

or a pharmaceutically acceptable salt thereof.

In embodiments of compounds of Formula (V), $R^7$ is hydrogen or $C_1$-$C_4$ alkyl (e.g. methyl or ethyl) optionally substituted by hydroxy, in particular $R^7$ is selected from hydrogen, methyl or hydroxyethyl.

In embodiments, a compound of Formula (I) is a compound according to Formula (V-a):

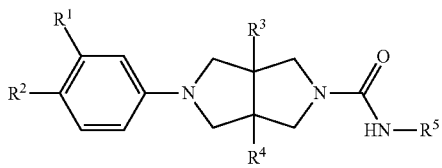

Formula (V-a)

or a pharmaceutically acceptable salt thereof.

In embodiments, a compound of Formula (I) is a compound according to Formula (V-b):

Formula (V-b)

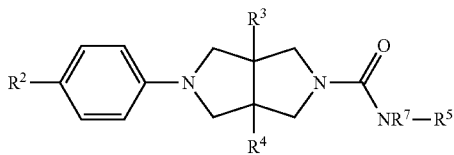

or a pharmaceutically acceptable salt thereof.

In embodiments of compounds of Formula (V-b), $R^7$ is hydrogen or $C_1$-$C_4$ alkyl (e.g. methyl or ethyl) optionally substituted by hydroxy, in particular $R^7$ is selected from hydrogen, methyl or hydroxyethyl.

In embodiments, a compound of Formula (I) is a compound according to Formula (V-c):

Formula (V-c)

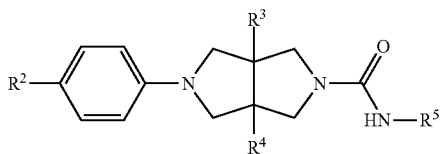

or a pharmaceutically acceptable salt thereof.

In embodiments of compounds of Formula (V-a) or (V-c), $R^5$ is not linked to —C(O)NR$^7$— by a nitrogen atom.

In embodiments of compounds of Formula (V-b), $R^5$ is not linked to —C(O)NH— by a nitrogen atom.

In embodiments of compounds as disclosed herein, in particular according to any one of Formulas (I), (I-a) to (I-i), (II-a) to (II-h), (III-a) to (III-i), (IV-a) to (IV-c), or (V-a) to (V-c), $R^2$ is selected from —O—Y$^1$—R$^{2a}$, —S—Y$^1$—R$^{2a}$, —SO$_2$—Y$^1$—R$^{2a}$ or —NR$^{2b}$R$^{2c}$.

In embodiments of compounds as disclosed herein, in particular according to any one of Formulas (I), (I-a) to (I-i), (II-a) to (II-h), (III-a) to (III-i), (IV-a) to (IV-c), or (V-a) to (V-c), $Y^1$ is a bond.

In embodiments of compounds as disclosed herein, in particular according to any one of Formulas (I), (I-a) to (I-i), (II-a) to (II-h), (III-a) to (III-i), (IV-a) to (IV-c), or (V-a) to (V-c), $R^2$ is selected from —O—R$^{2a}$, —S—R$^{2a}$, —SO$_2$—R$^{2a}$ or —NR$^{2b}$R$^{2c}$.

In embodiments of compounds as disclosed herein, in particular according to any one of Formulas (I), (I-a) to (I-i), (II-a) to (II-h), (III-a) to (III-i), (IV-a) to (IV-c), or (V-a) to (V-c), $R^2$ is selected from —O—R$^{2a}$ or —NR$^{2b}$R$^{2c}$.

In embodiments of compounds as disclosed herein, in particular according to any one of Formulas (I), (I-a) to (I-i), (II-a) to (II-h), (III-a) to (III-i), (IV-a) to (IV-c), or (V-a) to (V-c), $R^2$ is —O—R$^{2a}$.

In embodiments, a compound of Formula (I) is a compound according to Formula (VI-a) or (VI-b):

Formula (VI-a)

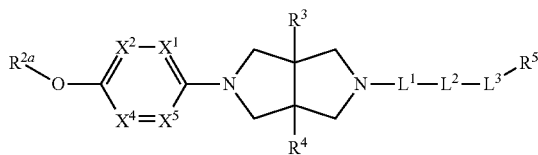

Formula (VI-b)

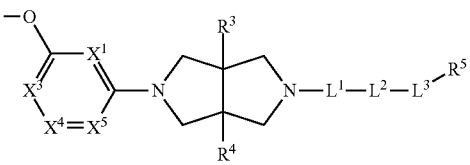

or a pharmaceutically acceptable salt thereof.

In embodiments, a compound of Formula (I) is a compound according to Formula (VI-a):

Formula (VI-a)

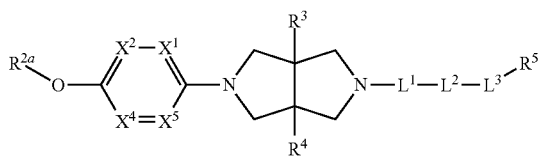

or a pharmaceutically acceptable salt thereof.

In embodiments, a compound of Formula (I) is a compound according to any one of Formulas (VII-a) to (VII-f):

Formula (VII-a)

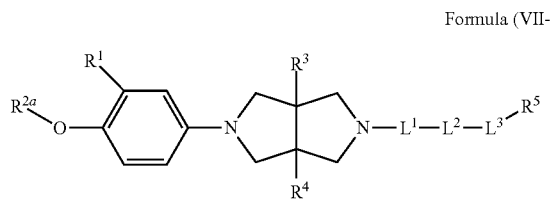

Formula (VII-b)

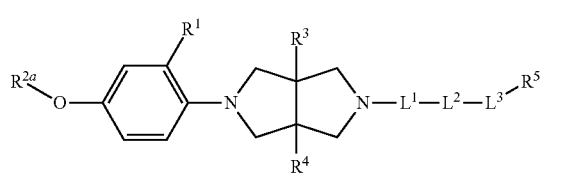

Formula (VII-c)

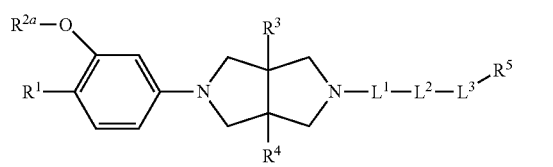

Formula (VII-d)

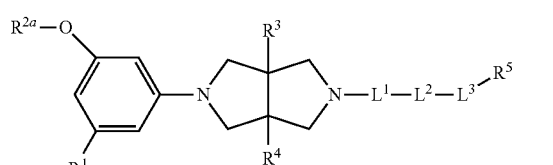

Formula (VII-e)

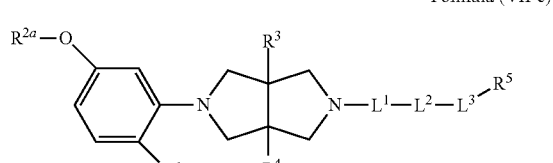

Formula (VII-f)

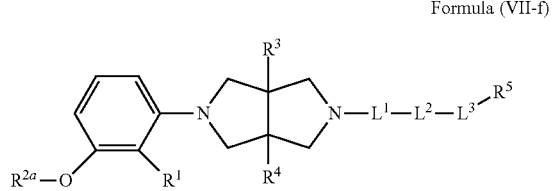

or a pharmaceutically acceptable salt thereof.

In embodiments of compounds of Formula (VII-a), (VII-b), (VII-c), (VII-d) or (VII-f), $R^1$ is hydrogen.

In embodiments of compounds of Formula (VII-a) is a compound according to Formula (VII-a-a):

Formula (VII-a-a)

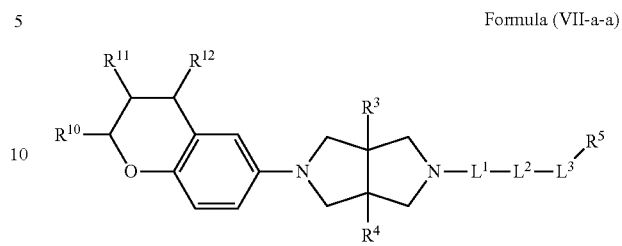

or a pharmaceutically acceptable salt thereof, wherein $R^{10}$, $R^{11}$ and $R^{12}$ is at each occurrence independently selected from hydrogen, halo, cyano, oxo, hydroxy, carboxy, $R^6$, —$OR^6$, —$C(O)R^6$ or —$C(O)OR^6$.

In embodiments of compounds of Formula (VII-a) is a compound according to Formula (VII-a-b):

Formula (VII-a-b)

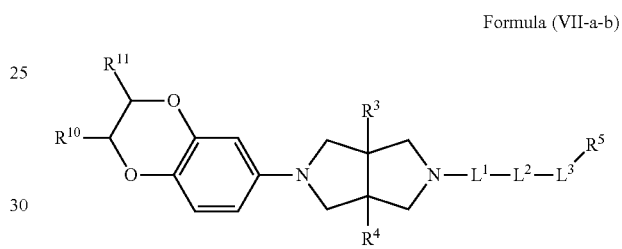

or a pharmaceutically acceptable salt thereof, wherein $R^{10}$ and $R^{11}$ is at each occurrence independently selected from hydrogen, halo, cyano, oxo, hydroxy, carboxy, $R^6$, —$OR^6$, —$C(O)R^6$ or —$C(O)OR^6$.

In embodiments of compounds of Formula (VII-a) is a compound according to Formula (VII-a-c):

Formula (VII-a-c)

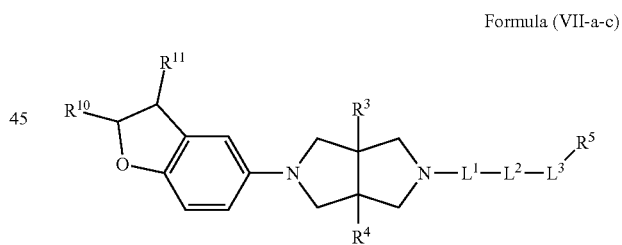

or a pharmaceutically acceptable salt thereof, wherein $R^{10}$ and $R^{11}$ is at each occurrence independently selected from hydrogen, halo, cyano, oxo, hydroxy, carboxy, $R^6$, —$OR^6$, —$C(O)R^6$ or —$C(O)OR^6$.

In embodiments, a compound of Formula (I) is a compound according to Formula (VIII-a) or (VIII-b):

Formula (VIII-a)

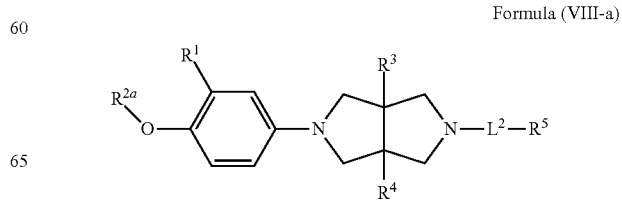

-continued

Formula (VIII-b)

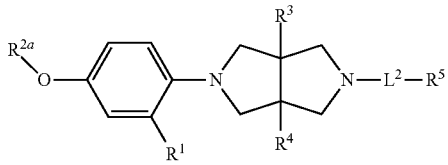

or a pharmaceutically acceptable salt thereof.

In embodiments, a compound of Formula (I) is a compound according to Formula (IX-a) or (IX-b):

Formula (IX-a)

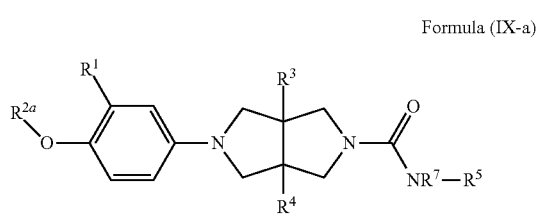

Formula (IX-b)

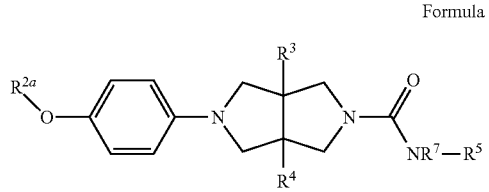

or a pharmaceutically acceptable salt thereof.

In embodiments of compounds of Formula (IX-a) or (IX-b), $R^7$ is hydrogen or $C_1$-$C_4$ alkyl (e.g. methyl or ethyl) optionally substituted by hydroxy, in particular $R^7$ is selected from hydrogen, methyl or hydroxyethyl.

In embodiments, a compound of Formula (I) is a compound according to Formula (IX-c):

Formula (IX-c)

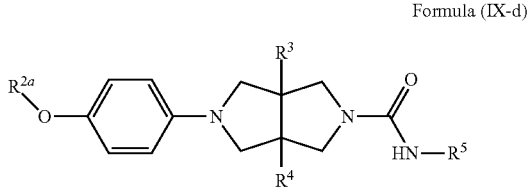

or a pharmaceutically acceptable salt thereof.

In embodiments of compounds of Formula (IX-c), $R^7$ is hydrogen or $C_1$-$C_4$ alkyl (e.g. methyl or ethyl) optionally substituted by hydroxy, in particular $R^7$ is selected from hydrogen, methyl or hydroxyethyl.

In embodiments of compounds of Formula (IX-a), (IX-b) or (IX-c), $R^5$ is not linked to —C(O)NR$^7$— by a nitrogen atom.

In embodiments, a compound of Formula (I) is a compound according to Formula (IX-d):

Formula (IX-d)

or a pharmaceutically acceptable salt thereof.

In embodiments of compounds of Formula (IX-d), $R^5$ is not linked to —C(O)NH— by a nitrogen atom.

In embodiments of compounds as disclosed herein, in particular compounds of Formulas (VI-a), (VI-b), (VII-a) to (VII-f), (VIII-a), (VIII-b) and (IX-a) to (IX-d), $R^{2a}$ is selected from unsubstituted $C_1$-$C_4$ alkyl (e.g. methyl or ethyl), $C_1$-$C_4$ alkyl substituted by $C_1$-$C_4$ alkoxy (e.g. ethyl substituted with methoxy), unsubstituted $C_3$-$C_6$ cycloalkyl (e.g. cyclopropyl), unsubstituted 3- to 6-membered monocyclic heterocycloalkyl (e.g. piperidinyl) or unsubstituted phenyl.

In embodiments of compounds as disclosed herein, in particular compounds of Formulas (VI-a), (VI-b), (VII-a) to (VII-f), (VIII-a), (VIII-b) and (IX-a) to (IX-d), $R^{2a}$ is unsubstituted $C_1$-$C_4$ alkyl, in particular methyl or ethyl.

In embodiments of compounds as disclosed herein, in particular according to any one of Formulas (I), (I-a) to (I-i), (II-a) to (II-h), (III-a) to (III-i), (IV-a) to (IV-c), (V-a) to (V-c), (VI-a), (VI-b), (VII-a) to (VII-f), (VIII-a), (VIII-b), or (IX-a) to (IX-d), $R^2$ is —O—$R^{2a}$ and $R^{2a}$ is selected from unsubstituted $C_1$-$C_4$ alkyl (e.g. methyl or ethyl), $C_1$-$C_4$ alkyl substituted by $C_1$-$C_4$ alkoxy (e.g. ethyl substituted with methoxy), unsubstituted $C_3$-$C_6$ cycloalkyl (e.g. cyclopropyl), unsubstituted 3- to 6-membered monocyclic heterocycloalkyl (e.g. piperidinyl) or unsubstituted phenyl.

In embodiments of compounds as disclosed herein, in particular according to any one of Formulas (I), (I-a) to (I-i), (II-a) to (II-h), (III-a) to (III-i), (IV-a) to (IV-c), (V-a) to (V-c), (VI-a), (VI-b), (VII-a) to (VII-f), (VIII-a), (VIII-b), or (IX-a) to (IX-d), $R^2$ is —O—$R^{2a}$ and $R^{2a}$ is unsubstituted $C_1$-$C_4$ alkyl, such as methyl or ethyl.

In embodiments of compounds as disclosed herein, in particular according to any one of Formulas (I), (I-a) to (I-i), (II-a) to (II-h), (III-a) to (III-i), (IV-a) to (IV-c), (V-a) to (V-c), (VI-a), (VI-b), (VII-a) to (VII-f), (VIII-a), (VIII-b), or (IX-a) to (IX-d), $R^2$ is —S—$R^{2a}$.

In embodiments of compounds as disclosed herein, in particular according to any one of Formulas (I), (I-a) to (I-i), (II-a) to (II-h), (III-a) to (III-i), (IV-a) to (IV-c), (V-a) to (V-c), (VI-a), (VI-b), (VII-a) to (VII-f), (VIII-a), (VIII-b), or (IX-a) to (IX-d), $R^2$ is —S—$R^{2a}$ and $R^{2a}$ is unsubstituted $C_1$-$C_4$ alkyl, such as methyl or ethyl.

In embodiments of compounds as disclosed herein, in particular according to any one of Formulas (I), (I-a) to (I-i), (II-a) to (II-h), (III-a) to (III-i), (IV-a) to (IV-c), (V-a) to (V-c), (VI-a), (VI-b), (VII-a) to (VII-f), (VIII-a), (VIII-b), or (IX-a) to (IX-d), $R^2$ is —SO$_2$—$R^{2a}$.

In embodiments of compounds as disclosed herein, in particular according to any one of Formulas (I), (I-a) to (I-i), (II-a) to (II-h), (III-a) to (III-i), (IV-a) to (IV-c), (V-a) to (V-c), (VI-a), (VI-b), (VII-a) to (VII-f), (VIII-a), (VIII-b), or (IX-a) to (IX-d), $R^2$ is —SO$_2$—$R^{2a}$ and $R^{2a}$ is unsubstituted $C_1$-$C_4$ alkyl, such as methyl or ethyl.

In embodiments of compounds as disclosed herein, in particular according to any one of Formulas (I), (I-a) to (I-i), (II-a) to (II-h), (III-a) to (III-i), (IV-a) to (IV-c), (V-a) to (V-c), (VI-a), (VI-b), (VII-a) to (VII-f), (VIII-a), (VIII-b), or (IX-a) to (IX-d), $R^2$ is —$NR^{2b}R^{2c}$.

In embodiments, a compound of Formula (I) is a compound according to Formula (X-a) or (X-b):

Formula (X-a)

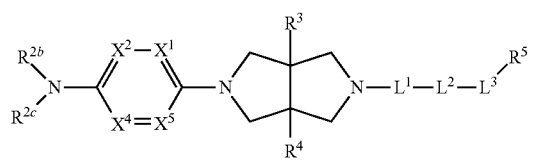

Formula (X-b)

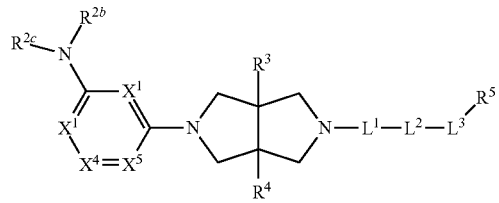

or a pharmaceutically acceptable salt thereof.

In embodiments, a compound of Formula (I) is a compound according to Formula (X-a):

Formula (X-a)

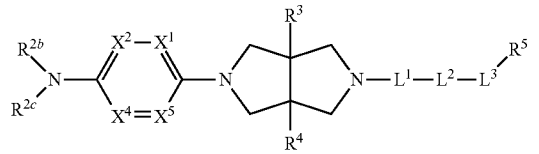

or a pharmaceutically acceptable salt thereof.

In embodiments, a compound of Formula (I) is a compound according to Formula (XI-a) or (XI-b):

Formula (XI-a)

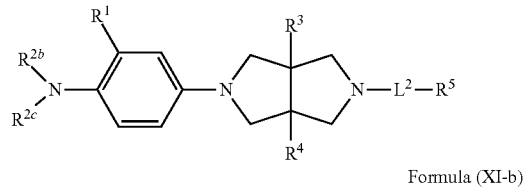

Formula (XI-b)

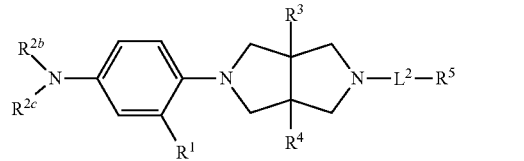

or a pharmaceutically acceptable salt thereof.

In embodiments, a compound of Formula (I) is a compound according to Formula (XII-a) or (XII-b):

Formula (XII-a)

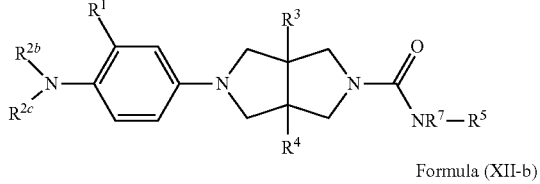

Formula (XII-b)

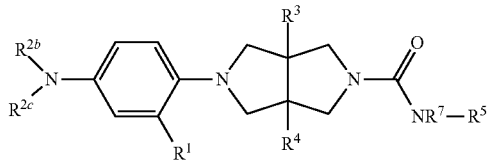

or a pharmaceutically acceptable salt thereof.

In embodiments of compounds of Formula (XII-a) or (XII-b), $R^7$ is hydrogen or $C_1$-$C_4$ alkyl (e.g. methyl or ethyl) optionally substituted by hydroxy, in particular $R^7$ is selected from hydrogen, methyl or hydroxyethyl.

In embodiments, a compound of Formula (I) is a compound according to Formula (XII-c):

Formula (XII-c)

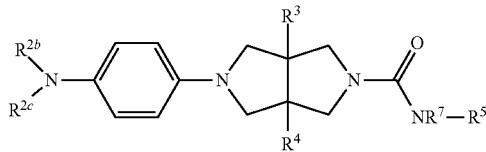

or a pharmaceutically acceptable salt thereof.

In embodiments of compounds of Formula (XII-c), $R^7$ is hydrogen or $C_1$-$C_4$ alkyl (e.g. methyl or ethyl) optionally substituted by hydroxy, in particular $R^7$ is selected from hydrogen, methyl or hydroxyethyl.

In embodiments of compounds of Formula (XII-a), (XII-b) or (XII-c), $R^5$ is not linked to —C(O)$NR^7$— by a nitrogen atom In embodiments, a compound of Formula (I) is a compound according to Formula (XII-d):

Formula (XII-d)

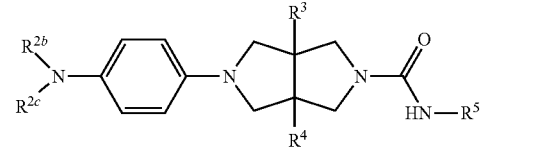

or a pharmaceutically acceptable salt thereof.

In embodiments of compounds of Formula (XII-d), $R^5$ is not linked to —C(O)NH— by a nitrogen atom.

In embodiments of compounds as disclosed herein, in particular compounds of Formulas (X-a), (X-b), (XI-a), (XI-b) and (XII-a) to (XII-d), $R^{2b}$ and $R^{2c}$ is each independently selected from $C_1$-$C_6$ alkyl optionally substituted by —NR⁷R⁸, where R⁷ and R⁸ is each independently selected from unsubstituted $C_1$-$C_4$ alkyl, in particular $R^{2b}$ is unsubstituted $C_1$-$C_4$ alkyl and $R^{2c}$ is $C_1$-$C_4$ alkyl substituted by —N(CH₃)₂.

Alternatively, in embodiments of compounds as disclosed herein, in particular compounds of Formulas (X-a), (X-b), (XI-a), (XI-b) and (XII-a) to (XII-d), $R^{2b}$ and $R^{2c}$ together with the nitrogen atom to which they are attached form a 3- to 7-membered heterocycloalkyl,
  optionally including one additional heteroatom selected from N or S in the ring,
  said heterocycloalkyl formed by $R^{2b}$ and $R^{2c}$ may be optionally substituted by one substituent independently selected from hydroxy or —SO₂R⁷;
any S in the ring of said heterocycloalkyl formed by $R^{2b}$ and $R^{2c}$ may be optionally oxidized; in particular $R^{2b}$ and $R^{2c}$ together with the nitrogen atom to which they are attached from:

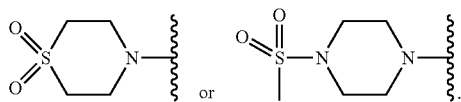 [SMILES: *N1CCS(=O)(=O)CC1 ; *N1CCN(S(C)(=O)=O)CC1]

In embodiments, a compound of Formula (I) is a compound according to Formula (XIII-a) or Formula (XIII-b):

Formula (XIII-a)

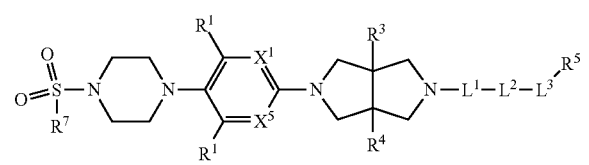

Formula (XIII-b)

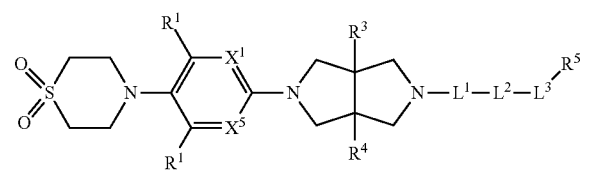

In embodiments of compounds of Formula (XIII-a) or (XIII-b), each of $X^1$ and $X^5$ is selected from $CR^1$ or N; provided only one of $X^1$ and $X^5$ can be N.

In embodiments of compounds of Formula (XIII-a) or (XIII-b), each of $X^1$ and $X^5$ is $CR^1$.

In particular embodiments of compounds of Formula (XIII-a) or (XIII-b), each of $X^1$ and $X^5$ is CH and each $R^1$ is hydrogen.

Particular compounds of the invention include, for example, compounds of any one of Formulas (I), (I-a) to (I-i), (II-a) to (II-h), (III-a) to (III-i), (IV-a) to (IV-c), (V-a) to (V-c), (VI-a), (VI-b), (VII-a) to (VII-f), (VII-a-a), (VII-a-b), (VIII-a), (VIII-b), or (IX-a) to (IX-d), (X-a), (X-b), (XI-a), (XI-b), (XII-a) to (XII-c), (XIII-a) or (XIII-b), or a pharmaceutically acceptable salt thereof, wherein, unless otherwise stated, each of $X^1$, $X^2$, $X^3$, $X^4$, $X^5$, $R^1$, $R^2$, $R^{2a}$, $R^{2b}$, $R^{2c}$, $Y^1$, $Y^2$, $R^3$, $R^4$, $R^5$, $R^6$, $R^7$, $R^8$, $R^9$, $R^{10}$, $R^{11}$, $R^{12}$, $L^1$, $L^2$, $L^3$, has any of the meanings defined hereinbefore or in any one or more of paragraphs (1) to (70) hereinafter:
1. $R^1$ is selected from hydrogen halo, cyano, hydroxy, $C_1$-$C_6$ alkyl, $C_2$-$C_6$ alkenyl, $C_2$-$C_6$ alkynyl, $C_1$-$C_6$ alkoxy, $C_1$-$C_6$ alkyl-carbonyl or $C_1$-$C_6$ alkoxy-carbonyl, where any alkyl, alkenyl, alkynyl or alkoxy in $R^1$ may be optionally substituted by one substituent selected from cyano, hydroxy, carboxy, —C(O)R⁶ or C(O)OR⁶, where R⁶ is $C_1$-$C_4$ alkyl.
2. $R^1$ is selected from hydrogen halo, cyano, $C_1$-$C_6$ alkyl, $C_2$-$C_6$ alkenyl or $C_2$-$C_6$ alkynyl, where any alkyl, alkenyl or alkynyl in $R^1$ may be optionally substituted by one substituent selected from cyano, hydroxy, carboxy, —C(O)R⁶ or C(O)OR⁶, where R⁶ is $C_1$-$C_4$ alkyl.
3. $R^1$ is selected from hydrogen halo, cyano, $C_1$-$C_6$ alkyl or $C_2$-$C_6$ alkenyl, where any alkyl and alkenyl in $R^1$ may be optionally substituted by one substituent selected from cyano, hydroxy, carboxy, —C(O)R⁶ or C(O)OR⁶, where R⁶ is $C_1$-$C_4$ alkyl.
4. $R^1$ is hydrogen, fluoro, cyano, methyl optionally substituted with cyano or carboxy, ethyl optionally substituted with cyano or carboxy, or ethenyl optionally substituted with cyano or carboxy.
5. $R^1$ is hydrogen.
6. $R^2$ is selected from —O—Y¹—$R^{2a}$, —S—Y¹—$R^{2a}$, —SO₂—Y¹—$R^{2a}$ or —NR$^{2b}$R$^{2c}$.
4. $Y^1$ is a bond.
5. $R^2$ is selected from —O—$R^{2a}$, —S—$R^{2a}$, —SO₂—$R^{2a}$ or —NR$^{2b}$R$^{2c}$.
6. $R^2$ is selected from —O—$R^{2a}$ or —NR$^{2b}$R$^{2c}$.
7. $R^2$ is —O—$R^{2a}$.
8. $R^{2a}$ is selected from unsubstituted $C_1$-$C_4$ alkyl (e.g. methyl or ethyl), $C_1$-$C_4$ alkyl substituted by $C_1$-$C_4$ alkoxy (e.g. ethyl substituted with methoxy), unsubstituted $C_3$-$C_6$ cycloalkyl (e.g. cyclopropyl), unsubstituted 3- to 6-membered monocyclic heterocycloalkyl (e.g. piperidinyl) or unsubstituted phenyl.
9. $R^{2a}$ is unsubstituted $C_1$-$C_4$ alkyl, in particular methyl or ethyl.
10. $R^2$ is —O—$R^{2a}$ and $R^{2a}$ is selected from unsubstituted $C_1$-$C_4$ alkyl (e.g. methyl or ethyl), $C_1$-$C_4$ alkyl substituted by $C_1$-$C_4$ alkoxy (e.g. ethyl substituted with methoxy), unsubstituted $C_3$-$C_6$ cycloalkyl (e.g. cyclopropyl), unsubstituted 3- to 6-membered monocyclic heterocycloalkyl (e.g. piperidinyl) or unsubstituted phenyl.
11. $R^2$ is —O—$R^{2a}$ and $R^{2a}$ is unsubstituted $C_1$-$C_4$ alkyl, such as methyl or ethyl.
12. $R^2$ is —S—$R^{2a}$.
13. $R^2$ is —S—$R^{2a}$ and $R^{2a}$ is unsubstituted $C_1$-$C_4$ alkyl, such as methyl or ethyl.
14. $R^2$ is —SO₂—$R^{2a}$.
15. $R^2$ is —SO₂—$R^{2a}$ and $R^{2a}$ is unsubstituted $C_1$-$C_4$ alkyl, such as methyl or ethyl.
16. $R^2$ is —NR$^{2b}$R$^{2c}$.
17. $R^2$ is —NR$^{2b}$R$^{2c}$ and $R^{2b}$ and $R^{2c}$ is each independently selected from $C_1$-$C_6$ alkyl optionally substituted by —NR⁷R⁸, where R⁷ and R⁸ is each independently selected from unsubstituted $C_1$-$C_4$ alkyl.
18. $R^2$ is —NR$^{2b}$R$^{2c}$ and $R^{2b}$ is unsubstituted $C_1$-$C_4$ alkyl and $R^{2c}$ is $C_1$-$C_4$ alkyl substituted by —N(CH₃)₂.
19. $R^2$ is —NR$^{2b}$R$^{2c}$ and $R^{2b}$ and $R^{2c}$ together with the nitrogen atom to which they are attached form a 3- to 7-membered heterocycloalkyl,
  optionally including one additional heteroatom selected from N or S in the ring,
  said heterocycloalkyl formed by $R^{2b}$ and $R^{2c}$ may be optionally substituted by one substituent independently selected from hydroxy or —SO₂R⁷;
any S in the ring of said heterocycloalkyl formed by $R^{2b}$ and $R^{2c}$ may be optionally oxidized.

20. $R^2$ is $-NR^{2b}R^{2c}$ and $R^{2b}$ and $R^{2c}$ together with the nitrogen atom to which they are attached form:

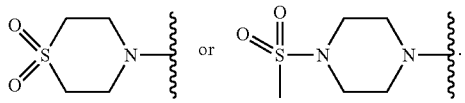 [SMILES: *N1CCS(=O)(=O)CC1 ; *N1CCN(S(C)(=O)=O)CC1]

21. $R^3$ and $R^4$ is each independently selected from hydrogen, hydroxy, carboxy, unsubstituted $C_1$-$C_6$ alkyl (e.g. methyl), unsubstituted $C_1$-$C_6$ alkoxy (e.g. methoxy), or unsubstituted $C_1$-$C_6$ alkoxycarbonyl (e.g. methoxycarbonyl), in particular $R^3$ and $R^4$ is each independently selected from hydrogen or unsubstituted $C_1$-$C_4$ alkyl (e.g. methyl).
22. $R^3$ and $R^4$ is the same type of substituent. For example, each of $R^3$ and $R^4$ is hydrogen or each of $R^3$ and $R^4$ is methyl.
23. Each of $R^3$ and $R^4$ is hydrogen.
24. $R^3$ and $R^4$ together with the carbon atom to which they are attached form an unsubstituted 3- to 7-membered cycloalkyl.
25. $R^5$ is selected from $C_1$-$C_6$ alkyl, $C_2$-$C_6$ alkenyl, $C_2$-$C_6$ alkynyl, $C_3$-$C_{12}$ cycloalkyl, 3- to 12-membered heterocycloalkyl, phenyl or 5- or 6-membered heteroaryl, where
any heterocycloalkyl or heteroaryl in $R^5$ includes 1, 2 or 3 heteroatoms selected from N, O or S in the ring;
any alkyl, alkenyl or alkynyl in $R^5$ may be optionally substituted by one, two or three substituents independently selected from halo, cyano, oxo, hydroxy, carboxy, nitro, $R^6$, $-OR^6$, $SO_2R^7$;
any cycloalkyl, heterocycloalkyl, in $R^5$ may be optionally substituted by one, two or three substituents independently selected from halo, cyano, oxo, nitro, $R^7$, $-OR^7$, $-SO_2R^7$;
any phenyl or heteroaryl in $R^5$ may be optionally substituted by one, two or three substituents independently selected from halo, cyano, nitro, $R^7$, $-OR^7$, $-SO_2R^7$.
26. $R^5$ is $C_1$-$C_6$ alkyl, such as methyl, ethyl, n-propyl, iso-propyl, n-butyl, sec-butyl and tert-butyl, optionally substituted by one, two or three substituents independently selected from halo, cyano, oxo, hydroxy, carboxy, nitro, $R^6$, $-OR^6$, $SO_2R^7$.
27. $R^5$ is $C_1$-$C_6$ alkyl, such as methyl, ethyl, n-propyl, iso-propyl, n-butyl, sec-butyl, and tert-butyl, optionally substituted by one, two or three substituents independently selected from cyano, hydroxy or $-SO_2CH_3$.
28. $R^5$ is $C_1$-$C_6$ alkyl, such as methyl, ethyl, n-propyl, iso-propyl, n-butyl, sec-butyl or tert-butyl, optionally substituted by one or two substituents independently selected from cyano, hydroxy or $-SO_2CH_3$.
29. $R^5$ is $-CH_2CH_3$, $-CH_2CH_2OH$, $-CH_2CH_2CH_2CN$, $-C(CH_3)_3$, $-CH_2CH_2CN$, $CH_2CH(OH)CN$, $-CH_2CH_2SO_2CH_3$ or $-CH_2CH_2CH_3$.
30. $R^5$ is $C_1$-$C_6$ alkyl, such as methyl, ethyl, n-propyl, iso-propyl, n-butyl, sec-butyl or tert-butyl, optionally substituted by one or two substituents independently selected from cyano or hydroxy.
31. $R^5$ is $-CH_2CH_3$, $-CH_2CH_2OH$, $-CH_2CH_2CH_2CN$ or $-C(CH_3)_3$.
32. $R^5$ is $C_2$-$C_6$ alkenyl, such as ethenyl, propenyl, butenyl, butadienyl, pentenyl, pentadienyl, hexenyl and hexadienyl, optionally substituted by one, two or three substituents independently selected from halo, cyano, oxo, hydroxy, carboxy, nitro, $R^6$, $-OR^6$, $SO_2R^7$.
33. $R^5$ is $C_2$-$C_6$ alkenyl, such as ethenyl, propenyl, butenyl, butadienyl, pentenyl, pentadienyl, hexenyl and hexadienyl, optionally substituted by one, two or three substituents independently selected from halo, cyano, oxo, hydroxy, carboxy, nitro, $R^6$, $-OR^6$, $SO_2R^7$.
34. $R^5$ is unsubstituted $C_2$-$C_6$ alkenyl, such as unsubstituted $C_2$-$C_4$ alkenyl.
35. $R^5$ is $C_2$-$C_6$ alkynyl, such as ethynyl, propynyl, butynyl, pentynyl and hexynyl, optionally substituted by one, two or three substituents independently selected from halo, cyano, oxo, hydroxy, carboxy, nitro, $R^6$, $-OR^6$, $SO_2R^7$.
36. $R^5$ is unsubstituted $C_2$-$C_6$ alkynyl, such as unsubstituted $C_2$-$C_4$ alkenyl.
37. $R^5$ is $C_3$-$C_{12}$ cycloalkyl, such as cyclopropyl, cyclobutyl, cyclopentyl, cyclohexyl, bicycle[2.1.1]hexane, bicycle[1.1.1]pentane or tricyclo[3.3.1.1]-decane, optionally substituted by one, two or three substituents independently selected from halo, cyano, oxo, nitro, $R^7$, $-OR^7$, $-SO_2R^7$.
38. $R^5$ is selected from unsubstituted $C_3$-$C_{10}$ cycloalkyl, such as cyclopropyl, cyclobutyl, cyclopentyl, cyclohexyl, bicycle[2.1.1]hexane, bicycle[1.1.1]pentane or tricyclo[3.3.1.1]-decane.
39. $R^5$ is selected from unsubstituted $C_3$-$C_6$ cycloalkyl, such as cyclopropyl, cyclobutyl, cyclopentyl or cyclohexyl.
40. $R^5$ is cyclohexyl.
41. $R^5$ is $C_3$-$C_{10}$ cycloalkyl, such as cyclopropyl, cyclobutyl, cyclopentyl, cyclohexyl, bicyclo[2.1.1]hexane, bicyclo[1.1.1]pentane or tricyclo[3.3.1.1]-decane, substituted by hydroxy.
42. $R^5$ is

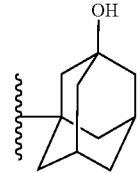

43. $R^5$ is 3- to 12-membered heterocycloalkyl including 1, 2 or 3 heteroatoms selected from N, O or S in the ring, such as pyrrolidinyl, thiomorpholinyl, morpholinyl, tetrahydropyranyl, piperazinyl and piperidinyl, optionally substituted by one, two or three substituents independently selected from halo, cyano, oxo, nitro, $R^7$, $-OR^7$, $-SO_2R^7$.
44. $R^5$ is selected from pyrrolidinyl, thiomorpholinyl, morpholinyl, tetrahydropyranyl, piperazinyl or piperidinyl, optionally substituted by one or two substituents independently selected from halo (e.g. fluoro) cyano, oxo, hydroxy or $-SO_2CH_3$.
45. $R^5$ is selected from:

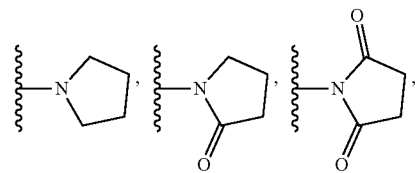

-continued

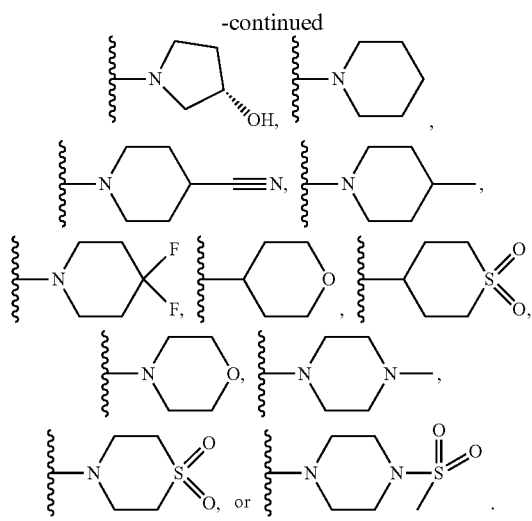

46. R⁵ is selected from:

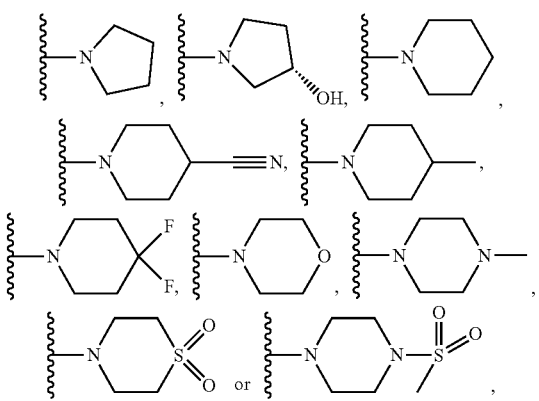

and L¹ is a bond, L³ is a bond, and L² is —C(O)—.

47. R⁵ is selected from:

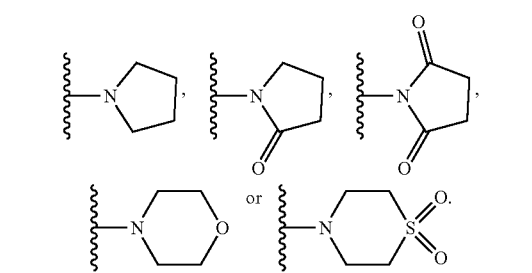

48. R⁵ is selected from:

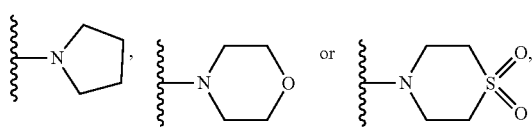

and L¹ is a bond, L³ is a bond, and L² is —C(O)—.

49. R⁵ is phenyl optionally substituted by one, two or three substituents independently selected from halo, cyano, oxo, nitro, R⁷, —OR⁷, —SO₂R⁷.
50. R⁵ is unsubstituted phenyl.
51. R⁵ is phenyl substituted by halo (e.g. fluoro), nitro or $C_1$-$C_4$ alkoxy (e.g. methoxy).
52. R⁵ is phenyl substituted by nitro.
53. R⁵ is

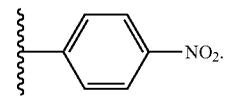

54. R⁵ is 5- or 6-membered heteroaryl including 1, 2 or 3 heteroatoms selected from N, O or S in the ring, optionally substituted by one, two or three substituents independently selected from halo, cyano, oxo, nitro, R⁷, —OR⁷, —SO₂R⁷.
55. R⁵ is a 5-membered heteroaryl, such as pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl, optionally substituted by one, two or three substituents independently selected from halo, cyano, oxo, nitro, R⁷, —OR⁷, —SO₂R⁷.
56. R⁵ is an unsubstituted 5-membered heteroaryl, such as pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl.
57. R⁵ is a 6-membered heteroaryl, such as pyridyl, pyrazinyl, pyridazinyl, pyrimidinyl and triazinyl, optionally substituted by one, two or three substituents independently selected from halo, cyano, oxo, nitro, R⁷, —OR⁷, —SO₂R⁷.
58. R⁵ is an unsubstituted 6-membered heteroaryl, such as pyridyl, pyrazinyl, pyridazinyl, pyrimidinyl and triazinyl.
59. R⁵ is unsubstituted pyridyl.
60. R⁵ is selected from $C_1$-$C_6$ alkyl, $C_3$-$C_{12}$ cycloalkyl, 3- to 12-membered heterocycloalkyl, phenyl or 5- or 6-membered heteroaryl, where
    any heterocycloalkyl or heteroaryl in R⁵ includes 1, 2 or 3 heteroatoms selected from N, O or S in the ring;
    any alkyl in R⁵ may be optionally substituted by cyano or hydroxy;
    any cycloalkyl, heterocycloalkyl, phenyl or heteroaryl in R⁵ may be optionally substituted by oxo, nitro or hydroxy.
61. R⁵ is selected from
    unsubstituted $C_1$-$C_6$ alkyl;
    $C_1$-$C_6$ alkyl substituted by one or two substituents independently selected from cyano or hydroxy;
    unsubstituted $C_3$-$C_{10}$ cycloalkyl;
    $C_3$-$C_{10}$ cycloalkyl substituted by hydroxy,
    unsubstituted 3- to 10-membered heterocycloalkyl;
    3- to 10-membered heterocycloalkyl substituted by hydroxy;
    unsubstituted phenyl; or
    phenyl substituted by nitro.
62. R⁵ is selected from
    unsubstituted methyl, unsubstituted ethyl, unsubstituted n-propyl, unsubstituted iso-propyl, unsubstituted n-butyl, unsubstituted sec-butyl, unsubstituted tert-butyl;

methyl substituted by cyano or hydroxy; ethyl substituted by cyano and/or hydroxy, n-propyl substituted by cyano and/or hydroxy, iso-propyl substituted by cyano and/or hydroxy, n-butyl substituted by cyano and/or hydroxy, sec-butyl substituted by cyano and/or hydroxy, tert-butyl substituted by cyano and/or hydroxy;

unsubstituted cyclopropyl, unsubstituted cyclobutyl, unsubstituted cyclopentyl, unsubstituted cyclohexyl;

cyclopropyl substituted by hydroxy, cyclobutyl substituted by hydroxy, cyclopentyl substituted by hydroxy, cyclohexyl substituted by hydroxy;

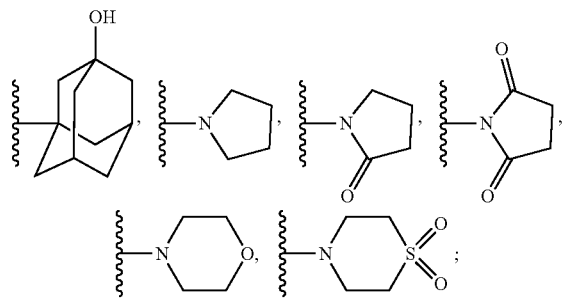

unsubstituted phenyl; or
phenyl substituted by nitro.
63. $R^5$ is selected from —$CH_2CH_3$, —$CH_2CH_2OH$, —$CH_2CH_2CH_2CN$, —$C(CH_3)_3$;

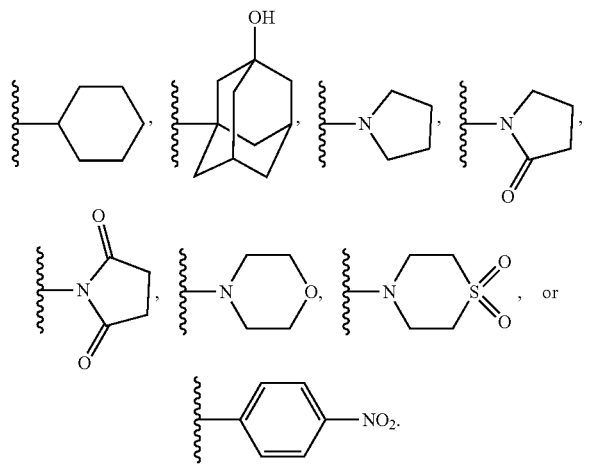

64. $L^1$ is selected from a bond or unsubstituted $C_1$-$C_4$ alkylene, in particular $L^1$ is a bond.
65. $L^3$ is selected from a bond or unsubstituted $C_1$-$C_4$ alkylene, in particular $L^3$ is a bond.
66. $L^1$ is selected from a bond or unsubstituted $C_1$-$C_4$ alkylene and $L^3$ is selected from a bond or unsubstituted $C_1$-$C_4$ alkylene.
67. $L^1$ a bond and $L^3$ is a bond.
68. $L^2$ is selected from a bond, —C(O)—, —C(O)O—, —C(O)NR$^7$—, —SO$_2$NR$^7$—, —SO$_2$— or —C(O)NR$^7$NR$^8$—, such as a bond, —C(O)—, —C(O)O—, —C(O)NH—, —C(O)N(CH$_3$)—, —C(O)N(—CH$_2$CH$_3$OH)—, —SO$_2$NH—, —SO$_2$— or —C(O)NHNH.
69. $L^2$ is selected from a bond, —C(O)—, —C(O)O— or —C(O)NR$^7$—, in particular $L^2$ is selected from a bond, —C(O)— or —C(O)NR$^7$—.

70. $R^3$ and $R^4$ are in cis configuration as shown in Formula (I-a).

In embodiments of compounds of Formula (I),
$R^1$ is hydrogen;
$R^2$ is —O—$R^{2a}$;
$R^{2a}$ is selected from unsubstituted $C_1$-$C_4$ alkyl (e.g. methyl or ethyl), $C_1$-$C_4$ alkyl substituted by $C_1$-$C_4$ alkoxy (e.g. ethyl substituted with methoxy), unsubstituted $C_3$-$C_6$ cycloalkyl (e.g. cyclopropyl), unsubstituted 3- to 6-membered monocyclic heterocycloalkyl (e.g. piperidinyl) or unsubstituted phenyl, in particular $R^{2a}$ is unsubstituted $C_1$-$C_4$ alkyl, such as methyl or ethyl;
$L^1$ is selected from a bond or unsubstituted $C_1$-$C_4$ alkylene, in particular $L^1$ is a bond;
$L^3$ is selected from a bond or unsubstituted $C_1$-$C_4$ alkylene, in particular $L^3$ is a bond;
$L^2$ is selected from a bond, —C(O)—, —C(O)O— or —C(O)NH—, in particular $L^2$ is selected from a bond, —C(O)— or —C(O)NH—;
$R^3$ and $R^4$ is each independently selected from hydrogen or unsubstituted $C_1$-$C_4$ alkyl (e.g. methyl); in particular each of $R^3$ and $R^4$ is hydrogen or each of $R^3$ and $R^4$ is methyl;
$R^5$ is selected from $C_1$-$C_6$ alkyl, $C_3$-$C_6$ cycloalkyl, 3- to 6-membered heterocycloalkyl, phenyl or 5- or 6-membered heteroaryl, where
  any heterocycloalkyl or heteroaryl in $R^5$ includes 1, 2 or 3 heteroatoms selected from N, O or S in the ring;
  any alkyl in $R^5$ may be optionally substituted by one, two or three substituents independently selected from halo, cyano, oxo, hydroxy, carboxy, nitro, $R^6$, —OR$^6$, —C(O)R$^6$, —C(O)OR$^6$, —OC(O)R$^6$, —C(O)NR$^6$R$^7$, —NR$^7$C(O)R$^8$, —NR$^6$R$^7$, —SO$_2$NR$^6$R$^7$, —NR$^7$SO$_2$R$^8$, —SR$^7$, —SO$_2$R$^7$, —SO$_2$OR$^7$, —OSO$_2$R$^7$, —NR$^8$SO$_2$NR$^6$R$^7$, —NR$^8$C(O)NR$^6$R$^7$, —NR$^7$C(O)OR$^8$ or —OC(O)NR$^6$R$^7$;
  any cycloalkyl, heterocycloalkyl, phenyl or heteroaryl in $R^5$ may be optionally substituted by one, two or three substituents independently selected from halo, cyano, oxo, nitro, $R^7$, —OR$^7$, —C(O)R$^7$, —OC(O)R$^7$, —C(O)OR$^7$, —C(O)NR$^7$R$^8$, —NR$^7$C(O)R$^8$, —NR$^7$R$^8$, —SO$_2$NR$^7$R$^8$, —NR$^7$SO$_2$R$^8$, —SR$^7$, —SO$_2$R$^7$, —SO$_2$OR$^7$, —OSO$_2$R$^7$, —NR$^7$SO$_2$NR$^8$R$^9$, —NR$^7$C(O)NR$^8$R$^9$, —NR$^7$C(O)OR$^8$ or —OC(O)NR$^7$R$^8$.

In embodiments of compounds of Formula (I), the compounds have the structure of Formula (VIII-c) or (VIII-d), Formula (VIII-c)
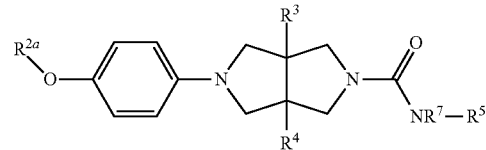

Formula (VIII-d)
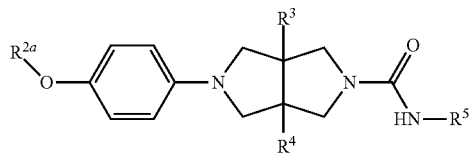

or a pharmaceutically acceptable salt thereof, wherein
$R^{2a}$ is unsubstituted $C_1$-$C_4$ alkyl;
$R^3$ and $R^4$ is each independently selected from hydrogen or unsubstituted $C_1$-$C_4$ alkyl (e.g. methyl), in particular each of $R^3$ and $R^4$ is hydrogen or each of $R^3$ and $R^4$ is methyl;
$R^5$ is selected from $C_1$-$C_6$ alkyl, $C_3$-$C_6$ cycloalkyl, 3- to 6-membered heterocycloalkyl, phenyl or 5- or 6-membered heteroaryl, where
any heterocycloalkyl or heteroaryl in $R^5$ includes 1, 2 or 3 heteroatoms selected from N, O or S in the ring;
any alkyl in $R^5$ may be optionally substituted by cyano or hydroxy;
any cycloalkyl, heterocycloalkyl, phenyl or heteroaryl in $R^5$ may be optionally substituted by oxo, nitro or hydroxy; and
$R^7$, when present, is $C_1$-$C_4$ alkyl optionally substituted by hydroxy.

In embodiments of compounds of Formula (I), the compounds have the structure of Formula (VIII-c') or (VIII-d'),

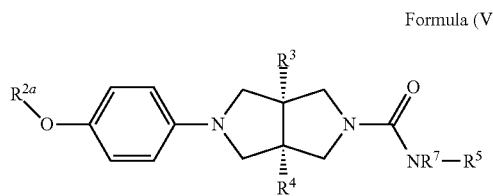

Formula (VIII-c')

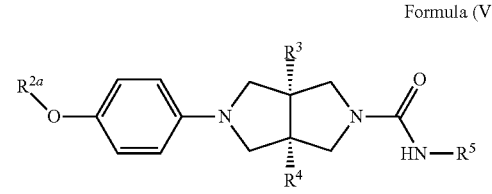

Formula (VIII-d')

or a pharmaceutically acceptable salt thereof, wherein
$R^{2a}$ is unsubstituted $C_1$-$C_4$ alkyl;
$R^3$ and $R^4$ is each independently selected from hydrogen or unsubstituted $C_1$-$C_4$ alkyl (e.g. methyl), in particular each of $R^3$ and $R^4$ is hydrogen or each of $R^3$ and $R^4$ is methyl;
$R^5$ is selected from $C_1$-$C_6$ alkyl, $C_3$-$C_6$ cycloalkyl, 3- to 6-membered heterocycloalkyl, phenyl or 5- or 6-membered heteroaryl, where
any heterocycloalkyl or heteroaryl in $R^5$ includes 1, 2 or 3 heteroatoms selected from N, O or S in the ring;
any alkyl in $R^5$ may be optionally substituted by cyano or hydroxy;
any cycloalkyl, heterocycloalkyl, phenyl or heteroaryl in $R^5$ may be optionally substituted by oxo, nitro or hydroxy; and
$R^7$, when present, is $C_1$-$C_4$ alkyl optionally substituted by hydroxy.

In embodiments of compounds of Formula (I), the compounds have the structure of Formula (VIII-d),

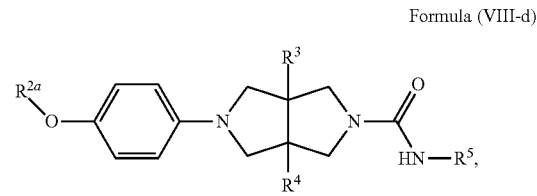

Formula (VIII-d)

in particular Formula (VIII-d')

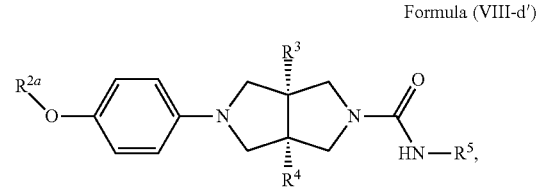

Formula (VIII-d')

or a pharmaceutically acceptable salt thereof, wherein
$R^{2a}$ is selected from $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkenyl, 3- to 6-membered monocyclic heterocyclyl, phenyl, or 5- or 6-membered heteroaryl, where
any alkyl, alkenyl, alkynyl, cycloalkyl, cycloalkenyl or heterocyclyl in $R^{2a}$ may be optionally substituted by one, two or three substituents independently selected from halo, cyano, oxo, hydroxy, carboxy, $R^6$, —$OR^6$, —$C(O)R^6$, —$C(O)OR^6$, —$OC(O)R^6$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$;
any phenyl or heteroaryl in $R^{2a}$ may be optionally substituted by one, two or three substituents independently selected from halo, cyano, carboxy, $R^6$, —$OR^6$, —$C(O)R^6$, —$C(O)OR^6$, —$OC(O)R^6$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$; and
any heterocyclyl or heteroaryl in $R^{2a}$ includes 1, 2 or 3 heteroatoms selected from N, O or S in the ring;
$R^3$ and $R^4$ is each independently selected from hydrogen, hydroxy, carboxy, $C_1$-$C_6$ alkyl, $C_1$-$C_6$ alkoxy, $C_1$-$C_6$ alkyl-carbonyl or $C_1$-$C_6$ alkoxy-carbonyl,
any alkyl or alkoxy in $R^3$ and $R^4$ may be optionally substituted by one, two or three substituents independently selected from halo, cyano, or hydroxy; or
$R^3$ and $R^4$ together with the carbon atom to which they are attached form a 3- to 7-membered cycloalkyl,
said cycloalkyl formed by $R^3$ and $R^4$ may be optionally substituted by one, two or three substituents independently selected from halo, cyano, hydroxy, carboxy, $R^6$, —$OR^6$, —$C(O)R^6$ or —$C(O)OR^6$;
$R^5$ is selected from hydrogen, $C_1$-$C_6$ alkyl, $C_2$-$C_6$ alkenyl, $C_2$-$C_6$ alkynyl, $C_3$-$C_{12}$ cycloalkyl, $C_3$-$C_{12}$ cycloalkenyl, 3- to 12-membered heterocyclyl, phenyl or 5- or 6-membered heteroaryl, where
any heterocyclyl or heteroaryl in $R^5$ includes 1, 2 or 3 heteroatoms selected from N, O or S in the ring;
any alkyl, alkenyl or alkynyl in $R^5$ may be optionally substituted by one, two or three substituents independently selected from halo, cyano, oxo, hydroxy, carboxy, nitro, $R^6$, —$OR^6$, —$C(O)R^6$, —$C(O)OR^6$, —$OC(O)R^6$, —$C(O)NR^6R^7$, —$NR^7C(O)R^8$, —$NR^6R^7$, —$SO_2NR^6R^7$, —$NR^7SO_2R^8$, —$SR^7$, —$SO_2R^7$, —$SO_2OR^7$, —$OSO_2R^7$, —$NR^8SO_2NR^6R^7$, —$NR^8C(O)NR^6R^7$, —$NR^7C(O)OR^8$ or —$OC(O)NR^6R^7$;

any cycloalkyl, cycloalkenyl, heterocyclyl, phenyl or heteroaryl in $R^5$ may be optionally substituted by one, two or three substituents independently selected from halo, cyano, oxo, nitro, $R^7$, —$OR^7$, —$C(O)R^7$, —$OC(O)R^7$, —$C(O)OR^7$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$;

In embodiments of compounds of Formula (I), the compounds have the structure of Formula (VIII-d),

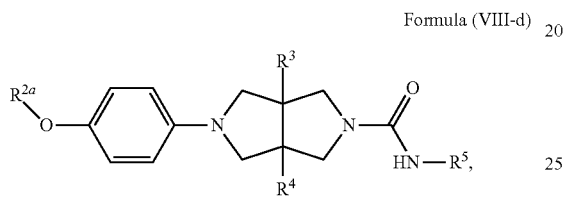

Formula (VIII-d)

in particular Formula (VIII-d')

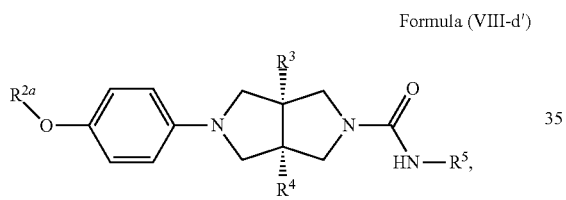

Formula (VIII-d')

or a pharmaceutically acceptable salt thereof, wherein
$R^{2a}$ is unsubstituted $C_1$-$C_4$ alkyl;
$R^3$ and $R^4$ is each independently selected from hydrogen or unsubstituted $C_1$-$C_4$ alkyl (e.g. methyl), in particular each of $R^3$ and $R^4$ is hydrogen or each of $R^3$ and $R^4$ is methyl; and
$R^5$ is selected from $C_1$-$C_6$ alkyl, $C_3$-$C_6$ cycloalkyl, 3- to 6-membered heterocycloalkyl, phenyl or 5- or 6-membered heteroaryl, where
any heterocycloalkyl or heteroaryl in $R^5$ includes 1, 2 or 3 heteroatoms selected from N, O or S in the ring;
any alkyl in $R^5$ may be optionally substituted by one, two or three substituents independently selected from halo, cyano, oxo, hydroxy, carboxy, nitro, $R^6$, —$OR^6$, —$C(O)R^6$, —$C(O)OR^6$, —$OC(O)R^6$, —$C(O)NR^6R^7$, —$NR^7C(O)R^8$, —$NR^6R^7$, —$SO_2NR^6R^7$, —$NR^7SO_2R^8$, —$SR^7$, —$SO_2R^7$, —$SO_2OR^7$, —$OSO_2R^7$, —$NR^8SO_2NR^6R^7$, —$NR^8C(O)NR^6R^7$, —$NR^7C(O)OR^8$ or —$OC(O)NR^6R^7$;

any cycloalkyl, heterocycloalkyl, phenyl or heteroaryl in $R^5$ may be optionally substituted by one, two or three substituents independently selected from halo, cyano, oxo, nitro, $R^7$, —$OR^7$, —$C(O)R^7$, —$OC(O)R^7$, —$C(O)OR^7$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$;

In embodiments of compounds of Formula (I), the compounds have the structure of Formula (VIII-d),

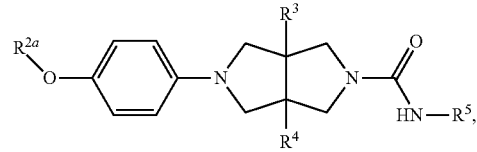

Formula (VIII-d)

in particular Formula (VIII-d')

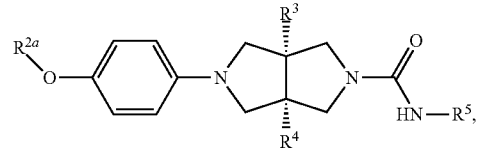

Formula (VIII-d')

or a pharmaceutically acceptable salt thereof, wherein
$R^{2a}$ is unsubstituted $C_1$-$C_4$ alkyl;
$R^3$ and $R^4$ is each independently selected from hydrogen or unsubstituted $C_1$-$C_4$ alkyl (e.g. methyl), in particular each of $R^3$ and $R^4$ is hydrogen or each of $R^3$ and $R^4$ is methyl; and
$R^5$ is selected from $C_1$-$C_6$ alkyl, $C_3$-$C_6$ cycloalkyl, 3- to 6-membered heterocycloalkyl, phenyl or 5- or 6-membered heteroaryl, where
any heterocycloalkyl or heteroaryl in $R^5$ includes 1, 2 or 3 heteroatoms selected from N, O or S in the ring;
any alkyl in $R^5$ may be optionally substituted by cyano or hydroxy;
any cycloalkyl, heterocycloalkyl, phenyl or heteroaryl in $R^5$ may be optionally substituted by oxo, nitro or hydroxy.

In embodiments of compounds of Formula (I), the compounds have the structure of Formula (XII-c) or (XII-d),

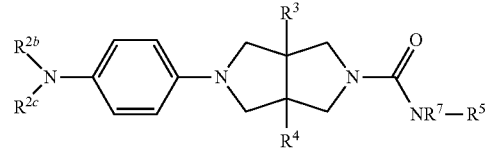

Formula (XII-c)

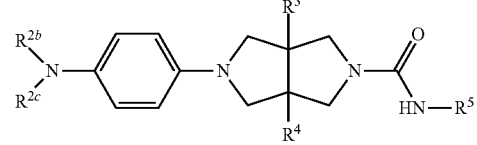

Formula (XII-d)

or a pharmaceutically acceptable salt thereof, wherein
$R^{2b}$ is unsubstituted $C_1$-$C_4$ alkyl,
$R^{2c}$ is $C_1$-$C_4$ alkyl substituted by —$N(CH_3)_2$;
$R^3$ and $R^4$ is each independently selected from hydrogen or unsubstituted $C_1$-$C_4$ alkyl (e.g. methyl), in particular each of $R^3$ and $R^4$ is hydrogen;

$R^5$ is selected from $C_1$-$C_6$ alkyl, $C_3$-$C_6$ cycloalkyl, 3- to 6-membered heterocycloalkyl, phenyl or 5- or 6-membered heteroaryl, where any heterocycloalkyl or heteroaryl in $R^5$ includes 1, 2 or 3 heteroatoms selected from N, O or S in the ring;

any alkyl in $R^5$ may be optionally substituted by cyano or hydroxy;

any cycloalkyl, heterocycloalkyl, phenyl or heteroaryl in $R^5$ may be optionally substituted by oxo, nitro or hydroxy; and $R^7$, when present, is $C_1$-$C_4$ alkyl optionally substituted by hydroxy.

In embodiments of compounds of Formula (I), the compounds have the structure of Formula (XII-c') or (XII-d'), Formula (XII-c')

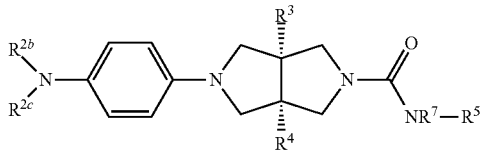

Formula (XII-d')

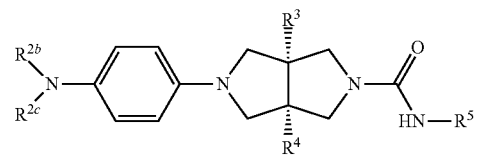

or a pharmaceutically acceptable salt thereof, wherein $R^{2b}$ is unsubstituted $C_1$-$C_4$ alkyl, $R^{2c}$ is $C_1$-$C_4$ alkyl substituted by —N(CH$_3$)$_2$;

$R^3$ and $R^4$ is each independently selected from hydrogen or unsubstituted $C_1$-$C_4$ alkyl (e.g. methyl), in particular each of $R^3$ and $R^4$ is hydrogen;

$R^5$ is selected from $C_1$-$C_6$ alkyl, $C_3$-$C_6$ cycloalkyl, 3- to 6-membered heterocycloalkyl, phenyl or 5- or 6-membered heteroaryl, where any heterocycloalkyl or heteroaryl in $R^5$ includes 1, 2 or 3 heteroatoms selected from N, O or S in the ring;

any alkyl in $R^5$ may be optionally substituted by cyano or hydroxy;

any cycloalkyl, heterocycloalkyl, phenyl or heteroaryl in $R^5$ may be optionally substituted by oxo, nitro or hydroxy; and $R^7$, when present, is $C_1$-$C_4$ alkyl optionally substituted by hydroxy.

In embodiments of compounds of Formula (I), the compounds have the structure of Formula (XII-c) or (XII-d):

Formula (XII-c)

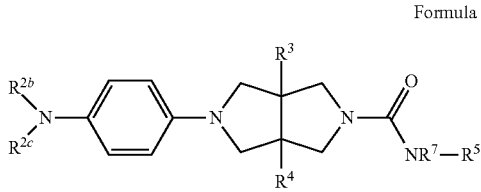

Formula (XII-d)

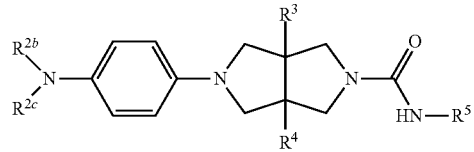

or a pharmaceutically acceptable salt thereof, wherein $R^{2b}$ and $R^{2c}$ together with the nitrogen atom to which they are attached form:

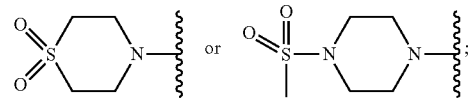 [SMILES: *N1CCS(=O)(=O)CC1 ; *N1CCN(S(C)(=O)=O)CC1]

$R^3$ and $R^4$ is each independently selected from hydrogen or unsubstituted $C_1$-$C_4$ alkyl (e.g. methyl), in particular each of $R^3$ and $R^4$ is hydrogen;

$R^5$ is selected from $C_1$-$C_6$ alkyl, $C_3$-$C_6$ cycloalkyl, 3- to 6-membered heterocycloalkyl, phenyl or 5- or 6-membered heteroaryl, where any heterocycloalkyl or heteroaryl in $R^5$ includes 1, 2 or 3 heteroatoms selected from N, O or S in the ring;

any alkyl in $R^5$ may be optionally substituted by cyano or hydroxy;

any cycloalkyl, heterocycloalkyl, phenyl or heteroaryl in $R^5$ may be optionally substituted by oxo, nitro or hydroxy; and $R^7$, when present, is $C_1$-$C_4$ alkyl optionally substituted by hydroxy.

In embodiments of compounds of Formula (I), the compounds have the structure of Formula (XII-c') or (XII-d'):

Formula (XII-c')

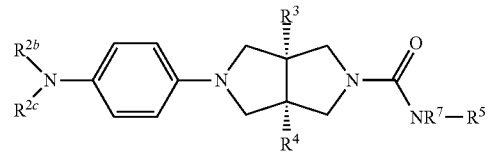

Formula (XII-d')

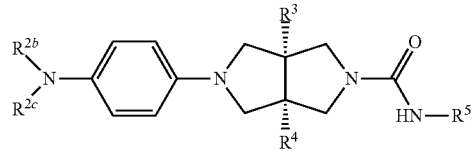

or a pharmaceutically acceptable salt thereof, wherein $R^{2b}$ and $R^{2c}$ together with the nitrogen atom to which they are attached form:

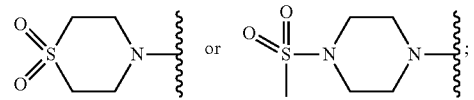 [SMILES: *N1CCS(=O)(=O)CC1 ; *N1CCN(S(C)(=O)=O)CC1]

$R^3$ and $R^4$ is each independently selected from hydrogen or unsubstituted $C_1$-$C_4$ alkyl (e.g. methyl), in particular each of $R^3$ and $R^4$ is hydrogen;

R⁵ is selected from $C_1$-$C_6$ alkyl, $C_3$-$C_6$ cycloalkyl, 3- to 6-membered heterocycloalkyl, phenyl or 5- or 6-membered heteroaryl, where
any heterocycloalkyl or heteroaryl in R⁵ includes 1, 2 or 3 heteroatoms selected from N, O or S in the ring;
any alkyl in R⁵ may be optionally substituted by cyano or hydroxy;
any cycloalkyl, heterocycloalkyl, phenyl or heteroaryl in R⁵ may be optionally substituted by oxo, nitro or hydroxy; and
R⁷, when present, is $C_1$-$C_4$ alkyl optionally substituted by hydroxy.

In an embodiment, the compound of Formula (I) is a compound selected from Table 1 or Table 1a:

TABLE 1

| Chemical name | Structure |
| --- | --- |
| cis-5-(4-Ethoxyphenyl)-N-(2-hydroxyethyl)hexahydro-pyrrolo[3,4-c]pyrrole-2(1H)-carboxamide | 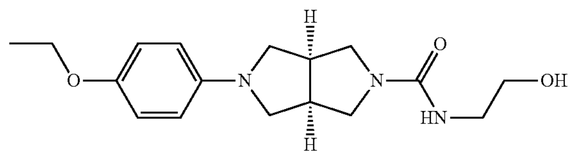 [SMILES: CCOc1ccc(N2C[C@H]3CN(C(=O)NCCO)C[C@H]3C2)cc1] |
| cis-4-(5-(4-Ethoxyphenyl)hexahydropyrrolo[3,4-c]pyrrol-2(1H)-yl)butanenitrile | 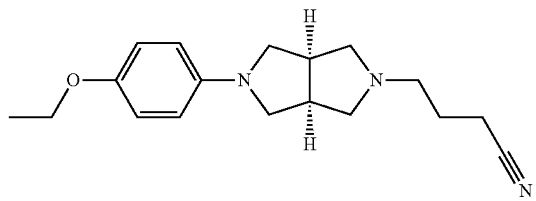 [SMILES: CCOc1ccc(N2C[C@H]3CN(CCCC#N)C[C@H]3C2)cc1] |
| cis-5-(4-Ethoxyphenyl)-N-(2-hydroxyethyl)-3a,6a-dimethylhexahydropyrrolo[3,4-c]pyrrole-2(1H)-carboxamide | 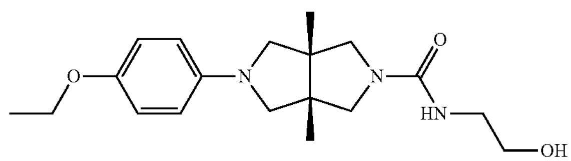 [SMILES: CCOc1ccc(N2C[C@]3(C)CN(C(=O)NCCO)C[C@]3(C)C2)cc1] |
| cis-5-(4-Ethoxyphenyl)-N-(3-(2-oxopyrrolidin-1-yl)propyl)hexahydro-pyrrolo[3,4-c]pyrrole-2(1H)-carboxamide | 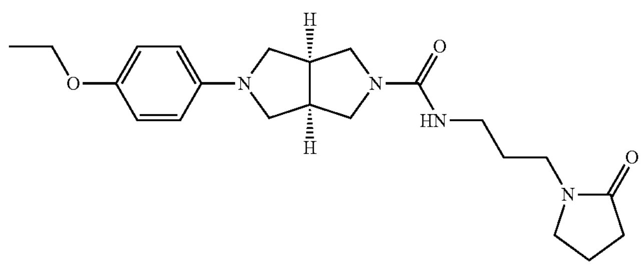 [SMILES: CCOc1ccc(N2C[C@H]3CN(C(=O)NCCCN4CCCC4=O)C[C@H]3C2)cc1] |
| cis-5-(4-Ethoxyphenyl)-N-((R)-2-hydroxypropyl)hexa-hydropyrrolo[3,4-c]pyrrole-2(1H)-carboxamide | 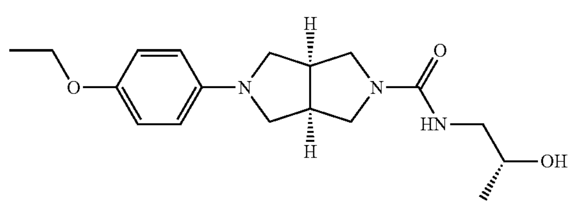 [SMILES: CCOc1ccc(N2C[C@H]3CN(C(=O)NC[C@@H](C)O)C[C@H]3C2)cc1] |
| cis-5-(4-Ethoxyphenyl)-N-((1r,3s,5R,7S)-3-hydroxy-adamantan-1-yl)hexahydropyrrolo[3,4-c]pyrrole-2(1H)-carboxamide | 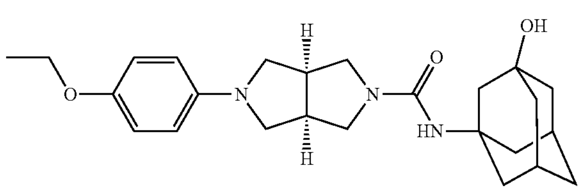 [SMILES: CCOc1ccc(N2C[C@H]3CN(C(=O)NC45CC6CC(CC(O)(C6)C4)C5)C[C@H]3C2)cc1] |
| cis-5-(4-(1,1-Dioxidothiomorpholino)phenyl)-N-ethylhexa-hydropyrrolo[3,4-c]pyrrole-2(1H)-carboxamide | 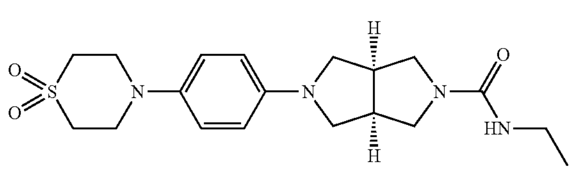 [SMILES: CCNC(=O)N1C[C@@H]2CN(c3ccc(N4CCS(=O)(=O)CC4)cc3)C[C@@H]2C1] |

TABLE 1-continued

| Chemical name | Structure |
|---|---|
| cis-5-(4-(1,1-Dioxidothiomorpholino)phenyl)-N-ethyl-3a,6a-dimethylhexahydropyrrolo[3,4-c]pyrrole-2(1H)-carboxamide | 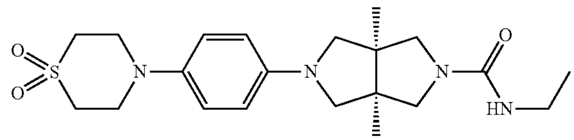 [SMILES: CCNC(=O)N1C[C@@]2(C)CN(c3ccc(N4CCS(=O)(=O)CC4)cc3)C[C@@]2(C)C1] |
| cis-N-Cyclohexyl-5-(4-(1,1-dioxidothiomorpholino)-phenyl)hexahydropyrrolo[3,4-c]pyrrole-2(1H)-carboxamide | 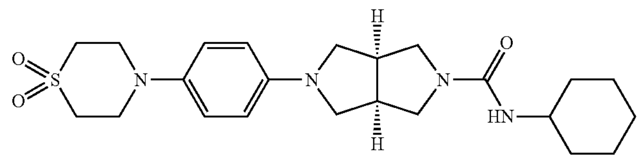 [SMILES: O=C(NC1CCCCC1)N1C[C@@H]2CN(c3ccc(N4CCS(=O)(=O)CC4)cc3)C[C@@H]2C1] |
| cis-N-tert-Butyl-5-(4-(1,1-dioxidothiomorpholino)phenyl)-hexahydropyrrolo[3,4-c]pyrrole-2(1H)-carboxamide | 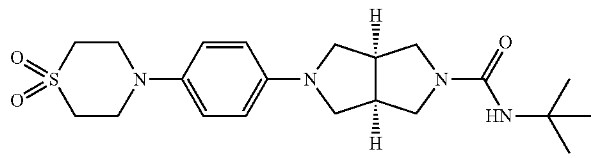 [SMILES: CC(C)(C)NC(=O)N1C[C@@H]2CN(c3ccc(N4CCS(=O)(=O)CC4)cc3)C[C@@H]2C1] |
| cis-5-(4-(1,1-Dioxidothiomorpholino)phenyl)-N-(2-hydroxyethyl)hexahydro-pyrrolo[3,4-c]pyrrole-2(1H)-carboxamide | 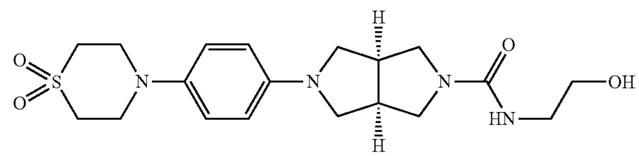 [SMILES: O=C(NCCO)N1C[C@@H]2CN(c3ccc(N4CCS(=O)(=O)CC4)cc3)C[C@@H]2C1] |
| cis-5-(4-(1,1-Dioxidothiomorpholino)phenyl)hexahydro-pyrrolo[3,4-c]pyrrol-2(1H)-yl)(morpholino)methanone | 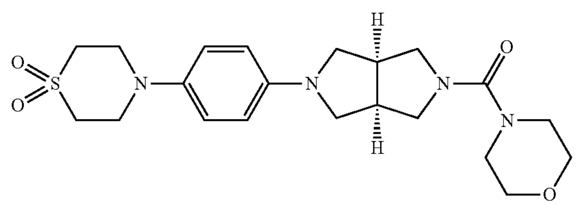 [SMILES: O=C(N1CCOCC1)N1C[C@@H]2CN(c3ccc(N4CCS(=O)(=O)CC4)cc3)C[C@@H]2C1] |
| cis-5-(4-Ethoxyphenyl)-N-ethyl-3a,6a-dimethylhexa-hydropyrrolo[3,4-c]pyrrole-2(1H)-carboxamide | 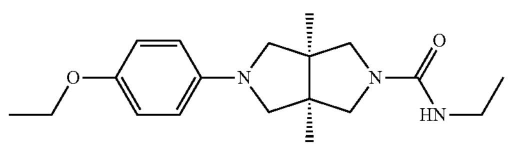 [SMILES: CCNC(=O)N1C[C@@]2(C)CN(c3ccc(OCC)cc3)C[C@@]2(C)C1] |
| cis-5-(4-Ethoxyphenyl)-N-ethylhexahydropyrrolo[3,4-c]pyrrole-2(1H)-carboxamide | 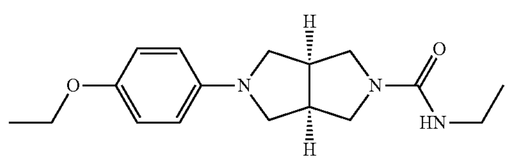 [SMILES: CCNC(=O)N1C[C@@H]2CN(c3ccc(OCC)cc3)C[C@@H]2C1] |
| cis-N-Ethyl-5-(4-methoxyphenyl)hexahydropyrrolo[3,4-c]pyrrole-2(1H)-carboxamide | 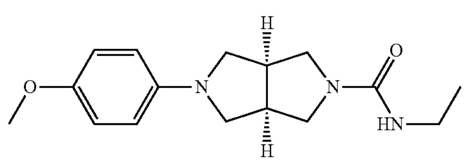 [SMILES: CCNC(=O)N1C[C@@H]2CN(c3ccc(OC)cc3)C[C@@H]2C1] |
| cis-N-Cyclohexyl-5-(4-methoxyphenyl)hexahydro-pyrrolo[3,4-c]pyrrole-2(1H)-carboxamide | 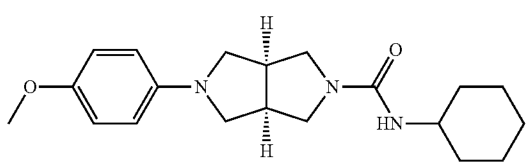 [SMILES: COc1ccc(N2C[C@H]3CN(C(=O)NC4CCCCC4)C[C@H]3C2)cc1] |

TABLE 1-continued

| Chemical name | Structure |
|---|---|
| cis-N-(2-Hydroxyethyl)-5-(4-methoxyphenyl)hexahydro-pyrrolo[3,4-c]pyrrole-2(1H)-carboxamide | 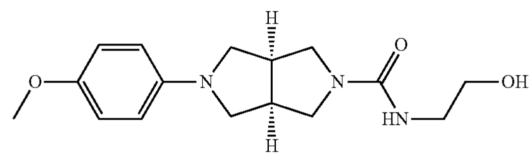 [SMILES: COc1ccc(N2C[C@H]3CN(C(=O)NCCO)C[C@H]3C2)cc1] |
| 4-Nitrophenyl 5-(4-ethoxyphenyl)hexahydropyrrolo[3,4-c]pyrrole-2(1H)-carboxylate | 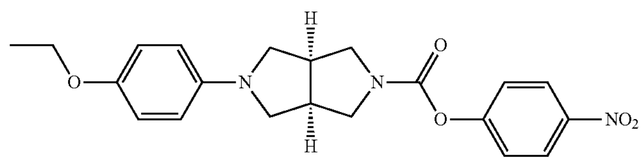 [SMILES: CCOc1ccc(N2C[C@H]3CN(C(=O)Oc4ccc([N+](=O)[O-])cc4)C[C@H]3C2)cc1] |
| cis-N-Ethyl-5-(4-((R)-3-hydroxypyrrolidin-1-yl)phenyl)-hexahydropyrrolo[3,4-c]pyrrole-2(1H)-carboxamide | 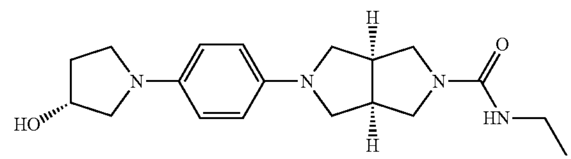 [SMILES: CCNC(=O)N1C[C@@H]2CN(c3ccc(N4CC[C@@H](O)C4)cc3)C[C@@H]2C1] |
| cis-5-(4-((3-(Dimethylamino)propyl)(methyl)amino)-phenyl)-N-ethylhexahydro-pyrrolo[3,4-c]pyrrole-2(1H)-carboxamide | 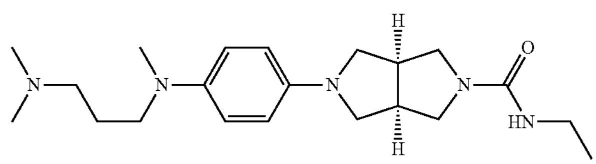 [SMILES: CCNC(=O)N1C[C@@H]2CN(c3ccc(N(C)CCCN(C)C)cc3)C[C@@H]2C1] |
| cis-4-(5-(4-Ethoxyphenyl)-3a,6a-dimethylhexahydro-pyrrolo[3,4-c]pyrrol-2(1H)-yl)butanenitrile | 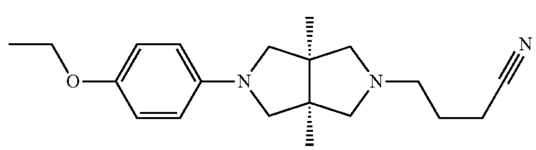 [SMILES: CCOc1ccc(N2C[C@]3(C)CN(CCCC#N)C[C@]3(C)C2)cc1] |
| cis-N-Ethyl-5-(4-(4-(methylsulfonyl)piperazin-1-yl)phenyl)hexahydro-pyrrolo[3,4-c]pyrrole-2(1H)-carboxamide | 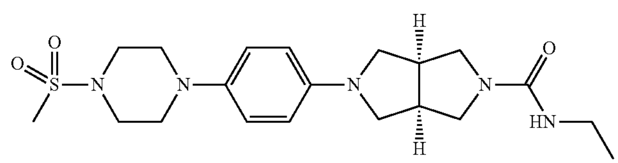 [SMILES: CCNC(=O)N1C[C@@H]2CN(c3ccc(N4CCN(S(C)(=O)=O)CC4)cc3)C[C@@H]2C1] |
| cis-4-(5-(4-(4-(Methylsulfonyl)piperazin-1-yl)phenyl)-hexahydropyrrolo[3,4-c]pyrrol-2(1H)-yl)butanenitrile | 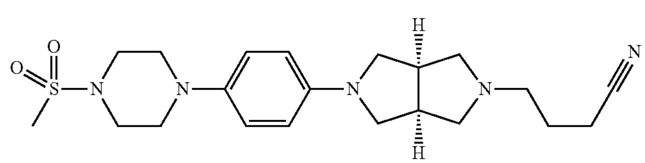 [SMILES: CS(=O)(=O)N1CCN(c2ccc(N3C[C@H]4CN(CCCC#N)C[C@H]4C3)cc2)CC1] |
| cis-4-(5-(4-((3-(Dimethylamino)propyl)(methyl)-amino)phenyl)hexahydro-pyrrolo[3,4-c]pyrrol-2(1H)-yl)butanenitrile | 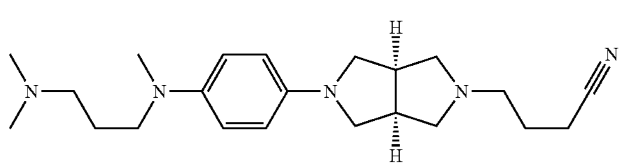 [SMILES: CN(C)CCCN(C)c1ccc(N2C[C@H]3CN(CCCC#N)C[C@H]3C2)cc1] |
| cis-5-(4-((3-(Dimethylamino)propyl)(methyl)amino)-phenyl)-N-(2-hydroxyethyl)hexahydropyrrolo[3,4-c]pyrrole-2(1H)-carboxamide | 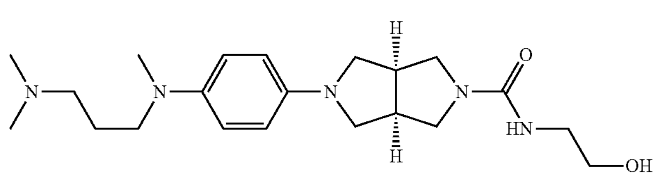 [SMILES: CN(C)CCCN(C)c1ccc(N2C[C@H]3CN(C(=O)NCCO)C[C@H]3C2)cc1] |

TABLE 1-continued

| Chemical name | Structure |
|---|---|
| cis-N-(2-Hydroxyethyl)-5-(4-(4-(methylsulfonyl)-piperazin-1-yl)phenyl)hexahydro-pyrrolo[3,4-c]pyrrole-2(1H)-carboxamide | 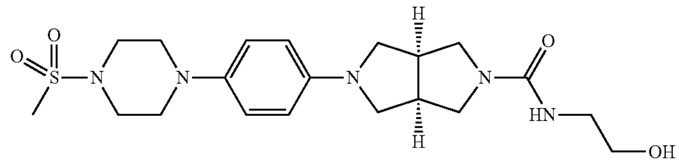 [SMILES: CS(=O)(=O)N1CCN(c2ccc(N3C[C@H]4CN(C(=O)NCCO)C[C@H]4C3)cc2)CC1] |
| cis-N-Ethyl-3a,6a-dimethyl-5-(4-(4-(methylsulfonyl)-piperazin-1-yl)phenyl)hexahydropyrrolo[3,4-c]pyrrole-2(1H)-carboxamide | 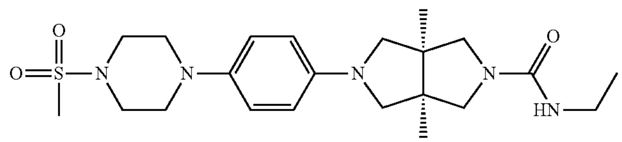 [SMILES: CCNC(=O)N1C[C@@]2(C)CN(c3ccc(N4CCN(S(C)(=O)=O)CC4)cc3)C[C@@]2(C)C1] |
| cis-N-(2-Hydroxyethyl)-3a,6a-dimethyl-5-(4-(4-(methylsulfonyl)piperazin-1-yl)phenyl)hexahydro-pyrrolo[3,4-c]pyrrole-2(1H)-carboxamide | 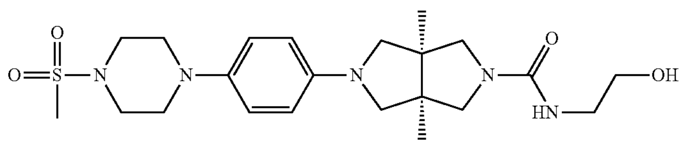 [SMILES: C[C@@]12CN(C(=O)NCCO)C[C@]1(C)CN(c1ccc(N3CCN(S(C)(=O)=O)CC3)cc1)C2] |
| cis-4-(3a,6a-Dimethyl-5-(4-(4-(methylsulfonyl)-piperazin-1-yl)phenyl)hexahydro-pyrrolo[3,4-c]pyrrol-2(1H)-yl)butanenitrile | 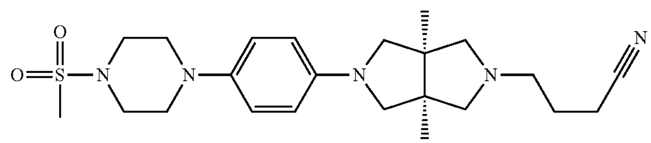 [SMILES: C[C@@]12CN(CCCC#N)C[C@]1(C)CN(c1ccc(N3CCN(S(C)(=O)=O)CC3)cc1)C2] |
| cis-5-(4-(1,1-Dioxidothiomorpholino)phenyl)-N-(2-hydroxyethyl)-3a,6a-dimethylhexahydropyrrolo[3,4-c]pyrrole-2(1H)-carboxamide | 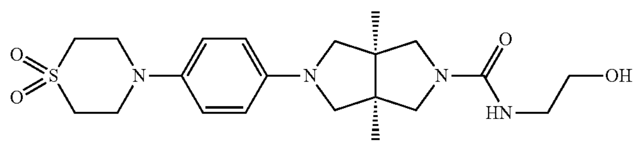 [SMILES: C[C@@]12CN(C(=O)NCCO)C[C@]1(C)CN(c1ccc(N3CCS(=O)(=O)CC3)cc1)C2] |
| cis-4-(3a,6a-Dimethyl-5-(4-(4-(methylsulfonyl)-piperazin-1-yl)phenyl)hexahydropyrrolo[3,4-c]pyrrol-2(1H)-yl)butanenitrile | 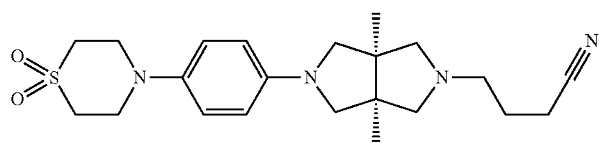 |
| cis-4-(5-(4-(1,1-Dioxidothiomorpholino)-phenyl)hexahydropyrrolo[3,4-c]pyrrol-2(1H)-yl)butanenitrile | 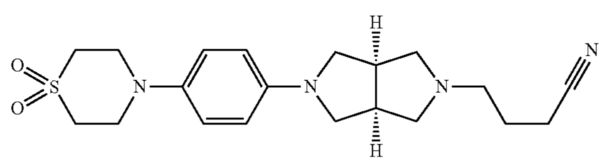 [SMILES: N#CCCCN1C[C@@H]2CN(c3ccc(N4CCS(=O)(=O)CC4)cc3)C[C@@H]2C1] |
| cis-(1,1-Dioxidothiomorpholino)-5-(4-(1,1-dioxidothiomorpholino)phenyl)-3a,6a-dimethylhexahydropyrrolo[3,4-c]pyrrol-2(1H)-yl)methanone | 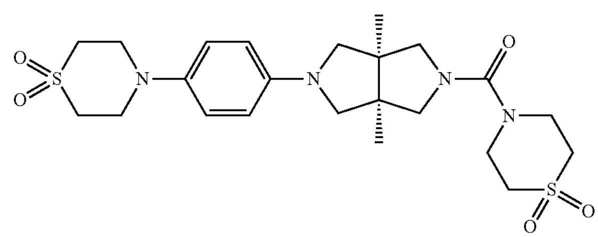 [SMILES: C[C@@]12CN(C(=O)N3CCS(=O)(=O)CC3)C[C@]1(C)CN(c1ccc(N3CCS(=O)(=O)CC3)cc1)C2] |
| cis-(1,1-Dioxidothiomorpholino)(5-(4-ethoxy-phenyl)hexahydropyrrolo[3,4-c]pyrrol-2(1H)-yl)methanone | 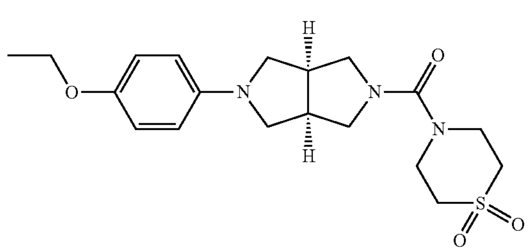 [SMILES: CCOc1ccc(N2C[C@H]3CN(C(=O)N4CCS(=O)(=O)CC4)C[C@H]3C2)cc1] |

TABLE 1-continued

| Chemical name | Structure |
| --- | --- |
| cis-2-(4-Ethoxyphenyl)-5-(2-(pyrrolidin-1-yl)ethyl)octahydropyrrolo[3,4-c]pyrrole | 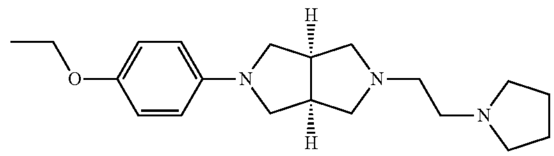 [SMILES: CCOc1ccc(N2C[C@H]3CN(CCN4CCCC4)C[C@H]3C2)cc1] |
| cis-1-(2-(5-(4-Ethoxyphenyl)hexahydro-pyrrolo[3,4-c]pyrrol-2(1H)-yl)ethyl)-pyrrolidine-2,5-dione | 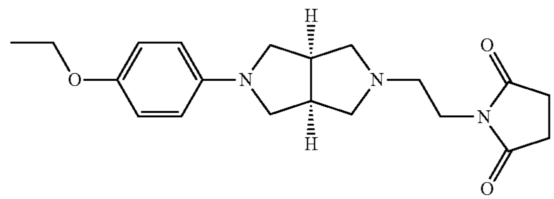 [SMILES: CCOc1ccc(N2C[C@H]3CN(CCN4C(=O)CCC4=O)C[C@H]3C2)cc1] |

TABLE 1a

| Chemical name | Structure |
| --- | --- |
| cis-5-(4-Ethoxyphenyl)-N-(2-hydroxyethyl)hexahydro-pyrrolo[3,4-c]pyrrole-2(1H)-carboxamide | 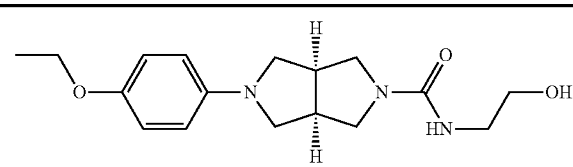 |
| cis-4-(5-(4-Ethoxyphenyl)hexahydropyrrolo[3,4-c]pyrrol-2(1H)-yl)butanenitrile | 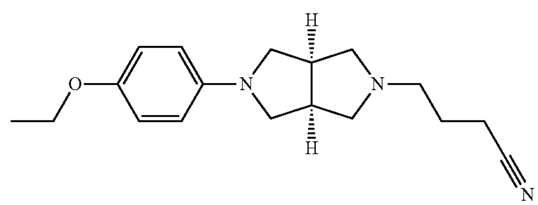 [SMILES: CCOc1ccc(N2C[C@H]3CN(CCCC#N)C[C@H]3C2)cc1] |
| cis-5-(4-Ethoxyphenyl)-N-(2-hydroxyethyl)-3a,6a-dimethylhexahydropyrrolo[3,4-c]pyrrole-2(1H)-carboxamide | 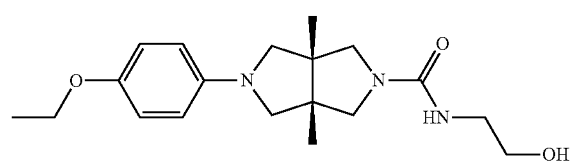 [SMILES: CCOc1ccc(N2C[C@]3(C)CN(C(=O)NCCO)C[C@]3(C)C2)cc1] |
| cis-5-(4-Ethoxyphenyl)-N-(3-(2-oxopyrrolidin-1-yl)propyl)hexahydro-pyrrolo[3,4-c]pyrrole-2(1H)-carboxamide | 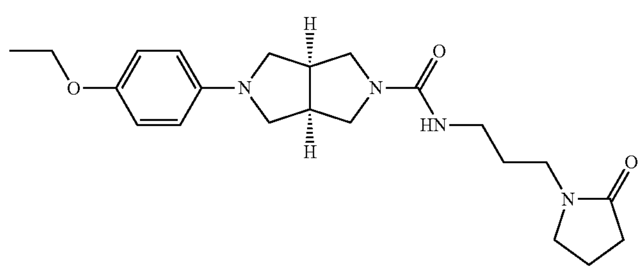 [SMILES: CCOc1ccc(N2C[C@H]3CN(C(=O)NCCCN4CCCC4=O)C[C@H]3C2)cc1] |
| cis-5-(4-Ethoxyphenyl)-N-((R)-2-hydroxypropyl)hexa-hydropyrrolo[3,4-c]pyrrole-2(1H)-carboxamide | 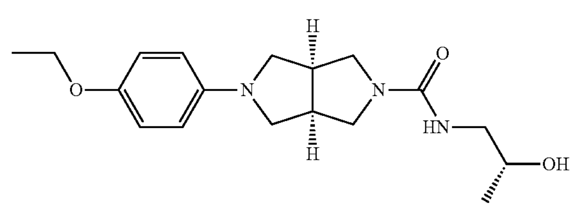 [SMILES: CCOc1ccc(N2C[C@H]3CN(C(=O)NC[C@@H](C)O)C[C@H]3C2)cc1] |

TABLE 1a-continued

| Chemical name | Structure |
|---|---|
| cis-5-(4-Ethoxyphenyl)-N-((1r,3s,5R,7S)-3-hydroxy-adamantan-1-yl)hexahydropyrrolo[3,4-c]pyrrole-2(1H)-carboxamide | 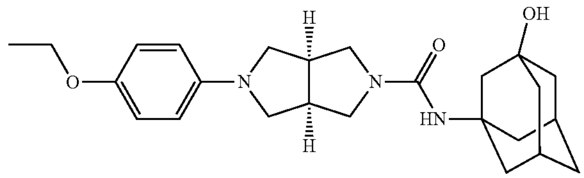 [SMILES: CCOc1ccc(N2C[C@H]3CN(C(=O)NC45CC6CC(CC(O)(C6)C4)C5)C[C@H]3C2)cc1] |
| cis-5-(4-(1,1-Dioxidothiomorpholino)phenyl)-N-ethylhexa-hydropyrrolo[3,4-c]pyrrole-2(1H)-carboxamide | 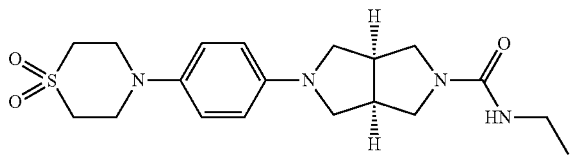 [SMILES: CCNC(=O)N1C[C@@H]2CN(c3ccc(N4CCS(=O)(=O)CC4)cc3)C[C@@H]2C1] |
| cis-5-(4-(1,1-Dioxidothiomorpholino)phenyl)-N-ethyl-3a,6a-dimethylhexahydropyrrolo[3,4-c]pyrrole-2(1H)-carboxamide | 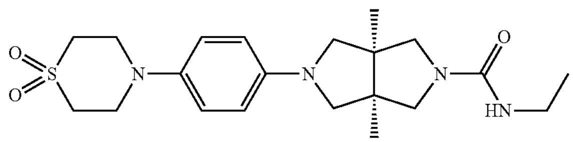 [SMILES: CCNC(=O)N1C[C@@]2(C)CN(c3ccc(N4CCS(=O)(=O)CC4)cc3)C[C@@]2(C)C1] |
| cis-N-Cyclohexyl-5-(4-(1,1-dioxidothiomorpholino)-phenyl)hexahydropyrrolo[3,4-c]pyrrole-2(1H)-carboxamide | 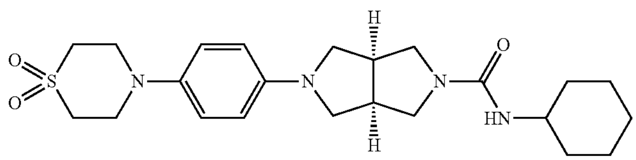 [SMILES: O=C(NC1CCCCC1)N1C[C@@H]2CN(c3ccc(N4CCS(=O)(=O)CC4)cc3)C[C@@H]2C1] |
| cis-N-tert-Butyl-5-(4-(1,1-dioxidothiomorpholino)phenyl)-hexahydropyrrolo[3,4-c]pyrrole-2(1H)-carboxamide | 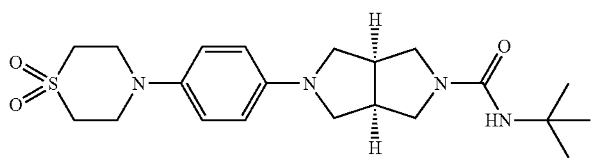 [SMILES: CC(C)(C)NC(=O)N1C[C@@H]2CN(c3ccc(N4CCS(=O)(=O)CC4)cc3)C[C@@H]2C1] |
| cis-5-(4-(1,1-Dioxidothiomorpholino)phenyl)-N-(2-hydroxyethyl)hexahydro-pyrrolo[3,4-c]pyrrole-2(1H)-carboxamide | 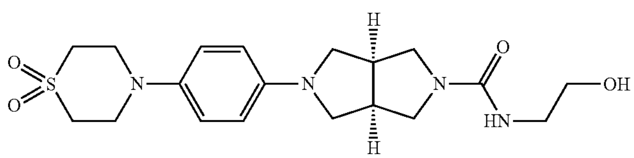 [SMILES: O=C(NCCO)N1C[C@@H]2CN(c3ccc(N4CCS(=O)(=O)CC4)cc3)C[C@@H]2C1] |
| cis-5-(4-(1,1-Dioxidothiomorpholino)phenyl)hexahydro-pyrrolo[3,4-c]pyrrol-2(1H)-yl)(morpholino)methanone | 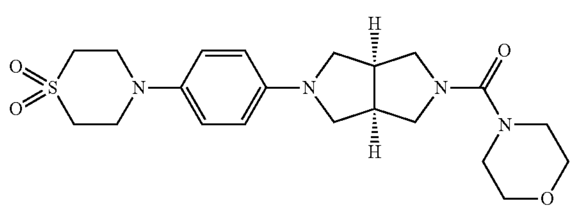 [SMILES: O=C(N1CCOCC1)N1C[C@@H]2CN(c3ccc(N4CCS(=O)(=O)CC4)cc3)C[C@@H]2C1] |
| cis-5-(4-Ethoxyphenyl)-N-ethyl-3a,6a-dimethylhexa-hydropyrrolo[3,4-c]pyrrole-2(1H)-carboxamide | 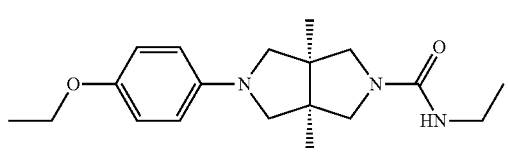 [SMILES: CCNC(=O)N1C[C@@]2(C)CN(c3ccc(OCC)cc3)C[C@@]2(C)C1] |
| cis-5-(4-Ethoxyphenyl)-N-ethylhexahydropyrrolo[3,4-c]pyrrole-2(1H)-carboxamide | 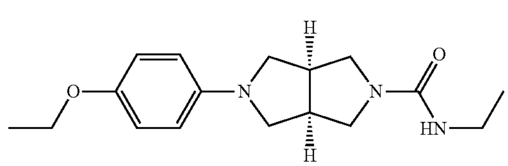 [SMILES: CCNC(=O)N1C[C@@H]2CN(c3ccc(OCC)cc3)C[C@@H]2C1] |

TABLE 1a-continued

| Chemical name | Structure |
|---|---|
| cis-N-Ethyl-5-(4-methoxyphenyl)hexahydropyrrolo[3,4-c]pyrrole-2(1H)-carboxamide | 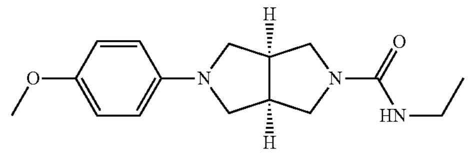 [SMILES: CCNC(=O)N1C[C@@H]2CN(c3ccc(OC)cc3)C[C@@H]2C1] |
| cis-N-Cyclohexyl-5-(4-methoxyphenyl)hexahydro-pyrrolo[3,4-c]pyrrole-2(1H)-carboxamide | 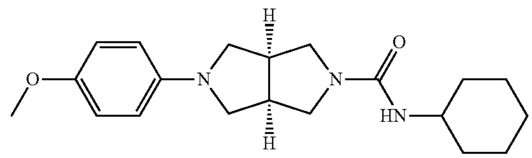 [SMILES: COc1ccc(N2C[C@H]3CN(C(=O)NC4CCCCC4)C[C@H]3C2)cc1] |
| cis-N-(2-Hydroxyethyl)-5-(4-methoxyphenyl)hexahydro-pyrrolo[3,4-c]pyrrole-2(1H)-carboxamide | 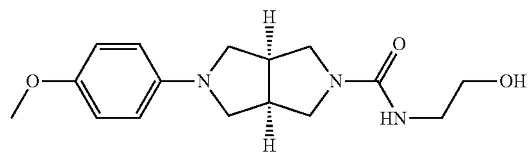 [SMILES: COc1ccc(N2C[C@H]3CN(C(=O)NCCO)C[C@H]3C2)cc1] |
| 4-Nitrophenyl 5-(4-ethoxyphenyl)hexahydropyrrolo[3,4-c]pyrrole-2(1H)-carboxylate | 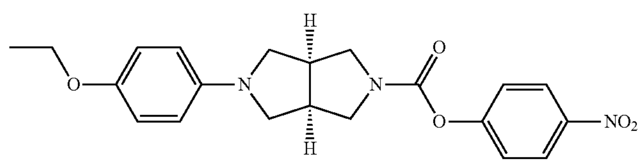 [SMILES: CCOc1ccc(N2C[C@H]3CN(C(=O)Oc4ccc([N+](=O)[O-])cc4)C[C@H]3C2)cc1] |
| cis-N-Ethyl-5-(4-((R)-3-hydroxypyrrolidin-1-yl)phenyl)-hexahydropyrrolo[3,4-c]pyrrole-2(1H)-carboxamide | 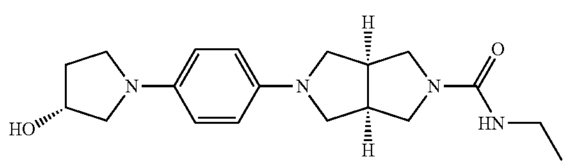 [SMILES: CCNC(=O)N1C[C@@H]2CN(c3ccc(N4CC[C@@H](O)C4)cc3)C[C@@H]2C1] |
| cis-5-(4-((3-(Dimethylamino)propyl)(methyl)amino)-phenyl)-N-ethylhexahydro-pyrrolo[3,4-c]pyrrole-2(1H)-carboxamide | 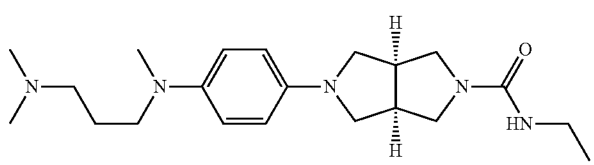 [SMILES: CCNC(=O)N1C[C@@H]2CN(c3ccc(N(C)CCCN(C)C)cc3)C[C@@H]2C1] |
| cis-4-(5-(4-Ethoxyphenyl)-3a,6a-dimethylhexahydro-pyrrolo[3,4-c]pyrrol-2(1H)-yl)butanenitrile | 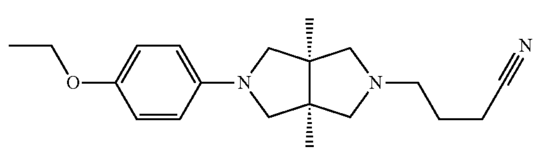 [SMILES: CCOc1ccc(N2C[C@]3(C)CN(CCCC#N)C[C@]3(C)C2)cc1] |
| cis-N-Ethyl-5-(4-(4-(methylsulfonyl)piperazin-1-yl)phenyl)hexahydro-pyrrolo[3,4-c]pyrrole-2(1H)-carboxamide | 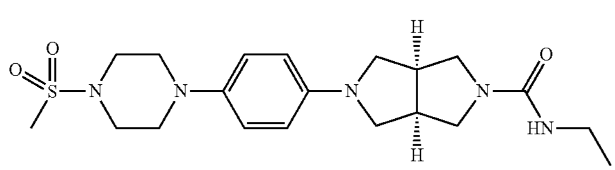 [SMILES: CCNC(=O)N1C[C@@H]2CN(c3ccc(N4CCN(S(C)(=O)=O)CC4)cc3)C[C@@H]2C1] |
| cis-4-(5-(4-(4-(Methylsulfonyl)piperazin-1-yl)phenyl)-hexahydropyrrolo[3,4-c]pyrrol-2(1H)-yl)butanenitrile | 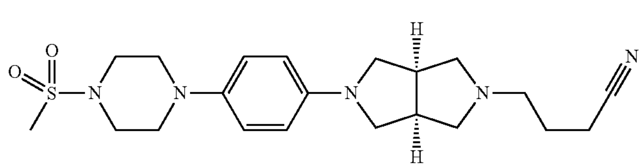 [SMILES: CS(=O)(=O)N1CCN(c2ccc(N3C[C@H]4CN(CCCC#N)C[C@H]4C3)cc2)CC1] |

TABLE 1a-continued

| Chemical name | Structure |
|---|---|
| cis-4-(5-(4-((3-(Dimethylamino)propyl)(methyl)-amino)phenyl)hexahydro-pyrrolo[3,4-c]pyrrol-2(1H)-yl)butanenitrile | 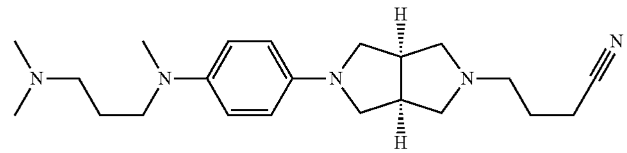 |
| cis-5-(4-((3-(Dimethylamino)propyl)(methyl)amino)-phenyl)-N-(2-hydroxyethyl)hexahydropyrrolo[3,4-c]pyrrole-2(1H)-carboxamide | 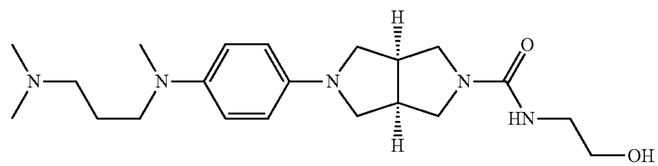 [SMILES: CN(C)CCCN(C)c1ccc(N2C[C@H]3CN(C(=O)NCCO)C[C@H]3C2)cc1] |
| cis-N-(2-Hydroxyethyl)-5-(4-(4-(methylsulfonyl)-piperazin-1-yl)phenyl)hexahydro-pyrrolo[3,4-c]pyrrole-2(1H)-carboxamide | 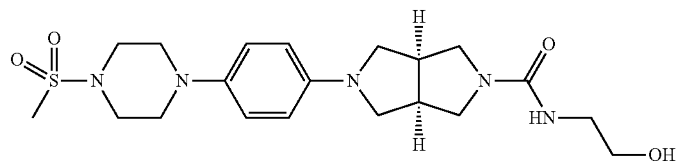 [SMILES: CS(=O)(=O)N1CCN(c2ccc(N3C[C@H]4CN(C(=O)NCCO)C[C@H]4C3)cc2)CC1] |
| cis-N-Ethyl-3a,6a-dimethyl-5-(4-(4-(methylsulfonyl)-piperazin-1-yl)phenyl)hexahydropyrrolo[3,4-c]pyrrole-2(1H)-carboxamide | 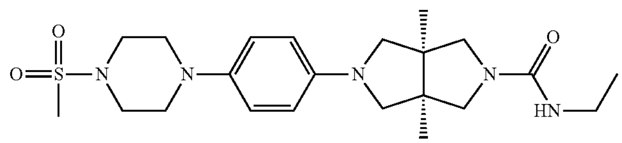 [SMILES: CCNC(=O)N1C[C@@]2(C)CN(c3ccc(N4CCN(S(C)(=O)=O)CC4)cc3)C[C@@]2(C)C1] |
| cis-N-(2-Hydroxyethyl)-3a,6a-dimethyl-5-(4-(4-(methylsulfonyl)piperazin-1-yl)phenyl)hexahydro-pyrrolo[3,4-c]pyrrole-2(1H)-carboxamide | 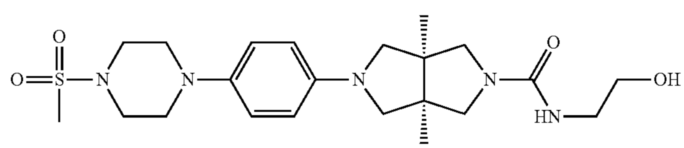 [SMILES: C[C@@]12CN(C(=O)NCCO)C[C@]1(C)CN(c1ccc(N3CCN(S(C)(=O)=O)CC3)cc1)C2] |
| cis-4-(3a,6a-Dimethyl-5-(4-(4-(methylsulfonyl)-piperazin-1-yl)phenyl)hexahydro-pyrrolo[3,4-c]pyrrol-2(1H)-yl)butanenitrile | 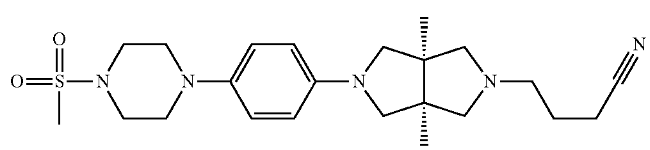 [SMILES: C[C@@]12CN(CCCC#N)C[C@]1(C)CN(c1ccc(N3CCN(S(C)(=O)=O)CC3)cc1)C2] |
| cis-5-(4-(1,1-Dioxidothiomorpholino)phenyl)-N-(2-hydroxyethyl)-3a,6a-dimethylhexahydropyrrolo[3,4-c]pyrrole-2(1H)-carboxamide | 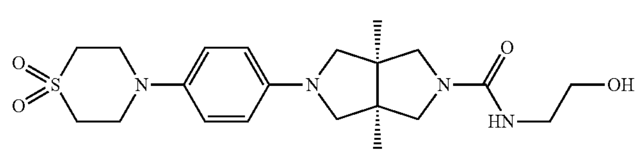 [SMILES: C[C@@]12CN(C(=O)NCCO)C[C@]1(C)CN(c1ccc(N3CCS(=O)(=O)CC3)cc1)C2] |
| cis-4-(3a,6a-Dimethyl-5-(4-(4-(methylsulfonyl)-piperazin-1-yl)phenyl)hexahydropyrrolo[3,4-c]pyrrol-2(1H)-yl)butanenitrile | 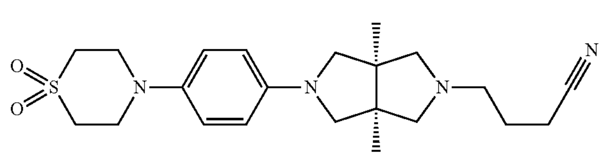 [SMILES: C[C@@]12CN(CCCC#N)C[C@]1(C)CN(c1ccc(N3CCS(=O)(=O)CC3)cc1)C2] |
| cis-4-(5-(4-(1,1-Dioxidothiomorpholino)-phenyl)hexahydropyrrolo[3,4-c]pyrrol-2(1H)-yl)butanenitrile | 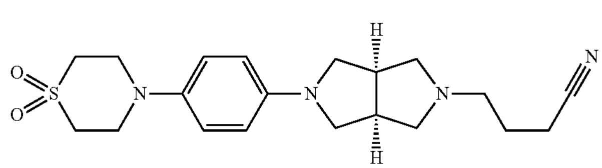 [SMILES: N#CCCCN1C[C@@H]2CN(c3ccc(N4CCS(=O)(=O)CC4)cc3)C[C@@H]2C1] |

TABLE 1a-continued

| Chemical name | Structure |
|---|---|
| cis-(1,1-Dioxidothiomorpholino)-5-(4-(1,1-dioxidothiomorpholino)phenyl)-3a,6a-dimethylhexahydropyrrolo[3,4-c]pyrrol-2(1H)-yl)methanone | 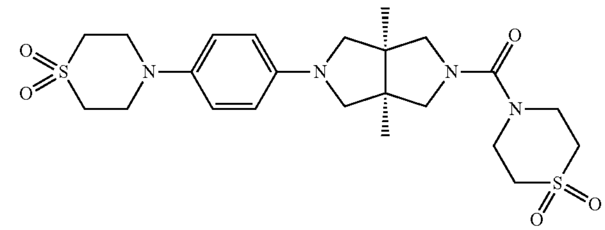 [SMILES: C[C@@]12CN(C(=O)N3CCS(=O)(=O)CC3)C[C@]1(C)CN(c1ccc(N3CCS(=O)(=O)CC3)cc1)C2] |
| cis-(1,1-Dioxidothiomorpholino)(5-(4-ethoxyphenyl)hexahydropyrrolo[3,4-c]pyrrol-2(1H)-yl)methanone | |
| cis-2-(4-Ethoxyphenyl)-5-(2-(pyrrolidin-1-yl)ethyl)octahydropyrrolo[3,4-c]pyrrole | 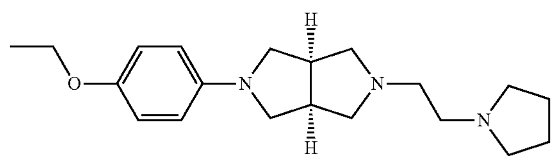 [SMILES: CCOc1ccc(N2C[C@H]3CN(CCN4CCCC4)C[C@H]3C2)cc1] |
| cis-1-(2-(5-(4-Ethoxyphenyl)hexahydro-pyrrolo[3,4-c]pyrrol-2(1H)-yl)ethyl)-pyrrolidine-2,5-dione | 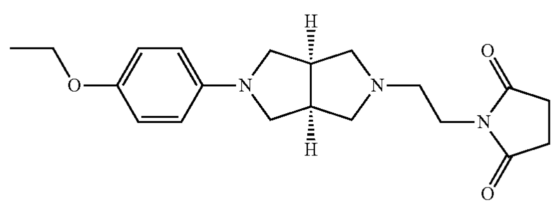 [SMILES: CCOc1ccc(N2C[C@H]3CN(CCN4C(=O)CCC4=O)C[C@H]3C2)cc1] |
| cis-5-(4-ethoxyphenyl)hexahydropyrrolo[3,4-c]pyrrol-2(1H)-yl)(morpholino)methanone | 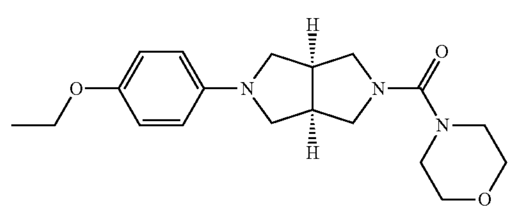 [SMILES: CCOc1ccc(N2C[C@H]3CN(C(=O)N4CCOCC4)C[C@H]3C2)cc1] |
| cis-N-(1,1-dioxidotetrahydro-2H-thiopyran-4-yl)-5-(4-ethoxyphenyl)hexa-hydropyrrolo[3,4-c]pyrrole-2(1H)-carboxamide | 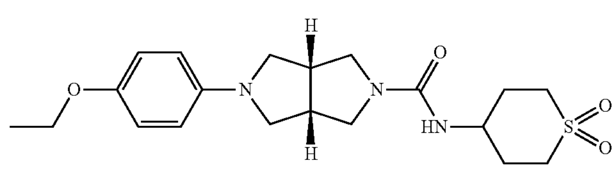 [SMILES: CCOc1ccc(N2C[C@H]3CN(C(=O)NC4CCS(=O)(=O)CC4)C[C@H]3C2)cc1] |
| cis-5-(4-ethoxyphenyl)-N-(tetrahydro-2H-pyran-4-yl)hexahydropyrrolo[3,4-c]pyrrole-2(1H)-carboxamide | 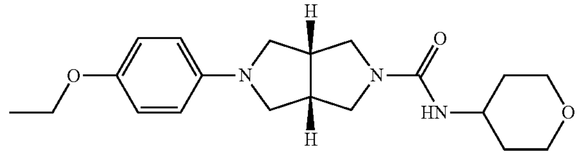 [SMILES: CCOc1ccc(N2C[C@H]3CN(C(=O)NC4CCOCC4)C[C@H]3C2)cc1] |

TABLE 1a-continued

| Chemical name | Structure |
|---|---|
| (4,4-difluoropiperidin-1-yl)(cis-5-(4-ethoxyphenyl)hexahydropyrrolo[3,4-c]pyrrol-2(1H)-yl)methanone | 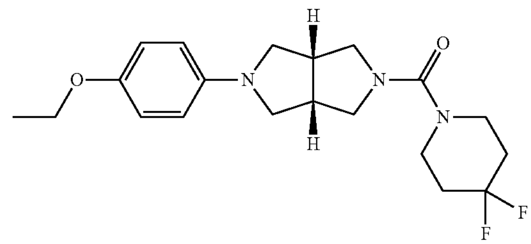 [SMILES: CCOc1ccc(N2C[C@H]3CN(C(=O)N4CCC(F)(F)CC4)C[C@H]3C2)cc1] |
| (cis-5-(4-ethoxyphenyl)hexahydro pyrrolo[3,4-c]pyrrol-2(1H)-yl)(4-(methylsulfonyl)piperazin-1-yl)methanone | 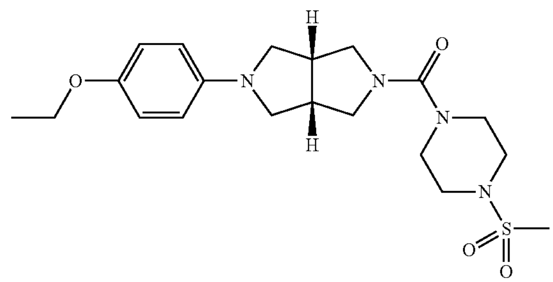 [SMILES: CCOc1ccc(N2C[C@H]3CN(C(=O)N4CCN(S(C)(=O)=O)CC4)C[C@H]3C2)cc1] |
| 1-(cis-5-(4-ethoxyphenyl)octahydro pyrrolo[3,4-c]pyrrole-2-carbonyl)piperidine-4-carbonitrile | 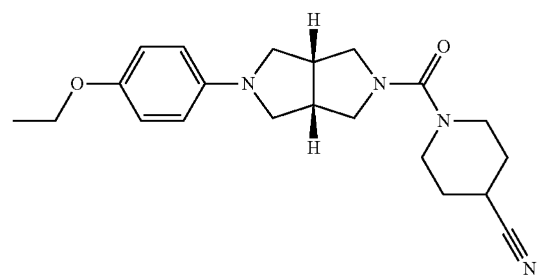 [SMILES: CCOc1ccc(N2C[C@H]3CN(C(=O)N4CCC(C#N)CC4)C[C@H]3C2)cc1] |
| cis-N-(2-cyanoethyl)-5-(4-ethoxyphenyl)-N-methylhexahydropyrrolo[3,4-c]pyrrole-2(1H)-carboxamide | | or a pharmaceutically acceptable salt of any of the foregoing compounds.

In an embodiment of the present invention the compound of formula (I) is a compound selected from:

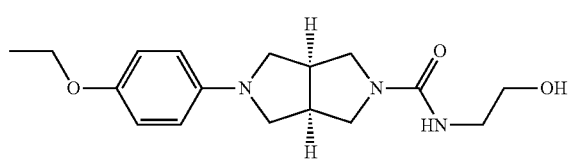

cis-5-(4-Ethoxyphenyl)-N-(2-hydroxyethyl)hexahydro-pyrrolo[3,4-c]pyrrole-2(1H)-carboxamide -continued

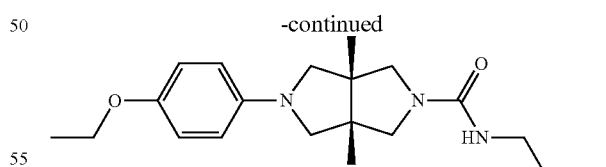

cis-5-(4-Ethoxyphenyl)-N-(2-hydroxyethyl)-3a,6a-dimethylhexahydropyrrolo[3,4-c]pyrrole-2(1H)-carboxamide or a pharmaceutically acceptable salt of any of these compounds.

Pharmaceutical Compositions

In accordance with another aspect, the present invention provides a pharmaceutical formulation comprising a compound of the invention, or a pharmaceutically acceptable salt thereof, and a pharmaceutically acceptable excipient.

Conventional procedures for the selection and preparation of suitable pharmaceutical formulations are described in, for example, "Pharmaceuticals—The Science of Dosage Form Designs", M. E. Aulton, Churchill Livingstone, 1988.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of a condition is an amount sufficient to symptomatically relieve in a warm-blooded animal, particularly a human the symptoms of the condition or to slow the progression of the condition.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the invention will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, a daily dose selected from 0.1 mg/kg to 100 mg/kg, 1 mg/kg to 75 mg/kg, 1 mg/kg to 50 mg/kg, 1 mg/kg to 20 mg/kg or 5 mg/kg to 10 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Suitably the compound of the invention is administered orally, for example in the form of a tablet, or capsule dosage form. The daily dose administered orally may be, for example a total daily dose selected from 1 mg to 2000 mg, 5 mg to 2000 mg, 5 mg to 1500 mg, 10 mg to 750 mg or 25 mg to 500 mg. Typically, unit dosage forms will contain about 0.5 mg to 0.5 g of a compound of this invention.

Therapeutic Uses and Applications

In accordance with another aspect, the present invention provides a compound of the invention, or a pharmaceutically acceptable salt thereof, for use as a medicament.

A further aspect of the invention provides a compound of the invention, or a pharmaceutically acceptable salt thereof, for use in the treatment of a disease or medical condition mediated by LOX.

Also provided is the use of a compound of the invention, or a pharmaceutically acceptable salt thereof in the manufacture of a medicament for the treatment of a disease or medical condition mediated by LOX.

Also provided is a method of treating a disease or medical condition mediated by LOX in a subject in need thereof, the method comprising administering to the subject an effective amount of a compound of the invention, or a pharmaceutically acceptable salt thereof.

Unless stated otherwise reference to the treatment of a disease or medical condition mediated by LOX is intended to encompass diseases or medical conditions mediated by any one of LOX, LOXL1, LOXL2, LOXL3 or LOXL4.

In the following sections of the application reference is made to a compound of the invention, or a pharmaceutically acceptable salt for use in the treatment of certain diseases or conditions. It is to be understood that any reference herein to a compound for a particular use is also intended to be a reference to (i) the use of the compound of the invention, or pharmaceutically acceptable salt thereof, in the manufacture of a medicament for the treatment of that disease or condition; and (ii) a method of treating the disease or condition in a subject, the method comprising administering to the subject a therapeutically effective amount of the compound of the invention, or pharmaceutically acceptable salt thereof.

The disease of medical condition mediated by LOX may be any of the diseases or medical conditions listed in this application.

As discussed in the background to the invention the role of the LOX family of may have distinct roles in diseases such as cancer. Accordingly the selective inhibition of a LOX may be advantageous. In one embodiment there is provided a compound of the invention, or pharmaceutically acceptable salt thereof, for use in the selective inhibition of LOX, LOXL1, LOXL2, LOXL3 or LOXL4. In other embodiments it may be advantageous to inhibit two or more members of the LOX family. Accordingly in another embodiment there is provided a compound of the invention, or pharmaceutically acceptable salt thereof, for use in the inhibition of two or more members of the LOX family selected from LOX, LOXL1, LOXL2, LOXL3 or LOXL4.

Proliferative Diseases—LOX and Cancer

A further aspect of the invention provides a compound of the invention, or a pharmaceutically acceptable salt thereof, for use in the treatment of a proliferative disease. The proliferative disease may be malignant or non-malignant.

As mentioned in the Background to the invention, LOX plays a critical role in primary cancer and metastasis. Evidence supporting this role of LOX in primary tumour growth and metastasis is described below.

Studies have shown that LOX plays a fundamental role in the growth of primary tumours in colorectal and lung cancer (Gao, Xiao et al. 2010, Baker, Cox et al. 2011) and glioblastoma (Mammoto, Jiang et al. 2013). PDAC KRAS$^{mut}$/p53$^{wt}$ cells (which endogenously express low levels of LOX) were engineered to express high levels of human LOX. In murine allograft models using these cells primary tumour growth is increased significantly (Miller, Morton et al. 2015). Lysyl oxidase activity participates in primary tumor growth in a transgenic mouse model of aggressive pancreatic ductal adenocarcinoma (PDAC) by directly impacting the senescence stability (Wiel, Augert et al. 2013).

Expression of LOX is elevated in more than 70% of breast cancer patients with Estrogen Receptor negative disease, in 80% of head and neck cancer patients, in 33% of primary colorectal carcinomas (CRC) and 48% of metastatic tissues from patients with CRC (Baker, Cox et al. 2011), and in cirrhotic HCC patients with a history of alcoholism (Huang, Ho et al. 2013). LOX is also overexpressed in lung adenocarcinoma (Wilgus, Borczuk et al. 2011), LKB1-mutant lung cancer (Gao, Xiao et al. 2010), aggressive prostate adenocarcinoma (Stewart, Gray et al. 2008), uveal melanoma (Abourbih, Di Cesare et al. 2010), oral and oropharyngeal squamous carcinoma (Albinger-Hegyi, Stoeckli et al. 2010), thyroid cancer (Boufraqech, Nilubol et al. 2015), clear cell renal cell carcinoma (Vitalba et al, 2016), myeloproliferative neoplasms, especially myelofibrosis (Papadantonakis, Matsuura et al. 2012, Tadmor, Bejar et al. 2013) and pancreatic cancer (Sansom 2012, Miller, Morton et al. 2015).

Lysyl-Oxidase-Like Isoforms and Cancer

LOXL2 is another member of the LOX family that is involved in the cross-linking of extracellular collagens and elastin (Vadasz, Kessler et al. 2005) (Kim, Kim et al. 2010). In addition to conserved C-terminal region, the LOXL2 protein has scavenger receptor cysteine-rich regions that are commonly found in cell surface receptors and adhesion molecules, as well as a cytokine receptor-like domain.

LOXL2 expression has been found upregulated in breast, gastric, colon, esophageal, head and neck, lung and laryngeal carcinomas, as reviewed in Barker et al (Barker, Cox et al. 2012) and in renal cells carcinoma (Hase, Jingushi et al. 2014) (Nishikawa, Chiyomaru et al. 2015). High LOXL2 expression has been associated with poor prognosis in patients with squamous cell carcinoma, laryngeal, oesophagus and breast cancer, increased metastases in colon and breast cancer, as well as drug resistance in pancreatic cancer cells—reviewed in Barker et al (Barker, Cox et al. 2012). Additionally, it has been shown that LOXL2 up-regulation increases the invasiveness of otherwise non-invasive breast cancer cells (Akiri, Sabo et al. 2003). Furthermore, LOXL2 and LOXL4 are required for metastatic niche formation in a breast orthotopic mouse model (Wong et al, 2011). LOXL2 expression is associated with lymph node metastasis, histological grades and poor prognosis in cholangiocarcinoma, and knockdown of LOXL2 reduces invasion and metastasis (Xu, Li et al. 2014). HCC metastasis relies on LOXL2, which is overexpressed in tumor tissues and sera of HCC patients (Wong, Tse et al. 2014).

LOXL2 transcription is regulated by HIF-1 and upregulation of LOXL2 in hypoxia has been shown to downregulate E-cadherin leading to epithelial to mesenchymal transition (EMT) (Schietke, Warnecke et al. 2010) which is a key step in tumour progression, invasion and metastasis. This is in agreement with other reports where LOXL2 was shown to be involved in both EMT and tumour progression in murine squamous and spindle cell carcinomas (Fong, Dietzsch et al. 2007) (Moreno-Bueno, Salvador et al. 2011). LOXL2 expression is positively associated in CRC (Offenberg, Brunner et al. 2008). LOXL2 has also been linked to Src kinase/focal adhesion kinase (Src/FAK) pathway activation, and this appears to be the major pathway where secreted LOXL2 induces gastric tumour cell invasion and metastasis (Peng, Ran et al. 2009).

In certain cancers such as basal-like breast carcinoma and larynx squamous cell carcinoma perinuclear expression of LOXL2 is a marker of tumour aggressiveness and poor prognostic (Moreno-Bueno, Salvador et al. 2011) (Peinado, Moreno-Bueno et al. 2008).

Barry-Hamilton et al. reported that LOXL2 antibody treatment significantly reduces bone metastases from intracardiac injection of breast carcinoma cells (Barry-Hamilton, Spangler et al. 2010). In addition, Barker et al have provided preclinical evidence that LOXL2 inhibition is highly effective against spontaneous lung, liver and bone metastases of mammary carcinoma cells (Barker, Chang et al. 2011). Therefore, LOXL2 also represents a promising therapeutic target for the treatment of primary and metastatic cancer.

As mentioned in the Background to the Invention it is thought that although LOX and LOXL2 are involved in similar extra-cellular processes, it appears that they have distinct roles.

Other members of the LOX family, LOXL1, LOXL3 and LOXL3 are also implicated in proliferative conditions including cancer (see Background to the Invention).

Accordingly in one embodiment there is provided a compound of the invention, or pharmaceutically acceptable salt thereof for use in the treatment of a cancer. In one embodiment the cancer is non-metastatic. Accordingly the compound of the invention, or a pharmaceutically acceptable salt thereof may be for use in the treatment of a primary tumour in a subject.

The Role of LOX in Cancer Metastasis

Elevated LOX expression is associated with metastasis and decreased patient survival (Baker, Cox et al. 2011, Wilgus, Borczuk et al. 2011) Increased LOX expression is associated with disease grade, increased distant metastasis and lower overall survival in breast cancer patients with oestrogen receptor (ER)-negative tumours (Erler, Bennewith et al. 2006), in head and neck cancer patients (Albinger-Hegyi, Stoeckli et al. 2010, Toustrup, Sorensen et al. 2011), gastric cancer (Kasashima, Yashiro et al. 2015), hepatocellular carcinoma (Zhu, Huang et al. 2015), non-small cells lung cancer (Liu, Ping et al. 2014) and astrocytomas (da Silva, Uno et al. 2015), laryngeal cancer (Se, 2017). LOX expression is a determinant of poor survival in pancreatic cancer (Miller, Morton et al. 2015). Inhibition of LOX eliminates metastasis in mice with orthotopically grown human breast cancer (Erler, Bennewith et al. 2006) and inhibits tumour angiogenesis in a human colorectal cancer model (Baker, Bird et al. 2013).

A polyclonal antibody that was raised against LOX and shown to inhibit its enzymatic activity, was able to block the metastatic spread of tumour cells to the lungs and livers of recipient mice in an orthotopic model of metastatic human breast cancer (Erler et al, 2006). Suppression of LOX expression using shRNA blocks metastatic spread of the breast cancer cells and that BAPN, the non-selective small molecule inhibitor of LOX can block metastatic tumour growth of these cells in mice (Erler et al, 2006). Furthermore, inhibition of tumour-secreted LOX by genetic (shRNA), antibody (Ab) or the irreversible non-selective small molecule inhibitor BAPN, significantly reduced invasion and metastasis of orthotopic human breast tumours or circulating human breast cancer cells (Bondareva, Downey et al. 2009, Erler, Bennewith et al. 2009, Levental, Yu et al. 2009), CRC (Baker, Cox et al. 2011), HCC (Huang, Ho et al. 2013), LKB1-mutant lung adenocarcinoma (Gao, Xiao et al. 2010), anaplastic thyroid cancer (Boufraqech, Nilubol et al. 2015) and PDAC in mice (Sansom 2012; Miller, Morton et al. 2015). High expression of LOX in primary breast tumours leads to osteolytic lesion formation; silencing or inhibition of LOX activity abrogates tumour-driven bone metastases (Cox, Rumney et al. 2015). LOX inhibition with BAPN and new inhibitor CCT365623 significantly reduce metastatic lung tumour burden in a mouse model of spontaneous breast cancer that metastasizes to the lungs (Tang et al, 2017).

LOX family members (especially LOX and LOXL2) play a critical role in the metastatic spread of cancer cells (Erler, Bennewith et al. 2006, Bondareva, Downey et al. 2009, Erler, Bennewith et al. 2009, Levental, Yu et al. 2009, Gao, Xiao et al. 2010). In response to hypoxia (a condition that occurs due to inadequate blood supply when solid tumours exceed about 1 $cm^3$ in size), cancer cells produce and secrete LOX into the circulation (Erler, Bennewith et al. 2009).

LOX regulates invasion of cancer cells in vitro. Thus, cancer cells expressing high levels of LOX show increased ability to invade 3D collagen I and Matrigel matrices (Kirschmann, Seftor et al. 2002) (Erler, Bennewith et al. 2006). Furthermore, experimental over-expression of LOX enhances invasion of cancer cells, whereas genetic knockdown of LOX using RNA interference (RNAi; with both short hairpin RNA [shRNA] or small interfering RNA [siRNA]) or antisense technology) inhibits the in vitro invasion activity of cancer cells (Kirschmann, Seftor et al. 2002) (Erler, Bennewith et al. 2006). Similarly, a non-selective small molecule inhibitor of LOX, beta-aminopropionitrile (BAPN) also blocks the in vitro invasion activity of several human cancer cell lines (Kirschmann, Seftor et al. 2002) (Erler, Bennewith et al. 2006). LOX enhances hypoxia-induced invasion and migration in cervical cancer cells mediated by the EMT which can be inhibited by BAPN (Yang, Li et al. 2013). These studies implicate LOX in the invasive behaviour of cancer cells.

One of the critical functions of LOX appears to be to act remotely to pre-condition the niche at future sites of metastasis. Tumour cell metastasis is facilitated by these "premetastatic niches" formed in destination organs using invading bone marrow-derived dendritic cells (BMDCs). This "nest-building" activity is initiated when LOX becomes deposited at discreet sites in the target organ (Erler, Bennewith et al. 2009). Studies have shown that bone marrow derived cell recruitment is an essential step in niche conditioning and metastatic spread of cancer (Kaplan et al, 2005). This mechanism underlines the importance of LOX for the invasive activity of cancer cells and for the earliest stages of metastasis, when the cancer cells first migrate out of the primary tumour. It has been shown that BMDCs and LOX co-localise in human metastatic tissue, and inhibition of LOX can prevent BMDC recruitment and metastasis in models of breast cancer metastasis (Erler, Bennewith et al. 2009).

In addition to its roles in the early phases of metastasis, there is evidence that LOX is necessary to maintain the growth of the cancer cells once they arrive at the new metastatic sites because inhibition of LOX causes regression of these lesions, even after the development of metastatic disease (Erler, Bennewith et al. 2006) (Erler, Bennewith et al. 2009) (Bondareva, Downey et al. 2009). It was shown that although depletion of LOX does not affect tumour cell proliferation on plastic, it suppresses their growth in recombinant basement membrane (Matrigel) matrices (Erler, Bennewith et al. 2006). Furthermore, cancer cells do not colonise the lungs efficiently when LOX is inhibited by shRNA (Erler et al, 2006) and it was found that metastatic lung tumours regress when mice are treated with LOX neutralising antibodies (Erler, Bennewith et al. 2006). Notably, the colonisation of the lung by human breast cancer cells was enhanced when the cells were co-injected with conditioned medium from cells expressing LOX, but this was blocked if the mice were treated with conditioned medium in the presence of BAPN or a LOX antibody (Erler, Bennewith et al. 2009). These findings demonstrate a requirement for tumour-secreted LOX to maintain metastatic growth.

LOX is essential for phosphorylation of the focal adhesion kinase (FAK) downstream of integrin signalling (Erler, Bennewith et al. 2006). FAK is a tyrosine kinase that interacts with several signalling molecules and is critical for cell survival (van Nimwegen and van de Water 2007). LOX-mediated collagen cross-linking results in increased tissue stiffness and activation of the FAK/SRC signalling in in vitro and in vivo models of CRC. Cells expressing high levels of enzymatically active LOX have an increased capacity to proliferate, invade and metastasize. Thus LOX have both cell-dependent and cell-autonomous roles in metastatic tumour growth at several levels: enhances the ability of cancer cells to invade locally, possibly by enhancing migration away from the primary site; conditions the future metastatic sites in preparation for the arrival of the BMDCs and then tumour cells; supports the survival/proliferation of the cancer cells once they colonise the niche.

Host response to tumour surgery can promote further lung metastases in a mechanism mediated by LOX. Blocking LOX activity reduces the risk of lung metastases following surgery (Chen, 2017).

Accordingly, the compound of the invention, or a pharmaceutically acceptable salt thereof may be for use in the treatment of metastatic cancer in a subject.

In another embodiment of the invention there is provided a compound of the invention, or a pharmaceutically acceptable salt thereof may be for use as an inhibitor of the motility of tumour cells. In another embodiment the compound of the invention, or a pharmaceutically acceptable salt thereof may be for use as an inhibitor of the dissemination and invasiveness of mammalian cancer cells leading to inhibition of metastatic tumour growth. In particular a compound of the invention, or a pharmaceutically acceptable salt thereof may be for use as an anti-invasive agent for use in the containment and/or treatment of solid tumour disease. In another embodiment a compound of the invention, or a pharmaceutically acceptable salt thereof may be for use in the prevention or inhibition of cancer metastasis.

LOX Family, Fibroblasts and Stroma

Cancer associated fibroblasts are recruited by cancer cells recruit fibroblasts through various growth factors and cytokines and form a myofibroblastic microenvironment that promotes cancer growth, survival, local invasion and metastasis (Karagiannis, Poutahidis et al. 2012). Persistent presence of myofibroblasts in cancer contributes to desmoplasia, a cancer-specific type of fibrosis. Desmoplasia and increased fibrosis have been associated with progression of several cancers such as breast, pancreatic, colorectal, gastric and hepatocellular (Barker, Cox et al. 2012). Desmoplasia is also an intrinsic mechanism of resistance to immunotherapy in stromally-rich tumours (Zhao and Subramanian, 2017). LOX and LOX family members have an essential role in extracellular matrix remodelling and desmoplasia (Levental, 2009; Xiao, 2012). Lysyl oxidase family members expression, either secreted by cancer cells or by activated fibroblasts, has been found associated with tumour ECM, tumour stroma or tumour-associated vasculature of several cancers, such as colorectal, pancreatic, breast, laryngeal, endometrial, testicular, hepatocellular, renal (reviewed in Barker et al (Barker, Cox et al. 2012)), gastric cancer (Kasashima, Yashiro et al. 2014), and to be involved in their progression and metastasis (Akiri, Sabo et al. 2003, Barry-Hamilton, Spangler et al. 2010, Barker, Bird et al. 2013) (Pickup, Laklai et al. 2013). Expression of LOXL4 is enhanced in keratocystic odontogenic tumors (KCOT) stromal tissues and primary KCOT stromal fibroblasts (Jiang, Sima et al. 2014)

In one embodiment there is provided a compound of the invention, or a pharmaceutically acceptable salt thereof for use in the treatment of desmoplasia.

As discussed herein, the compound of the invention, or a pharmaceutically acceptable salt thereof may be for use in the treatment of a cancer, which may be non-metastatic or metastatic and which may be a solid tumour or a haematological ("liquid") cancer selected from, for example:

(1) Carcinoma, including for example tumours derived from stratified squamous epithelia (squamous cell carcinomas) and tumours arising within organs or glands (adenocarcinomas). Examples include breast, colon, lung, prostate, ovary. esophageal carcinoma (including, but not limited to, esophageal adenocarcinoma and squamous cell carcinoma), basal-like breast carcinoma, basal cell carcinoma (a form of skin cancer), squamous cell carcinoma (various tissues), head and neck carcinoma (including, but not limited to, squamous cell carcinomas), stomach carcinoma (including, but not limited to, stomach adenocarcinoma, gastrointestinal stromal tumor), signet ring cell carcinoma, bladder carcinoma (including transitional cell carcinoma (a malignant neoplasm of the bladder)), bronchogenic carcinoma, colorectal carcinoma (including, but not limited to, colon carcinoma and rectal carcinoma), anal carcinoma, gastric carcinoma, lung carcinoma (including but not limited to small cell carcinoma (SCLC) and non-small cell carcinoma of the lung (NSCLC), lung adenocarcinoma, squamous cell carcinoma, large cell carcinoma, bronchioloalveolar carcinoma, and mesothelioma), neuroendocrine tumors (including but not limited to carcinoids of the gastrointestinal tract, breast, and other organs), adrenocortical carcinoma, thyroid carcinoma, pancreatic carcinoma (including, but not limited to, pancreatic ductal adenocarcinoma, pancreatic adenocarcinoma, acinar cell carcinoma, intraductal papillary mucinous neoplasm with invasive carcinoma, mucinous cystic neoplasm with invasive carcinoma, islet cell carcinoma and neuroendocrine tumors), breast carcinoma (including, but not limited to, ductal carcinoma, lobular carcinoma, inflammatory breast cancer, clear cell carcinoma, mucinous carcinoma), ovarian carcinoma (including, but not limited to, ovarian epithelial carcinoma or surface epithelial-stromal tumor including serous tumor, endometrioid tumor and mucinous cystadenocarcinoma, sex-cord-stromal tumor), liver and bile duct carcinoma (including, but not limited to, hepatocellular carcinoma, cholangiocarcinoma and hemangioma), prostate carcinoma, adenocarcinoma, brain tumours (including, but not limited to glioma, glioblastoma and medulloblastoma), germ cell tumors, sweat gland carcinoma, sebaceous gland carcinoma, papillary carcinoma, papillary adenocarcinoma, cystadenocarcinoma, kidney carcinoma (including, but not limited to, renal cell carcinoma, clear cell carcinoma and Wilm's tumor), medullary carcinoma, ductal carcinoma in situ or bile duct carcinoma, choriocarcinoma, seminoma, embryonal carcinoma, cervical carcinoma, uterine carcinoma (including, but not limited to, endometrial adenocarcinoma, uterine papillary serous carcinoma, uterine clear-cell carcinoma, uterine sarcomas and leiomyosarcomas, mixed mullerian tumors), testicular carcinoma, osteogenic carcinoma, epithelial carcinoma, sarcomatoid carcinoma, nasopharyngeal carcinoma, laryngeal carcinoma; oral and oropharyngeal squamous carcinoma;

(2) Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and hemangioendothelioma (blood vessels); liposarcoma (adipose tissue); glioma and astrocytoma (neurogenic connective tissue found in the brain); myxosarcoma (primitive embryonic connective tissue); chordoma, endotheliosarcoma, lymphangiosarcoma, lymphangioendotheliosarcoma, synovioma, Ewing's sarcoma, mesenchymous and mixed mesodermal tumor (mixed connective tissue types) and other soft tissue sarcomas;

(3) Myeloma and multiple myeloma;

(4) Hematopoietic tumours, including: myelogenous and granulocytic leukemia (malignancy of the myeloid and granulocytic white blood cell series); lymphatic, lymphocytic, and lymphoblastic leukemia (malignancy of the lymphoid and lymphocytic blood cell series); polycythemia vera and erythremia (malignancy of various blood cell products, but with red cells predominating); myelofibrosis.

(5) Lymphomas, including: Hodgkin and Non-Hodgkin lymphomas;

(6) Solid tumors of the nervous system including medulloblastoma, craniopharyngioma, ependymoma, pinealoma, hemangioblastoma, acoustic neuroma, oligodendroglioma, meningioma, neuroblastoma and schwannoma;

(7) Melanoma, uveal melanoma and retinoblastoma; and (8) Mixed Types, including, e.g., adenosquamous carcinoma, mixed mesodermal tumor, carcinosarcoma or teratocarcinoma.

In a particular embodiment a compound of the invention, or a pharmaceutically acceptable salt thereof may be for use in the treatment of a cancer selected from pancreatic, colorectal, breast and lung cancer.

A compound of the invention, or a pharmaceutically acceptable salt thereof the invention may be for use in the treatment of a benign proliferative disease. The benign disease may be a benign tumour, for example hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, moles, uterine fibroids, thyroid adenomas, adrenocortical adenomas or pituitary adenomas. The benign condition may be endometriosis or a keratocystic odontogenic tumor.

Fibrotic Diseases

As discussed in the Background to the invention, LOX and LOXL are implicated in fibrotic diseases. Accordingly a compound of the invention or a pharmaceutically acceptable salt thereof may be for use in the treatment of a fibrotic disorder. The fibrotic disorder may be a disorder characterised by excess fibrosis, e.g., an excess of fibrous connective tissue in a tissue or organ, e.g., triggered by a reparative or reactive process, e.g., in response to injury (e.g., scarring, healing) or excess fibrotic tissue arising from a single cell line (e.g., fibroma).

LOX has been implicated in the pathogenesis of renal fibrosis and its inhibition with the alleviation of the symptoms (Di Donato, Ghiggeri et al. 1997, Haase 2009, Chen, Lin et al. 2015). Hyperuricemia results in hypertension, intrarenal vascular disease, and renal injury and is associated with increased expression of lysyl oxidase (LOX) and fibronectin in kidneys (Yang, Wang et al. 2010). Increased LOX activity has been linked to delayed graft failure after renal transplant, potentially due to increased local fibrosis (Zhi, 2017)

Similar involvement of LOX or LOXL2 in the pathology of disease and reduction in symptoms has been demonstrated for lung fibrosis (Barry-Hamilton, Spangler et al. 2010) (Haase 2009, Cox, Bird et al. 2013, Chien, Richards et al. 2014).

LOX and LOXL2 are involved in liver fibrosis (Kagan 1994, Marshall and Smith 2011) (Ricard-Blum, Bresson-Hadni et al. 1996) (Smith and Van Vlasselaer 2011) (Georges, Hui et al. 2007), liver cirrhosis (the last stage of liver fibrosis) (Kagan 1994) and related diseases such as Wilson's disease and primary biliary cirrhosis (Vadasz, Kessler et al. 2005). Therapeutic indications for LOX family inhibitors (such as simtuzumab, a humanized LOXL2 antibody) included a number of fibrotic conditions: myelofibrosis (Primary myelofibrosis, Post Polycythemia Vera or Post Essential Thrombocythemia Myelofibrosis), idiopathic pulmonary fibrosis (IPF), liver fibrosis due to non-alcoholic steatohepatitis (NASH), HIV and/or Hepatitis C-infection or primary sclerosing cholangitis (PSC) and compensated liver cirrhosis due to NASH. Levels of lysyl oxidase are increased in patients with scleroderma and systemic sclerosis (Chanoki, Ishii et al. 1995) (Rimar, Rosner et al. 2014).

LOX inhibitors assist in collagen remodeling and re-establishment of collagen architecture in human Dupuytren's, keloid and scar fibroblasts (Priyanka, 2016).

The fibrotic disorder may be any of those discussed in the above three paragraphs. In one embodiment the compound of the invention or a pharmaceutically acceptable salt thereof may be for use in the treatment of a fibrotic disorder selected from:
  (i) a fibrotic condition affecting the lungs, for example pulmonary fibrosis secondary to cystic fibrosis; idiopathic pulmonary fibrosis; coal worker's progressive massive fibrosis; cryptogenic fibrosing alveolitis, chronic fibrosing interstitial pneumonia, interstitial lung disease (ILD), diffuse parenchymal lung disease (DPLD), emphysema and chronic obstructive pulmonary disease (COPD), or chronic asthma; or
  (ii) a fibrotic condition affecting the liver, for example cirrhosis, and associated conditions such as chronic viral hepatitis B or C, Wilson's disease, non-alcoholic fatty liver disease (NAFLD), alcoholic steatohepatitis (ASH), non-alcoholic steatohepatitis (NASH), primary biliary cirrhosis (PBC), biliary cirrhosis or autoimmune hepatitis; or
  (iii) a fibrotic condition affecting the kidneys, for example diabetic nephropathy, vesicoureteral reflux, tubulointerstitial renal fibrosis; glomerulonephritis or glomerular nephritis, including focal segmental glomerulosclerosis and membranous glomerulonephritis or mesangiocapillary glomerular nephritis;
  (iv) a fibrotic condition affecting the heart or vascular system, for example endomyocardial fibrosis; old myocardial infarction; atrial fibrosis; congestive heart failure, cardiomyopathy, hypertensive heart disease (HHD), hypertension (for example pulmonary hypertension) and fibrosis associated with hypertension, atherosclerosis, restenosis (e.g. coronary, carotid, and cerebral lesions), and heart disease associated with cardiac ischemic events; or
  (v) a fibrotic condition affecting the mediastinum, for example mediastinal fibrosis; or
  (vi) a fibrotic condition affecting bone, for example myelofibrosis, including primary myelofibrosis, post polycythemia vera or post essential thrombocythemia myelofibrosis; or
  (vii) a fibrotic condition affecting the retroperitoneum, for example retroperitoneal fibrosis skin; or
  (viii) a fibrotic condition affecting the skin, for example nephrogenic systemic fibrosis, keloid formation and scarring, systemic sclerosis or scleroderma; or
  (ix) a fibrotic condition affecting the GI tract, for example a fibrotic intestinal disorder, inflammatory bowel disease, ulcerative colitis or Crohn's disease; or
  (x) a fibrotic condition affecting connective tissue, for example arthrofibrosis; or capsulitis; or
  (xi) a fibrotic condition affecting the eye, for example ocular fibrosis following surgery or pseudoexfoliation syndrome glaucoma.

LOX Family, Angiogenesis and Vasculature Permeability

Angiogenesis, the formation of new blood vessels, is essential for tumor growth and progression.

LOX and LOXL2 are key players in promoting angiogenesis in a number of tumour models, such as colorectal (Baker, Bird et al. 2013), ovarian, lung cancer (Zaffryar-Eilot, Marshall et al. 2013), melanoma (Osawa, Ohga et al. 2013), glioblastoma (Mammoto, Jiang et al. 2013). LOX is overexpressed in tumour endothelial cells (Osawa, Ohga et al. 2013). Increased LOX tumour expression is associated with increased VEGF expression (Mammoto, Jiang et al. 2013), (Baker, Bird et al. 2013).

Additionally, LOXL2 inhibition led to the normalisation of vasculature and increased tumour perfusion in ovarian xenograft and lung allograft mice models (Zaffryar-Eilot, Marshall et al. 2013).

Excessive angiogenesis is involved in a number of diseases in addition to cancer discussed above. LOX mediates vascular permeability by modulating the stiffness of the endothelial barrier. Abnormal vascular permeability, such as present in diseases such as pulmonary edema and acute respiratory distress syndrome (ARDS) or endotoxin-induced lung injury can be normalised by LOX inhibition (Mammoto, Mammoto et al. 2013) (Ingber and Mammoto 2014).

Accordingly, a compound of the invention or a pharmaceutically acceptable salt thereof may be for use as an anti-angiogenic agent. A compound of the invention or a pharmaceutically acceptable salt thereof may be for use in vascular normalisation.

In one embodiment a compound of the invention or a pharmaceutically acceptable salt thereof may be for use in the treatment is treatment of pulmonary embolism, emphysema, pleural effusion, pulmonary oedema, brain swelling, plural effusion, pericardial effusion and ascites.

In one embodiment a compound of the invention or a pharmaceutically acceptable salt thereof may be for use in the treatment is treatment of ischemia; ischemic stroke, ischemic heart disease, cerebral infarct, peripheral vascular disease, elephantiasis, lymphatic obstruction.

In one embodiment, the treatment is treatment of age-related macular degeneration (AMD), diabetic retinopathy and retinopathy of prematurity.

Inflammatory Disorders

Exacerbated inflammation and lung barrier dysfunction are hallmarks of acute respiratory distress syndrome (ARDS), a condition with dangerously high rates of morbidity and mortality. Increased LOX activity has been associated with bacterial lipopolysaccharide (LPS) induced inflammation. Inhibition of LPS-induced ECM crosslinking and stiffening by LOX suppression reduced EC inflammatory activation and lung dysfunction. Thus LOX inhibitors can be useful for the treatment of ARDS (Mambetsariev, Tian et al. 2014). LOX and LOXL1 reduction and collagen crosslinking reduction have been associated with decreased inflammation in an Angiotensin II induced model of hypertension (Gonzalez, Rhaleb et al. 2014).

In an embodiment there is provided a compound of the invention, or a pharmaceutically acceptable salt thereof may be useful in the treatment of an inflammatory condition. The inflammatory condition may be any of those described herein. For example the compound of the invention, or a pharmaceutically acceptable salt thereof may be for use in the treatment of acute inflammation (e.g., mediated by an acute infection).

In an embodiment the compound of the invention, or a pharmaceutically acceptable salt thereof may be for use in the treatment of chronic inflammatory disease, for example a disease selected from inflammatory bowel diseases (e.g. Crohn's disease and ulcerative colitis), psoriasis, sarcoidosis, rheumatoid arthritis, osteoarthritis, psoriatic arthritis, Reiter's syndrome, traumatic arthritis, rubella arthritis, acute synovitis, gouty arthritis and spondylitis.

In an embodiment the compound of the invention, or a pharmaceutically acceptable salt thereof may be for use in the treatment of rheumatoid arthritis; osteoarthritis; psoriatic arthritis; Reiter's syndrome; traumatic arthritis; rubella arthritis; acute synovitis; gouty arthritis; or spondylitis; diabetes or gout.

In an embodiment the compound of the invention, or a pharmaceutically acceptable salt thereof may be for use in the treatment of psoriasis; eczema; sarcoidosis, allergic rhinitis; allergic conjunctivitis; asthma, acute respiratory distress syndrome, acute lung injury (ALI), acute respiratory distress syndrome (ARDS), endotoxin-induced lung injury, pulmonary inflammation, chronic obstructive pulmonary disease and systemic cachexia.

In an embodiment the compound of the invention, or a pharmaceutically acceptable salt thereof may be for use in the treatment of rheumatoid arthritis, osteoarthritis, psoriatic arthritis, Reiter's syndrome, traumatic arthritis, rubella arthritis, acute synovitis, gouty arthritis or spondylitis, diabetes or gout.

In an embodiment the compound of the invention, or a pharmaceutically acceptable salt thereof may be for use in the treatment of endotoxemia; toxic shock syndrome, inflammatory bowel disease, atherosclerosis, irritable bowel syndrome, Crohn's disease, ulcerative colitis, a bone resorption disease, osteoporosis, diabetes, reperfusion injury, graft versus host reaction, allograft rejection, sepsis, septic shock, endotoxic shock, Gram negative sepsis, glomerulonephritis, restenosis, vasculitis, or thrombosis.

In another embodiment the compound of the invention, or a pharmaceutically acceptable salt thereof may be for use in the treatment of polymyositis, systemic lupus or interstitial nephritis.

Cardiovascular Disease

Interrupting collagen crosslinking by LOX with BAPN treatment reduces myocardial fibrosis in a mouse model, which is useful as potential therapeutic targeting of collagen regulation and thereby age-related myocardial fibrosis (Rosin, Sopel et al. 2015). Increased expression of LOX is associated with myocardial fibrosis and cardiac dysfunction (Zibadi, Vazquez et al. 2010) (Gao, Xiao et al. 2010) (Lopez, Gonzalez et al. 2010). Left atrial myocardium of patients with atrial fibrillation express higher levels of lysyl oxidase and fibronectin expression as well as collagen crosslinking. Fibronectin upregulation is mediated by LOX in cardiac fibroblasts (Adam, Theobald et al. 2011). LOX inhibitors can be useful for the prevention of fibrotic atrial remodelling. Inhibition of LOX by using a blocking antibody reduced cardiac fibrosis and infarct expansion in a mouse model (Gonzalez-Santamaria, 2016).

Lysyl oxidases play a causal role in experimental pulmonary hypertension and inhibition with BAPN reduces the symptoms (Nave, Mizikova et al. 2014). LOX facilitate the formation of crosslinked and therefore insoluble collagen and the subsequent left ventricle stiffness and systolic dysfunction in patients with hypertensive heart disease (HHD) and heart failure (HF) of hypertensive origin (Lopez, Gonzalez et al. 2013) (Lopez, Querejeta et al. 2012). A role for LOXL1 has been suggested in cardiac hypertrophy and BAPN administration inhibits angiotensin II-induced cardiac hypertrophy in vivo (Ohmura, Yasukawa et al. 2012). LOX knockdown attenuates cardiac and vascular fibrosis in high fat diet induced obesity (Martinez-Martinez, 2016).

Lysyl oxidase inhibition has been proposed as a therapeutic method for decreasing or preventing recurrent restenosis (Nuthakki, Fleser et al. 2004) (Brasselet, Durand et al. 2005). Increased LOX activity has been observed in atherosclerosis (Kagan, Raghavan et al. 1981). LOX is overexpressed in other pathologies associated with increased thrombosis, such as myeloproliferative neoplasms, chronic kidney disease and arterial stenosis and enhances platelets aggregation (Shinobu et al, 2016).

Accordingly in an embodiment compound of the invention, or a pharmaceutically acceptable salt thereof may be for use in the treatment of a cardiovascular disease, for example any one of the diseases mentioned in this section, e.g. the treatment of atherosclerosis, myocardial fibrosis, prevention of fibrotic atrial remodelling, old myocardial infarction; congestive heart failure, cardiomyopathy, hypertensive heart disease (HHD), hypertension (for example pulmonary hypertension) and fibrosis associated with hypertension, restenosis (e.g. coronary, carotid, and cerebral lesions), and heart disease associated with cardiac ischemic events.

Neurological Conditions

As discussed in the Background to the Invention, LOX is associated with neurological conditions including Alzheimer's disease and other neurological conditions. Accordingly, in one embodiment there is provided a compound of the invention, or a pharmaceutically acceptable salt thereof may be for use in the treatment of a neurological condition mediated by LOX or LOXL. The neurological condition may be Alzheimer's disease (AD) and hereditary cerebral hemorrhage with amyloidosis of the Dutch type (HCHWA-D) or non-Alzheimer's dementia.

LOX is increased at the site of brain injury (Gilad, Kagan et al. 2001) and spinal cord injury and its inhibition lead to accelerated functional recovery in a unilateral spinal cord dissection model (Gilad and Gilad 2001). Accordingly a compound of the invention, or a pharmaceutically acceptable salt thereof may be for use in the treatment nerve damage, for example the promotion of nerve regrowth and/or recovery after spinal cord injury.

Pulmonary Diseases

LOXL2 and LOXL3 are likely to have a role in Primary Alveolar Proteinosis (PAP) since both are expressed in PAP tissue, but not normal lung tissue (Neufeld and Brekhman 2009). Excessive lysyl oxidase activity was linked to the pathologic pulmonary features of bronchopulmonary dysplasia (Kumarasamy, Schmitt et al. 2009). A compound of the invention, or a pharmaceutically acceptable salt thereof may be for use in the treatment of primary alveolar proteinosis (PAP) or bronchopulmonary dysplasia.

Eye Diseases

Increased LOXL2 levels have been associated with failure following glaucoma surgery and treatment with a LOXL2 antibody reduced pathological angiogenesis, inflammation, and ocular fibrosis (Park, Kim et al. 2014) (Van Bergen, Marshall et al. 2013) (Stalmans, Van Bergen et al. 2011). Expression of lysyl oxidase-type enzymes increases following laser-induced choroidal neovascularization (CNV) in a model of age-related macular degeneration (AMD), in parallel with fibrotic damage. Inhibition of LOX or LOXL2 prevents neovascularization and fibrosis following laser-induced CNV. Therefore LOX and LOXL inhibitors can be useful in the treatment of conditions characterized by neovascularization, such as age-related macular degeneration (AMD), diabetic retinopathy and retinopathy of prematurity (Stalmans, Marshall et al. 2010). LOXL1 expression is increased in the initial stages of abnormal fibrogenesis in pseudoexfoliation syndrome/glaucoma tissues (Zenkel, Krysta et al. 2011) (Schlotzer-Schrehardt, Pasutto et al. 2008).

A compound of the invention, or a pharmaceutically acceptable salt thereof may be for use in the treatment of an ocular condition mediated by LOX or a LOXL, for example any of the ocular conditions listed in the paragraph above.

Other Diseases

LOX is the main isoenzyme expressed in human adipose tissue and that its expression is strongly upregulated in samples from obese patients. 8-aminopropionitrile reduces body weight gain and improves the metabolic profile in diet-induced obesity in rats (Miana, Galan et al. 2015) and reduces local adipose tissue inflammation (Halberg, Khan et al. 2009). In an embodiment a compound of the invention, or a pharmaceutically acceptable salt thereof may be for use in the treatment of obesity.

LOX has been suggested as a new therapeutic target in bacterial infections and subsequent fibrotic complications. LOX is upregulated in infections with *Staphylococcus aureus* and inhibition with BAPN influences resulting abscesses morphology and collagenisation (Beerlage, Greb et al. 2013). LOX is implicated also in some parasitic diseases: LOX and LOXLs are upregulated in the early stages of liver granuloma development in schistosomiasis (Decitre, Gleyzal et al. 1998), and BAPN inhibition reduces the size of the granulomas and reduces the egg load in combination with antiparasitic drug PZQ compared to PZQ alone (Giboda, Zenka et al. 1992), In one embodiment, the compound is for use in the treatment of a bacterial infection, for example infection with *Staphylococcus Aureus*. The compound of the invention may be for use in the treatment or prevention of infection associated fibrosis, for example to prevent or inhibit abscess formation associated with the infection. The formation of abscesses can provide a favourable microenvironment for the bacteria to multiply. Inhibition of abscess formation may be beneficial in that it may provide enhanced exposure of the bacteria to antibiotics at the site of infection, because the shielding effect provided by the abscess would be reduced or eliminated. Thus, combination treatments comprising a compound of the invention together with an antibiotic agent may provide an enhanced antibacterial effect. The compound of the invention may also be for use in the prevention or inhibition of tissue fibrosis following eradication of the infection and healing of the infection sites.

In one embodiment, the compound is for use in the treatment of a parasitic infection, for example schistosomiasis.

EGFR Mediated Conditions

Elevated levels of the epidermal growth factor receptor (EGFR), a growth-factor-receptor tyrosine kinase, and/or its ligands is observed in many cancer types and is involved in the promotion of tumour growth. EGFR inhibitors have been directed to a number of cancer types, including NSCLC, pancreatic cancer, squamous cells carcinoma, skin cancer, thyroid, colorectal, prostate, gastric, renal, breast, head and neck cancers, glioma, meningiomas, mesothelioma, cervical carcinomas epidermal carcinomas (reviewed in Bianco et al (Bianco, Gelardi et al. 2007)). Elevated EGFR was found to act as a strong indicator of poor prognosis in head and neck, ovarian, cervical, bladder and oesophageal cancers (Nicholson, Gee et al. 2001). EGFR inhibitors have also been proposed for the treatment of metastatic prostate cancer (Ree, Bratland et al. 2008), biliary cancer such as cholangiocarcinoma with a mutation in ERRFI1 (Borad, Carpten et al. 2014).

Blockade of the kinase activity of EGFR does not reach maximum therapeutic efficacy. LOX inhibitors reduce the level of surface EGFR suggesting the possibility that these compounds will have an effect on reducing EGFR activation (Tang et al, 2017).

EGFR inhibition has been targeted as treatment for a number of other diseases, such as prevention and treatment of obesity (Threadgill and Barrick 2007), treatment of Alzheimer's disease (Ma 2013), treatment of *Chlamydia* infection and related diseases (Tsang and Furdui 2015), treatment of viral diseases (Jung 2010), promotion of axon regeneration (He and Koprivica 2007), treatment of genetic skin disorders characterized by hyperkeratosis, keratinocyte hyperplasia, and/or ichthyosis (Alexandrescu 2009).

Given the role of LOX inhibition in modulating the surface EGFR levels and EGFR signalling, LOX inhibitors could be useful in the treatment of diseases which can be targeted by EGFR inhibition.

In an embodiment, there is provided a compound of the invention, or a pharmaceutically acceptable salt thereof, for use in the treatment of a disorder (e.g., a disease) that is ameliorated by the inhibition of EGFR. The EGFR mediated condition may be, for example, any of those listed in this section or elsewhere in the description. The compound of the invention, or a pharmaceutically acceptable salt thereof may be for use in the treatment of a cancer which over-expresses EGFR. The cancer over-expressing EGFR may be, for example NSCLC, pancreatic cancer, squamous cells carcinoma, skin cancer, thyroid, colorectal, prostate, renal, breast, head and neck cancers, glioma, mesothelioma, epidermal carcinomas ovarian, cervical, bladder and oesophageal cancers or a biliary cancer such as cholangiocarcinoma.

In an embodiment, there is provided a compound of the invention, or a pharmaceutically acceptable salt thereof, for use in the treatment of wherein the compound is for use in the treatment a fibrotic disease, such as liver fibrosis, lung fibrosis, kidney fibrosis, cardiac fibrosis, myelofibrosis or schleroderma.

In one embodiment, the compound is for use in the treatment of a viral infection, for example Rhinovirus, influenza virus, parainfluenza virus, coronavirus, adenovirus, respiratory syncytial virus, picornavirus, metapneumovirus, hantavirus, measles virus, Epstein-Barr virus, herpes simplex virus or cytomegalovirus.

In one embodiment, the compound is for use in the treatment of *Chlamydia* infection.

In one embodiment, the compound is for use in the treatment of a genetic skin disorder, for example a keratinization disorder is selected from among Darier's disease, Hailey-Hailey disease, erythrodermic autosomal recessive lamellar ichthyosis, nonerythrodermic autosomal recessive lamellar ichthyosis, autosomal dominant lamellar ichthyosis, bullous congenital ichthyosiform erythroderma, palmoplantar keratoderma, erythrokeratodermia variabilis, verrucous epidermal nevi, pityriasis rubra pilaris, Netherton syndrome, idiopathic vulgaris, ichthyosis vulgaris, monilethrix, keratosis piliaris, bullous ichthyosiform erythroderma, nonbullous congenital ichthyosis, Sjogren-Larsson syndrome, erythrokeratodermica variabilis, hyperkeratosis lenticularis perstans, eythrokeratodermia figurate variabilis, mutilating keratoderma of Vohwinkel, Harlequin ichthyosis and Tay's syndrome.

LOX and EGFR

In one aspect, the present invention relates to a lysyl oxidase inhibitor for use in the treatment or prevention of a cancer associated with overexpression of EGFR.

In another aspect, the present invention relates to the use of a lysyl oxidase inhibitor in the manufacture of a medicament for the treatment or prevention of a cancer associated with overexpression of EGFR.

Suitably, in all aspects, the cancer may be selected from the group consisting of: NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers and a biliary cancer such as cholangiocarcinoma.

Suitably, in all aspects, the lysyl oxidase inhibitor may be a compound of the present invention or a pharmaceutical composition of the present invention.

Suitably, in all aspects of the invention, the lysyl oxidase inhibitor of the invention may downregulate expression of MATN2 and/or activate SMAD2. Suitably, the lysyl oxidase inhibitor of the invention may downregulate expression of HTRA1. Optionally, in all aspects of the invention, the lysyl inhibitor of the invention may inhibit maturation of lysyl oxidase and/or inhibit the catalytic activity of lysyl oxidase. Suitably, the lysyl oxidase inhibitor of the invention may not inhibit MAO-A and/or MAO-B.

In a further aspect, the present invention relates to a method of treating or preventing cancer in a subject, said method comprising administering a therapeutically effective amount of a lysyl oxidase inhibitor of the invention to said subject, wherein said subject has a cancer associated with overexpression of EGFR.

Optionally, the method may comprise determining the level EGFR in a biological sample of said subject, and administering a lysyl oxidase inhibitor of the invention to said subject when the presence of EGFR is determined to be overexpressed in the biological sample.

Optionally, the method may further comprise the steps of determining the level of MATN2, pSMAD2 or HTRA1 or combinations thereof in a biological sample of said subject, and administering a lysyl oxidase inhibitor of the invention to said subject when:
  a) the level of MATN2 is greater than a reference sample; and/or
  b) the level of pSMAD2 is lower than a reference sample; and/or
  c) the level of HTRA1 is greater than a reference sample.

Optionally, said subject may have a cancer selected from the group consisting of: NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers and a biliary cancer such as cholangiocarcinoma.

Suitably, in all aspects of the invention, the lysyl oxidase inhibitor of the invention may downregulate expression of MATN2 or HTRA1 and/or activate SMAD2. Optionally, in all aspects of the invention, the lysyl inhibitor of the invention may inhibit maturation of lysyl oxidase and/or inhibit the catalytic activity of lysyl oxidase. Suitably, the lysyl oxidase inhibitor of the invention may not inhibit MAO-A and/or MAO-B.

Disclosed herein, is a method of increasing the sensitivity rate (efficacy rate) of a lysyl oxidase inhibitor of the invention to treat cancer in a patient population said method comprising selecting a sub population which overexpresses an EGFR and/or MATN2 and/or HTRA1 biomarker. Optionally, said subgroup may underexpress pSMAD2.

Disclosed herein is also a method of identifying a subject having increased likelihood of responsiveness or sensitivity to a lysyl oxidase inhibitor of the invention comprising:
  a) determining the level of one or more of EGFR, MATN2, and HTRA1 in a biological sample of the subject;
wherein increased levels EGFR, MATN2, HTRA1 or a combination thereof compared to a reference sample indicates an increased likelihood of responsiveness or sensitivity to a lysyl oxidase inhibitor in the subject.

Disclosed herein is also a method of identifying a subject having responsiveness or sensitivity to a lysyl oxidase inhibitor of the invention comprising:
  a) determining the level of one or more of EGFR, MATN2, and HTRA1 in a biological sample of the subject;
wherein increased levels one or more of EGFR, MATN2, and HTRA1 compared to a reference sample identifies the subject as having responsiveness or sensitivity to a lysyl oxidase inhibitor.

Optionally, in all these methods, the methods may comprise a further step of administering a therapeutically effective amount of a lysyl oxidase inhibitor of the invention when the subject is identified as having increased likelihood of responsiveness of sensitivity to a lysyl oxidase inhibitor.

In a further aspect, the present invention relates to a method of determining a treatment regimen for a subject with cancer, comprising:
  a) determining the level one or more of EGFR, MATN2, and HTRA1 in a biological sample; and
  b) administering a treatment regimen comprising a therapeutically effective amount of a lysyl oxidase inhibitor of the invention, when levels one or more of EGFR, MATN2, and HTRA1 are elevated compared to a reference sample.

Biomarkers

As disclosed herein, a clinical test is useful to predict response to LOX inhibition therapy, preferably prior to a subject commencing LOX inhibition therapy. Such a test will inform the clinician whether the patient is likely to respond to LOX inhibition therapy or not, and enable the clinician to commence alternative therapy if the patient is predicted to be unlikely to respond. This will benefit the patient by targeting their treatment with an appropriate therapy early, rather than relying on the current "trial and error" approach. Such a test will therefore enable better of targeting of LOX inhibition therapy to patients early in their disease, when maximum effect can be achieved, and may result in greater access to these drugs as they are used in a more cost-efficient manner.

This enables likely responders and non-responders to be identified, so that non-responders may be provided alternative treatment, and those who are not non-responders (and therefore may be a moderate or good responder) may be provided LOX inhibition therapy. As a result thereof, LOX inhibition therapies may therefore be used in a more targeted and cost-efficient manner.

For the purposes of the biomarker and stratification aspects disclosed herein a "LOX inhibitor" is an agent which is able to reduce the expression, reduce the catalytic activity or prevent maturation of LOX. Suitably the LOX inhibitor is a compound of the invention, or a pharmaceutically acceptable salt thereof.

Any suitable source of lysyl oxidase may be employed for the determination of LOX inhibition. The enzyme can be derived, isolated, or recombinantly produced from any source known in the art, including yeast, microbial, and mammalian, that will permit the generation of a suitable product that can generate a detectable reagent or will be biologically active in a suitable assay. In one embodiment, the lysyl oxidase is of human, bovine, or other mammalian origin. See, e.g., Williams, et al., Anal. Biochem. 113:336 (1985); Kirschmann et al., supra; Cancer Res. 62:4478-83 (2002); LOX may be obtained from Accession No. NP00238 (preprotein sequence); Accession No. NM02317 (DNA sequence). A functional fragment or a derivative of lysyl oxidase that still substantially retains its enzymatic activity catalyzing the oxidation of lysyl oxidase can also be used. The lysyl oxidase enzyme can sometimes be the pre-proprotein, proprotein, the protein, or a biologically active fragment thereof.

The enzymatic activity of lysyl oxidase can be assessed by any suitable method. Exemplary methods of assessing lysyl oxidase activity include that of Trackman et al., Anal. Biochem. 113:336-342 (1981); Kagan, et al., Methods Enzymol. 82A:637-49 (1982); Palamakumbura et al., Anal. Biochem. 300:245-51 (2002); Albini et al., Cancer Res. 47: 3239-45 (1987); Kamath et al, Cancer Res. 61:5933-40 (2001); for example.

The enzymatic activity of the lysyl oxidase may be assessed by detecting and/or quantitating "lysyl oxidase byproducts," such as $H_2O_2$ production; collagen pyridinium residues ammonium production; aldehyde product production; lysyl oxidation, or deoxypyridinoline (Dpd). One may also detect and quantitate cellular invasive capacity in vitro; cellular adhesion and growth in vitro; and metastatic growth in vivo. In vivo models include, but are not limited to suitable syngeneic models, human tumor xenograft models, orthotopic models, metastatic models, transgenic models, and gene knockout models. See, e.g., Teicher, Tumors Models in Cancer Research (Humana Press 2001).

A compound is an inhibitor of lysyl oxidase expression or biological activity when the compound reduces the expression or activity or lysyl oxidase relative to that observed in the absence of the compound. In one embodiment, a compound is an inhibitor of lysyl oxidase when the compound reduces the incidence of metastasis relative to the observed in the absence of the compound and, in further testing, inhibits metastatic tumor growth.

The tumor inhibition can be quantified using any convenient method of measurement. For example, the incidence of metastasis can be assessed by examining relative dissemination (e.g., number of organ systems involved) and relative tumor burden in these sites. Metastatic growth can be ascertained by microscopic or macroscopic analysis, as appropriate. Tumor metastasis can be reduced by about 10%, 20%, 30%, 40%, 50%, 60%, 70%, 80%, 90%, 95% or greater.

Lysyl oxidase expression may be assessed using promoter analysis. Any convenient system for promoter activity analysis can be employed. Typically, the reporter gene system allows promoter activity to be detected using the lysyl oxidase promoter attached to a reporter molecule such that promoter activity results in the expression of the reporter molecule. See, e.g., Ausubel et al., Current Protocols in Molecular Biology (John Wiley & Sons, current edition) at chapter 9.6.

Also, LOX may be inhibited by degradation of its mRNA. An approach to this form of gene regulation is described in Wilson et al. "Modulation of LDL receptor mRNA stability by phorbol esters in human liver cell culture models," Lipid Res. 38, 437-446 (1997).

The lysyl oxidase inhibitor compounds of the present invention may be used in the LOX inhibition therapy described herein.

Disclosed herein is a method for prediction of response to anti-LOX inhibition therapy, using biomarkers indicative of a favourable response.

Throughout this section, the terms patient and subject are used interchangeably herein to refer to an individual for whom it is desirable to determine likely response to LOX inhibition therapy. Such an individual may have, or be predisposed to having, or expected to develop, cancer.

A biomarker as used herein is a biologically derived indicator of a process, event, or condition. Biomarkers can be used in methods of diagnosis, e.g. clinical screening, and prognosis assessment and in monitoring the results of therapy, identifying patients most likely to respond to a particular therapeutic treatment, drug screening and development. A biomarker may be a gene, exhibiting differential expression between responders and non-responders to LOX inhibition therapy. Expression of a biomarker gene (transcription and optionally translation) may be determined by measuring an expression product of the gene, referred to herein as a target molecule. A combination of two or more biomarkers may be referred to herein as a panel or a genetic signature which correlates with likely response to LOX inhibition therapy.

Predicting response means making a determination of the likely effect of treatment in a subject. Prediction typically means an assessment made prior to commencing the relevant treatment, although it is understood that a prediction of the likely response to a particular treatment may be made whilst a subject is receiving an alternative treatment. Predicting response to therapy, within the scope of the present invention may also include making an assessment of likely continued response to LOX inhibition therapy. Therefore, prediction of response may include a determination of likely response during a course of LOX inhibition therapy.

A sample may be selected from the group comprising tissue sample, such as a biopsy sample; and a body fluid sample. A body fluid sample may be a blood sample. A blood sample may be a peripheral blood sample. It may be a whole blood sample, or cellular extract thereof. In one embodiment, preferably the sample is a tissue sample.

The level of a target molecule herein refers to a measure of the amount of a target molecule in a sample. The level may be based upon a measure of one type of target molecule indicative of expression specific for a particular biomarker (i.e. DNA, RNA or protein). The level may alternatively be based upon a measure of a combination of two or more types of target molecule indicative of expression specific for a particular biomarker (i.e. two or more of DNA, RNA and protein). The level of a target molecule may be expressed as a direct measure of the amount of target molecule (for example concentration (mg/vol sample) or RPKM).

Elevated level means an increase in level (i.e. amount) of a target molecule compared to the level of the same target molecule in a subject who does not have cancer. An elevated level includes any statistically significant increase compared to the control. The level of a target molecule indicative of expression of a biomarker in a subject which does not have cancer or a disease associated with overexpression of EGFR may be referred to as a reference value or baseline value.

The elevated level of the target molecule representative of gene expression may be assessed by comparing the amount of the target molecule present in the patient sample under investigation with a reference value indicative of the amount of the target molecule in a control sample.

References herein to the "same" level of target molecule or biomarker expression indicate that the biomarker expression of the sample is identical to the reference or baseline value. References herein to a "similar" level of target molecule or biomarker expression indicate that the biomarker expression of the sample is not identical to the reference or baseline value but the difference between them is not statistically significant i.e. the levels have comparable quantities.

Suitable control samples for determination of a reference value or baseline value may be derived from individuals without a disease associated with overexpression of EGFR and without cancer. A control sample may be age matched with the patient undergoing investigation. Reference values or baseline value may be obtained from suitable individuals and used as a general reference value for multiple analysis.

Favourable response to LOX inhibition therapy may include, without limitation, treatment or prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms. Thus, favourable response to LOX inhibition therapy includes delay or reduction of proliferation of tumour growth and/or delay of metastasis.

Target molecules as used herein may be selected from the group consisting of: a biomarker protein; and nucleic acid encoding the biomarker protein. The nucleic acid may be DNA or RNA. In an embodiment the nucleic acid is mRNA. Reference herein to a target molecule may include one type of biological molecule (i.e. DNA or RNA or protein) or a combination of two or more types of such biological molecules, all indicative of the expression of the same biomarker.

A binding partner may be selected from the group comprising: complementary nucleic acids; aptamers; receptors, antibodies or antibody fragments. By a specific binding partner is meant a binding partner capable of binding to at least one such target molecule in a manner that can be distinguished from non-specific binding to molecules that are not target molecules. A suitable distinction may, for example, be based on distinguishable differences in the magnitude of such binding.

One or more target molecules may be used, where each target molecule is indicative of the expression of a different biomarker selected from the group consisting of: EGFR, MATN2, HTRA1 and pSMAD2. Two or more or three or more, target molecules, each being indicative of the expression of a different biomarker selected from the group consisting of: EGFR, MATN2, HTRA1 and pSMAD2, may be used.

A target molecule indicative of the expression of EGFR may be used.

A target molecule indicative of the expression of MATN2 may be used.

Two or more target molecules or three or more biomarkers, each being indicative of the expression of a different biomarker, may be used. For example, wherein the biomarkers are EGFR and MATN2; MATN2 and pSMAD2 or EGFR and pSMAD2.

Thus, the disclosed method identifies an expression signature which identifies subjects who are unlikely to respond or are likely to respond to LOX inhibition therapy. The signature may be characterized by an up regulation of MATN2, an upregulation of EGFR, an upregulation of homotrimeric HTRA1, a down regulation of pSMAD2 or a combination thereof.

A method of increasing the sensitivity (efficacy) rate or identifying increased likelihood of response to LOX inhibitors in accordance with the present invention will preferably be carried out in vitro, but it will be appreciated that a method of the invention may also be carried out in vivo.

A level of a target molecule may be investigated using a binding partner for the target molecule. A binding partner may be specific for a target molecule. A binding partner specific to a target molecule will be capable of binding to at least one such target molecule in a manner that can be distinguished from non-specific binding to molecules that are not target molecules. A suitable distinction may, for example, be based on distinguishable differences in the magnitude of such binding.

Reference to a protein target may include precursors or variants produced on translation of the transcripts produced when the gene is expressed. Therefore, where a protein undergoes modification between first translation and its mature form, the precursor and/or the mature protein may be used as suitable target molecules. As above, techniques by which protein target molecules may be preserved within a patient sample, thus facilitating its detection, will be well known to those skilled in the art. A protein target may be found within a cell of a patient sample or may be secreted or released from the cell.

Where the target molecule is a protein, a binding partner may be used to determine the level of the protein in a sample obtained from the subject. A suitable binding partner may be is selected from the group consisting of: aptamers; receptors, and antibodies or antibody fragments. Suitable methods for determining the level of a protein in a sample are available in the art. For example, in certain embodiments of the methods or devices of the invention the binding partner is an antibody, or antibody fragment, and the detection of the target molecules utilises an immunological method. The immunological method may be an enzyme-linked immunosorbent assay (ELISA) including variants such as sandwich ELISAs; radioimmunoassays (RIA) or the immunological method may utilise a lateral flow device. Other suitable techniques may include multiplex assays such as Luminex or proteomic MRM or fluorescence activated cell sorting (FACS); chemiluminescence.

A binding partner may be labelled, for example using a reporter moiety such as a fluorophore, chromogenic substrate or chromogenic enzyme. Where it is desired that the invention will make use of reporter moieties, the reporter moieties may be directly attached to the binding partners, for instance utilising labelled antibodies. Alternatively, the reporter moieties may be attached to reporter molecules that interact with the binding partners, for instance utilising antibodies indirectly attached to a reporter moiety by means of biotin/avidin complex.

When the target molecule is a nucleic acid, binding partners may be complementary nucleic acids and aptamers, for example provided in a microarray or chip. Methods for determining the level of a nucleic acid target molecule in a sample are available in the art. A suitable target molecule representative of gene expression may comprise an RNA transcript translatable to yield a protein. mRNA of this sort will typically be found within a patient sample. In particular, the transcriptome of white blood cells, for example neutrophils, of a patient sample have been found to provide a biomarker signature with improved sensitivity and specificity for determining non-responders and/or good responders to anti-TNF therapy, and the use of mRNA and in particular the transcriptome may represent a preferred embodiment. Use of mRNA as the target molecule has advantages in that the assays for detecting mRNA (such as quantitative rtPCR or the like) tend to be cheaper than methods for detecting protein (such as ELISAs). mRNA assays can be more readily multiplexed, allowing for high throughput analysis; nucleic acids generally show greater stability than their protein counterparts; and processing of the sample to obtain and amplify nucleic acid is generally simpler than for protein.

Techniques by which mRNA may be collected, purified and amplified as necessary, are well known to those skilled in the art. Transcriptome analysis may be used for determining biomarker expression. Suitable techniques for determining the level of RNA in a sample, for example by transcriptome analysis, may include hybridization techniques, for example by detecting binding to a nucleic acid library, quantitative PCR, and high throughput sequencing including tag based sequencing such as SAGE (serial analysis of gene expression) and RNA-seq.

The above examples are non-limiting, and any appropriate assay by which the presence or elevated levels of a requisite target molecule may be detected may be used. It will be appreciated that suitable assays may be determined with reference to the nature of the target molecule to be detected and/or the nature of the patient sample to be used.

Multiple samples may be processed simultaneously, sequentially or separately. Multiple samples may be processed simultaneously, for example in a high throughput method.

Suitably, kits for carrying out the stratification or biomarker methods disclosed herein may be provided. Such kits may contain compounds by which the presence or elevated levels of a requisite target molecule may be detected, such as antibodies to one or more biomarkers of the present invention. Optionally, the kit may further comprise one or more of a set of instructions for use, a chart providing reference or baseline values for at least the biomarker to de detected using the kits; and reagents.

Once the amounts or concentrations of the target molecules in the patient sample have been determined, this information may be used as the basis of an assessment of the predicted response to LOX inhibition therapy, which may, in turn, be used to suggest a suitable course of treatment for the patient. The assessment may be qualitative or quantitative.

An elevated level of a biomarker may include at least 10%, 15, 20, 30, 40 50, 60, 70, 80, 90 or 100% or more increase compared to the baseline or reference value level. In one embodiment, an elevated level may be 1 fold or more difference relative to the baseline or reference value, such as a fold difference of 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 15 or 20 or any ranges there between. In one embodiment, the higher level is between a 1 and 15 fold difference relative to the baseline level, such as between a 1.5 and 12 fold difference relative to the baseline level. In a further embodiment, the higher level is between a 1 and 7 fold difference relative to the baseline level. It is appreciated that elevation levels may differ from the same biomarker depending on the target molecule being used. Where nucleic acid and protein target molecules are used for any particular biomarker, an elevated level may be expressed individually for a target molecule, or may be expressed as a sum or average of the target molecules.

The method may produce a quantitative output, based upon elevation values for a biomarker or a sum or biomarkers. Alternatively, the method may provide a qualitative output, based on likely response, for example yes/no; elevated; non-elevated; responder/non-responder; good, moderate or low based on EULAR criteria, etc. Where the levels of two or more target molecules are determined, a composite score may be determined, which may be compared to a composite score of reference values for the same target molecules.

The disclosed methods or devices may further involve investigating physiological measurements of the patient.

In accordance with the invention, there is provided a method for treating a subject having cancer, wherein it was previously determined (or previously estimated) that the cancer is associated with overexpression of EGFR compared to a reference value, the method comprising administering an therapeutically effective amount of a LOX Inhibitor of the invention to the subject.

In a further embodiment, there is provided a method for treating a subject having cancer, wherein it was previously determined (or previously estimated) that a target molecule indicative of expression of MATN2 is increased in a sample from the subject compared to a reference value, the method comprising administering an therapeutically effective amount of a LOX Inhibitor of the invention to the subject.

In a further embodiment, there is provided a method for treating a subject having cancer, wherein it was previously determined (or previously estimated) that a target molecule indicative of expression of homotrimeric HTRA1 is increased in a sample from the subject compared to a reference value, the method comprising administering a therapeutically effective amount of a LOX Inhibitor of the invention to the subject.

In a further embodiment, there is provided a method for treating a subject having cancer, wherein it was previously determined (or previously estimated) that a target molecule indicative of expression of pSMAD2 is decreased in a sample from the subject compared to a reference value, the method comprising administering a therapeutically effective amount of a LOX Inhibitor of the invention to the subject.

LOX inhibitors can disrupt EGFR membrane localisation, block EGFR signalling and, thereby, suppress tumour growth in cancers associated with overexpression of EGFR.

As such, LOX inhibitors will have particular utility in the treatment of cancers associated with overexpression of EGFR.

In one aspect, the present invention relates to a lysyl oxidase inhibitor of the invention for use in the treatment or prevention of a cancer associated with overexpression of EGFR.

In another aspect, the present invention relates to the use of a lysyl oxidase inhibitor of the invention in the manufacture of a medicament for the treatment or prevention of a cancer associated with overexpression of EGFR.

In a further aspect, the present invention relates to a method of treating or preventing cancer in a subject, said method comprising administering a therapeutically effective amount of a lysyl oxidase inhibitor of the invention to said subject, wherein said subject has a cancer or has a predisposition for a cancer associated with overexpression of EGFR.

Optionally, the method may comprise determining the level EGFR in a biological sample of said subject, and administering a lysyl oxidase inhibitor of the invention to said subject when the presence of EGFR is determined to be overexpressed in the biological sample.

By "EGFR overexpression" it is meant the presence of increased copies of the EGFR gene or increased EGFR protein (preferably at the surface) in or on a cancer cell compared to a non-cancerous cell of the same tissue type. Thus, in one embodiment overexpression may be defined as at least a two-fold amplification of the EGFR gene, as determined by fluorescent in-situ hybridization (FISH), or as a positive staining using anti-EGFR antibodies in an immunohistochemistry (IHC) assay. In addition, or in the alternative, overexpression may be measured by the fraction of cell membrane labelled with a specific antibody; thus overexpression of EGFR may be defined as at least 1% or at least 2% or at least 3% membranous staining and 1+ (or 2+ or 3+) intensity, or at least 10% membranous staining. Furthermore, cells may be classified as cells that do not express, or have undetectable levels of EGFR, cells expressing low levels of EGFR (about 1000 to about 100,00 receptors/cell), medium levels of EGFR (about 10,000 to about 100,000 receptors/cell) and cells expressing high levels of EGFR (about $1 \times 10^6$ or more receptors/cell). Therefore, the cancer susceptible to treatment using a LOX inhibitor of the present invention are cancers characterized by two-fold or greater amplification of the EGFR gene, positive (1+, 2+, or 3+) IHC assay, at least 1%, or at least 10% membranous staining, medium or high levels of EGFR and preferably cancer cells characterized by high levels of EGFR. Suitably, overexpression may be determined using anti-EGFR antibodies (preferably anti-HER1) in an immunohistochemistry (IHC) assay.

Optionally, the method may further comprise the steps of determining the level of MATN2, pSMAD2 or both MATN2 and pSMAD2 in a biological sample of said subject, and administering a lysyl oxidase inhibitor of the invention to said subject when:
a) the level of MATN2 is greater than a reference sample;
b) the level of pSMAD2 is lower than a reference sample; or
c) the level of MATN2 is greater than a reference sample and the level of pSMAD2 is lower than a reference sample.

Suitably, the cancer may be selected from the group consisting of: NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers and a biliary cancer such as cholangiocarcinoma.

Optionally, in all aspects of the invention, the lysyl oxidase inhibitor may inhibit maturation of lysyl oxidase and/or inhibit the catalytic activity of lysyl oxidase. Suitably, the lysyl oxidase inhibitor may not inhibit MAO-A and/or MAO-B. Suitably, inhibition of MAO-A and/or MAO-B may be determined using the in vitro oxidase-A/-B activity assay as described in the Examples. Suitably, the lysyl oxidase inhibitor may not inhibit DAO and/or hERG.

Disclosed herein is also a method of increasing the sensitivity rate (efficacy rate) of a lysyl oxidase inhibitor of the invention to treat cancer in a patient population said method comprising selecting a sub population which overexpresses an EGFR and, optionally overexpresses MATN2 and/or HTRA1. Optionally, said subgroup may also exhibit reduced expression of pSMAD2.

By "increased likelihood of responsiveness or sensitivity to a LOX inhibitor" it is meant a higher prediction of a favourable effects associated with LOX inhibition therapy.

In a further aspect, the present invention relates to a method of determining a treatment regimen for a subject with cancer, comprising:
a) determining the level of EGFR (and optionally MATN2 or HTRA1) in a biological sample; and
b) administering a treatment regimen comprising a therapeutically effective amount of a lysyl oxidase inhibitor of the invention, when levels of EGFR (and optionally increased MATN2 and/or HTRA1) are elevated compared to a reference sample.

MATN2

Matrilin2 (MATN2) is a secreted protein with 10 EGF-like repeats (Wagener, R. et al. The matrilins-adaptor proteins in the extracellular matrix. FEBS Lett 579, 3323-3329, doi:10.1016/j.febslet.2005.03.018 (2005)). A protein sequence of human MATN2 may be obtained from uniprot (Universal protein resource) reference O00339-1.

It was shown in WO 2017/141049 A1 that recombinant human MATN2 increase the levels of EGFR at the surface of the cell and thus MATN2 strongly enhances EGF-induced EGFR activation. Without wishing to be bound by theory, it is believed that MATN2 binding traps EGFR at the cell surface to present it to EGF for activation.

It has been surprisingly found that LOX inhibitors can downregulate expression of MATN2 which leads to increased internalisation of EGFR. Accordingly, the LOX inhibitors of the invention may have particular utility in the treatment of cancers having elevated levels of MATN2 compared to a reference sample.

Suitably, levels of MATN2 may be determined using immunofluorescence using a commercially available anti-human MATN2 antibody (e.g. from R&D). For example, the sample may be subjected to incubation with primary anti-MATN2 antibodies followed by fluorescence secondary antibodies (such as those available from Life Technologies) and then the levels determined using confocal imaging. An identical procedure is carried out on a reference sample so that it can be determined if MATN2 levels are increased.

Thus, MATN2 (optionally in combination with EGFR) may be used as a biomarker to predict responsiveness or sensitivity of a patient suffering from cancer to treatment with a lysyl oxidase inhibitor of the invention. Optionally, one or more further biomarkers may be used such as pSMAD2.

Disclosed herein is also a method of increasing the sensitivity rate (efficacy rate) of a lysyl oxidase inhibitor of the invention to treat cancer in a patient population said method comprising selecting a sub population which has enhanced expression of MATN2. Optionally, said subgroup may also exhibit reduced expression of pSMAD2.

Disclosed herein is also a method of identifying a subject having increased likelihood of responsiveness or sensitivity to a lysyl oxidase inhibitor of the invention comprising:
   a) determining the level of MATN2 in a biological sample of the subject;
wherein increased levels MATN2 compared to a reference sample indicates an increased likelihood of responsiveness or sensitivity to a lysyl oxidase inhibitor in the subject.

Disclosed herein is also a method of identifying a subject having responsiveness or sensitivity to a lysyl oxidase inhibitor of the invention comprising:
   a) determining the level of MATN2 in a biological sample of the subject;
wherein increased levels MATN2 compared to a reference sample identifies the subject as having responsiveness or sensitivity to a lysyl oxidase inhibitor of the invention.

Optionally, in all methods disclosed herein, the methods may comprise a further step of administering a therapeutically effective amount of a lysyl oxidase inhibitor when the subject is identified has have increased likelihood of responsiveness of sensitivity to a lysyl oxidase inhibitor.

Disclosed herein is also a method of determining a treatment regimen for a subject with cancer, comprising:
   a) determining the level of MATN2 in a biological sample; and
   b) administering a treatment regimen comprising a therapeutically effective amount of a lysyl oxidase inhibitor, when levels MATN2 are elevated compared to a reference sample.

SMAD2

Smad proteins are signal transducers and transcriptional modulators that mediate multiple signaling pathways. SMAD2 mediates the signal of the transforming growth factor (TGF)-beta, and thus regulates multiple cellular processes, such as cell proliferation, apoptosis, and differentiation. This protein is recruited to the TGF-beta receptors through its interaction with the Smad anchor for receptor activation (SARA) protein. In response to TGF-beta signal, this protein is phosphorylated by the TGF-beta receptors. A human protein sequence may be obtained from uniprot (Universal protein resource) reference Q15796.

It was shown in WO 2017/141049 A1 that strong activation of SMAD2 in LOX deficient cells and that TGFβ1 downregulates MATN2 mRNA. Without wishing to be bound by theory, it is believed that LOX inhibitors may activate SMAD2 which will lead to the downregulation of MATN2. Accordingly, activation of SMAD2 (which may be measured by upregulation of phospho-SMAD2 (pSMAD2)) will lead to a reduction of EGFR at the cell surface. Thus, SMAD2 may be used as a biomarker to determine response to treatment with a LOX inhibitor.

Suitably, levels of pSMAD2 may be determined using an anti-pSMAD2 antibody (such as those commercially available from Millipore).

HTRA1

HTRA1 is a secreted serine protease known to block TGFβ1 signalling by cleaving mature TGFβ1. A protein sequence for HTRA1 may be obtained from uniprot (Universal protein resource) reference Q92743 version 1.

It was shown in WO 2017/141049 A1 that LOX depletion reduces the levels of extracellular homotrimeric HTRA1, the active form of this enzyme and HTRA1 suppresses SMAD2 activation and rescues MATN2 expression in LOX depleted cells. Without wishing to be bound by theory, it is believed that reducing HTRA1 will activate SMAD2 causing a reduction in the expression of MATN2 mRNA. It was shown in WO 2017/141049 A1 that MATN2 binding traps EGFR at the cell surface to present it to EGF for activation, it is believed that elevated protein stability of HTRA1 will indicate an increased likelihood of response to treatment with a LOX inhibitor. Hence, HTRA1 may be used as a biomarker.

Accordingly, the LOX inhibitors may have particular utility in the treatment of cancers having elevated levels of HTRA1 compared to a reference sample.

Suitably, levels of HTRA1 may be determined using immunofluorescence using a commercially available anti-human HTRA1 antibody (anti-human HTRA1 antibody, R&D). For example, the sample may be subjected to incubation with primary anti-HTRA1 antibodies followed by fluorescence secondary antibodies (such as those available from Life Technologies) and then the levels determined using confocal imaging. An identical procedure is carried out on a reference sample so that it can be determined if HTRA1 levels are increased.

Disclosed herein is a method of determining a treatment regimen for a subject with cancer, comprising:
   a) determining the level of HTRA1 in a biological sample; and
   b) administering a treatment regimen comprising a therapeutically effective amount of a lysyl oxidase inhibitor, when levels HTRA1 are elevated compared to a reference sample.

In Vitro Methods

The present invention also provides in vitro methods of internalising EGFR or reducing EGFR expression in a cell, said method comprising the step of contacting the cell with a LOX inhibitor of the invention.

In another aspect, the present invention further comprises an in vitro method of downregulating MATN2 expression in a cell, comprising the step of contacting the cell with a LOX inhibitor of the invention.

In a further aspect, the present invention also provides upregulating pSMAD2 in a cell comprising contacting a cell with a LOX inhibitor of the invention.

Suitably, in all aspects, the cell may be a cell-line, preferably a mammalian cell line.

Suitably, the cell may be a cancer cell, preferably a cancer cell associated with overexpression of EGFR.

Combination Therapies e.g. for the Treatment of Cancer

LOX inhibition can be a useful method for improving the efficacy of other drugs or addressing resistance to drug treatment through a number of mechanisms. Specific inhibition of LOX with siRNA can induce apoptosis of laryngeal cancer Hep-2 cells and enhance the sensitivity of Hep-2 cells to chemotherapeutic drugs such as cisplatin (Dong, Lu et al. 2014) and to radiation (Dong, Xin et al. 2014). LOX-expression and secretion is increased in response to ionizing radiation (IR) and hypoxia, suggesting that LOX may contribute towards an IR-induced migratory phenotype in sub-lethally-irradiated tumor cells and tumor progression; therefore LOX inhibitors can be used in combination with radiotherapy to reduce side effects in surrounding tissues receiving a reduced radiation dose (Shen, Sharma et al. 2014). LOX and LOXL2 inhibition can alter vascular permeability or normalise vasculature in a tumour environment, which can enhance the delivery or effectiveness of drugs (Ingber and Mammoto 2014) (Marshall, Spangler et al. 2012), for example improved efficacy of treatment in ovarian xenograft and lung allograft mice models with chemotherapeutic agents such as taxol (Zaffryar-Eilot, Marshall et al. 2013). Pharmacological inhibition of lysyl oxidases improved drug delivery and reversed the negative effect of VEGF ablation on drug delivery and therapeutic response in anti-VEGF-resistant tumors (Roehrig et al, 2017). The extracellular matrix has been proposed to have an important role in the resistance to chemotherapeutics. It has been shown that inhibition of LOX for cells grown in collagen (as a surrogate of ECM) reverses their collagen-dependent increased resistance to chemotherapeutics such as erlotinib, cisplatin or methotrexate (Smith and Holzer 2010). Drug diffusion and efficacy is reduced by the enzymatic action of LOX and LOXLs on the ECM in a 3D cell culture (not in 2D) and sensitivity to doxorubicin and paclitaxel can be restored by inhibition with BAPN (Schuetze, Roehrig et al. 2015). LOX inhibition synergized with gemcitabine to kill tumors and significantly prolonged tumor-free survival in a pancreatic mouse model. This was associated with stromal alterations and increased infiltration of macrophages and neutrophils into tumors. Therefore, targeting LOX could improve outcome in surgically resectable disease (Miller, Morton et al. 2015).

The compounds of the invention may be used alone to provide a therapeutic effect. The compounds of the invention may also be used in combination with one or more additional anti-tumour agent and/or radiotherapy.

Such chemotherapy may include one or more of the following categories of anti-cancer agents:

antiproliferative/antineoplastic drugs and combinations thereof, such as alkylating agents (for example cisplatin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5-fluorouracil and tegafur, raltitrexed, methotrexate, pemetrexed, leucovorin, cytosine arabinoside, floxuridine, cytarabine, 6-mercaptopurine, 6-thioguanine, fludarabine phosphate, pentostatine, and gemcitabine and hydroxyurea, and trifluridine with trifluracil); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors; eribulin); proteasome inhibitors, for example carfilzomib and bortezomib; interferon therapy; and topoisomerase inhibitors (for example epipodophyllotoxins like etoposide and teniposide, amsacrine, topotecan, irinotecan, mitoxantrone and camptothecin); bleomcin, dactinomycin, daunorubicin, doxorubicin, epirubicin, idarubicin, ara-C, paclitaxel (Taxol™), nabpaclitaxel, docetaxel, mithramycin, deoxyco-formycin, mitomycin-C, L-asparaginase, interferons (especially IFN-alpha), etoposide, teniposide, DNA-demethylating agents, (for example, azacitidine or decitabine); and histone de-acetylase (HDAC) inhibitors (for example vorinostat, MS-275, panobinostat, romidepsin, valproic acid, mocetinostat (MGCD0103) and pracinostat SB939; and belinostat, panobinostat); trabectedin;

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride; and navelbene, CPT-II, anastrazole, letrazole, capecitabine, cyclophosphamide, ifosamide, and droloxafine; and abiraterone, Enzalutamide; analogues of somatostatin such as lanreotide;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-HER2 antibody pertuzumab; the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), afatinib, vandetanib, osimertinib and rociletinib) erbB2 tyrosine kinase inhibitors such as lapatinib) and antibodies to costimulatory molecules such as CTLA-4, 4-IBB and PD-I, or antibodies to cytokines (IL-10, TGF-beta); small molecule inhibitors of fibroblasts growth factor receptor family, such as ponatinib, nintedanib, levitinib, dovitinib, lucitanib, danusertinib, PD173074, PD-166866, AZD4547, BGJ398, LY2874455, TAS-120, ARQ 087, JNJ42756493, BLU9931, DEBIO 1347, FGF401, BAY-1163877, FIIN-2, H3B-6527, PRN1371, BLU554, S49076, SU5416; antibodies that block FGF ligand binding (ligand traps), such as FP-1039; antibodies that hinder FGFR dimerization such as MFGR1877S; inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, sorafenib, tipifarnib and lonafarnib, vemurafenib, dabrafenib), inhibitors of cell signalling through MEK (such as trametinib, cobimetinib) and/or AKT kinases, c-kit inhibitors, abl kinase inhibitors such as ponatinib, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors or CDK4/CDK6 inhibitors such as palbociclib, ribociclib and abemaciclib; CCR2, CCR4 or CCR$^6$ antagonists; mTOR kinase inhibitors such as Everolimus; Janus kinase family inhibitors such as ruxolitinib; Brunton's tyrosine kinase inhibitors such as Ibrutinib; anaplastic lymphoma kinase—ALK—such as ceritinib, crizotinib, alectinib; c-Met kinase inhibitors such as cabozantinib; hedgehog signalling pathway inhibitors such as vismodegib, sonidegib; and RAF kinase inhibitors such as BAL3833 or other RAF inhibitors described in WO2006043090, WO2009077766, WO2011092469 or WO2015075483;

(v) antiangiogenic agents such as those which inhibit the effects of vascular endothelial growth factor, [for example the anti-vascular endothelial cell growth factor antibody bevacizumab (Avastin™), anti-VEGF2 antibody ramucirumab; recombinant fusion protein ziv-aflibercept]; thalidomide; pomalidomide; lenalidomide; and for example, a VEGF receptor tyrosine kinase inhibitor such as regorafenib, vandetanib, vatalanib, sunitinib, axitinib and pazopanib and lenvatinib;

(vi) gene therapy approaches, including for example approaches to replace aberrant genes such as aberrant p53 or aberrant BRCA1 or BRCA2; oncolytic viruses such as talimogene laherparepvec;

(vii) immunotherapy approaches, including for example antibody therapy such as denosumab, obinutuzumab, blinatomumab, dinutuximab, idarucizumab, daratumumab, durvalumab, necitumumab, elotuzumab, olaratumab, alemtuzumab, rituximab, ibritumomab tiuxetan (Zevalin®) and ofatumumab; interferons such as interferon α, peginterferon alpha-2b; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); toll-like receptor modulators for example TLR-7 or TLR-9 agonists; PD-1, PD-L1, PD-L2 and CTL4-A modulators (for example Nivolumab, pembrolizumab, atezolizumab), antibodies and vaccines; other IDO inhibitors (such as indoximod); anti-PD-1 monoclonal antibodies (such as MK-3475 and nivolumab); anti-PDL1 monoclonal antibodies (such as MEDI-4736 and RG-7446); anti-PDL2 monoclonal antibodies; and anti-CTLA-4 antibodies (such as ipilumumab); antibody-drug conjugates such as Brentuximab vedotin, trastuzumab emtansine.

(viii) cytotoxic agents for example fludaribine (fludara), cladribine, pentostatin (Nipent™);

(ix) targeted therapies, for example PI3K inhibitors, for example idelalisib and perifosine; SMAC (second mitochondria derived activator of caspases) mimetics, also known as Inhibitor of Apoptosis Proteins (IAP) antagonists (IAP antagonists). These agents act to suppress IAPs, for example XIAP, cIAP1 and cIAP2, and thereby re-establish cellular apoptotic pathways. Particular SMAC mimetics include Birinapant (TL32711, TetraLogic Pharmaceuticals), LCL161 (Novartis), AEG40730 (Aegera Therapeutics), SM-164 (University of Michigan), LBW242 (Novartis), ML101 (Sanford-Burnham Medical Research Institute), AT-406 (Ascenta Therapeutics/University of Michigan), GDC-0917 (Genentech), AEG35156 (Aegera Therapeutic), and HGS1029 (Human Genome Sciences); and agents which target ubiquitin proteasome system (UPS), for example, bortezomib, ixazomib, carfilzomib, marizomib (NPI-0052), and MLN9708; and DNA repair inhibitors such as Olaparib, rucaparib; antiapoptotic BCL proteins family inhibitors such as venetoclax.

(xii) chimeric antigen receptors, anticancer vaccines and arginase inhibitors.

The additional anti-tumour agent may be a single agent or one or more of the additional agents listed herein.

Particular anti-cancer agents which may be used together with a compound of the invention include for example:

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

In some embodiments in which a combination treatment is used, the amount of the compound of the invention and the amount of the other pharmaceutically active agent(s) are, when combined, therapeutically effective to treat a targeted disorder in the patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the compound of the invention and an approved or otherwise published dosage range(s) of the other pharmaceutically active compound(s).

According to a further aspect of the invention, there is provided a compound of the invention as defined hereinbefore and an additional anti-cancer agent as defined hereinbefore, for use in the conjoint treatment of cancer.

According to a further aspect of the invention, there is provided a pharmaceutical product comprising a compound of the invention as defined hereinbefore and an additional anti-cancer agent as defined hereinbefore for the conjoint treatment of cancer.

According to a further aspect of the invention, there is provided a method of treatment of a human or animal subject suffering from a cancer comprising administering to the subject a therapeutically effective amount of a compound of the invention, or a pharmaceutically acceptable salt thereof simultaneously, sequentially or separately with an additional anti-cancer agent as defined hereinbefore.

According to a further aspect of the invention, there is provided a compound of the invention, or a pharmaceutically acceptable salt thereof for use simultaneously, sequentially or separately with an additional anti-cancer agent as defined hereinbefore, in the treatment of a cancer.

The compound of the invention may also be used be used in combination with radiotherapy. Suitable radiotherapy treatments include, for example X-ray therapy, proton beam therapy or electron beam therapies. Radiotherapy may also encompass the use of radionuclide agents, for example $^{131}$I, $^{32}$P, $^{90}$Y, $^{89}$Sr, $^{153}$Sm or $^{223}$Ra. Such radionuclide therapies are well known and commercially available.

According to a further aspect of the invention, there is provided a compound of the invention, or a pharmaceutically acceptable salt thereof as defined hereinbefore for use in the treatment of cancer conjointly with radiotherapy.

According to a further aspect of the invention, there is provided a method of treatment of a human or animal subject suffering from a cancer comprising administering to the subject a therapeutically effective amount of a compound of the invention, or a pharmaceutically acceptable salt thereof simultaneously, sequentially or separately with radiotherapy.

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl or trifluoroacetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively, an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3 \cdot OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

Abbreviations

The following abbreviations are used:
DCM: dichloromethane
DMF: N,N-Dimethyl formamide
DMSO: dimethyl sulfoxide
DIPEA: N,N-Diisopropylethylamine
DCl: Deuterium chloride
HPLC: high performance liquid chromatography
min: minute(s)
h: hour(s)
rt: Room temperature
RPM: rounds per minute
TFA: trifluoroacetic acid
THF: tetrahydrofuran
TFE: 2,2,2-trifluoroethanol
Boc: tert-butyloxycarbonyl
Me: methyl
Et: ethyl
Bu: butyl
$^t$Bu: tert-butyl
Ac: acetyl
Bn: benzyl
NaO$^t$Bu: sodium-tert-butoxide
Et$_3$N: Triethylamine
EtOAc: ethyl acetate
AcOH: acetic acid
XPhos: 2-Dicyclohexylphosphino-2',4',6'-triisopropylbiphenyl
Pd(OAc)$_2$: palladium(II) acetate
MeOH: methanol
BuOH: butanol
Et$_2$O: diethyl ether
EtNCO: ethyl isocyanate
CDCl$_3$: deuterated chloroform
(CD$_3$)$_2$SO: deuterated dimethyl sulfoxide (DMSO)
NMR: nuclear magnetic resonance
HRMS: high resolution mass spectroscopy General Procedures GP1

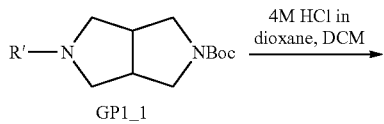

GP1_1

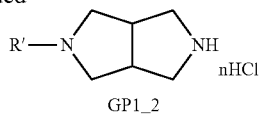

4 M HCl in dioxane was added to carbamate GP1_1 (neat or in DCM), and the mixture was stirred at rt for 1-4 h. The solvent was removed under reduced pressure (alternatively, the mixture can be centrifuged at 3000 RPM for 5 minutes, and the solvent subsequently removed by decantation) to afford the amine hydrochloride GP1_2, which can be further purified in its free base form if necessary.

General Procedures GP2

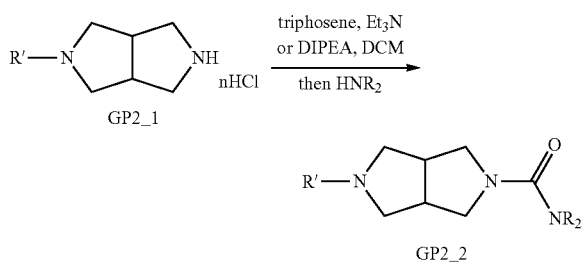

Triphosgene was added to a mixture of Et₃N or DIPEA and amine or amine hydrochloride GP2_1 in DCM at 0° C. and the reaction mixture was stirred for 0.5-1 h. HNR₂ was then added and the mixture was stirred for a further 1-16 h. The mixture was diluted with DCM and the organic phase was washed with H₂O, dried over MgSO₄, filtered and the solvent was removed under reduced pressure. The crude could be further purified by chromatography to afford urea GP2_2 if necessary.

General Procedures GP3

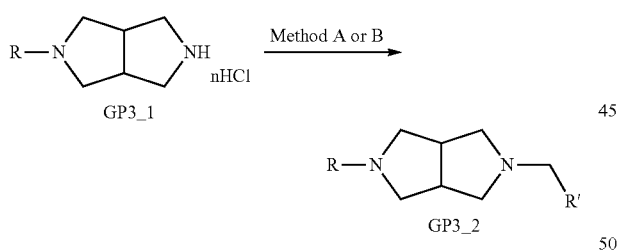

Method A—Alkyl bromide BrCH₂R' (eg. 4-bromobutanenitrile) was added to a mixture of amine or amine hydrochloride GP3_1 and Et₃N or K₂CO₃ in DMF and the reaction mixture was stirred for 1-16 h. After diluting with EtOAc, the organic phase was washed with H₂O (3×) and brine, dried over MgSO₄, filtered and the solvent was removed under reduced pressure to afford nitrile GP3_2, which could be further purified by chromatography if necessary.

Method B—Alkyl bromide BrCH₂R' (eg. 4-bromobutanenitrile) was added to a mixture of amine or amine hydrochloride GP3_1 and Et₃N in MeCN and the reaction mixture was stirred at 75° C. for 1-16 h. After diluting with EtOAc, the organic phase was washed with H₂O (3×) and brine, dried over MgSO₄, filtered and the solvent was removed under reduced pressure to afford nitrile GP3_2, which could be further purified by chromatography if necessary.

General Procedures GP4

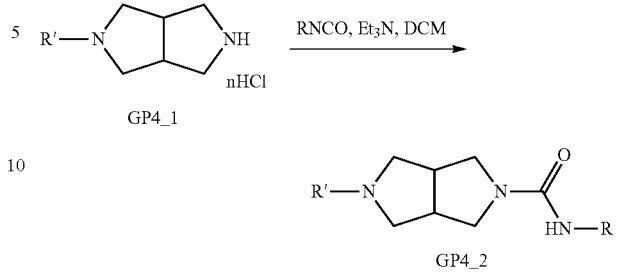

Isocyanate RNCO was added to a mixture of amine or amine hydrochloride GP4_1 and Et₃N in DCM and the reaction mixture was stirred at rt for 1 h. The solvent was removed under reduced pressure. The crude could be further purified by chromatography to afford urea GP4_2 if necessary.

General Procedures GP5

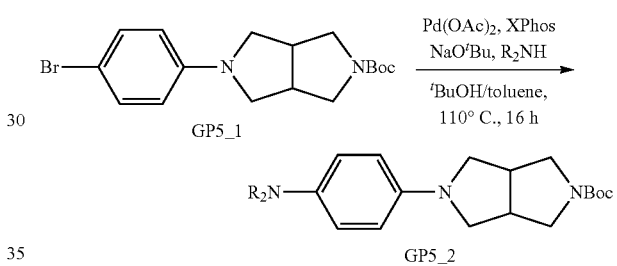

A mixture of aryl bromide GP5_1, R²NH, Pd(OAc)₂, XPhos and NaO$^t$Bu in $^t$BuOH/toluene (1:5) was degassed with Argon and stirred at 110° C. for 16 h. The mixture was cooled to rt and the solvent was removed under reduced pressure. The crude could be further purified by chromatography to afford aniline GP5_2 if necessary.

General Procedures GP6

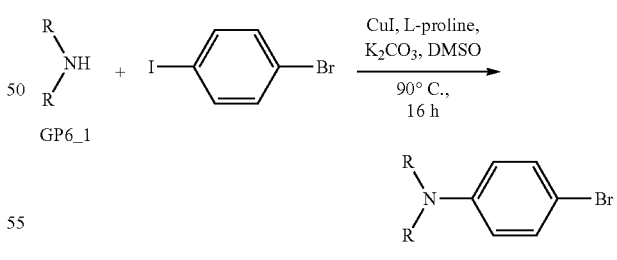

A mixture of amine GP6_1, 4-bromo-1-iodobenzene, CuI, L-proline, K₂CO₃ and DMSO was stirred at 90° C. for 16 h. After cooling to rt, the mixture was diluted with EtOAc. The organic phase was washed with H₂O (3×) and brine, dried over MgSO₄, filtered and the solvent was removed under reduced pressure. The crude could be further purified by column chromatography to afford aniline GP6_2 if necessary.

General Procedures GP7

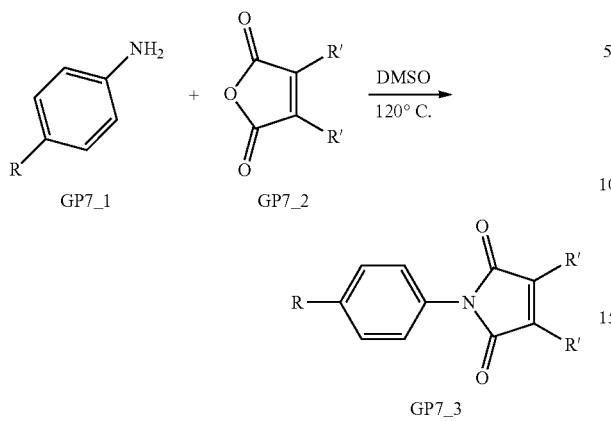

A mixture of aniline GP7_1, anhydride GP7_2 and DMSO (or AcOH) was stirred at 120° C. for ~20 h. After cooling to rt, the mixture was diluted with dichloromethane and washed with water. The organic phase was dried (MgSO$_4$), filtered and concentrated in vacuo to afford maleimide GP7_3, which can be further purified by chromatography if necessary. Alternatively, the mixture of aniline GP7_1, anhydride GP7_2 in ethanol was stirred at reflux for 4 h. After cooling to rt and concentration in vacuo, maleimide GP7_3 was obtained by recrystallisation from ethanol.

General Procedures GP8

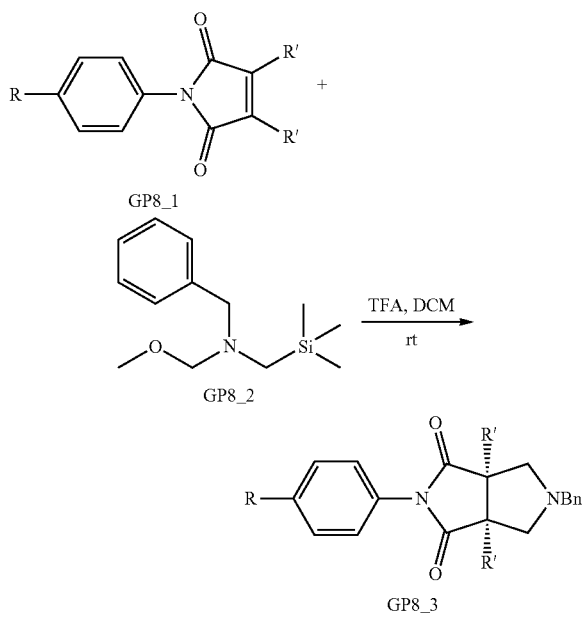

A mixture of N-(methoxymethyl)-N-(trimethylsilylmethyl)benzylamine GP8_2 maleimide GP8_1 and TFA in DCM was stirred at rt for ~20 h. The reaction mixture was diluted with DCM and washed with a saturated sodium bicarbonate solution. The organic layer was dried (MgSO$_4$), filtered and concentrated in vacuo to afford maleimide GP8_3, which can be further purified by chromatography if necessary.

General Procedures GP9

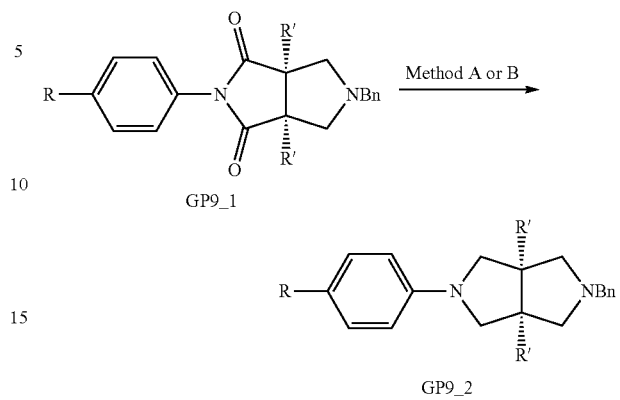

Method A—lithium aluminium hydride (1 M in Et$_2$O) was added dropwise to a solution of maleimide GP9_1 and tetrahydrofuran at 0° C. The reaction was stirred at rt for ~20 h. The reaction mixture was cooled to 0° C. and a small amount of water was carefully added, followed by a small amount of 10% aqueous sodium hydroxide and water. The resulting suspension was filtered and the filtrate was dried and concentrated in vacuo to afford aniline GP9_2, which can be further purified by chromatography if necessary.

Method B—Borane-tetrahydrofuran complex (1 M in THF) was added dropwise to a solution of maleimide GP9_1 and tetrahydrofuran at 0° C. The reaction was stirred at 60° C. for ~20 h. The reaction mixture was cooled to 0° C. and ethanol was carefully added. The mixture was stirred at 60° C. for 1 h and concentrated in vacuo to afford aniline GP9_2, which can be further purified by chromatography if necessary.

General Procedures GP10

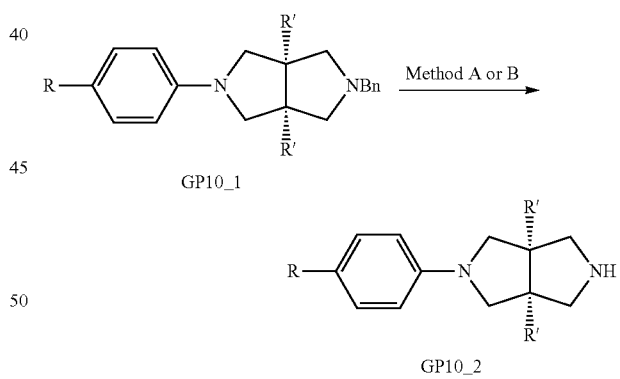

Method A—a mixture of N-benzylpyrrolidine GP10_1, palladium black (or Pd(OH)$_2$ or Pd/C) and cyclohexadiene (up to 5 equiv.) in 2,2,2-trifluoroethanol was stirred at 70-80° C. After 30 min, an additional portion of cyclohexadiene (up to 5 equiv.) was added. The reaction was stirred for a further 1-3 h. After cooling to rt, the reaction mixture was filtered through celite and concentrated in vacuo to afford amine GP10_2 which could be further purified by chromatography if necessary.

Method B—a mixture of N-benzylpyrrolidine GP10_1, palladium black (or Pd(OH)$_2$ or Pd/C) and ammonium formate (up to 10 equiv.) in methanol was stirred at 60° C. for 3-16 h. After cooling to rt, the reaction mixture was filtered through celite and concentrated in vacuo to afford amine GP10_2 which could be further purified by chromatography if necessary.
Analytical Methods Flash chromatography was performed on a Biotage Isolera or a Combiflash Rf+ flash purification system using prepacked silica gel cartridges with HPLC grade solvents.

Liquid chromatography mass spectrometry (LCMS) and high-resolution mass spectrometry (HRMS) analyses of chemical compounds were performed on an Agilent 1200 series HPLC and diode array detector coupled to a 6210 time-of-flight mass spectrometer with a multimode ESI source or a Waters Acquity UPLC and diode array detector coupled to a Waters G2 QToF, SQD or QDa mass spectrometer fitted with a multimode ESI/APCI source.

1H and 13C NMR spectra were recorded on a Bruker 500 MHz or a 300 MHz spectrometer using an internal deuterium lock.

Example 1: cis-5-(4-Ethoxyphenyl)-N-(2-hydroxyethyl)hexahydropyrrolo[3,4-c]pyrrole-2(1H)-carboxamide

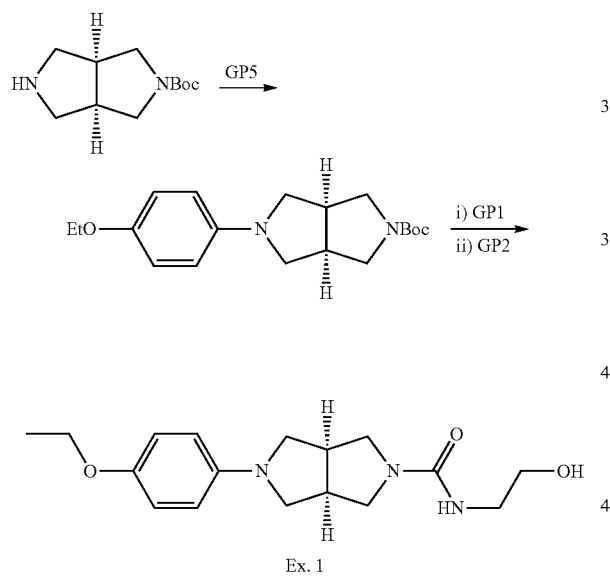

Ex. 1 tert-Butyl 5-(4-ethoxyphenyl)-hexahydropyrrolo[3,4-c]pyrrole-2(1H)-carboxylate was prepared using general procedures GP5—from tert-butyl-hexahydropyrrolo[3,4-c]pyrrole-2(1H)-carboxylate (5.0 g, 23.6 mmol), p-phenetidine (3.57 mL, 23.6 mmol), Pd(OAc)$_2$ (265 mg, 5%), XPhos (1.0 g, 10%), NaO$^t$Bu (2.72 g, 28.3 mmol) and toluene/$^t$BuOH (4:1; 118 mL); 110° C., 16 h. Chromatography (EtOAc/cyclohexane 0→30%) gave a light brown gum (7.0 g, 89%), which can be further purified by precipitation from cold toluene. $^1$H NMR (500 MHz, CDCl$_3$) δ 6.89-6.81 (m, 2H), 6.56-6.48 (m, 2H), 3.98 (q, J=7.0 Hz, 2H), 3.68-3.59 (m 2H), 3.50-3.41 (m 2H), 3.38 (d, J=10.5 Hz, 1H), 3.25 (d, J=10.5 Hz, 1H), 3.17 (dd, J=9.3, 3.6 Hz, 2H), 2.98 (s, 2H), 1.46 (s, 9H), 1.38 (t, J=7.0 Hz, 3H). $^{13}$C NMR (126 MHz, CDCl$_3$) δ 154.49, 150.52, 142.67, 115.95, 112.99, 79.36, 64.28, 53.01, 50.77 and 50.40, 42.29 and 41.37, 28.50, 15.04. HRMS calcd for C$_{19}$H$_{29}$N$_2$O$^3$ (M+H$^+$) 333.2159. found 333.2173.

The title compound was prepared using general procedures GP1 and GP2—from i) tert-butyl 5-(4-ethoxyphenyl)-hexahydropyrrolo[3,4-c]pyrrole-2(1H)-carboxylate (40 mg, 0.12 mmol) and 4.0 M HCl in 1,4-dioxane (151 μL, 0.60 mmol); rt, 1 h. ii) Triethylamine (252 μL, 1.81 mmol), triphosgene (50 mg, 0.17 mmol) and ethanolamine (165 μL, 2.74 mmol). Chromatography (MeOH/EtOAc 5→10%) gave a white solid (25 mg, 0.08 mmol, 65%). $^1$H NMR (500 MHz, CDCl$_3$) δ 6.86 (d, J=9.0 Hz, 2H), 6.52 (d, J=9.0 Hz, 2H), 4.71 (t, J=5.7 Hz, 1H), 3.98 (q, J=7.0 Hz, 2H), 3.75-3.69 (m, 2H), 3.67 (dd, J=10.1, 7.2 Hz, 2H), 3.57 (br s, 1H), 3.48 (dd, J=9.5, 7.2 Hz, 2H), 3.43-3.39 (m, 2H), 3.36 (dd, J=10.5, 3.7 Hz, 2H), 3.21 (dd, J=9.5, 3.7 Hz, 2H), 3.10-3.00 (m, 2H), 1.39 (t, J=7.0 Hz, 3H). $^{13}$C NMR (126 MHz, CDCl$_3$) δ 157.87, 150.61, 142.48, 115.93, 113.04, 64.27, 63.47, 53.01, 50.55, 43.60, 42.02, 15.04. HRMS calcd for C$_{17}$H$_{26}$N$_3$O$_3$ (M+H$^+$) 320.1969. found 320.2049.

Example 2: cis-4-(5-(4-Ethoxyphenyl)hexahydropyrrolo[3,4-c]pyrrol-2(1H)-yl)butanenitrile

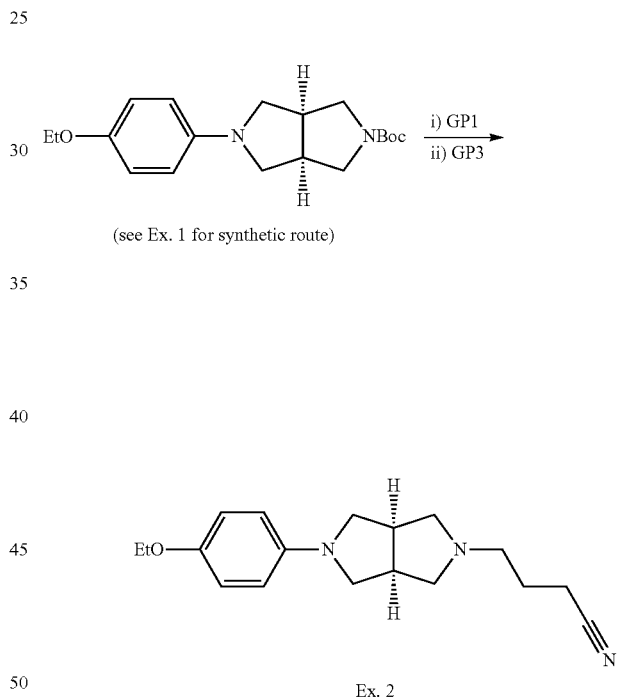

(see Ex. 1 for synthetic route)

Ex. 2

The title compound was prepared using general procedure GP1 and GP3—from i) tert-butyl 5-(4-ethoxyphenyl)-hexahydropyrrolo[3,4-c]pyrrole-2(1H)-carboxylate (20 mg, 0.06 mmol) and HCl (4.0 M in dioxane, 75 μL); rt, 1 h. ii) triethylamine (50 μL, 0.36 mmol), diisopropylethylamine (21 μL, 0.12 mmol) and 4-bromobutyronitrile (9 μL, 0.09 mmoL), THF (1.0 mL); rt, 16 h. A colourless oil was obtained without further purification (3 mg, 17%). $^1$H NMR (500 MHz, CDCl$_3$) δ 6.85 (d, J=9.0 Hz, 2H), 6.67 (d, J=9.0, 2H), 3.99 (q, J=7.0 Hz, 2H), 3.28-2.97 (m, 6H), 2.81-2.66 (m, 2H), 2.55-2.41 (m, 6H), 2.04-1.91 (m, 1H), 1.39 (t, J=7.0, 4H). HRMS calcd for C$_{18}$H$_{26}$N$_3$O (M+H$^+$) 300.2070. found 300.1979.

Example 3: cis-5-(4-Ethoxyphenyl)-N-(2-hydroxyethyl)-3a,6a-dimethylhexahydropyrrolo[3,4-c]pyrrole-2(1H)-carboxamide

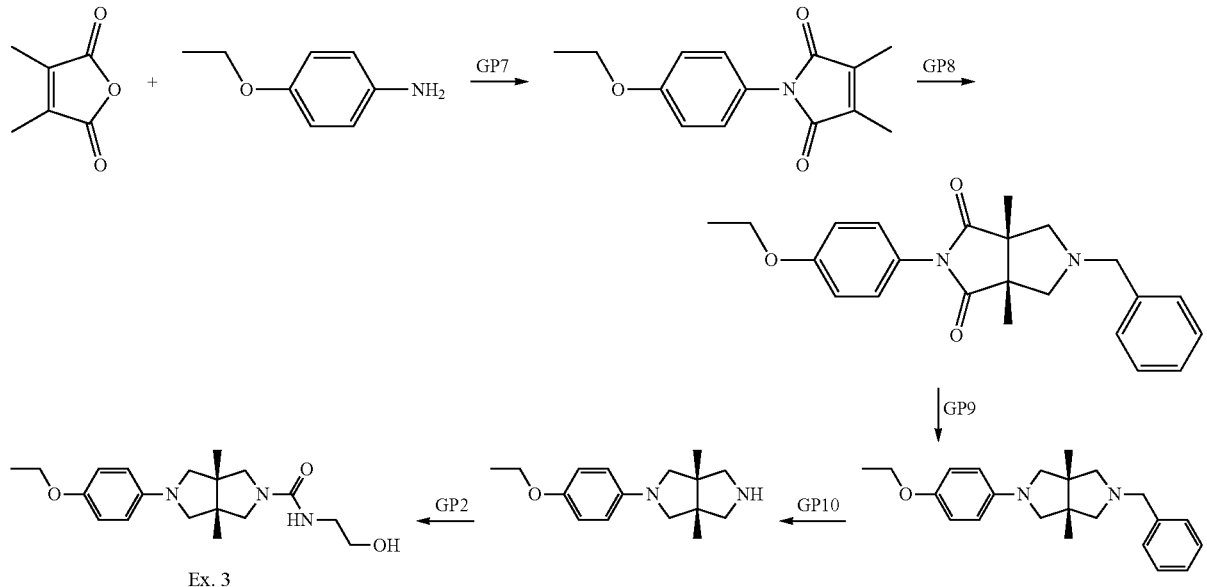

Ex. 3

1-(4-Ethoxyphenyl)-3,4-dimethyl-1H-pyrrole-2,5-dione was prepared using general procedure GP7—from p-phenetidine (2.55 mL, 19.8 mmol) and 2,3-dimethyl maleic anhydride (5.00 g, 39.6 mmol) in DMSO (11.7 mL); 120° C., 16 h. Purification by chromatography (toluene) gave 1-(4-ethoxyphenyl)-3,4-dimethyl-1H-pyrrole-2,5-dione as a bright yellow crystalline solid (4.95 g, 100%). $^1$H NMR (500 MHz, CDCl$_3$) δ 7.21 (d, J=9.0, 2H), 6.94 (d, J=9.0, 2H), 4.02 (d, J=7.0, 2H), 2.02 (s, 6H), 1.40 (t, J=7.0, 3H). $^{13}$C NMR (126 MHz, CDCl$_3$) δ 171.20, 158.13, 137.28, 127.28, 124.48, 114.82, 63.65, 14.77, 8.85. HRMS calcd for C$_{14}$H$_{16}$NO$_3$ (M+H$^+$) 246.1125. found 246.1127.

2-Benzyl-5-(4-ethoxyphenyl)-3a,6a-dimethyloctahydropyrrolo[3,4-c]pyrrole was prepared using general procedure GP8 and GP9—from i) N-(methoxymethyl)-N-(trimethylsilylmethyl)-benzylamine (4.08 mL, 15.9 mmol), TFA (93 µL, 1.22 mmol), 1-(4-ethoxyphenyl)-3,4-dimethyl-1H-pyrrole-2,5-dione (3.00 g, 12.2 mmol) and DCM (30 mL); rt, 16 h. ii) Lithium aluminium hydride (1.0 M in diethyl ether, 36.6 mL, 36.6 mmol), THF (123 mL) and DCM (100 mL); rt, 16 h. A colourless oil was obtained which was used immediately in the subsequent transformation. $^1$H NMR (500 MHz, CDCl$_3$) δ 7.38-7.17 (m, 5H), 6.86 (d, J=9.0, 2H), 6.63 (d, J=9.0, 2H), 4.00 (q, J=7.0, 2H), 3.58 (s, 2H), 3.34 (d, J=9.0, 2H), 3.04 (d, J=9.0, 2H), 2.74 (d, J=9.2, 2H), 2.41 (d, J=9.1, 2H), 1.40 (t, J=7.0, 3H), 1.13 (s, 6H). $^{13}$C NMR (126 MHz, CDCl$_3$) δ 151.00, 143.96, 139.54, 128.45, 128.15, 126.74, 115.69, 114.73, 67.98, 64.20, 63.57, 59.76, 49.55, 21.56, 15.06. HRMS calcd for C$_{23}$H$_{31}$N$_2$O (M+H$^+$) 351.2431. found 351.2372.

2-(4-Ethoxyphenyl)-3a,6a-dimethyloctahydropyrrolo[3,4-c]pyrrole was prepared using general procedure GP10—from Pd(OH)$_2$ (20% on carbon, 470 mg), crude 2-benzyl-5-(4-ethoxyphenyl)-3a,6a-dimethyloctahydropyrrolo[3,4-c]pyrrole (12.2 mmol), ammonium formate (7.69 g, 122 mmol) and methanol (400 mL). 70° C., 6 h. The crude was redissolved in ethyl acetate (100 mL) and water (150 mL). The pH of the aqueous layer was adjusted to 13 with NaOH. The layers were separated and the aqueous layer extracted with ethyl acetate until there was no product left in the aqueous layer by TLC. The combined organic layers were dried (MgSO$_4$) and evaporated in vacuo to give (3aR,6aS)-2-(4-ethoxyphenyl)-3a,6a-dimethylhexahydropyrrolo[3,4-c]pyrrole as a white solid (3.17 g, 100% over three steps). $^{13}$C NMR (126 MHz, CDCl$_3$) δ 151.11, 142.03, 115.84, 113.51, 64.18, 59.46, 55.37, 50.22, 18.90, 15.01.

The title compound was prepared using general procedure GP2—from 2-(4-ethoxyphenyl)-3a,6a-dimethylhexahydropyrrolo[3,4-c]pyrrole (1.00 g, 3.85 mmol), triphosgene (1.48 g, 5.00 mmol), diisopropylethylamine (3.34 mL, 19.2 mmol), ethanolamine (3.48 mL, 57.7 mmol) and DCM (53 mL); rt, 16 h. Purification by chromatography (MeOH/EtOAc 0→20%) gave a colourless oil (963 mg, 72%). $^1$H NMR (300 MHz, CDCl$_3$) δ 6.85 (d, J=9.0, 2H), 6.42 (d, J=9.0, 2H), 4.78 (t, J=5.5, 1H), 4.97 (q, J=7.0, 2H), 3.68 (t, J=5.0, 2H), 3.53 (d, J=10.0, 2H), 3.46-3.27 (m, 6H), 3.21 (d, J=9.3, 2H), 2.11 (s, 1H), 1.38 (t, J=7.0, 3H), 1.16 (s, 6H). $^{13}$C NMR (126 MHz, CDCl$_3$) δ 157.91, 150.30, 142.16, 116.09, 112.04, 64.39, 63.69, 58.75, 56.32, 49.62, 43.66, 18.92, 15.05. HRMS calcd for C$_{19}$H$_{30}$N$_3$O$_3$ (M+H$^+$) 348.2282. found 348.2276.

Example 4: cis-5-(4-Ethoxyphenyl)-N-(3-(2-oxopyrrolidin-1-yl)propyl)hexahydro-pyrrolo[3,4-c]pyrrole-2(1H)-carboxamide

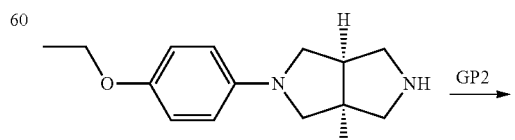

(See Ex. 1 for synthetic route)

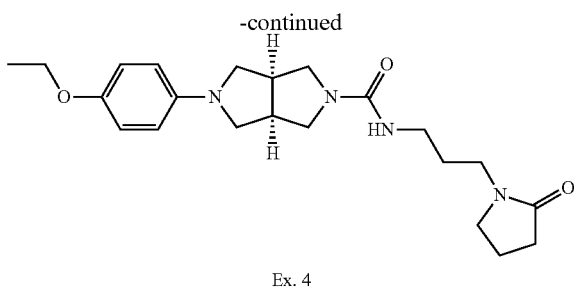

Ex. 4

The title compound was prepared using general procedure GP2—from 2-(4-ethoxyphenyl)hexahydropyrrolo[3,4-c]pyrrole (100 mg, 0.43 mmol), diisopropylethylamine (375 μL, 2.16 mmol), triphosgene (165 mg, 0.56 mmol), N-(3-aminopropyl)-2-pyrrolidine (603 μL, 4.30 mmol), DCM (6.0 mL); rt, 16 h. Purification by chromatography (MeOH/EtOAc 5→30%) gave a colourless oil (87 mg, 0.22 mmol, 51%). $^{1}$H NMR (500 MHz, CDCl$_3$) δ 6.82 (d, J=8.8, 2H), 6.49 (d, J=8.8, 2H), 5.75 (t, J=6.3, 1H), 3.96 (q, J=7.0, 2H), 3.69 (dd, J=10.2, 7.3, 2H), 3.46 (dd, J=8.3, 7.7, 2H), 3.42-3.29 (m, 6H), 3.21-3.11 (m, 4H), 3.05-2.97 (m, 2H), 2.40 (t, J=7.9, 2H), 2.04 (d, J=7.5, 2H), 1.71-1.60 (m, 2H), 1.36 (t, J=7.0, 3H). $^{13}$C NMR (126 MHz, CDCl$_3$) δ 176.01, 156.93, 150.44, 142.66, 115.90, 112.99, 64.25, 53.07, 50.29, 47.29, 42.00, 39.26, 35.94, 30.89, 26.47, 17.90, 15.04. HRMS calcd for C$_{22}$H$_{33}$N$_4$O$_3$ (M+H$^+$) 401.2547. found 401.5243.

Example 5: cis-5-(4-Ethoxyphenyl)-N—((R)-2-hydroxypropyl)hexahydropyrrolo[3,4-c]pyrrole-2(1H)-carboxamide

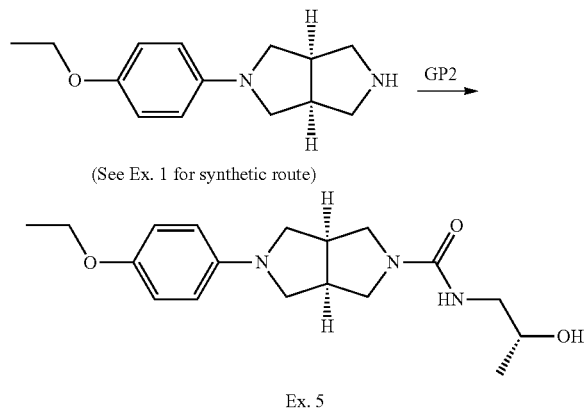

Ex. 5

The title compound was prepared using general procedure GP2—from 2-(4-ethoxyphenyl)hexahydropyrrolo[3,4-c]pyrrole (100 mg, 0.43 mmol), triethylamine (300 μL, 2.16 mmol), triphosgene (166 mg, 0.56 mmol), (R)-(−)-1-amino-2-propanol (203 μL, 2.58 mmol) and DCM (6.0 mL). Purification by chromatography (MeOH/EtOAc 0→15%) gave a colourless oil (25 mg, 0.07 mmol, 17%). $^{13}$C NMR (126 MHz, CDCl$_3$) δ 157.79, 150.64, 142.50, 115.94, 113.06, 68.24, 64.26, 53.01, 50.56, 48.35, 42.03, 20.80, 15.03. HRMS calcd for C$_{18}$H$_{28}$N$_3$O$_3$ (M+H$^+$) 334.2125. found 334.2115.

Example 6: cis-5-(4-Ethoxyphenyl)-N-((1r,3s,5R,7S)-3-hydroxyadamantan-1-yl)hexahydropyrrolo[3,4-c]pyrrole-2(1H)-carboxamide

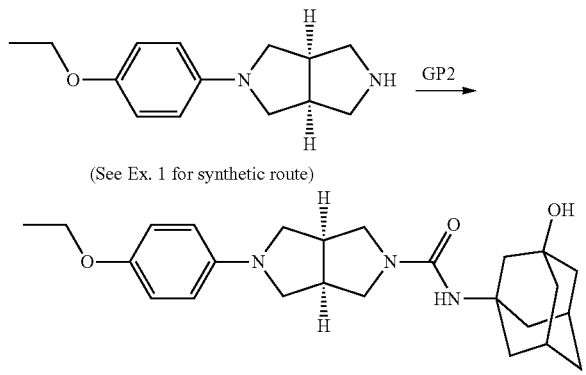

Ex. 6

The title compound was prepared using general procedure GP2—from 2-(4-ethoxyphenyl)hexahydropyrrolo[3,4-c]pyrrole (100 mg, 0.43 mmol), triethylamine (300 μL, 2.16 mmol), triphosgene (166 mg, 0.56 mmol), 3-amino-1-adamantol (432 mg, 2.58 mmol) and DCM (6.0 mL). Purification by chromatography (MeOH/EtOAc 0→15%) gave a colourless oil (22 mg, 0.05 mmol, 12%). $^{13}$C NMR (126 MHz, CDCl$_3$) δ 155.73, 150.56, 142.57, 115.94, 112.97, 69.36, 64.26, 53.81, 52.99, 50.15, 50.01, 44.17, 42.06, 41.26, 35.03, 30.75, 15.03. HRMS calcd for C$_{25}$H$_{36}$N$_3$O$_3$ (M+H$^+$) 426.2751. found 426.2736.

Example 7: cis-5-(4-(1,1-Dioxidothiomorpholino)phenyl)-N-ethylhexahydropyrrolo[3,4-c]pyrrole-2(1H)-carboxamide

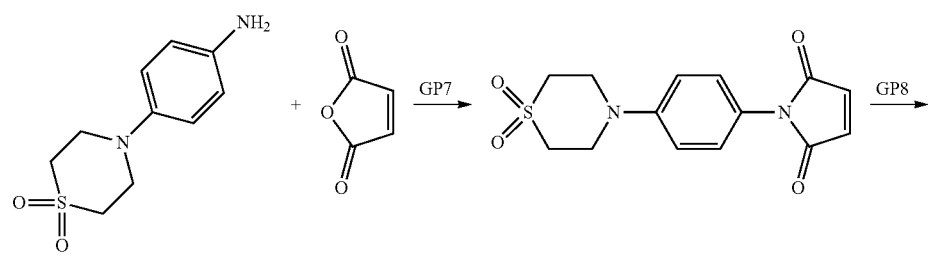

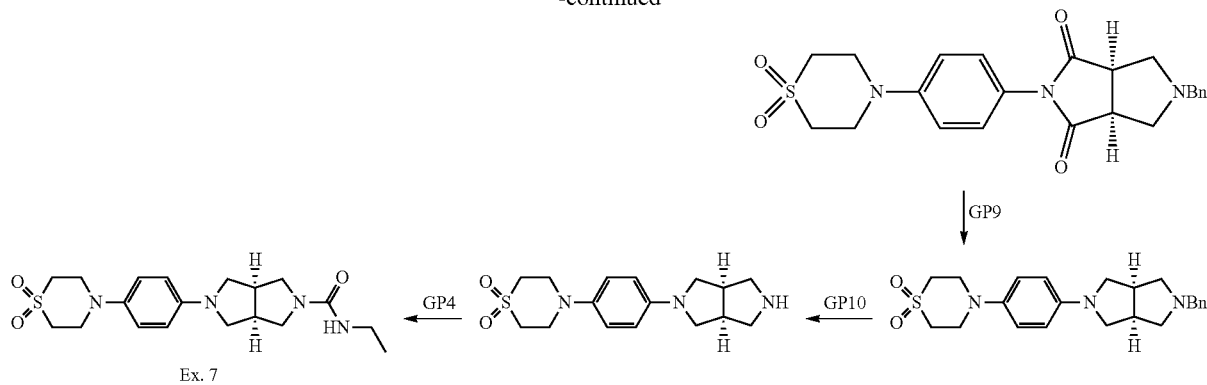

1-(4-(1,1-Dioxidothiomorpholino)phenyl)-1H-pyrrole-2,5-dione was synthesised according to general procedures GP7—from maleic anhydride (2.60 g, 26.5 mmol), 4-(4-aminophenyl)-thiomorpholine 1,1-dioxide (3.0 g, 13.3 mmol) and DMSO (9 mL); 120° C., 23 h. A pale yellow solid obtained which didn't require further purification (3.65 g, 76%). $^1$H NMR ((CD$_3$)$_2$SO, 500 MHz): 3.14 (4H, t, J=5.1 Hz), 3.83 (4H, t, J=5.1 Hz), 7.12 (2H, d, J=9.1 Hz), 7.15 (2H, s), 7.19 (2H, d, J=9.1 Hz); $^{13}$C NMR ((CD$_3$)$_2$SO, 125 MHz): 47.0, 50.3, 116.1, 123.2, 128.5, 135.1, 147.4, 170.8. HRMS (ESI +ve). found 307.0742 [M+H$^+$]; C$_{14}$H$_{15}$N$_2$O$_4$S requires 307.0747.

5-benzyl-2-(4-(1,1-dioxidothiomorpholino)phenyl)tetrahydropyrrolo[3,4-c]pyrrole-1,3(2H,3aH)-dione was synthesised according to general procedures GP8—from N-(methoxymethyl)-N-(trimethylsilylmethyl)benzylamine (2.2 mL, 8.32 mmol), 1-(4-(1,1-dioxidothiomorpholino)phenyl)-1H-pyrrole-2,5-dione (1.96 g, 6.40 mmol) and TFA (49 µL, 0.64 mmol) in DCM (20 mL); rt, 17 h. The crude residue was suspended in dichloromethane (40 mL) and diethyl ether (50 mL) was added. The resultant suspension was filtered to afford pure (2.27 g, 81%) as a off-white powder. $^1$H NMR ((CD$_3$)$_2$SO, 500 MHz): 2.50 (4H, a-t, J=5.2 Hz), 3.12 (4H, t, J=5.2 Hz), 3.35 (2H, dd, J=5.6, 9.8 Hz), 3.42 (2H, d, J=9.8 Hz), 3.65 (2H, s), 3.91 (4H, t, J=5.2 Hz), 7.00-7.03 (4H, m), 7.25-7.34 (7H, m); $^{13}$C NMR ((CD$_3$)$_2$SO, 125 MHz): 44.67, 46.96, 50.29, 56.45, 57.88, 116.02, 124.16, 127.47, 128.13, 128.60, 128.77, 138.82, 147.67, 179.43. HRMS (ESI +ve). found 440.1628 [M+H$^+$]; C$_{23}$H$_{26}$N$_3$O$_4$S requires 440.1639.

4-(4-(5-Benzylhexahydropyrrolo[3,4-c]pyrrol-2(1H)-yl)phenyl)thiomorpholine 1,1-dioxide was synthesised according to general procedures GP9—from borane-tetrahydrofuran complex (1.0 M in THF, 52.0 mL, 52.0 mmol), 5-benzyl-2-(4-(1,1-dioxidothiomorpholino)phenyl)tetrahydropyrrolo[3,4-c]pyrrole-1,3(2H,3aH)-dione (2.26 g, 5.14 mmol) and THF (70 mL); 80° C., 22 h. The crude residue was purified by chromatography (methanol/ethyl acetate 0→20%) to afford a white powder (1.44 g, 68%). $^1$H NMR ((CD$_3$)$_2$SO, 500 MHz): 2.35 (2H, dd, J=3.1, 9.0 Hz), 2.64 (2H, dd, J=6.3, 9.0 Hz), 2.80-2.87 (2H, m), 2.97 (2H, dd, J=3.2, 9.2 Hz), 3.14 (4H, t, 5.2 Hz), 3.26 (2H, dd, J=7.8, 9.2 Hz), 3.53-3.55 (6H, m), 6.61 (2H, d, J=9.0 Hz), 6.92 (2H, d, J=9.0 Hz), 7.21-7.32 (5H, m); $^{13}$C NMR ((CD$_3$)$_2$SO, 125 MHz): 41.59, 49.26, 50.62, 55.26, 59.33, 60.48, 115.24, 119.02, 127.22, 128.62, 128.82, 139.65, 140.55, 144.10. HRMS (ESI +ve). found 412.2045 [M+H$^+$]; C$_{23}$H$_{30}$N$_3$O$_2$S requires 412.2059.

The title compound was synthesised according to general procedures GP10 and GP4—from i) Palladium black (100 mg), 4-(4-(5-benzylhexahydropyrrolo[3,4-c]pyrrol-2(1H)-yl)phenyl)thiomorpholine 1,1-dioxide (1.0 g, 2.43 mmol), 4-cyclohexadiene (2.3 mL, 24.3 mmol) 2,2,2-trifluoroethanol (40 mL); 75° C., 1 h. ii) Et$_3$N (3.4 mL, 24.3 mmol), EtNCO (87.1 µL, 1.10 mmol) and DCM (20 mL); rt, 16 h. The crude was purified by chromatography (methanol/ethyl acetate 0→10%) to afford the desired compound (761 mg, 80% over two steps). $^1$H NMR (CDCl$_3$, 500 MHz): 1.15 (3H, t, J=7.2 Hz), 3.04-3.10 (2H, m), 3.16 (4H, t, J=5.4 Hz), 3.22 (2H, dd, J=2.9, 9.1 Hz), 3.28 (2H, dq, J=5.5, 7.2 Hz), 3.35 (2H, dd, J=3.8, 10.0 Hz), 3.47-3.53 (2H, m), 3.63-3.70 (6H, m), 4.17 (1H, t, J=5.5 Hz), 6.53 (2H, d, J=8.6 Hz), 6.93 (2H, d, J=8.6 Hz); $^{13}$C NMR (CDCl$_3$, 125 MHz): 15.76, 35.48, 42.02, 50.08, 50.23, 51.27, 52.56, 112.88, 120.28, 139.79, 143.67, 156.79. HRMS (ESI +ve). found 393.1940 [M+H$^+$]; C$_{19}$H$_{29}$N$_4$O$_3$S requires 393.1960.

Example 8: cis-5-(4-(1,1-Dioxidothiomorpholino)phenyl)-N-ethyl-3a,6a-dimethylhexahydropyrrolo[3,4-c]pyrrole-2(1H)-carboxamide

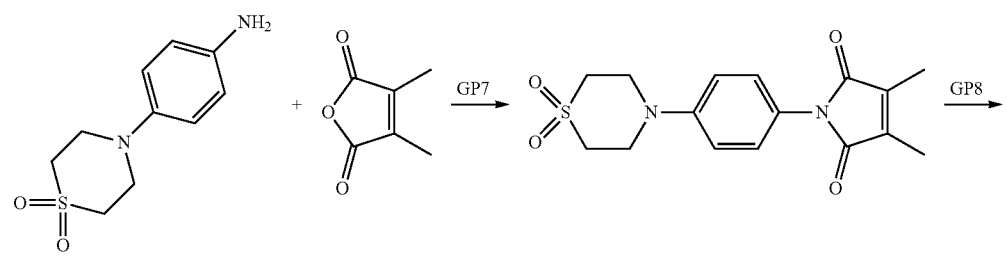

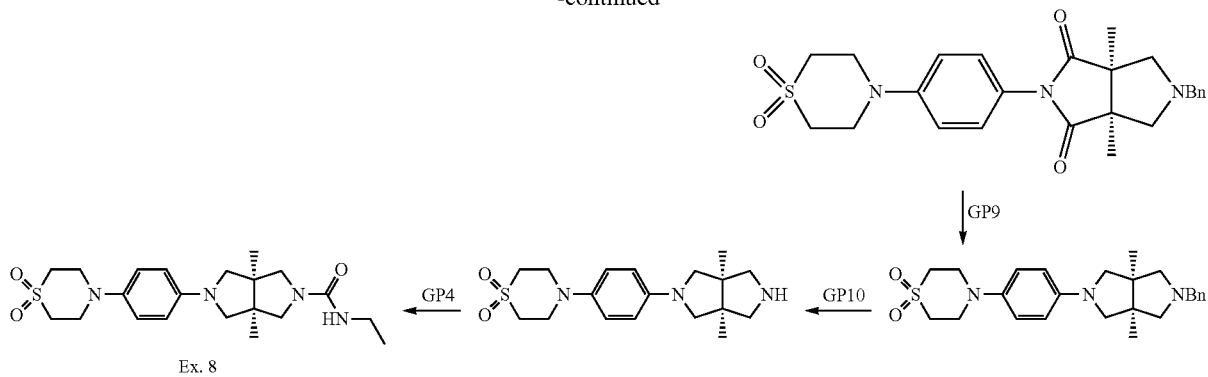

1-(4-(1,1-Dioxidothiomorpholino)phenyl)-3,4-dimethyl-1H-pyrrole-2,5-dione was synthesised according to general procedures GP7—from 2,3-dimethylmaleic anhydride (3.34 g, 26.5 mmol), 4-(4-aminophenyl)-thiomorpholine 1,1-dioxide (3.0 g, 13.3 mmol) and DMSO (6 mL); 120° C., 17 h. The crude residue was recrystallised from DCM and diethyl ether to afford a yellow powder (3.59 g, 81%). $^1$H NMR (CDCl$_3$, 500 MHz): 2.04 (6H, s), 3.11 (4H, t, J=5.2), 3.86 (4H, t, J=5.2 Hz), 6.98 (2H, d, J=9.0 Hz), 7.26 (2H, d, J=9.0 Hz); $^{13}$C NMR (CDCl$_3$, 125 MHz): 8.93, 47.78, 50.45, 116.71, 124.93, 127.36, 137.47, 146.52, 171.12. HRMS (ESI +ve). found 336.1046 [M+H$^+$]; C$_{16}$H$_{19}$N$_2$O$_4$S requires 336.1053.

5-Benzyl-2-(4-(1,1-dioxidothiomorpholino)phenyl)-3a,6a-dimethyltetrahydropyrrolo[3,4-c]pyrrole-1,3(2H,3aH)-dione was synthesised according to general procedures GP8—from N-(methoxymethyl)-N-(trimethylsilylmethyl)benzylamine (2.0 mL, 7.78 mmol), 1-(4-(1,1-dioxidothiomorpholino)phenyl)-3,4-dimethyl-1H-pyrrole-2,5-dione (2.0 g, 5.98 mmol) and TFA (46 µL, 0.60 mmol) in DCM (20 mL); rt, 20 h. The crude was recrystallised from DCM and diethyl ether to afford a pale-yellow solid (2.60 g, 93%). $^1$H NMR ((CD$_3$)$_2$SO, 500 MHz): 1.23 (6H, s), 2.17 (2H, d, J=9.6 Hz), 3.14 (4H, t, J=5.0 Hz), 3.22 (2H, d, J=9.6 Hz), 3.54 (2H, s), 3.84 (4H, t, J=5.0 Hz), 7.10 (2H, d, J=9.1 Hz), 7.14 (2H, d, J=9.2 Hz), 7.22-7.26 (3H, m), 7.31 (2H, t, J=7.2 Hz); $^{13}$C NMR ((CD$_3$)$_2$SO, 125 MHz): 15.40, 46.48, 49.85, 51.43, 57.24, 64.39, 115.50, 123.60, 126.99, 127.73, 128.02, 128.28, 138.21, 147.27, 181.28. HRMS (ESI +ve). found 468.1948 [M+H$^+$]; C$_{25}$H$_{30}$N$_3$O$_4$S requires 468.1952;

4-(4-(5-Benzyl-3a,6a-dimethylhexahydropyrrolo[3,4-c]pyrrol-2(1H)-yl)phenyl)thiomorpholine 1,1-dioxide was synthesised according to general procedures GP9 — from borane-tetrahydrofuran complex (1 M in THF, 45.0 mL, 45.0 mmol), 5-benzyl-2-(4-(1,1-dioxidothiomorpholino)phenyl)-3a,6a-dimethyltetrahydropyrrolo[3,4-c]pyrrole-1,3(2H,3aH)-dione (2.1 g, 4.49 mmol) and THF (60 mL); 80° C., 16 h. The crude was recrystallised from DCM and diethyl ether to afford a white solid (1.37 g, 70%). $^1$H NMR ((CD$_3$)$_2$SO, 500 MHz): 1.06 (6H, s), 2.33 (2H, d, J=9.0 Hz), 2.62 (2H, d, J=9.0 Hz), 2.93 (2H, d, J=9.2 Hz), 3.13 (4H, t, J=5.0 Hz), 3.25 (2H, d, J=9.2 Hz), 3.51 (2H, s), 3.53 (4H, t, J=5.0 Hz), 6.56 (2H, d, J=8.9 Hz), 6.90 (2H, d, J=8.9 Hz), 7.20-7.31 (5H, m); $^{13}$C NMR ((CD$_3$)$_2$SO, 125 MHz): 21.19, 48.75, 48.95, 50.1, 58.97, 62.69, 67.53, 114.45, 118.51, 126.66, 128.12, 128.16, 139.17, 139.91, 143.60. HRMS (ESI +ve). found 440.2366 [M+H$^+$]; C$_{25}$H$_{33}$N$_3$O$_2$S requires 440.2366.

The title compound was synthesised according to general procedures GP10 and GP4—from i) Palladium black (10 mg), 4-(4-(5-benzyl-3a,6a-dimethylhexahydropyrrolo[3,4-c]pyrrol-2(1H)-yl)phenyl)thiomorpholine 1,1-dioxide (100 mg, 0.23 mmol), ammonium acetate (143 mg, 2.28 mmol) and 2,2,2-trifluoroethanol (TFE, 5 mL); 75° C., 1 h. ii) triethylamine (316 µL, 2.27 mmol), ethyl isocyanate (18 µL, 0.23 mmol) and dichloromethane (4 mL); rt, 2 h. The crude residue was purified by chromatography (methanol/ethyl acetate 0→30%) to afford a white crystalline solid (10 mg, 10%). $^1$H NMR ((CD$_3$)$_2$SO, 500 MHz): 0.99 (3H, t, J=7.1 Hz), 1.07 (6H, s), 3.01 (2H, dq, J=5.5, 7.1 Hz), 3.14 (4H, t, J=5.2 Hz), 3.16 (2H, d, J=9.5 Hz), 3.19 (2H, d, J=10.2 Hz), 3.27 (2H, d, J=9.5 Hz), 3.36 (2H, d, J=10.2 Hz), 3.50 (4H, t, J=5.2 Hz), 6.02 (1H, t, J=5.5 Hz), 6.43 (2H, d, J=9.1 Hz), 6.92 (2H, d, J=9.1 Hz); $^{13}$C NMR ((CD$_3$)$_2$SO, 125 MHz): 16.21, 19.09, 35.05, 49.32, 49.66, 50.74, 56.52, 58.80, 112.41, 119.67, 139.59, 143.26, 157.01. HRMS (ESI +ve). found 421.2267 [M+H$^+$]; C$_{21}$H$_{33}$N$_4$O$_3$S requires 421.2268.

Example 9: cis-N-Cyclohexyl-5-(4-(1,1-dioxidothiomorpholino)phenyl)hexahydropyrrolo[3,4-c]pyrrole-2(1H)-carboxamide

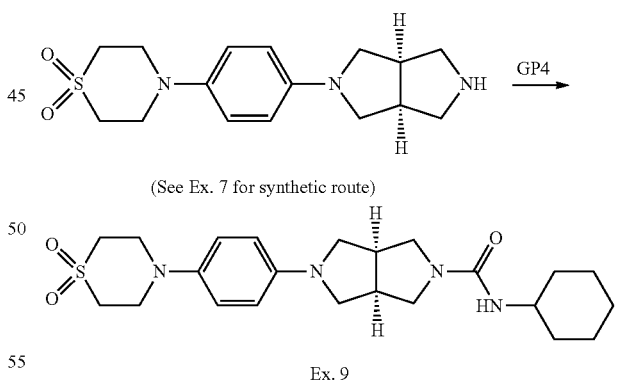

(See Ex. 7 for synthetic route)

Ex. 9

The title compound was prepared using general procedure GP4—from crude 4-(4-hexahydropyrrolo[3,4-c]pyrrol-2(1H)-yl)phenyl)thiomorpholine 1,1-dioxide (0.252 mmol) with triethylamine (0.34 mL, 2.42 mmol), cyclohexyl isocyanate (31 µL, 0.24 mmol) and dichloromethane (2.0 mL); rt, 20 h. Purification by chromatography (MeOH/EtOAc 0→10%) gave the desired compound (94 mg, 87% over two steps). $^1$H NMR ((CD$_3$)$_2$SO, 500 MHz): 1.03-1.07 (1H, m), 1.11-1.25 (4H, m), 1.53-1.56 (1H, m), 1.65-1.67 (2H, m), 1.71-1.73 (2H, m), 2.92-2.96 (2H m), 3.05 (2H, dd, J=3.4, 9.7 Hz), 3.12-3.16 (6H, m), 3.33-3.37 (3H, m), 3.48-3.51 (6H, m), 5.72 (1H, d, J=8.0 Hz), 6.50 (2H, d, J=8.9 Hz), 6.92 (2H, d, J=8.9 Hz); $^{13}$C NMR ((CD$_3$)$_2$SO, 125 MHz): 25.58, 25.83, 33.71, 41.66, 49.27, 49.53, 50.70, 50.89, 53.32, 113.49, 119.44, 139.98, 143.39, 156.39. HRMS (ESI +ve). found 447.2416 [M+H$^+$]; C$_{23}$H$_{35}$N$_4$O$_3$S requires 447.2424.

Example 10: cis-N-tert-Butyl-5-(4-(1,1-dioxidothiomorpholino)phenyl)hexahydropyrrolo[3,4-c]pyrrole-2(1H)-carboxamide

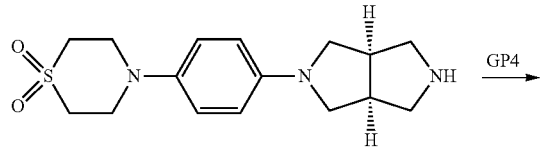

(See Ex. 7 for synthetic route)

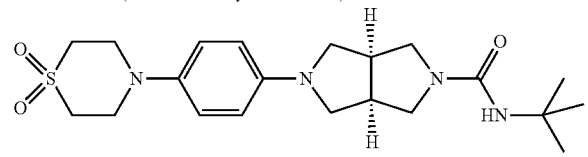

Ex. 10

The title compound was prepared using general procedure GP4—from crude 4-(4-(hexahydropyrrolo[3,4-c]pyrrol-2(1H)-yl)phenyl)thiomorpholine 1,1-dioxide (0.352 mmol) with triethylamine (0.33 mL, 2.35 mmol), tert-butylisocyanate (27 µL, 0.24 mmol) and dichloromethane (2.0 mL); rt, 20 h. Purification by chromatography (MeOH/EtOAc 0→10%) gave the desired compound (84 mg, 85% over two steps). $^1$H NMR ((CD$_3$)$_2$SO, 500 MHz): 1.25 (9H, s), 2.91-2.97 (2H, m), 3.07 (2H, dd, J=3.4, 9.5 Hz), 3.13-3.18 (6H, m), 3.36 (2H, dd, J=7.3, 9.5 Hz), 3.48-3.53 (6H, m), 5.24 (1H, s), 6.52 (2H, d, J=9.0 Hz), 6.93 (2H, d, J=9.0 Hz); $^{13}$C NMR ((CD$_3$)$_2$SO, 125 MHz): 29.70, 41.70, 49.54, 50.29, 50.71, 50.92, 53.33, 113.47, 119.45, 139.97, 143.40, 156.62. HRMS (ESI +ve). found 421.2270 [M+H$^+$]; C$_{21}$H$_{33}$N$_4$O$_3$S requires 421.2268.

Example 11: cis-5-(4-(1,1-Dioxidothiomorpholino)phenyl)-N-(2-hydroxyethyl)hexahydro-pyrrolo[3,4-c]pyrrole-2(1H)-carboxamide

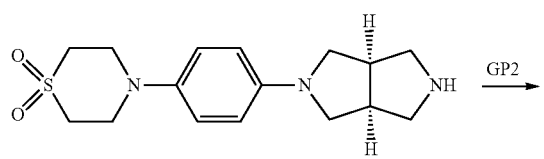

(See Ex. 7 for synthetic route)

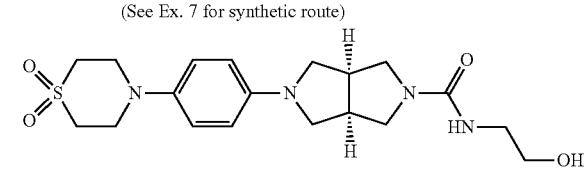

Ex. 11

The title compound was prepared using general procedure GP2—from 4-(4-(hexahydropyrrolo[3,4-c]pyrrol-2(1H)-yl)phenyl)thiomorpholine 1,1-dioxide (0.121 mmol), N,N-diisopropylethylamine (0.21 mL, 1.21 mmol), triphosgene (22 mg, 0.07 mmol) and ethanolamine (181 µL, 3.03 mmol), DCM (3.0 mL). Purification by chromatography (MeOH/EtOAc 0→15%) gave the desired compound (31 mg, 63% over two steps). $^{13}$C NMR (CDCl$_3$, 125 MHz): 41.69, 43.16, 49.52, 50.70, 50.84, 53.28, 61.28, 113.48, 119.44, 139.98, 143.37, 157.23. HRMS (ESI +ve). found 409.1895 [M+H$^+$]; C$_{19}$H$_{29}$N$_4$O$_4$S requires 409.1904.

Example 12: cis-5-(4-(1,1-Dioxidothiomorpholino)phenyl)hexahydropyrrolo[3,4-c]pyrrol-2(1H)-yl)(morpholino)methanone

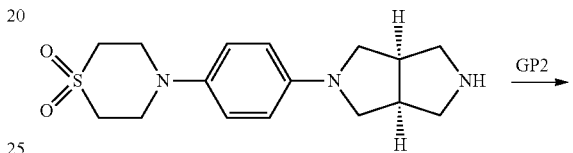

(See Ex. 7 for synthetic route)

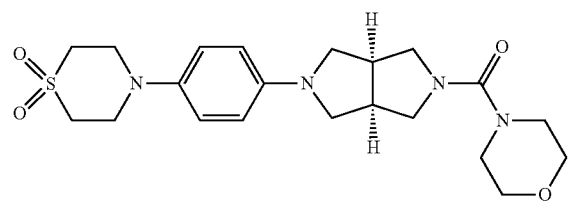

Ex. 12

The title compound was prepared using general procedure GP2—from crude 4-(4(hexahydropyrrolo[3,4-c]pyrrol-2(1H)-yl)phenyl)thiomorpholine 1,1-dioxide (0.242 mmol), N,N-diisopropylethylamine (0.21 mL, 1.21 mmol), triphosgene (22 mg, 0.07 mmol), ethanolamine (181 µL, 3.03 mmol) and DCM (3.0 mL). Purification by chromatography (MeOH/EtOAc 0→15%) gave the desired compound (37 mg, 70% over two steps). $^{13}$C NMR ((CD$_3$)$_2$SO, 125 MHz): 41.74, 46.86, 47.29, 49.50, 50.68, 52.90, 66.36, 113.63, 119.39, 140.02, 143.41, 162.17. HRMS (ESI +ve). found 435.2072 [M+H$^+$]; C$_{21}$H$_{31}$N$_4$O$_4$S requires 435.2075.

Example 13: cis-5-(4-Ethoxyphenyl)-N-ethyl-3a,6a-dimethylhexahydropyrrolo[3,4-c]pyrrole-2(1H)-carboxamide

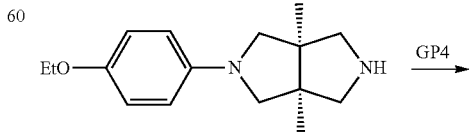

(See Ex. 3 for synthetic route)

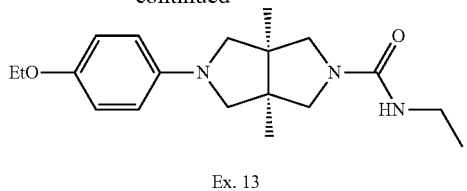

Ex. 13

The title compound was prepared using general procedure GP4—from 2-(4-ethoxyphenyl)-3a,6a-dimethyltetrahydropyrrolo[3,4-c]pyrrole (360 mg, 1.38 mmol), with triethylamine (1.93 mL, 13.8 mmol), ethyl isocyanate (110 µL, 1.38 mmol) and dichloromethane (7.0 mL); rt, 20 h. Purification by chromatography (MeOH/EtOAc 0→10%) gave the desired compound (458 mg, quant.). $^1$H NMR ((CD$_3$)$_2$SO, 500 MHz): 0.99 (3H, t, J=7.2 Hz), 1.06 (6H, s), 1.26 (3H, t, J=7.2 Hz), 3.01 (2H, td, J=5.7, 7.2 Hz), 3.11 (2H, d, J=9.4 Hz), 3.18 (2H, d, J=10.6 Hz), 3.25 (2H, d, J=9.4 Hz), 3.35 (2H, d, J=10.6 Hz), 3.89 (2H, q, J=7.2 Hz), 6.00 (1H, t, J=5.7 Hz), 6.40 (2H, d, J=9.0 Hz), 6.77 (2H, d, J=9.0 Hz); $^{13}$C NMR ((CD$_3$)$_2$SO, 125 MHz): 14.9, 15.7, 18.7, 34.6, 48.9, 56.1, 58.6, 63.4, 112.0, 115.6, 142.4, 149.5, 156.5. HRMS (ESI +ve). found 354.2141 [M+Na$^+$]; C$_{19}$H$_{29}$N$_3$NaO$_2$ requires 354.2152.

Example 14: cis-5-(4-Ethoxyphenyl)-N-ethylhexahydropyrrolo[3,4-c]pyrrole-2(1H)-carboxamide

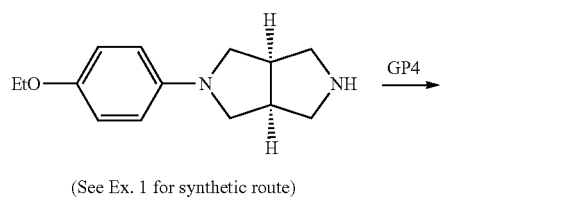

(See Ex. 1 for synthetic route)

Ex. 14

The title compound was prepared using general procedure GP4—from crude 2-(4-ethoxyphenyl)-octahydropyrrolo[3,4-c]pyrrole (~3.00 mmol), with triethylamine (4.2 mL, 30.1 mmol), ethyl isocyanate (240 µL, 3.01 mmol) and dichloromethane (7.0 mL); rt, 16 h. Purification by chromatography (MeOH/EtOAc 0→10%) gave the desired compound (715 mg, 78%) as a off-white solid. $^1$H NMR ((CD$_3$)$_2$SO, 500 MHz): 0.99 (3H, t, J=7.3 Hz), 1.27 (3H, t, J=7.2 Hz), 2.91-3.05 (6H, m), 3.15 (2H, dd, J=3.8, 10.5 Hz), 3.32-3.35 (2H, m), 3.49 (2H, dd, J=7.5, 10.5 Hz), 3.90 (2H, q, J=7.2 Hz), 6.08 (1H, t, J=5.6 Hz), 6.49 (2H, d, J=9.0 Hz), 6.78 (2H, d, J=9.0 Hz); $^{13}$C NMR ((CD$_3$)$_2$SO, 125 MHz): 14.8, 15.8, 34.6, 41.2, 50.4, 53.2, 63.3, 113.1, 115.4, 142.6, 149.9, 156.5. HRMS (ESI +ve). found 326.1831 [M+Na$^+$]; C$_{17}$H$_{25}$N$_3$NaO$_2$ requires 326.1839.

Example 15: cis-N-Ethyl-5-(4-methoxyphenyl)hexahydropyrrolo[3,4-c]pyrrole-2(1H)-carboxamide

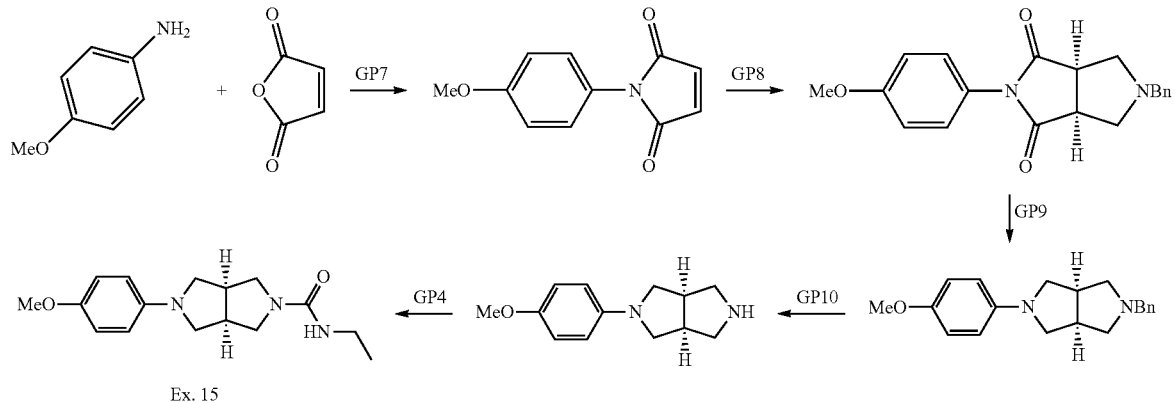

Ex. 15

1-(4-Methoxyphenyl)-1H-pyrrole-2,5-dione was prepared using general procedure GP7—from 4-methoxyaniline (9.0 g, 73.1 mmol), maleic anhydride (14.3 g, 146.2 mmol) and DMSO (27 mL); 120° C., 19 h. Yellow solid obtained and was used without further purification (15.8 g, quant.). $^1$H NMR ((CD$_3$)$_2$SO, 500 MHz): 3.78 (3H, s), 7.02 (2H, d, J=9.1 Hz), 7.15 (2H, s), 7.23 (2H, d, J=9.1 Hz); $^{13}$C NMR ((CD$_3$)$_2$SO, 125 MHz): 55.4, 114.1, 124.1, 128.3, 134.6, 158.6, 170.2.

5-Benzyl-2-(4-methoxyphenyl)tetrahydropyrrolo[3,4-c]pyrrole-1,3(2H,3aH)-dione was prepared using general procedure GP8—from N-(methoxymethyl)-N-(trimethylsilylmethyl)benzylamine (13.0 mL, 39.4 mmol), 1-(4-methoxyphenyl)-1H-pyrrole-2,5-dione (8.0 g, 39.4 mmol) and TFA (0.30 mL, 3.94 mmol) in DCM (80 mL); rt ° C., 17 h. The crude was purified by chromatography (ethyl acetate/cyclohexane 0→100%) to afford a pale yellow solid (10.5 g, 79%). $^1$H NMR ((CD$_3$)$_2$SO, 500 MHz): 2.39-2.42 (2H, m), 3.14 (2H, d, J=9.4 Hz), 3.39 (2H, d, J=7.2 Hz), 3.60 (2H, s), 3.79 (3H, s), 7.05 (2H, d, J=8.9 Hz), 7.14 (2H, s, J=8.9 Hz), 7.23-7.26 (3H, m), 7.33 (2H, t, J=7.7 Hz); $^{13}$C NMR ((CD$_3$)$_2$SO, 125 MHz): 44.2, 55.4, 56.0, 57.4, 114.2, 125.1, 127.0, 128.0, 128.1, 128.3, 138.3, 158.9, 178.9. HRMS (ESI +ve). found 359.1353 [M+Na$^+$]; C$_{20}$H$_{20}$N$_2$NaO$_6$ requires 359.1366.

2-Benzyl-5-(4-methoxyphenyl)octahydropyrrolo[3,4-c]pyrrole was prepared using general procedure GP9—from lithium aluminium hydride (1 M in Et₂O, 94 mL, 94 mmol), 5-benzyl-2-(4-methoxyphenyl)tetrahydropyrrolo[3,4-c]pyrrole-1,3(2H,3aH)-dione (10.5 g, 31.2 mmol) in a 2:1 mixture of tetrahydrofuran and dichloromethane (300 mL); rt, 21 h. The crude was purified by flash chromatography (ethyl acetate/cyclohexane) to afford a pale-brown solid (10.6 g, quant.). ¹H NMR ((CD₃)₂SO, 500 MHz): 2.34 (2H, dd, J=3.5, 9.2 Hz), 2.63 (2H, dd, J=6.8, 9.2 Hz), 2.78-2.89 (2H, m), 2.94 (2H, dd, J=3.5, 9.2 Hz), 3.24 (2H, dd, J=7.8, 9.2 Hz), 3.53 (2H, s), 3.66 (3H, s), 6.61 (2H, d, J=9.2 Hz), 6.79 (2H, d, J=9.2 Hz), 7.20-7.24 (1H, m), 7.26-7.31 (4H, m); ¹³C NMR ((CD₃)₂SO, 125 MHz): 41.2, 55.1, 55.2, 58.8, 60.0, 114.4, 114.9, 126.7, 128.1, 128.3, 139.2, 143.5, 151.3. HRMS (ESI +ve). found 309.1955 [M+H⁺]; C₂₀H₂₄N₂O requires 309.1961.

2-(4-Methoxyphenyl)octahydropyrrolo[3,4-c]pyrrole was prepared using general procedure GP10—from Palladium black (100 mg), -2-benzyl-5-(4-methoxyphenyl)octahydropyrrolo[3,4-c]pyrrole (1.0 g, 3.24 mmol) and 1,4-cyclohexadiene (3.1 mL, 32.4 mmol×2) in 2,2,2-trifluoroethanol (TFE, 25 mL); 85° C., 1 h. An off-white solid was obtained which was used with further purification (860 mg, quant.).

The title compound was prepared using general procedure GP4—from crude 2-(4-methoxyphenyl)octahydropyrrolo[3,4-c]pyrrole (~1.08 mmol), triethylamine (1.5 mL, 10.8 mmol), ethyl isocyanate (86 μL, 1.08 mmol) and dichloromethane (4.0 mL); rt, 16 h. Purification by chromatography (MeOH/EtOAc 0→10%) gave the desired compound (197 mg, 63%) as an off-white solid. ¹H NMR ((CD₃)₂SO, 500 MHz): 0.99 (3H, t, J=6.9 Hz), 2.93-2.97 (2H, m), 2.99-3.05 (4H, m), 3.15 (2H, dd, J=3.9, 10.7 Hz), 3.34 (2H, dd, J=7.1, 9.5 Hz), 3.49 (2H, dd, J=7.3, 10.7 Hz), 3.65 (3H, s), 6.09 (1H, t), 6.51 (2H, d, J=9.0 Hz), 6.79 (2H, d, J=9.0 Hz); ¹³C NMR ((CD₃)₂SO, 125 MHz): 15.8, 34.6, 41.2, 50.4, 53.2, 55.3, 113.1, 114.6, 142.7, 150.7, 156.5. HRMS (ESI +ve). found 290.1861 [M+H⁺]; C₁₆H₂₄N₃O₂ requires 290.1863.

Example 16: cis-N-Cyclohexyl-5-(4-methoxyphenyl)hexahydropyrrolo[3,4-c]pyrrole-2(1H)-carboxamide

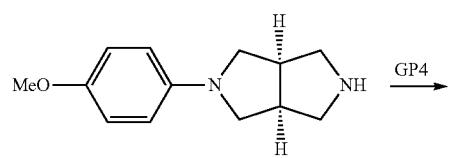

(See Ex. 15 for synthetic route)

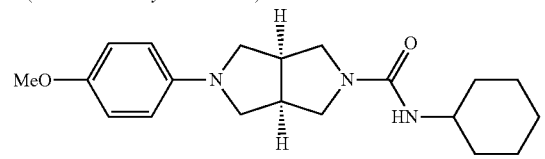

Ex. 16

The title compound was prepared using general procedure GP4—from crude 2-(4-methoxyphenyl)octahydropyrrolo[3,4-c]pyrrole (~1.08 mmol), triethylamine (1.5 mL, 10.8 mmol), cyclohexyl isocyanate (140 μL, 1.08 mmol) and DCM (4.0 mL); rt, 16 h. Purification by chromatography (MeOH/EtOAc 0→15%) gave the desired compound (260 mg, 70%) as an off-white solid. ¹H NMR ((CD₃)₂SO, 500 MHz): 1.01-1.26 (4H, m), 1.53-1.57 (2H, m), 1.64-1.74 (4H, m), 2.92-2.98 (2H, m), 3.04 (2H, dd, J=3.4, 9.5 Hz), 3.15 (2H, dd, J=3.6, 10.6 Hz), 3.22-3.40 (3H, m), 3.49 (2H, dd, J=7.7, 11.0 Hz), 3.65 (3H, s), 5.73 (1H, d, J=8.2 Hz), 6.51 (2H, d, J=9.2 Hz), 6.79 (2H, d, J=9.2 Hz); ¹³C NMR ((CD₃)₂SO, 125 MHz): 25.1, 25.4, 33.3, 41.2, 48.8, 50.5, 53.2, 55.3, 113.1, 114.6, 142.7, 150.7, 155.9. HRMS (ESI +ve). found 344.2335 [M+H⁺]; C₂₀H₃₀N₃O₂ requires 344.2333.

Example 17: cis-N-(2-Hydroxyethyl)-5-(4-methoxyphenyl)hexahydropyrrolo[3,4-c]pyrrole-2(1H)-carboxamide

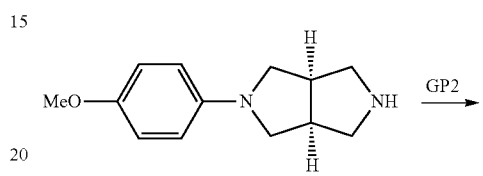

(See Ex. 15 for synthetic route)

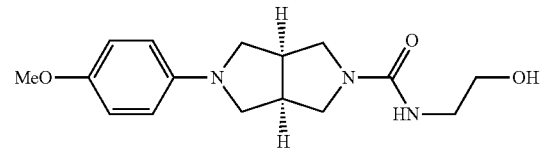

Ex. 17

The title compound was prepared using general procedure GP2—from crude 2-(4-methoxyphenyl)octahydropyrrolo[3,4-c]pyrrole (~1.08 mmol), diisopropylethylamine (1.9 mL, 10.8 mmol), triphosgene (193 mg, 0.65 mmol), ethanolamine (1.6 mL, 27.0 mmol), DCM (4.0 mL); rt, 1 h. Purification by chromatography (MeOH/EtOAc 0→10%) gave the desired compound (202 mg, 61%) as an off-white solid. ¹H NMR ((CD₃)₂SO, 500 MHz): 2.94-2.97 (2H, m), 3.03-3.10 (4H, m), 3.15 (2H, dd, J=3.7, 10.9 Hz), 3.32-3.38 (4H, m), 3.50 (2H, dd, J=7.3, 10.1 Hz), 3.65 (3H, s), 4.63 (1H, t, J=5.6 Hz), 6.10 (1H, t, J=5.4 Hz), 6.51 (2H, d, J=9.1 Hz), 6.79 (2H, d, J=9.1 Hz); ¹³C NMR ((CD₃)₂SO, 125 MHz): 41.3, 42.7, 50.5, 53.1, 55.3, 60.8, 113.1, 114.6, 142.7, 150.7, 156.8. HRMS (ESI +ve). found 306.1807 [M+H⁺]; C₁₆H₂₄N₃O₃ requires 306.1812.

Example 18: 4-Nitrophenyl 5-(4-ethoxyphenyl)hexahydropyrrolo[3,4-c]pyrrole-2(1H)-carboxylate

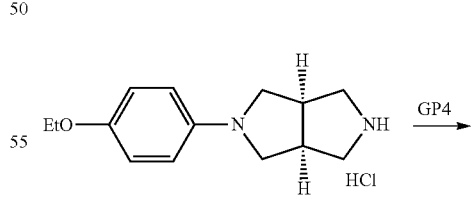

(See Ex. 1 for synthetic route)

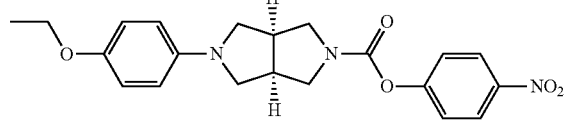

Ex. 18

The title compound was synthesised according to general procedures GP4—from 4-nitrophenyl chloroformate (500 mg, 2.5 mmol), 2-(4-ethoxyphenyl)octahydropyrrolo[3,4-c] pyrrole hydrochloride (600 mg, 2.2 mmol), trimethylamine (980 uL, 7 mmol) in THF (20 mL); rt, 48 h. The crude was purified by chromatography (EtOAc/cyclohexane 0→45%) to afford the desired compound (400 mg, 46%). $^1$H NMR (500 MHz, DMSO-$d_6$) δ 8.30-8.23 (m, 2H), 7.48-7.41 (m, 2H), 6.84-6.77 (m, 2H), 6.53 (d, J=8.9 Hz, 2H), 3.95-3.83 (m, 3H), 3.70 (dd, J=11.4, 7.5 Hz, 1H), 3.49 (dd, J=11.1, 4.6 Hz, 1H), 3.39-3.30 (m, 3H), 3.20 (td, J=9.6, 4.0 Hz, 2H), 3.08 (dtd, J=13.7, 7.2, 6.7, 3.7 Hz, 2H), 1.27 (t, J=6.9 Hz, 3H). MS (ESI) m/z 398 [M+H]+.

Example 19: cis-N-Ethyl-5-(4-((R)-3-hydroxypyrrolidin-1-yl)phenyl)hexahydro-pyrrolo[3,4-c]pyrrole-2(1H)-carboxamide 5H), 6.55 (br, 4H), 4.59 (d, J=15.0 Hz, 1H), 4.57 (d, J=15.0 Hz, 1H), 4.32 (m, 1H), 3.68-2.92 (m, 14H), 2.24-2.09 (m, 2H), 1.42 (s, 9H).

5-(4-((R)-3-(Benzyloxy)pyrrolidin-1-yl)phenyl)-N-ethyl-hexahydropyrrolo[3,4-c]pyrrole-2(1H)-carboxamide was synthesised according to general procedures GP1 and GP4—from i) tert-butyl 5-(4-((R)-3-(benzyloxy)pyrrolidin-1-yl)phenyl)hexahydropyrrolo[3,4-c]pyrrole-2(1H)-carboxylate (392 mg, 0.847 mmol), 4 M HCl in dioxane (4.2 mL) and DCM (4.2 mL); rt, 1 h. ii) Et$_3$N (590 μL, 4.23 mmol), EtNCO (87.1 μL, 1.10 mmol) and DCM (6.3 mL); rt, 16 h. Chromatography (THF/DCM 0→60%), beige solid (210 mg, 57%). $^1$H NMR (500 MHz, Acetone-$d_6$) δ 7.44-7.18 (m, 5H), 6.54 (br, 4H), 5.43 (br, 1H), 4.59 (d, J=15.0 Hz, 1H), 4.57 (d, J=15.0 Hz, 1H), 4.32 (m, 1H), 3.67-2.96 (m, 16H), 2.23-2.10 (m, 2H), 1.04 (t, J=7.2 Hz, 3H). MS (ESI) m/z 435 (M+H)$^+$

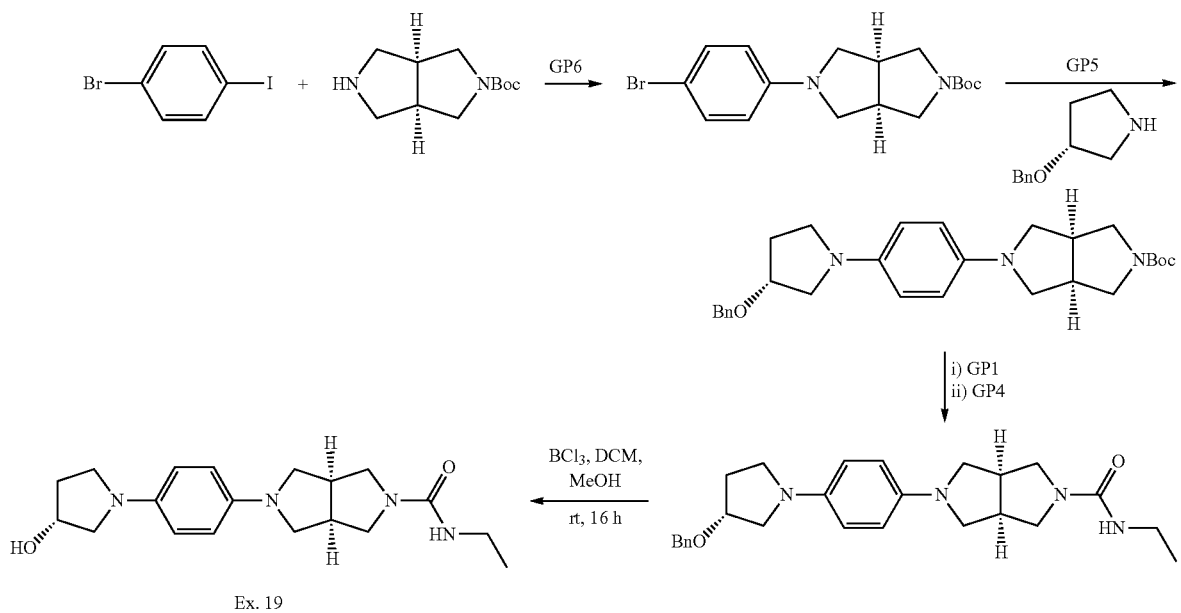

Ex. 19 tert-Butyl 5-(4-bromophenyl)hexahydropyrrolo[3,4-c]pyrrole-2(1H)-carboxylate was synthesised according to general procedures GP6—from 4-bromo-1-iodobenzene (1.39 g, 4.90 mmol), tert-butyl hexahydropyrrolo[3,4-c]pyrrole-2(1H)-carboxylate (800 mg, 3.77 mmol), CuI (72.1 mg, 10%), L-proline (86.8 mg, 20%), K$_2$CO$_3$ (67.7 mg, 4.90 mmol) and DMSO (19 mL); 90° C., 16 h. Chromatography (EtOAc/cyclohexane 0→25%), white solid (753 mg, 54%). $^1$H NMR (500 MHz, Acetone-$d_6$) δ 7.31-7.25 (m, 2H), 6.55-6.50 (m, 2H), 3.67-3.55 (m, 2H), 3.55-3.44 (m, 2H), 3.26 (dd, J=11.4, 3.9 Hz, 2H), 3.23-3.14 (m, 2H), 3.11-3.01 (m, 2H), 1.42 (s, 9H). MS (ESI) m/z 367/369 (M+H)$^+$ tert-Butyl 5-(4-((R)-3-(benzyloxy)pyrrolidin-1-yl)phenyl)hexahydropyrrolo[3,4-c]pyrrole-2(1H)-carboxylate was synthesised according to general procedures GP5—from Pd(OAc)$_2$ (20.0 mg, 5%), XPhos (65.2 mg, 10%), NaO$^t$Bu (157 mg, 1.64 mmol), tert-butyl 5-(4-bromophenyl)hexahydropyrrolo[3,4-c]pyrrole-2(1H)-carboxylate (500 mg, 1.37 mmol), (R)-3-(benzyloxy)pyrrolidine (290 mg, 1.64 mmol) and $^t$BuOH/toluene (1:5, 13.6 mL); 100° C., 16 h. Chromatography (EtOAc/cyclohexane 0→60%), white solid (397 mg, 63%). $^1$H NMR (500 MHz, Acetone-$d_6$) δ 7.44-7.19 (m, A mixture of 5-(4-((R)-3-(Benzyloxy)pyrrolidin-1-yl)phenyl)-N-ethylhexahydro-pyrrolo[3,4-c]pyrrole-2(1H)-carboxamide (210 mg, 0.484 mmol), BCl$_3$ (1.0 M in DCM; 2.42 mL, 2.42 mmol) and DCM (2.9 mL) was stirred at rt for 16 h. MeOH (2.9 mL) was added and the mixture was stirred at rt for 2 h, followed by the carefully addition of Et$_3$N (2.9 mL). After stirring for a further 0.5 h, the mixture was diluted with DCM (10 mL). The solution was washed with 0.5 M NaOH (20 mL), dried over MgSO$_4$, filtered and the solvent was removed under reduced pressure. The crude was purified by chromatography (THF/DCM 0→100%) to afford the title compound as a beige solid (139 mg, 84%). $^1$H NMR (500 MHz, DCl/Methanol-$d_4$ with DCM as internal standard) δ 7.59-7.52 (m, 2H), 7.11-7.06 (m, 2H), 4.71 (m, 1H), 3.93 (dd, J=12.3, 4.6 Hz, 1H), 3.86-3.80 (m, 2H), 3.79-3.70 (m, 4H), 3.57-3.49 (m, 3H), 3.45 (dd, J=10.7, 4.5 Hz, 2H), 3.30-3.26 (m, 4H), 2.40 (m, 1H), 2.26-2.19 (m, 1H), 1.17 (t, J=7.2 Hz, 3H). $^{13}$C NMR (126 MHz, DCl/Methanol-$d_4$ with DCM as internal standard) δ 158.46, 145.60, 139.00, 122.70, 117.28, 70.59, 66.06, 58.21, 56.10, 51.76, 42.72, 37.29, 35.13, 15.44. HRMS (ESI) for C$_{19}$H$_{29}$N$_4$O$_2$ ([M+H]$^+$): Calculated 345.2290. Observed 345.2272.

Example 20: cis-5-(4-((3-(Dimethylamino)propyl)(methyl)amino)phenyl)-N-ethylhexahydro-pyrrolo[3,4-c]pyrrole-2(1H)-carboxamide

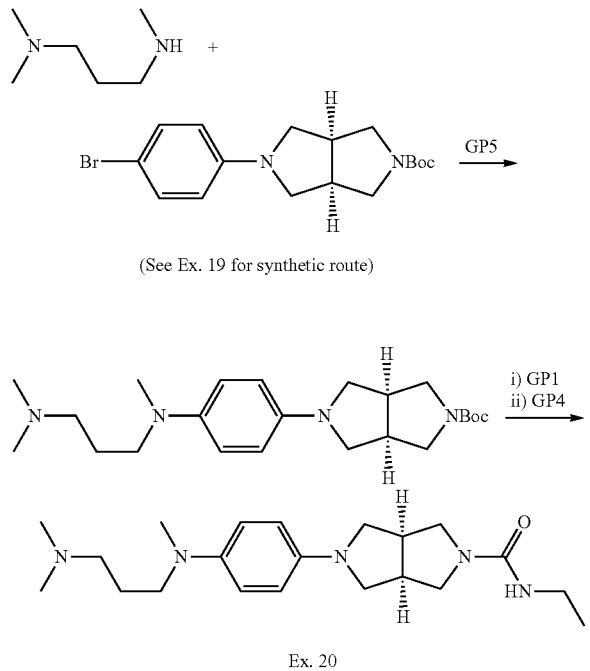

(See Ex. 19 for synthetic route)

Ex. 20 tert-Butyl 5-(4-((3-(dimethylamino)propyl)(methyl)amino)phenyl)hexahydropyrrolo-[3,4-c]pyrrole-2(1H)-carboxylate was synthesised according to general procedures GP5—from Pd(OAc)$_2$ (10.0 mg, 5%), XPhos (32.6 mg, 10%), NaO$^t$Bu (78.7 mg, 0.820 mmol), tert-butyl 5-(4-bromophenyl)hexahydropyrrolo[3,4-c]pyrrole-2(1H)-carboxylate (250 mg, 0.683 mmol), N,N,N-trimethylpropane-1,3-diamine (120 µL, 0.820 mmol) and $^t$BuOH/toluene (1:5, 6.8 mL); 100° C., 16 h. Chromatography (20% Et$_3$N in THF/DCM 0→60%), brown oil (197 mg, 72%). $^1$H NMR (500 MHz, Acetone-d$_6$) δ 6.78-6.69 (m, 2H), 6.59-6.52 (m, 2H), 3.69-3.54 (m, 2H), 3.44-3.34 (m, 2H), 3.31-3.20 (m, 4H), 3.18-3.09 (m, 2H), 3.01 (s, 2H), 2.79 (s, 3H), 2.25 (t, J=6.9 Hz, 2H), 2.15 (s, 6H), 1.70-1.61 (m, 2H), 1.43 (s, 9H). MS (ESI) m/z 403 (M+H)$^+$.

The title compound was synthesised according to general procedures GP1 and GP4—from i) tert-butyl 5-(4-((3-(dimethylamino)propyl)(methyl)amino)phenyl)hexahydro-pyrrolo[3,4-c]pyrrole-2(1H)-carboxylate (85 mg, 0.211 mmol), 4 M HCl in dioxane (1.5 mL) and DCM (1.5 mL); rt, 1 h. ii) Et$_3$N (441 µL, 3.16 mmol), EtNCO (21.7 µL, 0.274 mmol) and DCM (3.0 mL); rt, 16 h. Chromatography (20% Et$_3$N in THF/DCM 0→80%), brown solid (49 mg, 63%). $^1$H NMR (500 MHz, DCl/Methanol-d$_4$ with DCM as internal standard) δ 7.67-7.55 (m, 2H), 6.89-6.77 (m, 2H), 3.82-3.62 (m, 6H), 3.40 (dd, J=10.9, 3.8 Hz, 2H), 3.36-3.30 (m, 2H), 3.29-3.18 (m, 9H), 2.87 (s, 6H), 2.12-1.99 (m, 2H), 1.16 (t, J=7.2 Hz, 3H). $^{13}$C NMR (126 MHz, DCl/Methanol-d$_4$ with DCM as internal standard) δ 158.77, 149.11, 130.79, 123.21, 114.97, 56.87, 55.37, 53.83, 51.79, 46.68, 43.59, 42.98, 37.10, 21.97, 15.72. HRMS (ESI) for C$_{21}$H$_{36}$N$_5$O ([M+H]$^+$): Calculated 374.2920. Observed 374.2916.

Example 21: cis-4-(5-(4-Ethoxyphenyl)-3a,6a-dimethylhexahydropyrrolo[3,4-c]pyrrol-2(1H)-yl)butanenitrile

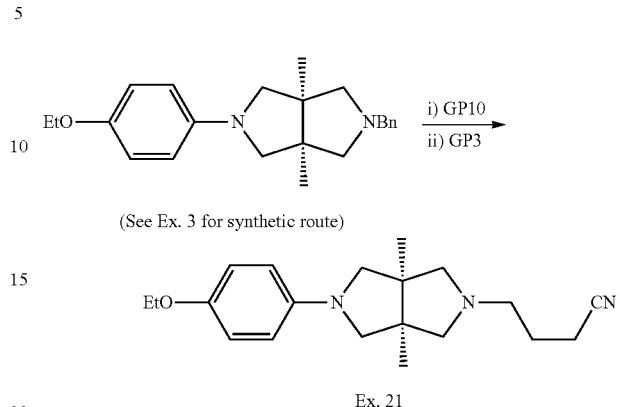

(See Ex. 3 for synthetic route)

Ex. 21

2-(4-Ethoxyphenyl)-3a,6a-di methylhexahydropyrrolo[3,4-c]pyrrole was synthesised according to general procedures GP10—from 2-benzyl-5-(4-ethoxyphenyl)-3a,6a-dimethyl-hexahydropyrrolo[3,4-c]pyrrole (1.0 g, 2.85 mmol), 10% Pd/C (606 mg, 20%), cyclohexadiene (2.70 mL, 28.5 mmol) and 2,2,2-trifluoroethanol (14.3 mL); 70° C., 3 h. The crude was purified by chromatography (2N NH$_3$ in MeOH/DCM 0→35%) to afford as a pink solid (536 mg, 72%). $^1$H NMR (500 MHz, Methanol-d$_4$) δ 6.81-6.77 (m, 2H), 6.64-6.56 (m, 2H), 3.95 (d, J=7.1 Hz, 1H), 3.93 (d, J=7.0 Hz, 1H), 3.41 (d, J=9.4 Hz, 2H), 3.04 (d, J=11.6 Hz, 2H), 2.91 (d, J=9.4 Hz, 2H), 2.78 (d, J=11.6 Hz, 2H), 1.33 (t, J=7.0 Hz, 3H), 1.11 (s, 6H). MS (ESI) m/z 261 (M+H)$^+$.

The title compound was synthesised according to general procedures GP3—from 4-bromobutanenitrile (243 µL, 2.45 mmol), 2-(4-ethoxyphenyl)-3a,6a-dimethylhexahydro-pyrrolo[3,4-c]pyrrole (530 mg, 2.04 mmol) and Et$_3$N (341 µL, 2.45 mmol) in DMF (10.2 mL); rt, 16 h. Chromatographic purification (THF/cyclohexane 0→50%) afforded a light brown oil (330 mg, 50%). $^1$H NMR (500 MHz, Acetone-d$_6$) δ 6.81-6.75 (m, 2H), 6.63-6.56 (m, 2H), 3.95 (d, J=7.0 Hz, 1H), 3.92 (d, J=7.0 Hz, 1H), 3.30 (d, J=9.1 Hz, 2H), 2.97 (d, J=9.1 Hz, 2H), 2.70 (d, J=8.8 Hz, 2H), 2.53-2.44 (m, 4H), 2.40 (d, J=9.0 Hz, 2H), 1.82-1.73 (m, 2H), 1.30 (t, J=7.0 Hz, 3H), 1.12 (s, 6H). $^{13}$C NMR (126 MHz, Acetone-d$_6$) δ 152.07, 144.90, 120.71, 116.14, 115.62, 68.74, 64.32, 64.25, 54.17, 50.11, 25.19, 21.70, 15.32, 14.91. HRMS (ESI) for C$_{20}$H$_{30}$N$_3$O ([M+H]$^+$): Calculated 328.2383. Observed 328.2390.

Example 22: cis-N-Ethyl-5-(4-(4-(methylsulfonyl)piperazin-1-yl)phenyl)hexahydro-pyrrolo[3,4-c]pyrrole-2(1H)-carboxamide

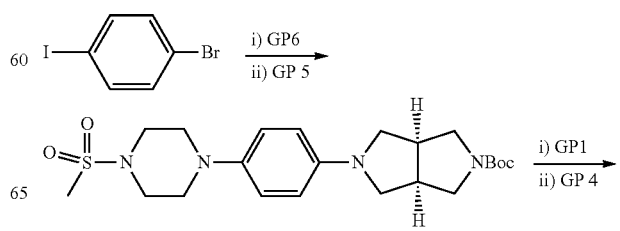

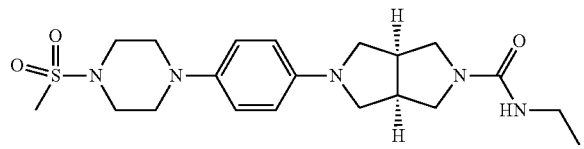

Ex. 22

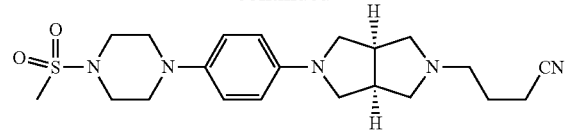

Ex. 23

1-(4-Bromophenyl)-4-(methylsulfonyl) piperazine was synthesised according to general procedures GP6—from 4-bromo-1-iodobenzene (2.0 g, 7.07 mmol), 1-(methylsulfonyl)piperazine (1.16 g, 7.07 mmol), CuI (135 mg, 10%), L-proline (81.3 mg, 10%), $K_2CO_3$ (1.17 g, 8.48 mmol) and DMSO (23.6 mL); 90° C., 16 h. Chromatography (THF/cyclohexane 0→10%), white solid (619 mg, 27%). $^1$H NMR (500 MHz, Chloroform-d) δ 7.45-7.35 (m, 2H), 6.93-6.82 (m, 2H), 3.47-3.38 (m, 4H), 3.32-3.25 (m, 4H), 2.85 (s, 3H). MS (ESI) m/z 319/321 (M+H)$^+$.

tert-Butyl 5-(4-(4-(methylsulfonyl)piperazin-1-yl)phenyl)hexahydropyrrolo[3,4-c]pyrrole-2(1H)-carboxylate was synthesised according to general procedures GP5—from Pd(OAc)$_2$ (56.7 mg, 5%), XPhos (184 mg, 10%), NaO$^t$Bu (444 mg, 4.63 mmol), tert-butyl hexahydropyrrolo[3,4-c]pyrrole-2(1H)-carboxylate (981 mg, 4.63 mmol), 1-(4-bromophenyl)-4-(methylsulfonyl)piperazine (1.23 g, 3.86 mmol) and $^t$BuOH/toluene (1:5, 19.3 mL); 100° C., 16 h. Chromatography (THF/DCM 0→100%, then 20% Et$_3$N in THF 100%), yellow solid (839 mg, 48%). MS (ESI) m/z 451 (M+H)$^+$.

The title compound was synthesised according to general procedures GP1 and GP4—from i) tert-butyl 5-(4-(4-(methylsulfonyl)piperazin-1-yl)phenyl)hexahydropyrrolo[3,4-c]pyrrole-2(1H)-carboxylate (200 mg, 0.444 mmol), 4 M HCl in dioxane (1.5 mL) and DCM (1.5 mL); rt, 1 h. ii) Et$_3$N (371 μL, 2.66 mmol), EtNCO (45.7 μL, 0.577 mmol) and DCM (3.0 mL); rt, 16 h. Chromatography (acetone/DCM 0→80%), white solid (125 mg, 67%). $^1$H NMR (500 MHz, DCl/Methanol-d$_4$ with DCM as internal standard) δ 7.67-7.61 (m, 2H), 6.90-6.83 (m, 2H), 3.83-3.71 (m, 10H), 3.70-3.63 (m, 2H), 3.42 (dd, J=10.9, 3.8 Hz, 2H), 3.37-3.33 (m, 2H), 3.29-3.19 (m, 4H), 3.03 (s, 3H), 1.16 (t, J=7.2 Hz, 3H). $^{13}$C NMR (126 MHz, DCl/Methanol-d$_4$ with DCM as internal standard) δ 158.59, 148.26, 133.08, 122.80, 115.27, 56.06, 54.24, 51.76, 44.44, 42.84, 37.15, 35.98, 15.53. HRMS (ESI) for $C_{20}H_{32}N_5O_3S$ ([M+H]$^+$): Calculated 422.2220. Observed 422.2203.

Example 23: cis-4-(5-(4-(4-(Methylsulfonyl)piperazin-1-yl)phenyl)hexahydropyrrolo[3,4-c]pyrrol-2(1H)-yl)butanenitrile

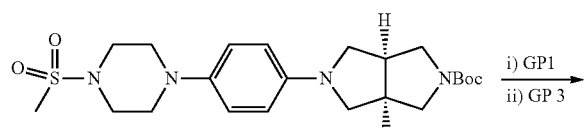

(see Ex. 22 for synthetic route)

The title compound was synthesised according to general procedures GP1 and GP3—from i) tert-butyl 5-(4-(4-(methylsulfonyl)piperazin-1-yl)phenyl)hexahydropyrrolo[3,4-c]pyrrole-2(1H)-carboxylate (200 mg, 0.444 mmol), 4 M HCl in dioxane (1.5 mL) and DCM (1.5 mL); rt, 1 h. ii) $K_2CO_3$ (368 mg, 2.66 mmol), 4-bromobutanenitrile (132 μL, 1.35 mmol) and DMF (3.0 mL); 90° C., 16 h. Chromatography (20% Et$_3$N in THF/DCM 0→80%), white solid (55 mg, 30%). $^1$H NMR (500 MHz, DMSO-d$_6$) δ 6.91-6.82 (m, 2H), 6.64-6.55 (m, 2H), 3.31-3.19 (m, 6H), 3.08-3.00 (m, 4H), 2.94 (dd, J=9.1, 3.2 Hz, 2H), 2.91 (s, 3H), 2.85-2.78 (m, 2H), 2.65-2.57 (m, 2H), 2.47 (t, J=7.1 Hz, 2H), 2.41 (t, J=6.9 Hz, 2H), 2.39-2.33 (m, 2H), 1.70 (p, J=7.1 Hz, 2H). $^{13}$C NMR (126 MHz, DMSO-d$_6$) δ 143.67, 142.35, 120.65, 118.33, 114.58, 59.95, 54.92, 53.14, 49.90, 45.54, 41.05, 33.75, 23.90, 14.19. HRMS (ESI) for $C_{21}H_{32}N_5O_2S$ ([M+H]$^+$): Calculated 418.2271. Observed 418.2254.

Example 24: cis-4-(5-(4-((3-(Dimethylamino)propyl)(methyl)amino)phenyl)hexahydro-pyrrolo[3,4-c]pyrrol-2(1H)-yl)butanenitrile

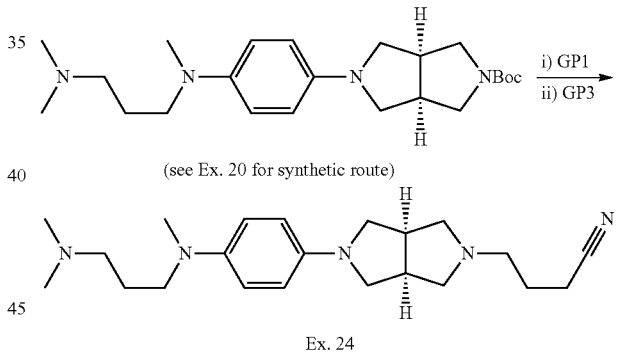

Ex. 24

The title compound was synthesised according to general procedures GP1 and GP3—from i) tert-butyl 5-(4-((3-(dimethylamino)propyl)(methyl)amino)phenyl)-hexahydropyrrolo[3,4-c]pyrrole-2(1H)-carboxylate (200 mg, 0.498 mmol), 4 M HCl in dioxane (1.5 mL) and DCM (1.5 mL); rt, 1 h. ii) $K_2CO_3$ (412 mg, 2.99 mmol), 4-bromobutanenitrile (742 μL, 7.46 mmol) and DMF (2.5 mL); 90° C., 16 h. Chromatography (20% Et$_3$N in THF/DCM 0→60%), colourless oil (95 mg, 52%). $^1$H NMR (500 MHz, DCl/Methanol-d$_4$ with DCM as internal standard) for a mixture of the two major rotamers δ 7.62-7.56 (m, 2H), 7.01-6.92 (m, 2H), 4.06 (m, 1H), 3.77-3.57 (m, 5H), 3.56-3.31 (m, 6H), 3.29-3.19 (m, 6H), 3.07-2.98 (m, 1H), 2.86 (s, 6H), 2.66 (q, J=7.2 Hz, 2H), 2.20-2.11 (m, 2H), 2.08-1.99 (m, 2H). $^{13}$C NMR (126 MHz, DCl/Methanol-d$_4$ with DCM as internal standard) for a mixture of the two major rotamers δ 150.24, 149.28, 131.81, 131.45, 125.91, 122.92, 122.82, 122.72, 119.75, 116.51, 116.39, 60.43, 59.80, 56.65, 56.57, 55.19, 55.16, 54.85, 53.69, 53.34, 46.40, 46.26, 43.41, 41.76, 41.65, 22.95, 22.75, 21.79, 14.92, 14.89. HRMS (ESI) for $C_{22}H_{36}N_5$ ([M+H]$^+$): Calculated 370.2965. Observed 370.2960.

Example 25: cis-5-(4-((3-(Dimethylamino)propyl)(methyl)amino)phenyl)-N-(2-hydroxyethyl)hexahydropyrrolo[3,4-c]pyrrole-2(1H)-carboxamide

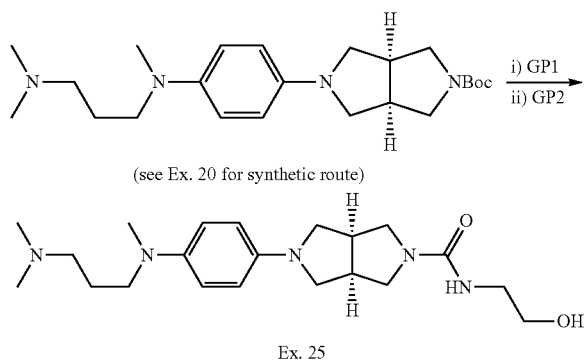

(see Ex. 20 for synthetic route)

Ex. 25

The title compound was synthesised according to general procedures GP1 and GP2—from i) tert-butyl 5-(4-((3-(dimethylamino)propyl)(methyl)amino)phenyl)hexahydro-pyrrolo[3,4-c]pyrrole-2(1H)-carboxylate (200 mg, 0.498 mmol), 4 M HCl in dioxane (1.5 mL) and DCM (1.5 mL); rt, 1 h. ii) triphosgene (73.8 mg, 0.249 mmol), DIPEA (519 μL, 2.99 mmol) and DCM (2.5 mL), rt, 1 h then ethanolamine (90.1 μL, 1.49 mmol); rt ° C., 16 h. Chromatography (20% Et$_3$N in EtOH/DCM 0→60%), brown solid (23 mg, 12%). $^1$H NMR (500 MHz, DCl/Methanol-d$_4$ with DCM as internal standard) δ 7.61-7.54 (m, 2H), 6.86-6.75 (m, 2H), 3.80-3.57 (m, 8H), 3.43-3.28 (m, 6H), 3.27-3.15 (m, 7H), 2.86 (s, 6H), 2.08-1.97 (m, 2H). $^{13}$C NMR (126 MHz, DCl/Methanol-d$_4$ with DCM as internal standard) δ 159.21, 149.09, 130.40, 122.99, 114.60, 62.22, 56.71, 55.23, 53.55, 51.54, 46.54, 44.26, 43.46, 42.88, 21.85. HRMS (ESI) for $C_{21}H_{36}N_5O_2$ ([M+H]$^+$): Calculated 390.2864. Observed 390.2850.

Example 26: cis-N-(2-Hydroxyethyl)-5-(4-(4-(methylsulfonyl)piperazin-1-yl)phenyl)hexahydro-pyrrolo[3,4-c]pyrrole-2(1H)-carboxamide

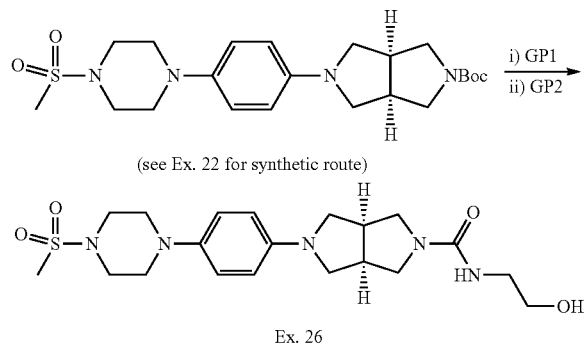

(see Ex. 22 for synthetic route)

Ex. 26

The title compound was synthesised according to general procedures GP1 and GP2—from i) tert-butyl 5-(4-(4-(methylsulfonyl)piperazin-1-yl)phenyl)hexahydropyrrolo[3,4-c]pyrrole-2(1H)-carboxylate (200 mg, 0.444 mmol), 4 M HCl in dioxane (1.5 mL) and DCM (1.5 mL); rt, 1 h. ii) triphosgene (52.7 mg, 0.178 mmol), DIPEA (463 μL, 2.66 mmol) and DCM (2.5 mL), rt, 1 h then ethanolamine (80.4 μL, 1.33 mmol); rt ° C., 16 h. Chromatography (propan-2-ol/DCM 0→45%), white solid (42 mg, 22%). $^1$H NMR (500 MHz, DCl/Methanol-d$_4$ with DCM as internal standard) δ 7.67-7.61 (m, 2H), 6.94-6.85 (m, 2H), 3.82-3.72 (m, 10H), 3.70-3.63 (m, 4H), 3.49-3.43 (m, 2H), 3.41-3.34 (m, 4H), 3.28-3.21 (m, 2H), 3.03 (s, 3H). $^{13}$C NMR (126 MHz, DCl/Methanol-d$_4$ with DCM as internal standard) δ 159.19, 148.13, 133.19, 122.81, 122.81, 122.71, 115.36, 62.21, 56.05, 54.31, 51.76, 44.53, 44.44, 42.87, 35.97. HRMS (ESI) for $C_{20}H_{32}N_5O_4S$ ([M+H]$^+$): Calculated 438.2170. Observed 438.2154.

Example 27: cis-N-Ethyl-3a,6a-dimethyl-5-(4-(4-(methylsulfonyl)piperazin-1-yl)phenyl)hexahydropyrrolo[3,4-c]pyrrole-2(1H)-carboxamide

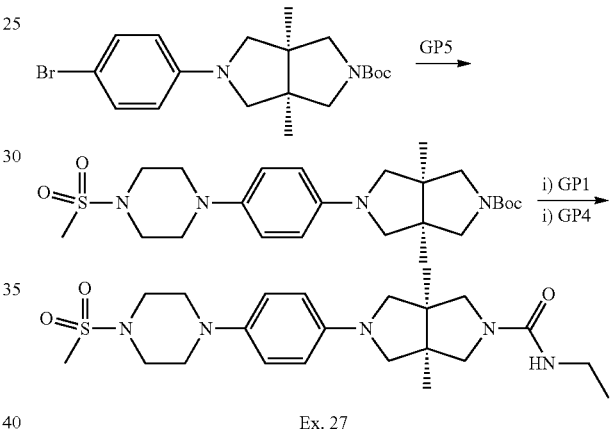

Ex. 27 tert-Butyl 3a,6a-dimethyl-5-(4-(4-(methylsulfonyl)piperazin-1-yl)phenyl)hexahydropyrrolo[3,4-c]pyrrole-2(1H)-carboxylate was synthesised according to general procedures GP5—from Pd(OAc)$_2$ (37.3 mg, 5%), XPhos (121 mg, 10%), NaO$^t$Bu (292 mg, 3.05 mmol), tert-butyl 5-(4-bromophenyl)-3a,6a-dimethylhexahydropyrrolo[3,4-c]pyrrole-2(1H)-carboxylate (1.0 g, 3.07 mmol), 1-(methylsulfonyl)piperazine (499 mg, 3.05 mmol) and tBuOH/toluene (1:5, 12.7 mL); 100° C., 6 h. Chromatography (THF/cyclohexane 0→60), orange solid (702 mg, 48%). 1H NMR (500 MHz, Acetone-d6) δ 6.95-6.90 (m, 2H), 6.52-6.45 (m, 2H), 3.46 (d, J=11.1 Hz, 2H), 3.38 (d, J=9.5 Hz, 2H), 3.36-3.26 (m, 6H), 3.25-3.20 (m, 2H), 3.12-3.06 (m, 4H), 2.87 (s, 3H), 1.43 (s, 9H), 1.15 (s, 6H). MS (ESI) m/z 479 (M+H)+.

The title compound was synthesised according to general procedures GP1 and GP4—from i) tert-Butyl 3a,6a-dimethyl-5-(4-(4-(methylsulfonyl)piperazin-1-yl)phenyl)hexahydropyrrolo[3,4-c]pyrrole-2(1H)-carboxylate (200 mg, 0.418 mmol), 4 M HCl in dioxane (2.0 mL) and DCM (2.0 mL); rt, 1 h. ii) Et$_3$N (350 μL, 2.51 mmol), EtNCO (40.0 μL, 0.502 mmol) and DCM (2.8 mL); rt, 16 h. Chromatography (THF/cyclohexane 0→50%), white solid (182 mg, 97%). $^1$H NMR (500 MHz, DCl/Methanol-d$_4$ with DCM as internal standard) δ 7.64-7.57 (m, 2H), 6.70-6.64 (m, 2H), 3.83-3.73 (m, 8H), 3.55 (d, J=10.8 Hz, 2H), 3.48 (d, J=10.1 Hz, 2H), 3.43 (d, J=10.7 Hz, 2H), 3.35-3.31 (m, 2H), 3.25 (q, J=7.2 Hz, 2H), 3.03 (s, 3H), 1.19 (s, 6H), 1.15 (t, J=7.2 Hz, 3H).

HRMS (ESI) for $C_{22}H_{36}N_5O_3S$ ([M+H]$^+$): Calculated 450.2533. Observed 450.2503.

Synthesis of tert-Butyl 5-(4-bromophenyl)-3a,6a-dimethylhexahydropyrrolo[3,4-o]pyrrole-2(1H)-carboxylate

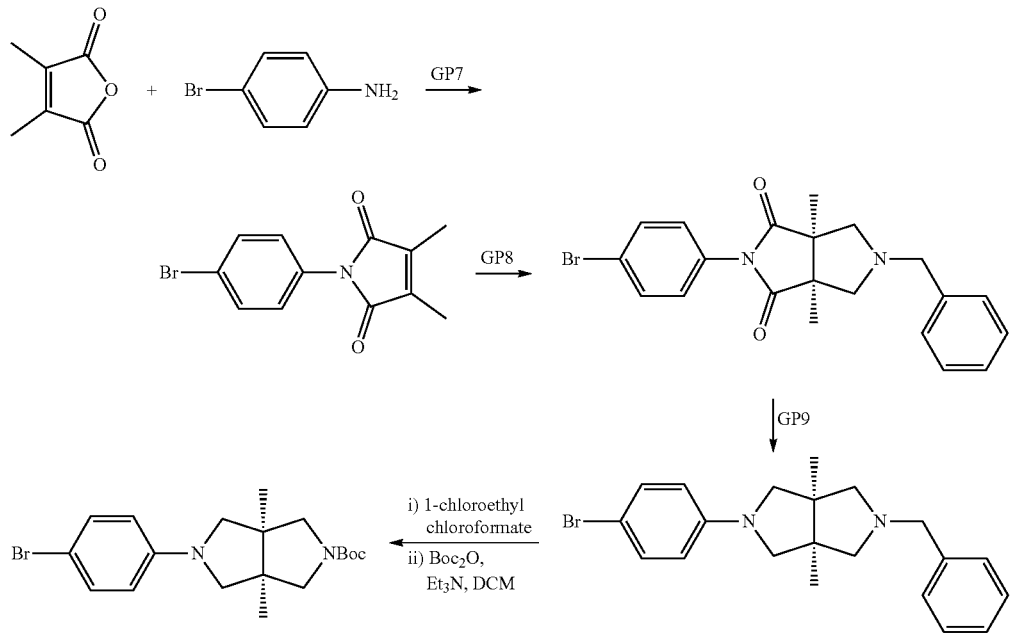

1-(4-Bromophenyl)-3,4-dimethyl-1H-pyrrole-2,5-dione was synthesised according to general procedures GP7—from 4-bromoaniline (1.37 g, 7.94 mmol), 3,4-dimethylfuran-2,5-dione (1.0 g, 7.94 mmol) and AcOH (8.0 mL); 100° C., 16 h. The crude was purified by chromatography (EtOAc/cyclohexane 0→50%) to afford a white solid (1.74 g, 79%). $^1$H NMR (500 MHz, Chloroform-d) δ 7.61-7.56 (m, 2H), 7.31-7.26 (m, 2H), 2.07 (s, 6H). MS (ESI) m/z 280/282 (M+H)$^+$.

5-Benzyl-2-(4-bromophenyl)-3a,6a-dimethyltetrahydropyrrolo[3,4-c]pyrrole-1,3(2H,3aH)-dione was synthesised according to general procedures GP8—from N-benzyl-1-methoxy-N-((trimethylsilyl)methyl)methanamine (39.0 g, 165 mmol), trifluoroacetic acid (2.90 mL, 30%) and 1-(4-bromophenyl)-3,4-dimethyl-1H-pyrrole-2,5-dione (35.4 g, 127 mmol) in DCM (211 mL); rt, 20 h. The crude was recrystallized from EtOAc/cyclohexane to afford a white crystalline solid (38.5 g, 73%). $^1$H NMR (500 MHz, Acetone-d$_6$) δ 7.74-7.67 (m, 2H), 7.35-7.21 (m, 7H), 3.59 (s, 2H), 3.42-3.34 (m, 2H), 2.28-2.23 (m, 2H), 1.33 (s, 6H). MS (ESI) m/z 413/415 (M+H)$^+$.

2-Benzyl-5-(4-bromophenyl)-3a,6a-dimethyloctahydropyrrolo[3,4-c]pyrrole was synthesised according to general procedures GP9—from BH$_3$·THF (1.0 M; 194 mL, 194 mmol), 5-benzyl-2-(4-bromophenyl)-3a,6a-dimethyltetrahydropyrrolo[3,4-c]pyrrole-1,3(2H,3aH)-dione (20.0 g, 48.4 mmol) and 1,4-dioxane (194 mL); 90° C., 16 h. The crude was purified by chromatography (THF/cyclohexane 0→25%) to afford a colourless syrup (13.8 g, 74%). $^1$H NMR (500 MHz, Chloroform-d) δ 7.34-7.19 (m, 7H), 6.51-6.44 (m, 2H), 3.60 (s, 2H), 3.39 (d, J=9.3 Hz, 2H), 3.08 (d, J=9.3 Hz, 2H), 2.78 (d, J=9.2 Hz, 2H), 2.47-2.38 (m, 2H), 1.13 (s, 6H). MS (ESI) m/z 385/387 (M+H)$^+$.

1-Chloroethyl chloroformate (4.62 mL, 42.8 mmol) was added to a solution of 2-benzyl-5-(4-bromophenyl)-3a,6a-dimethyloctahydropyrrolo[3,4-c]pyrrole (13.7 g, 35.7 mmol) in MeCN (119 mL) and the mixture was stirred at 70° C. for 1 h. After cooling to rt, the solvent was removed under reduced pressure. DCM (119 mL) was added, followed by Et$_3$N (14.9 mL, 107 mmol) and Boc$_2$O (9.82 mL, 42.8 mmol) and the mixture was stirred at rt for 16 h. The solvent was removed under reduced pressure. Cyclohexane (200 mL) was added and the suspension was stirred for 10 min. The mixture was filtered and the solids were washed with more cyclohexane portions. The filtrates were collected and the solvent was removed under reduced pressure. The crude was purified by chromatography (EtOAc/cyclohexane 0→20%) to afford tert-butyl 5-(4-bromophenyl)-3a,6a-dimethylhexahydropyrrolo[3,4-c]pyrrole-2(1H)-carboxylate as a white solid (14.1 g, quant.). $^1$H NMR (500 MHz, Chloroform-d) δ 7.32-7.28 (m, 2H), 6.40-6.35 (m, 2H), 3.62-3.12 (m, 8H), 1.46 (s, 9H), 1.14 (s, 6H). MS (ESI) m/z 339/341 (M-$^t$Bu+2H)$^+$.

Example 28: cis-N-(2-Hydroxyethyl)-3a,6a-dimethyl-5-(4-(4-(methylsulfonyl)piperazin-1-yl)phenyl)hexahydropyrrolo[3,4-c]pyrrole-2(1H)-carboxamide

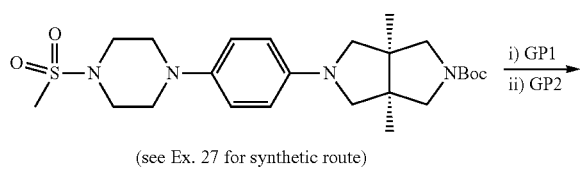

(see Ex. 27 for synthetic route)

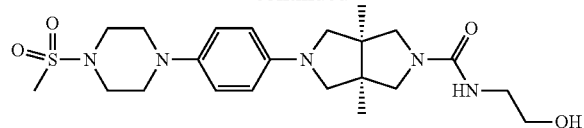

Ex. 28

The title compound was synthesised according to general procedures GP1 and GP2—from i) tert-Butyl 3a,6a-dimethyl-5-(4-(4-(methylsulfonyl)piperazin-1-yl)phenyl)hexahydropyrrolo[3,4-c]pyrrole-2(1H)-carboxylate (200 mg, 0.418 mmol), 4 M HCl in dioxane (2.0 mL) and DCM (2.0 mL); rt, 1 h. ii) triphosgene (49.7 mg, 0.167 mmol), DIPEA (437 μL, 2.51 mmol) and DCM (2.8 mL), rt, 15 min then ethanolamine (101 μL, 1.67 mmol); rt, 16 h. Chromatography (20% Et$_3$N in THF/DCM 0→100%), light yellow solid (103 mg, 53%). $^1$H NMR (500 MHz, DCl/Methanol-d$_4$ with DCM as internal standard) δ 7.65-7.57 (m, 2H), 6.72-6.64 (m, 2H), 3.84-3.72 (m, 8H), 3.65 (t, J=5.5 Hz, 2H), 3.58 (d, J=10.8 Hz, 2H), 3.51-3.43 (m, 4H), 3.39-3.32 (m, 4H), 3.04 (s, 3H), 1.20 (s, 6H). $^{13}$C NMR (500 MHz, DCl/Methanol-d$_4$ with DCM as internal standard) δ 159.40, 149.80, 130.76, 122.97, 113.35, 62.31, 58.93, 57.57, 56.54, 50.72, 44.53, 44.46, 36.14, 18.71. HRMS (ESI) for C$_{22}$H$_{36}$N$_5$O$_4$S ([M+H]$^+$): Calculated 466.2483. Observed 466.2450.

Example 29: cis-4-(3a,6a-Dimethyl-5-(4-(4-(methylsulfonyl)piperazin-1-yl)phenyl)hexahydro-pyrrolo[3,4-c]pyrrol-2(1H)-yl)butanenitrile

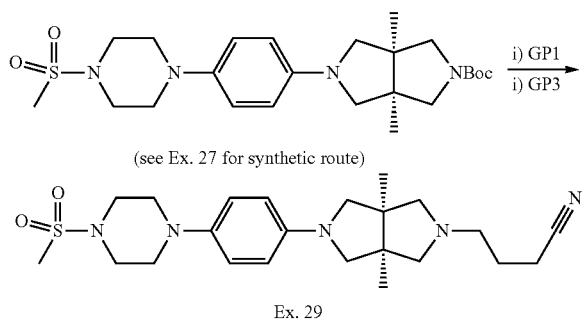

Ex. 29

The title compound was synthesised according to general procedures GP1 and GP3—from i) tert-Butyl 3a,6a-dimethyl-5-(4-(4-(methylsulfonyl)piperazin-1-yl)phenyl)hexahydropyrrolo[3,4-c]pyrrole-2(1H)-carboxylate (200 mg, 0.418 mmol), 4 M HCl in dioxane (2.0 mL) and DCM (2.0 mL); rt, 1 h. ii) K$_2$CO$_3$ (346 mg, 2.51 mmol), 4-bromobutanenitrile (166 μL, 1.67 mmol) and DMF (2.8 mL); rt, 16 h. Chromatography (20% Et$_3$N in THF/DCM 0→60%), white solid (100 mg, 54%). $^1$H NMR (500 MHz, DCl/Methanol-d$_4$ with DCM as internal standard) for a mixture of rotamers δ 7.68-7.61 (m, 2H), 6.89-6.81 (m, 2H), 3.94-3.71 (m, 12H), 3.44-3.32 (m, 4H), 3.14 (dd, J=10.6, 1.8 Hz, 2H), 3.03 (s, 3H), 2.63 (t, J=7.3 Hz, 2H), 2.23-2.11 (m, 2H), 1.31 (s, 3H), 1.30 (s, 3H). $^{13}$C NMR (126 MHz, DCl/Methanol-d$_4$ with DCM as internal standard) for a mixture of rotamers δ 150.12, 149.97, 132.25, 132.08, 122.91, 122.82, 119.78, 115.61, 115.18, 65.89, 65.50, 60.97, 60.42, 56.36, 56.20, 55.96, 54.78, 51.31, 50.91, 44.33, 36.03, 22.80, 19.54, 19.51, 14.91. HRMS (ESI) for C$_{23}$H$_{36}$N$_5$O$_2$S ([M+H]$^+$): Calculated 446.2864. Observed 446.2566.

Example 30: cis-5-(4-(1,1-Dioxidothiomorpholino)phenyl)-N-(2-hydroxyethyl)-3a,6a-dimethylhexahydropyrrolo[3,4-c]pyrrole-2(1H)-carboxamide

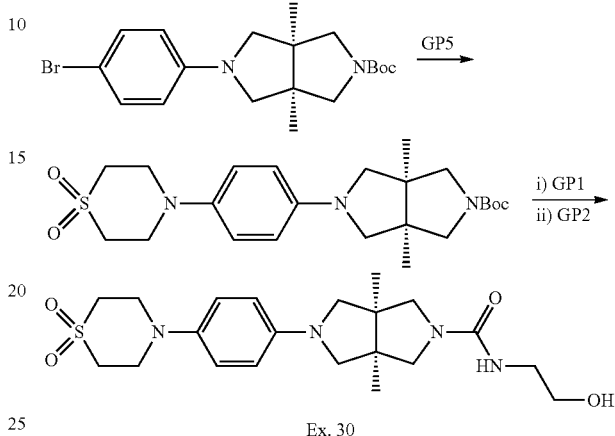

Ex. 30 tert-Butyl 5-(4-(1,1-dioxidothiomorpholino)phenyl)-3a,6a-dimethylhexahydro-pyrrolo[3,4-c]pyrrole-2(1H)-carboxylate was synthesised according to general procedures GP5—from Pd(OAc)$_2$ (37.3 mg, 5%), XPhos (121 mg, 10%), NaO$^t$Bu (292 mg, 3.05 mmol), tert-butyl 5-(4-bromophenyl)-3a,6a-dimethylhexahydropyrrolo[3,4-c]pyrrole-2(1H)-carboxylate (1.0 g, 3.07 mmol), thiomorpholine 1,1-dioxide (411 mg, 3.05 mmol) and $^t$BuOH/toluene (1:5, 12.7 mL); 100° C., 6 h. Chromatography (THF/cyclohexane 0→60), yellow foam (668 mg, 49%). $^1$H NMR (500 MHz, Acetone-d$_6$) δ 7.01-6.94 (m, 2H), 6.51-6.44 (m, 2H), 3.61-3.55 (m, 4H), 3.46 (d, J=11.1 Hz, 2H), 3.38 (d, J=9.5 Hz, 2H), 3.34-3.19 (m, 4H), 3.12-3.07 (m, 4H), 1.42 (s, 9H), 1.15 (s, 6H). MS (ESI) m/z 450 (M+H)$^+$.

The title compound was synthesised according to general procedures GP1 and GP2—from i) tert-butyl 5-(4-(1,1-dioxidothiomorpholino)phenyl)-3a,6a-dimethylhexahydropyrrolo[3,4-c]pyrrole-2(1H)-carboxylate (200 mg, 0.445 mmol), 4 M HCl in dioxane (2.0 mL) and DCM (2.0 mL); rt, 1 h. ii) triphosgene (52.9 mg, 0.178 mmol), DIPEA (465 μL, 2.67 mmol) and DMF (3.0 mL), rt, 15 min then ethanolamine (107 μL, 1.78 mmol); rt, 16 h. Chromatography (20% Et$_3$N in THF/DCM 0→80%), light yellow foam (55 mg, 28%). $^1$H NMR (500 MHz, Methanol-d$_4$) $^1$H NMR (500 MHz, Methanol-d$_4$) δ 6.96 (s, 2H), 6.49 (s, 2H), 3.67-3.45 (m, 8H), 3.36 (s, 8H), 3.18-3.12 (m, 4H), 1.16 (s, 6H). HRMS (ESI) for C$_{21}$H$_{33}$N$_4$O$_4$S ([M+H]$^+$): Calculated 437.2217. Observed 437.2177.

Example 31: cis-4-(3a,6a-Dimethyl-5-(4-(4-(methylsulfonyl)piperazin-1-yl)phenyl)hexahydropyrrolo[3,4-c]pyrrol-2(1H)-yl)butanenitrile

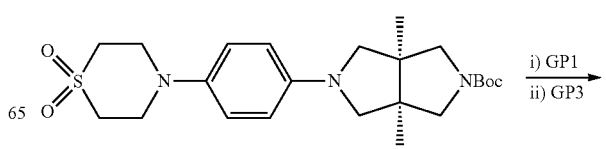

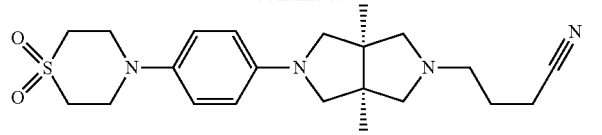

Ex. 31

The title compound was synthesised according to general procedures GP1 and GP3—from i) tert-butyl 5-(4-(1,1-dioxidothiomorpholino)phenyl)-3a,6a-dimethylhexahydropyrrolo[3,4-c]pyrrole-2(1H)-carboxylate (200 mg, 0.445 mmol), 4 M HCl in dioxane (2.0 mL) and DCM (2.0 mL); rt, 1 h. ii) $K_2CO_3$ (369 mg, 2.67 mmol), 4-bromobutanenitrile (177 μL, 1.78 mmol) and DMF (3.0 mL); rt, 16 h. Chromatography (20% $Et_3N$ in THF/DCM 0→40%), light yellow solid (105 mg, 56%). $^1$H NMR (500 MHz, DCl/Methanol-$d_4$ with DCM as internal standard) δ 7.54-7.48 (m, 2H), 7.42-7.21 (m, 2H), 4.15-3.96 (m, 7H), 3.76 (s, 2H), 3.60 (dt, J=11.3, 4.8 Hz, 4H), 3.54-3.35 (m, 5H), 2.70-2.64 (m, 2H), 2.25-2.16 (m, 2H), 1.42 (s, 6H). HRMS (ESI) for $C_{22}H_{33}N_4O_2S$ ([M+H]$^+$): Calculated 417.2319. Observed 417.2302.

Example 32: cis-4-(5-(4-(1,1-Dioxidothiomorpholino)phenyl)hexahydropyrrolo[3,4-c]pyrrol-2(1H)-yl)butanenitrile

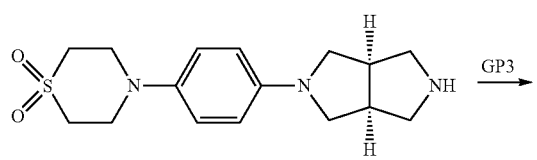

Ex. 32

The title compound was synthesised according to general procedures GP3—from 4-bromobutanenitrile (52.0 μL, 0.523 mmol), 4-(4-(hexahydropyrrolo[3,4-c]pyrrol-2(1H)-yl)phenyl)thiomorpholine 1,1-dioxide (140 mg, 0.436 mmol), $K_2CO_3$ (120 mg, 0.872 mmol) and DMF (4.4 mL); 60° C., 3 h. Chromatographic purification (THF/DCM 0→100%) afforded a white solid (116 mg, 69%). $^1$H NMR (500 MHz, Acetone-$d_6$) δ 6.97 (dd, J=8.7, 1.9 Hz, 2H), 6.68-6.64 (m, 2H), 3.66-3.59 (m, 4H), 3.42-3.35 (m, 2H), 3.15-3.09 (m, 4H), 3.04 (dd, J=9.2, 3.4 Hz, 2H), 2.94-2.88 (m, 2H), 2.70-2.64 (m, 2H), 2.52-2.47 (m, 6H), 1.81 (p, J=6.9 Hz, 2H). $^{13}$C NMR (126 MHz, Acetone) δ 145.31, 141.56, 138.29, 120.01, 115.64, 60.95, 55.92, 54.03, 51.67, 50.33, 42.51, 25.29, 14.97. HRMS (ESI) for $C_{20}H_{29}N_4O_2S$ ([M+H]$^+$): Calculated 389.2006. Observed 389.1987.

Example 33: cis-(1,1-Dioxidothiomorpholino)-5-(4-(1,1-dioxidothiomorpholino)phenyl)-3a,6a-dimethylhexahydropyrrolo[3,4-c]pyrrol-2(1H)-yl)methanone

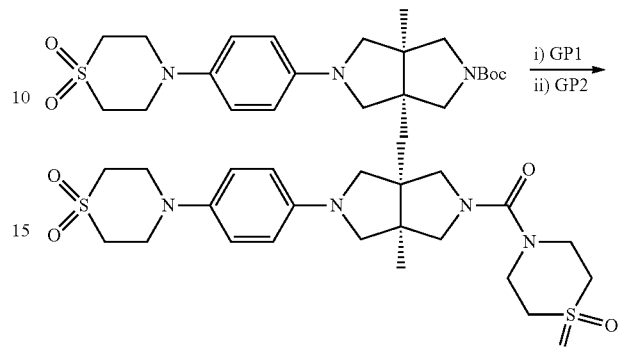

Ex. 33

The title compound was synthesised using general procedures GP1 and GP2 from i) tert-butyl 5-(4-(1,1-dioxidothiomorpholino)phenyl)-3a,6a-dimethylhexahydropyrrolo[3,4-c]pyrrole-2(1H)-carboxylate (130 mg, 0.289 mmol) and 4 M HCl in dioxane (2.9 mL) at rt for 1 h then ii) triphosgene (43 mg, 0.145 mmol), TEA (403 μL, 2.89 mmol) and DCM (3.0 mL at rt for 15 min then thiomorpholine-1,1-dioxide (195.3 mg, 1.45 mmol) at rt for 2 days. Purification by chromatography (MeOH/EtOAc 0→5%) then preparative HPLC (MeOH/$H_2O$ 40→100%+0.1% HCOOH) gave a white solid (26.6 mg, 18%). $^1$H NMR (500 MHz, DMSO-$d_6$) δ 6.94-6.89 (m, 2H), 6.43-6.39 (m, 2H), 3.60-3.45 (m, 10H), 3.34-3.26 (m, 4H), 3.16-3.08 (m, 10H), 1.06 (s, 6H). HRMS calcd for $C_{23}H_{35}N_4O_5S_2$ (M+H$^+$) 511.2049. found 511.2015.

Example 34: cis-(1,1-Dioxidothiomorpholino)(5-(4-ethoxyphenyl)hexahydropyrrolo[3,4-c]pyrrol-2(1H)-yl)methanone

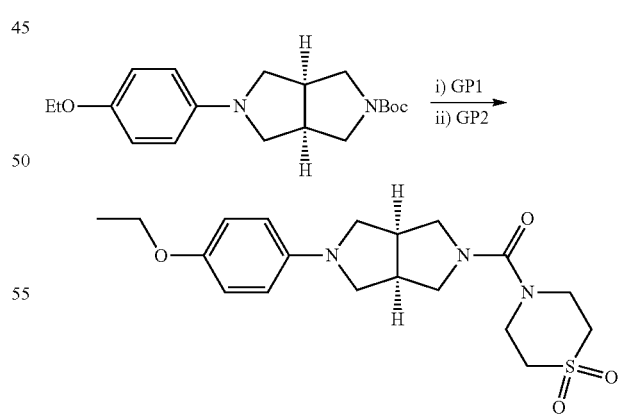

Ex. 34

The title compound was prepared using general procedures GP1 and GP2 from i) tert-butyl-5-(4-ethoxyphenyl)-hexahydropyrrolo[3,4-c]pyrrole-2(1H)-carboxylate (87.1 mg, 0.26 mmol) and HCl (4.0 M in dioxane, 1.31 mL) at rt for 1 h, then ii) N,N-diisopropylethylamine (182 μL, 1.05 mmol), triphosgene (38.9 mg, 0.13 mmol), thiomorpholine-1,1-dioxide (141.7 mg, 1.05 mmol) and dichloromethane (2.0 mL) at rt for 16 h. Purification by chromatography (MeOH/EtOAc 0→10%) then preparative HPLC (MeOH/H$_2$O 10→100%+0.1% HCOOH) gave a white solid (27.6 mg, 27%). $^1$H NMR (300 MHz, DMSO-d$_6$) δ 6.83-6.75 (m, 2H), 6.54-6.47 (m, 2H), 3.90 (q, J=6.9 Hz, 2H), 3.70-3.52 (m, 6H), 3.38-3.23 (m, 4H), 3.18-3.03 (m, 6H), 3.00-2.80 (m, 2H), 1.27 (t, J=7.0 Hz, 3H); HRMS calcd for C$_{19}$H$_{28}$N$_3$O$_4$S (M+H$^+$) 394.1801. found 394.1759.

Example 35: cis-2-(4-Ethoxyphenyl)-5-(2-(pyrrolidin-1-yl)ethyl)octahydropyrrolo[3,4-c]pyrrole

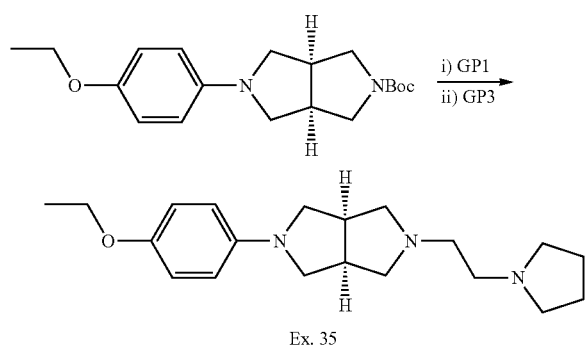

Ex. 35

The title compound was synthesised according to general procedures GP1 and GP3—from i) tert-butyl 5-(4-ethoxyphenyl)hexahydropyrrolo[3,4-c]pyrrole-2(1H)-carboxylate (200 mg, 0.60 mmol) and 4 M HCl in dioxane (1.0 mL, 4.0 mmol); rt, 1 h. ii) Triethylamine (0.25 mL, 1.8 mmol), 1-(2-chloroethyl)pyrrolidine hydrochloride (123 mg, 0.72 mmol) and acetonitrile (3 mL); 75° C., 24 h. The crude was purified by chromatography (basic alumina; 50-100% ethyl acetate/cyclohexane then 0-15% MeOH/ethyl acetate) to give as an off-white solid (52 mg, 26% yield). $^1$H NMR (CDCl$_3$, 500 MHz) δ 6.82 (d, 2H, J=9.0 Hz), 6.63 (d, 2H, J=9.0 Hz), 3.97 (q, 2H, J=7.0 Hz), 3.22-3.19 (m, 2H), 3.14 (dd, 2H, J=9.3, 2.4 Hz), 2.98-2.88 (m, 4H), 2.62 (s, 4H), 2.54 (br s, 4H), 2.32 (dd, 2H, J=8.4, 4.2 Hz), 1.78-1.76 (m, 4H), 1.37 (t, 3H, J=7.0 Hz); $^{13}$C NMR (CDCl$_3$, 125 MHz) δ 151.2, 143.8, 115.6, 115.1, 64.1, 61.3, 55.3, 55.0, 54.8, 54.5, 41.7, 23.4, 15.0; LCMS m/z 330.2538 found (M+H)$^+$, 330.2540 calculated for C$_{20}$H$_{32}$N$_3$O.

Example 36: cis-1-(2-(5-(4-Ethoxyphenyl)hexahydropyrrolo[3,4-c]pyrrol-2(1H)-yl)ethyl)-pyrrolidine-2,5-dione

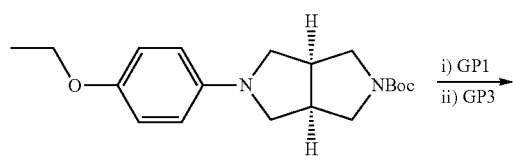

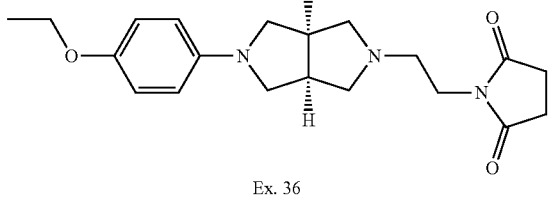

Ex. 36

The title compound was synthesised according to general procedures GP1 and GP3—from i) tert-butyl 5-(4-ethoxyphenyl)hexahydropyrrolo[3,4-c]pyrrole-2(1H)-carboxylate (300 mg, 0.90 mmol), 4 M HCl in dioxane (1.12 mL, 4.5 mmol); rt, 1 h. ii) Triethylamine (0.5 mL, 3.6 mmol), 2-bromoethyl succinimide (222 mg, 1.08 mmol) and acetonitrile (4.5 mL); 70° C., 72 h. The crude was purified by chromatography (basic alumina; 20-100% ethyl acetate/cyclohexane, then silica, 75-100% (9.5:0.5 ethyl acetate: triethylamine)/cyclohexane then 0-10% methanol/(9.5:0.5 ethyl acetate:triethylamine), to give an off-white solid (180 mg, 56% yield). $^1$H NMR (CDCl$_3$, 500 MHz) δ 6.81 (d, 2H, J=9.0 Hz, ArH), 6.61 (d, 2H, J=9.0 Hz), 3.96 (q, 2H, J=7.0 Hz), 3.63 (t, 2H, J=6.4 Hz), 3.33-3.26 (m, 2H), 2.99 (dd, 2H, J=9.1, 2.4 Hz), 2.86 (br s, 2H), 2.71 (br s, 2H), 2.66-2.62 (m, 2H), 2.58 (s, 4H), 2.51 (dd, 2H, J=8.9, 3.2 Hz), 1.37 (t, 3H, J=7.0 Hz); LCMS m/z 358.2117 found (M+H)$^+$, 358.2125. calculated for C$_{20}$H$_{28}$N$_3$O$_3$.

Example 37: cis-5-(4-Ethoxyphenyl)hexahydropyrrolo[3,4-c]pyrrol-2(1H)-yl)(morpholino)methanone

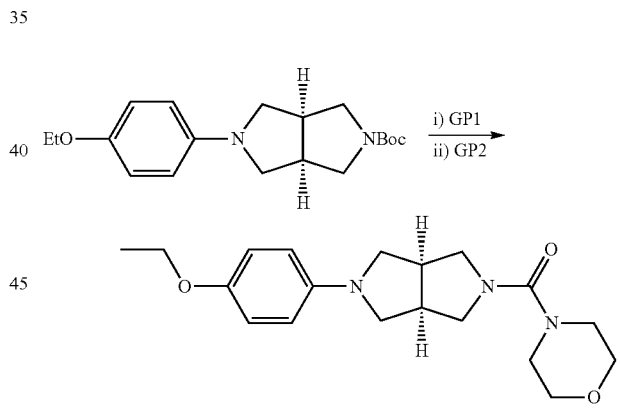

The title compound was prepared using general procedures GP1 and GP2 from i) tert-butyl-5-(4-ethoxyphenyl)-hexahydropyrrolo[3,4-c]pyrrole-2(1H)-carboxylate (259 mg, 0.78 mmol) and HCl (4.0 M in dioxane, 7 mL) at rt for 4 h, then ii) N,N-diisopropylethylamine (679 μL, 3.90 mmol), triphosgene (116 mg, 0.39 mmol), morpholine (336 μL, 3.90 mmol) and dichloromethane (6 mL) at −20° C. for 1h then rt for 16 h. Recrystallisation (acetonitrile) gave cis-5-(4-ethoxyphenyl)hexahydropyrrolo[3,4-c]pyrrol-2(1H)-yl)(morpholino)methanone as a colourless solid (198 mg, 74%). $^1$H NMR (300 MHz, DMSO-d$_6$) δ 6.78 (d, J=9.0 Hz, 2H), 6.50 (d, J=9.0 Hz, 2H), 3.90 (q, J=7.0 Hz, 2H), 3.69-3.49 (m, 6H), 3.45-3.27 (m, 2H), 3.22 (dd, J=11.0, 4.0 Hz, 2H), 3.17-3.09 (m, 4H), 3.04 (dd, J=9.5, 4.0 Hz, 2H), 2.98-2.86 (m, 2H), 1.27 (t, J=7.0 Hz, 3H); MS (ES+) m/z=346 (M+H$^+$, 100).

Example 38: cis-N-(1,1-dioxidotetrahydro-2H-thiopyran-4-yl)-5-(4-ethoxyphenyl)hexa-hydropyrrolo[3,4-c]pyrrole-2(1H)-carboxamide

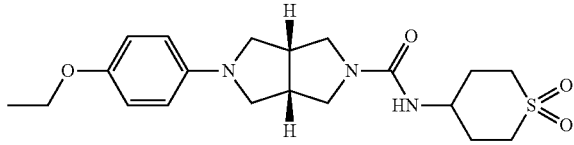 [SMILES: CCOc1ccc(N2C[C@H]3CN(C(=O)NC4CCS(=O)(=O)CC4)C[C@H]3C2)cc1]

tert-Butyl 5-(4-ethoxyphenyl)hexahydropyrrolo[3,4-c]pyrrole-2(1H)-carboxylate (120 mg, 0.36 mmol) was dissolved in 4 M HCl in dioxane (2.3 mL, 9.0. mmol) and the reaction mixture was stirred at room temperature under nitrogen for 1 hour before concentrating in vacuo and drying under vacuum. The flask was then purged with nitrogen and the residue was dissolved in anhydrous dichloromethane (5 mL). Diisopropylethylamine (0.38 mL, 2.16 mmol) then triphosgene (53 mg, 0.18 mmol) were added to the solution, which was stirred at room temperature under nitrogen for 1 hour before adding 4-aminotetrahydro-2H-thiopyran 1,1-dioxide (107 mg, 0.72 mmol), with continued stirring for 48 hours. The reaction mixture was then separated between dichloromethane (20 mL) and saturated aq. NaHCO$_3$ (20 mL). The aqueous phase was extracted with dichloromethane (2×20 mL) and the combined organic extracts were washed with brine (50 mL), dried over anhydrous sodium sulfate, filtered and concentrated to give the crude product, which was purified using flash column chromatography over basic alumina, eluting with 80-100% ethyl acetate/petroleum ether then 0-30% methanol/ethyl acetate, to give the title compound (25 mg, 17% yield) as a white solid. $^1$H NMR (CDCl$_3$, 300 MHz) δ 6.84 (d, 2H, J=9.0 Hz), 6.51 (d, 2H, J=9.0 Hz), 4.17 (d, 1H, J=7.5 Hz), 3.96 (q, 3H, J=6.9 Hz), 3.66-3.60 (m, 2H), 3.49-3.43 (m, 2H), 3.32 (dd, 2H, J=9.9, 3.2 Hz), 3.19 (dd, 2H, J=9.4, 3.0 Hz), 3.12-3.00 (m, 6H), 2.36-2.26 (m, 2H), 2.14-2.00 (m, 2H), 1.37 (t, 3H, J=7.0 Hz) ppm; LCMS m/z 408.1 found (M+H)$^+$, 408.1952 calculated for C$_{20}$H$_{30}$N$_3$O$_4$S.

Example 39: cis-5-(4-ethoxyphenyl)-N-(tetrahydro-2H-pyran-4-yl)hexahydropyrrolo[3,4-c]pyrrole-2(1H)-carboxamide

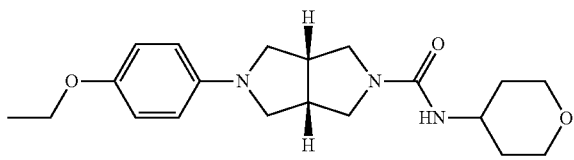 [SMILES: CCOc1ccc(N2C[C@H]3CN(C(=O)NC4CCOCC4)C[C@H]3C2)cc1]

tert-Butyl 5-(4-ethoxyphenyl)hexahydropyrrolo[3,4-c]pyrrole-2(1H)-carboxylate (100 mg, 0.30 mmol) was dissolved in 4 M HCl in dioxane (1.9 mL, 7.5 mmol) and the reaction mixture was stirred at room temperature under nitrogen for 1 hour before concentrating in vacuo and drying under vacuum. The flask was then purged with nitrogen and the residue was dissolved in anhydrous dichloromethane (4 mL). Diisopropylethylamine (0.31 mL, 1.82 mmol) then triphosgene (45 mg, 0.15 mmol) were added to the solution, which was stirred at room temperature under nitrogen for 1 hour before adding 4-aminotetrahydropyran (0.078 mL, 0.75 mmol), with continued stirring for 72 hours. The reaction mixture was then separated between dichloromethane (20 mL) and saturated aq. NaHCO$_3$ (20 mL). The aqueous phase was extracted with dichloromethane (2×20 mL) and the combined organic extracts were washed with brine (50 mL), dried over anhydrous sodium sulfate, filtered and concentrated to give the crude product, which was washed with 0-30% ethyl acetate/petroleum ether to give the title compound (91 mg, 84% yield) as an off-white solid. $^1$H NMR (CDCl$_3$, 300 MHz) δ 6.84 (d, 2H, J=9.0 Hz), 6.53 (d, 2H, J=9.0 Hz), 4.00-3.91 (m, 5H), 3.63 (dd, 2H, J=10.0, 7.5 Hz), 3.50-3.42 (m, 4H), 3.33 (dd, 2H, J=10.1, 3.9 Hz), 3.19 (dd, 2H, J=9.4, 3.7 Hz), 3.08-3.01 (m, 2H), 1.94-1.89 (m, 2H), 1.55-1.43 (m, 3H), 1.37 (t, 3H, J=7.0 Hz) ppm; LCMS m/z 360.1 found (M+H)$^+$, 360.2282. calculated for C$_{20}$H$_{30}$N$_3$O$_3$.

Example 40: (4,4-difluoropiperidin-1-yl)(cis-5-(4-ethoxyphenyl)hexahydro pyrrolo[3,4-c]pyrrol-2(1H)-yl)methanone

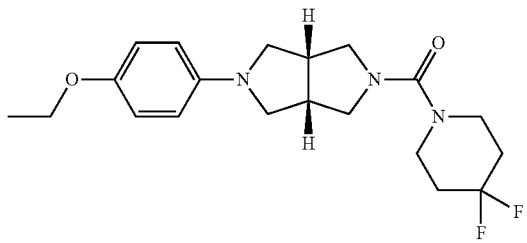 [SMILES: CCOc1ccc(N2C[C@H]3CN(C(=O)N4CCC(F)(F)CC4)C[C@H]3C2)cc1]

tert-Butyl 5-(4-ethoxyphenyl)hexahydropyrrolo[3,4-c]pyrrole-2(1H)-carboxylate (100 mg, 0.30 mmol) was dissolved in 4 M HCl in dioxane (1.9 mL, 7.5. mmol) and the reaction mixture was stirred at room temperature under nitrogen for 1 hour before concentrating in vacuo and drying under vacuum. The flask was then purged with nitrogen and the residue was dissolved in anhydrous dichloromethane (4 mL). Diisopropylethylamine (0.31 mL, 1.81 mmol) then triphosgene (45 mg, 0.15 mmol) were added to the solution, which was stirred at room temperature under nitrogen for 1 hour before adding 4,4-difluoropiperidine hydrochloride (119 mg, 0.75 mmol), with continued stirring for 72 hours. The reaction mixture was then separated between dichloromethane (20 mL) and saturated aq. NaHCO$_3$ (20 mL). The aqueous phase was extracted with dichloromethane (2×20 mL) and the combined organic extracts were washed with brine (50 mL), dried over anhydrous sodium sulfate, filtered and concentrated to give the crude product, which was purified using flash column chromatography over basic alumina, eluting with 10% methanol/dichloromethane, to give the title compound (102 mg, 89% yield) as an off-white solid. $^1$H NMR (CDCl$_3$, 300 MHz) δ 6.84 (d, 2H, J=9.0 Hz), 6.53 (d, 2H, J=9.0 Hz), 3.97 (q, 2H, J=7.0 Hz), 3.74 (dd, 2H, J=10.9, 7.6 Hz), 3.46-3.30 (m, 6H), 3.17 (dd, 2H, J=9.5, 3.6 Hz), 3.01-2.95 (m, 2H), 2.06-1.90 (m, 6H), 1.37 (t, 3H, J=7.0 Hz) ppm; $^{19}$F NMR (CDCl$_3$, 282 MHz) δ −97.2 ppm; LCMS m/z 380.1 found (M+H)$^+$, 380.2144. calculated for C$_{20}$H$_{28}$N$_3$O$_2$F$_2$.

Example 41: (cis-5-(4-ethoxyphenyl)hexahydropyrrolo[3,4-c]pyrrol-2(1H)-yl)(4-(methylsulfonyl)piperazin-1-yl)methanone

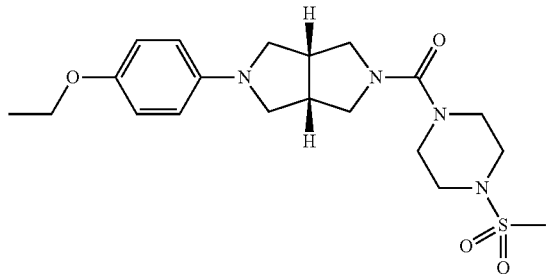 [SMILES: CCOc1ccc(N2C[C@H]3CN(C(=O)N4CCN(S(C)(=O)=O)CC4)C[C@H]3C2)cc1]

tert-Butyl 5-(4-ethoxyphenyl)hexahydropyrrolo[3,4-c]pyrrole-2(1H)-carboxylate (100 mg, 0.30 mmol) was dissolved in 4 M HCl in dioxane (1.9 mL, 7.5. mmol) and the reaction mixture was stirred at room temperature under nitrogen for 1 hour before concentrating in vacuo and drying under vacuum. The flask was then purged with nitrogen and the residue was dissolved in anhydrous dichloromethane (4 mL). Diisopropylethylamine (0.31 mL, 1.81 mmol) then triphosgene (45 mg, 0.15 mmol) were added to the solution, which was stirred at room temperature under nitrogen for 1 hour before adding 1-(methylsulfonyl)piperazine (124 mg, 0.75 mmol), with continued stirring for 72 hours. The reaction mixture was then separated between dichloromethane (20 mL) and saturated aq. NaHCO$_3$ (20 mL). The aqueous phase was extracted with dichloromethane (2×20 mL) and the combined organic extracts were washed with brine (50 mL), dried over anhydrous sodium sulfate, filtered and concentrated to give the crude product, which was washed with 20% ethyl acetate/petroleum ether then purified using flash column chromatography over basic alumina, eluting with 5-20% methanol/dichloromethane, to give the title compound (122 mg, 96% yield) as an off-white solid. $^1$H NMR (DMSO-d$_6$, 300 MHz) δ 6.78 (d, 2H, J=9.0 Hz), 6.50 (d, 2H, J=9.0 Hz), 3.90 (q, 2H, J=7.0 Hz), 3.62 (dd, 2H, J=10.9, 7.3 Hz), 3.29-3.22 (m, 8H), 3.12-3.05 (m, 8H), 2.87 (s, 3H), 1.27 (t, 3H, J=7.0 Hz) ppm; LCMS m/z 423.1 found (M+H)$^+$, 423.2061 calculated for C$_{20}$H$_{31}$N$_4$O$_4$S.

Example 42: 1-(cis-5-(4-ethoxyphenyl)octahydropyrrolo[3,4-c]pyrrole-2-carbonyl)piperidine-4-carbonitrile

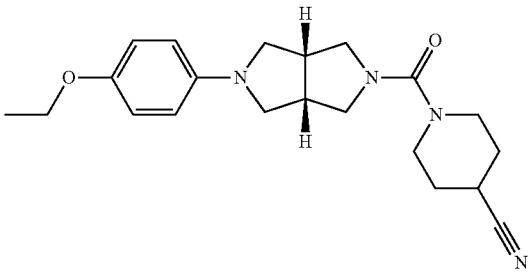 [SMILES: CCOc1ccc(N2C[C@H]3CN(C(=O)N4CCC(C#N)CC4)C[C@H]3C2)cc1]

tert-Butyl 5-(4-ethoxyphenyl)hexahydropyrrolo[3,4-c]pyrrole-2(1H)-carboxylate (100 mg, 0.30 mmol) was dissolved in 4 M HCl in dioxane (1.9 mL, 7.5 mmol) and the reaction mixture was stirred at room temperature under nitrogen for 1 hour before concentrating in vacuo and drying under vacuum. The flask was then purged with nitrogen and the residue was dissolved in anhydrous dichloromethane (4 mL). Diisopropylethylamine (0.31 mL, 1.82 mmol) then triphosgene (45 mg, 0.15 mmol) were added to the solution, which was stirred at room temperature under nitrogen for 1 hour before adding 4-carbonitrile piperidine (0.084 mL, 0.75 mmol), with continued stirring for 72 hours. The reaction mixture was then separated between dichloromethane (20 mL) and saturated aq. NaHCO$_3$ (20 mL). The aqueous phase was extracted with dichloromethane (2×20 mL) and the combined organic extracts were washed with brine (50 mL), dried over anhydrous sodium sulfate, filtered and concentrated to give the crude product, which was purified using flash column chromatography over basic alumina, eluting with 0-20% methanol/dichloromethane, to give the title compound (95 mg, 86% yield) as a white solid. $^1$H NMR (CDCl$_3$, 300 MHz) δ 6.84 (d, 2H, J=9.0 Hz), 6.53 (d, 2H, J=9.0 Hz), 3.97 (q, 2H, J=7.0 Hz), 3.72 (dd, 2H, J=10.9, 7.6 Hz), 3.53-3.40 (m, 5H), 3.30 (dd, 2H, J=11.0, 4.4 Hz), 3.22-3.11 (m, 5H), 3.00-2.94 (m, 2H), 1.91-1.79 (m, 3H), 1.37 (t, 3H, J=7.0 Hz) ppm; LCMS m/z 369.1 found (M+H)$^+$, 369.2285 calculated for C$_{21}$H$_{29}$N$_4$O$_2$.

Example 43: cis-N-(2-cyanoethyl)-5-(4-ethoxyphenyl)-N-methylhexahydro pyrrolo[3,4-c]pyrrole-2(1H)-carboxamide

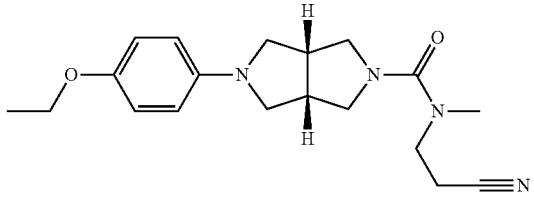 [SMILES: CCOc1ccc(N2C[C@H]3CN(C(=O)N(C)CCC#N)C[C@H]3C2)cc1]

tert-Butyl 5-(4-ethoxyphenyl)hexahydropyrrolo[3,4-c]pyrrole-2(1H)-carboxylate (100 mg, 0.30 mmol) was dissolved in 4 M HCl in dioxane (1.9 mL, 7.5 mmol) and the reaction mixture was stirred at room temperature under nitrogen for 1 hour before concentrating in vacuo and drying under vacuum. The flask was then purged with nitrogen and the residue was dissolved in anhydrous dichloromethane (4 mL). Diisopropylethylamine (0.31 mL, 1.82 mmol) then triphosgene (45 mg, 0.15 mmol) were added to the solution, which was stirred at room temperature under nitrogen for 1 hour before adding 3-(methylamino)propanenitrile (0.07 mL, 0.75 mmol), with continued stirring for 72 hours. The reaction mixture was then separated between dichloromethane (20 mL) and saturated aq. NaHCO$_3$ (20 mL). The aqueous phase was extracted with dichloromethane (2×20 mL) and the combined organic extracts were washed with brine (50 mL), dried over anhydrous sodium sulfate, filtered and concentrated to give the crude product, which was purified using flash column chromatography over basic alumina, eluting with 0-20% methanol/dichloromethane, to give the title compound (86 mg, 83% yield) as a white solid. $^1$H NMR (CDCl$_3$, 300 MHz) δ 6.84 (d, 2H, J=9.0 Hz), 6.53 (d, 2H, J=9.0 Hz), 3.97 (q, 2H, J=7.0 Hz), 3.71 (dd, 2H, J=10.9, 7.6 Hz), 3.49-3.40 (m, 5H), 3.35 (dd, 2H, J=10.9, 4.2 Hz), 3.18 (dd, 2H, J=9.5, 3.6 Hz), 2.95 (s, 3H), 2.65 (td, 3H, J=6.6, 5.4 Hz), 1.37 (t, 3H, J=7.0 Hz) ppm; LCMS m/z 343.1 found (M+H)$^+$, 343.2129. calculated for C$_{19}$H$_{27}$N$_4$O$_2$.

Biology: Materials and Methods
LOX Activity in Cysts Assay (Tang et al, 2017).
Cell Culture and Transfection Cell lines were purchased from American Type Culture Collection (ATCC). Cells were assessed for *Mycoplasma* contamination and were found to be negative. MDCK cell lines were cultured in Dulbecco's Modified Eagle Medium (DMEM):F12 media supplemented with 10% foetal bovine serum (FBS) and 1% Penicillin Streptomycin solution (Pen Strep). Cells were incubated at 37° C. in a humidified incubator with 5% CO2. Lipofectamine 3000 or lentivirus was used to transfect MDCK cells with GFP constructs and cells were selected with G418 (Life Technologies) at 5 mg/ml. Cell culture reagents were purchased from Life Technologies.

To produce MDCK cysts, cells were cultured on Matrigel (Corning) with 2% Matrigel supplemented in DMEM with 10% FBS. Cysts were allowed to form for 10 days before subsequent studies.

Cloning of LOX Expression Constructs

Mouse LOX cDNA was purchased from OriGene. Full length LOX cDNA was then PCR cloned into pEGFP-N1 (Clonetech), or biosensor vector proGFP2-N1 (Hanson, 2004) using the following primers, GAGAGAGCTAG-CATGCGTTTCGCCTGGG (forward primer) and TCTCTCCTCGAGATACGGTGAAATTGTGCAGCC (reverse primer). For the insertion into pEGFP-N1 or proGFP2-N1, NheI and XhoI restriction sites were added to forward and reverse primers accordingly. Mutant LOX constructs were made using QuickChange II site-directed mutagenesis kit (Agilent Technologies) following manufacture's protocol using LOX-GFP as template. To generate, roGFP2 versions of LOX mutant constructs, LOX mutant cDNA was transferred from pEGFP-N1 to proGFP2-N1 using NheI and XhoI.

Confocal Imaging and Imaging Analysis

Photomicrographs of live MDCK cysts with a Leica TCS SP8 X confocal system were used to image the biosensor. The oxidised biosensor was excited using a 405 nm laser, while the reduced biosensor was excited with a 488 nm laser. Emission of the biosensor was recorded at 500 nm~530 nm range using sequential scans. Ratio images were generated following a published protocol {Kardash, 2011 #376}. Note, while the published protocol generates YFP/CFP ratio images, we used it to generate Oxidised/Reduced (roGFP2 ratio) ratio images. The roGFP2 ratio at the basal surface of MDCK cysts was used to indicate LOX inhibition. LOX inhibitors were added 30 min prior to imaging.

The inhibition of LOX in cysts treated with LOX inhibitors compared to control (DMSO vehicle treated) cysts is shown in Table 2. For clarity, readout for DMSO treated cysts represents 0% inhibition (no inhibition) and readout for BAPN at 1 mM is used as 100% inhibition (full inhibition).

TABLE 2

Inhibition of LOX in the cyst

| Example | LOX biosensor inhibition (cyst) @ 10 μM | LOX biosensor IC50 (cyst) [μM] |
|---|---|---|
| 1 | — | <0.56 |
| 2 | 65% | |
| 3 | 100% | 1.62 |
| 9 | 100% | |
| 18 | 97% | |

TABLE 2-continued

Inhibition of LOX in the cyst

| Example | LOX biosensor inhibition (cyst) @ 10 μM | LOX biosensor IC50 (cyst) [μM] |
|---|---|---|
| 28 | 94% | |
| 30 | 59% | |
| 32 | 100% | |
| 37 | 100% | |
| 42 | 72% | |

In Vivo Assessment of LOX Inhibitors
Animal Procedures

All procedures involving animals were approved by the Animal Welfare and Ethical Review Body of the Institute of Cancer Research and Cancer Research UK Manchester Institute in accordance with National Home Office regulations under the Animals (Scientific Procedures) Act 1986 and according to the guidelines of the Committee of the National Cancer Research Institute Tumour size was determined by caliper measurements of tumour length, width and depth and volume was calculated as volume=0.5236× length×width×depth (mm). In accordance with our license to perform animal experiments, animals were excluded from the experiments if they displayed signs of distress, excessive bodyweight loss (>20%) or illness.

Oral Tolerability of LOX Inhibitors

Two CD1, NCR or Balb/c female mice at 6 weeks of age were dosed po by metal gavage once a day for 4 consecutive days with suspension of the test compound at the dose planned for therapy (200 mg/kg/day) in 5.25% Tween20/saline (v:v) or 5% DMSO in water at 0.2 ml per 20 g bodyweight.

The mice were observed for up to 15 days after last dose and their bodyweight measured every 4 days. A compound is considered tolerated if the bodyweight does not fall by >20% for over 72 hrs.

Compounds of this invention tested in vivo show good tolerability at the dose tested and exhibit <5% bodyweight loss or show bodyweight gain in the tolerability study and in further longer therapy studies.

In Vivo Tumour Models Studies

PDAC allografts: CD1 nu/nu female mice at 6 weeks of age were inoculated subcutaneously in the right flank with $2\times10^6$ PDAC KPC TRP53 R172H (p53 mut) cells at 100 ul suspension per animal. In other examples, CD1 nu/nu female mice at 5-6 weeks of age were inoculated subcutaneously in the right flank with 2-8×$10^6$ PDAC KP$^{fl}$C (LOX H1 clone) cells at 100 ul suspension per animal (p53 wt, LOX o/e). The origin and generation of these cell lines is reported in Miller et al, 2015. In some examples, the oral dosing by metal gavage commences two hours after cells inoculation or one day after cells inoculation, at 0.2 ml/20 g bodyweight per animal once daily for 2-4 weeks, with compound dissolved in 5.25% tween20/saline or 5% DMSO/water. In other examples, groups of 7-8 mice were assigned to treatment following stratified allocation of tumour volumes with a median size of circa 100 mm$^3$. Oral dosing by metal gavage commenced around day 10, at 0.2 ml/20 g bodyweight per animal once daily for 2 weeks, with compound dissolved in 5.25% tween20/saline or 5% DMSO/water. Control animals received a similar dosage of vehicle (5.25% tween20/saline or 5% DMSO/water). Tumours and weights are measured twice weekly using calipers. At the end of the study the animals are culled, and samples taken, fixed or snap frozen in liquid nitrogen. Frozen samples kept at −80 degree centigrade until being analysed and the fixed samples stained according to the desired marker.

SW620 xenografts: NCr mice were inoculated subcutaneously in the right flank with $5 \times 10^6$ SW620 cells at 100 ul suspension per animal. Groups of 7-8 mice were assigned to treatment following stratified allocation of tumour volumes with a median size of circa 100 $mm^3$. Dosing commenced around day 10-13 at 0.2 ml/20 g bodyweight per animal once daily for 2 weeks. Dosing was administrated orally by metal gavage, at 0.2 ml/20 g bodyweight, compound dissolved in 5.25% tween20/saline or 5% DMSO/water. Control animals received a similar dosage of vehicle (5.25% tween20/saline or 5% DMSO/water). Tumours and weights are measured twice weekly using calipers. At the end of the study the animals are culled, and samples taken, fixed or snap frozen in liquid nitrogen. Frozen samples are kept at −80 degree centigrade until being analysed and the fixed samples stained according to the desired marker.

MDA-MB-231 xenografts. Ncr nude female mice at 6 weeks old from Charles River were injected into the third upper nipple mammary fat pad with MDA-MB-231 Luc $4 \times 10^6$ in 100 ul PB (50:50 Matrigel). When tumours reach a mean of 80 mm 3 around 10 days post cell inoculation the animals are allocated in 4 groups of 8. LOX inhibitor treatment is then administrated by oral gavage dosing, at 0.2 ml/20 g bodyweight once daily for up to 28 consecutive days. Tumours and weights are measured twice weekly using calipers and the animals can be imaged using non-invasive method by bioluminescence using IVIS 200 imaging machine, weekly using 150 mg/kg luciferin administrate intraperitoneal or subcutaneous. At the end of the study the animals are culled, and samples taken, fixed or snap frozen in liquid nitrogen. Frozen samples kept at −80 degree centigrade until being analyzed and the fixed samples stained according to desired marker.

LOX Inhibitor Treatment of a Transgenic Mouse Breast Cancer Model

MMTV-PyMT (Guy et al, 1992) (FVB) female mice were randomized by non-statistical methods to LOX inhibitor treatment groups from day 70 post-birth, when animals had no detectable tumour. Mice were treated daily by oral gavage with LOX inhibitor in vehicle, or daily vehicle (5% DMSO/2.5% Tween20 in water) by oral gavage. Tumour size was determined unblinded by caliper measurements of tumour length, width and depth and volume was calculated as $0.5236 \times length \times width \times depth$ (mm). In all experiments, mice were humanely killed and mammary tumours and lungs were collected when the primary tumours reached ethical limits or signs of ill health.

For therapeutic efficacy assessment, the ratio of average tumour volume between compound treated and vehicle control treated (T/C) is calculated. Reduction in tumour volume in the compound treated group compared to vehicle-treated control group results in T/C<1. The efficacy of LOX inhibitors described in this invention, as measured by T/C in a pancreatic cancer model, a colorectal cancer model and a breast cancer model is shown in Table 3 and is significant (p<0.05) for all the data presented.

For lung metastases quantification, all mouse tissue samples were fixed in 10% formalin (Sigma) and embedded in paraffin. Samples were sectioned and hematoxylin and eosin (H&E) stained. Samples were imaged with a Leica SCN400 slide scanner. Lung metastases were manually selected using Pen tool in ImageScope. Lung metastases number was counted and area was measured using ImageScope. The investigator was blinded to the experimental groups. The ratio of average metastases surface between compound treated and vehicle control treated (T/C) is calculated. The ratio of average metastases numbers between compound treated and vehicle control treated (T/C) is also calculated. Reduction in metastases area and/or in metastases number in the compound treated group compared to vehicle-treated control group results in T/C<1. The antimetastatic efficacy of LOX inhibitors described in this invention, as measured by T/C in a model of breast cancer metastasizing to lungs is shown in Table 3 and is significant (p<0.05) for all the data presented.

TABLE 3

| Example | PDAC R172H (p53 mut) (mouse pancreatic carcinoma) - primary tumour a) R172H (p53mut) b) p53wt, LOX o/e | SW620 human colorectal carcinoma cells (mutant RAS) - primary tumour | MDA-MB-231 human breast adenocarcinoma - primary tumour | MMT-PyMT breast transgenic model - primary tumour | MMT-PyMT breast transgenic model - metastases a) Count b) Area |
|---|---|---|---|---|---|
| 1 | a) 0.54 b) 0.35 | 0.55 | 0.29 | 0.3 (@67 mpk) | a) 0.14 (@67 mpk) b) 0.02 (@67 mpk) |
| 3 | a) 0.58 b) 0.42 | | | | |

Significant, p<0.05
All values are T/C, all doses are 200 mg/kg po qd unless otherwise stated

REFERENCES

Guy, C. T., Cardiff, R. D. & Muller, W. J. Induction of mammary tumors by expression of polyomavirus middle T oncogene: a transgenic mouse model for metastatic disease. Mol Cell Biol 12, 954-961 (1992)

Hanson, G. T., Aggeler, R., Oglesbee, D., Cannon, M., Capaldi, R. A., Tsien, R. Y., Remington J. S. (2004). Investigating mitochondrial redox potential with redox-sensitive green fluorescent protein indicators. J. Biol. Chem. 279, 13044-13053.

Abourbih, D. A., et al. (2010). "Lysyl oxidase expression and inhibition in uveal melanoma." Melanoma research 20(2): 97-106.

Adam, O., et al. (2011). "Increased lysyl oxidase expression and collagen cross-linking during atrial fibrillation." J. Mol. Cell. Cardiol. 50(4): 678-685.

Akiri, G., et al. (2003). "Lysyl oxidase-related protein-1 promotes tumor fibrosis and tumor progression in vivo." Cancer research 63(7): 1657-1666.

Albinger-Hegyi, A., et al. (2010). "Lysyl oxidase expression is an independent marker of prognosis and a predictor of lymph node metastasis in oral and oropharyngeal squamous cell carcinoma (OSCC)." International journal of cancer Journal international du cancer 126(11): 2653-2662.

Alexandrescu, D. T. (2009). "Treatment of skin disorders with EGFR inhibitors". WO2009091889A1

Anderson, C., et al. (2007). "Chemical genetics suggests a critical role for lysyl oxidase in zebrafish notochord morphogenesis." Mol Biosyst 3(1): 51-59.

Aslam, T., et al. (2015). "Optical molecular imaging of lysyl oxidase activity—detection of active fibrogenesis in human lung tissue." Chemical Science 6(8): 4946-4953.

Baker, A.-M., et al. (2013). "Lysyl oxidase plays a critical role in endothelial cell stimulation to drive tumor angiogenesis." Cancer research 73(2): 583-594.

Baker, A.-M., et al. (2011). "The role of lysyl oxidase in SRC-dependent proliferation and metastasis of colorectal cancer." Journal of the National Cancer Institute 103(5): 407-424.

Barker, H. E., et al. (2013). "Tumor-Secreted LOXL2 Activates Fibroblasts through FAK Signaling." Molecular Cancer Research 11(11): 1425-1436.

Barker, H. E., et al. (2011). "LOXL2-mediated matrix remodeling in metastasis and mammary gland involution." Cancer research 71(5): 1561-1572.

Barker, H. E., et al. (2012). "The rationale for targeting the LOX family in cancer." Nature reviews Cancer 12(8): 540-552.

Barry-Hamilton, V., et al. (2010). "Allosteric inhibition of lysyl oxidase-like-2 impedes the development of a pathologic microenvironment." Nat Med 16(9): 1009-1017.

Beerlage, C., et al. (2013). "Hypoxia-inducible factor 1-regulated lysyl oxidase is involved in *Staphylococcus aureus* abscess formation." Infect. Immun. 81(7): 2562-2573.

Bianco, R., et al. (2007). "Rational bases for the development of EGFR inhibitors for cancer treatment." The International Journal of Biochemistry & Cell Biology 39(7-8): 1416-1431.

Bondareva, A., et al. (2009). "The lysyl oxidase inhibitor, beta-aminopropionitrile, diminishes the metastatic colonization potential of circulating breast cancer cells." PLoS One 4(5): e5620.

Borad, M. J., et al. (2014). "Targeted chemotherapy of cancer using EGFR inhibitors". WO2014145751A2

Boufraqech, M., et al. (2015). "miR30a Inhibits LOX Expression and Anaplastic Thyroid Cancer Progression." Cancer research 75(2): 367-377.

Brasselet, C., et al. (2005). "Collagen and elastin cross-linking: A mechanism of constrictive remodeling after arterial injury." Am. J. Physiol. 289(5, Pt. 2): H2228-H2233.

Burchardt, E. R. (2006). "Preparation of 2-phenyl-3-pyridazinones as lysyl oxidase inhibitors". DE102004056226A1

Burke A. A., et al (2017) Comparing hydrazine-derived reactive groups as inhibitors of quinone-dependent amine oxidases, Journal of Enzyme Inhibition and Medicinal Chemistry, 32:1, 496-503, Carrington, M. J., et al. (1984). "The inhibition of lysyl oxidase in vivo by isoniazid and its reversal by pyridoxal. Effect on collagen cross-linking in the chick embryo." Biochem J 221(3): 837-843.

Chang, J. et al (2017) Pre-clinical evaluation of small molecule LOXL2 inhibitors in breast cancer. Oncotarget, 8(16):26066-26078

Chanoki, M., et al. (1995). "Increased expression of lysyl oxidase in skin with scleroderma." Br J Dermatol 133(5): 710-715.

Chen, W.-C., et al. (2015). "Matrix-Stiffness—Regulated Inverse Expression of Krüppel-Like Factor 5 and Krüppel-Like Factor 4 in the Pathogenesis of Renal Fibrosis." The American Journal of Pathology 185(9): 2468-2481.

Chen, R T et al. (2017) "Blocking Surgically Induced Lysyl Oxidase Activity Reduces the Risk of Lung Metastases". Cell Reports 19(4), 774-784

Chien, J. W., et al. (2014). "Serum lysyl oxidase-like 2 levels and idiopathic pulmonary fibrosis disease progression." European Respiratory Journal 43(5): 1430-1438.

Cox, T. R., et al. (2013). "LOX-Mediated Collagen Cross-linking Is Responsible for Fibrosis-Enhanced Metastasis." Cancer research 73(6): 1721-1732.

Cox, T. R., et al. (2015). "The hypoxic cancer secretome induces pre-metastatic bone lesions through lysyl oxidase." Nature 522(7554): 106-110.

Crowley, V. et al. (2016). "Development of Glucose Regulated Protein 94-Selective Inhibitors Based on the Bnlm and Radamide Scaffold." J Med. Chem. 59, 3471-3488.

Curtis, M. et al. (2013). "Phenicol antibacterials." US2013/0237502A1.

da Silva, R., et al. (2015). "LOX Expression and Functional Analysis in Astrocytomas and Impact of IDH1 Mutation." PLoS One 10(3): e0119781.

Decitre, M., et al. (1998). "Lysyl oxidase-like protein localizes to sites of de novo fibrinogenesis in fibrosis and in the early stromal reaction of ductal breast carcinomas." Lab. Invest. 78(2): 143-151.

Dentillo, D. B., et al. (2010). "Deregulation of LOXL1 and HTRA1 Gene Expression in Endometriosis." Reproductive Sciences 17(11): 1016-1023.

Di Donato, A., et al. (1997). "Lysyl oxidase expression and collagen cross-linking during chronic adriamycin nephropathy." Nephron 76(2): 192-200.

Dong, K.-f., et al. (2014). "Effects on apoptosis and chemosensitivity in human laryngeal cancer Hep-2 cells by silencing the lysyl oxidase gene expression." Zhongguo Xiandai Yixue Zazhi 24(29): 13-17.

Dong, K., et al. (2014). "Effects of lox gene expression on proliferation, invasion and radiosensitivity of laryngeal cancer hep-2 cells." Tianjin Yiyao 42(5): 417-420.

Erler, J. T., et al. (2009). "Hypoxia-induced lysyl oxidase is a critical mediator of bone marrow cell recruitment to form the premetastatic niche." Cancer Cell 15(1): 35-44.

Erler, J. T., et al. (2006). "Lysyl oxidase is essential for hypoxia-induced metastasis." Nature 440(7088): 1222-1226.

Fong, S. F., et al. (2007). "Lysyl oxidase-like 2 expression is increased in colon and esophageal tumors and associated with less differentiated colon tumors." Genes Chromosomes Cancer 46(7): 644-655.

Gao, Y., et al. (2010). "LKB1 inhibits lung cancer progression through lysyl oxidase and extracellular matrix remodeling." Proceedings of the National Academy of Sciences 107(44): 18892-18897.

Georges, P. C., et al. (2007). "Increased stiffness of the rat liver precedes matrix deposition: implications for fibrosis." Am. J. Physiol. 293(6, Pt. 1): G1147-G1154.

Giboda, M., et al. (1992). "Experimental schistosomiasis mansoni: modulation of granulomas by inhibition of collagen cross-link formation. Preliminary report." Ann Trop Med Parasitol 86(6): 631-636.

Gilad, G. M. and V. H. Gilad (2001). "3-Aminopropionitrile treatment can accelerate recovery of mice after spinal cord injury." Eur. J. Pharmacol. 430(1): 69-72.

Gilad, G. M., et al. (2001). "Lysyl oxidase, the extracellular matrix-forming enzyme, in rat brain injury sites." Neurosci. Lett. 310(1): 45-48.

Gilad, G. M., et al. (2005). "Evidence for increased lysyl oxidase, the extracellular matrix-forming enzyme, in Alzheimer's disease brain." Neurosci Lett 376(3): 210-214.

Goeroegh, T., et al. (2007). "Selective upregulation and amplification of the lysyl oxidase like-4 (LOXL4) gene in head and neck squamous cell carcinoma." J Pathol 212 (1): 74-82.

Gonzalez-Santamaria, J et al, (2016) "Matrix cross-linking lysyl oxidases are induced in response to myocardial infarction and promote cardiac dysfunction". Cardiovascular Research 109, (1), 67-78.

Gonzalez, G. E., et al. (2014). "N-acetyl-seryl-aspartyl-lysyl-proline reduces cardiac collagen cross-linking and inflammation in angiotensin II-induced hypertensive rats." Clin. Sci. 126(1): 85-94.

Gopalan Balasubramanian. (1990) "Biphenyl-substituted guanidine derivatives useful as hypoglycaemic agents." U.S. Pat. No. 5,302,720.

Haase, V. H. (2009). "Pathophysiological Consequences of HIF Activation." Annals of the New York Academy of Sciences 1177(1): 57-65.

Halberg, N., et al. (2009). "Hypoxia-inducible factor 1α induces fibrosis and insulin resistance in white adipose tissue." Mol. Cell. Biol. 29(16): 4467-4483.

Hase, H., et al. (2014). "LOXL2 Status Correlates with Tumor Stage and Regulates Integrin Levels to Promote Tumor Progression in ccRCC." Molecular Cancer Research 12(12): 1807-1817.

He, Z. and V. Koprivica (2007). "EGFR inhibitors promote axon regeneration". WO2007008338A1

Herranz, N., et al. (2012). "Lysyl Oxidase-like 2 Deaminates Lysine 4 in Histone H3." Molecular Cell 46(3): 369-376.

Hornstra, I. K., et al. (2003). "Lysyl oxidase is required for vascular and diaphragmatic development in mice." J Biol Chem 278(16): 14387-14393.

Huang, C.-S., et al. (2013). "Long-term ethanol exposure-induced hepatocellular carcinoma cell migration and invasion through lysyl oxidase activation are attenuated by combined treatment with pterostilbene and curcumin analogues." Journal of Agricultural and Food Chemistry 61(18): 4326-4335.

Hynes, J. et al. (2009). "Imidazopyridine and imidazopyrazine compounds useful as kinase inhibitors." WO2009/155388A1.

Ingber, D. E. and A. Mammoto (2014). "Methods of altering vascular permeability by changing the mechanical properties of extracellular matrixes using agents such as lysyl oxidase (LOX)-modulating agents and uses for treatment of diseases". WO2014152122A2

Jiang, W.-P., et al. (2014). "Identification of the involvement of LOXL4 in generation of keratocystic odontogenic tumors by RNA-Seq analysis." In J Oral Sci 6(1): 31-38.

Jourdan-Le Saux, C., et al. (1994). "Lysyl oxidase cDNA of myofibroblast from mouse fibrotic liver." Biochem Biophys Res Commun 199(2): 587-592.

Jung, B. (2010). "Use of quinazoline derivatives for the treatment of viral diseases". WO2010026029A1

Kagan, H. M. (1994). "Lysyl oxidase: mechanism, regulation and relationship to liver fibrosis." Pathol Res Pract 190(9-10): 910-919.

Kagan, H. M. and W. Li (2003). "Lysyl oxidase: properties, specificity, and biological roles inside and outside of the cell." Journal of cellular biochemistry 88(4): 660-672.

Kagan, H. M., et al. (1981). "Changes in aortic lysyl oxidase activity in diet-induced atherosclerosis in the rabbit." Arteriosclerosis 1(4): 287-291.

Karagiannis, G. S., et al. (2012). "Cancer-Associated Fibroblasts Drive the Progression of Metastasis through both Paracrine and Mechanical Pressure on Cancer Tissue." Molecular Cancer Research 10(11): 1403-1418.

Kasashima, H., et al. (2014). "Lysyl oxidase-like 2 (LOXL2) from stromal fibroblasts stimulates the progression of gastric cancer." Cancer Letters 354(2): 438-446.

Kasashima, H., et al. (2015). "Lysyl oxidase is associated with the epithelial-mesenchymal transition of gastric cancer cells in hypoxia." Gastric Cancer: 1-12.

Kim, Y.-M., et al. (2010). "The human lysyl oxidase-like 2 protein functions as an amine oxidase toward collagen and elastin." Mol. Biol. Rep. 38(1): 145-149.

Kim, Y., et al. (1999). "Coexpression of the lysyl oxidase-like gene (LOXL) and the gene encoding type III procollagen in induced liver fibrosis." Journal of cellular biochemistry 72(2): 181-188.

Kirschmann, D. A., et al. (2002). "A molecular role for lysyl oxidase in breast cancer invasion." Cancer research 62(15): 4478-4483.

Kumarasamy, A., et al. (2009). "Lysyl oxidase activity is dysregulated during impaired alveolarization of mouse and human lungs." Am. J. Respir. Crit. Care Med. 180 (12): 1239-1252.

Lee, G.-H., et al. (2011). "Lysyl oxidase-like-1 enhances lung metastasis when lactate accumulation and monocarboxylate transporter expression are involved." Oncology Letters 2(5): 831-838.

Levene, C. I., et al. (1992). "Inhibition of chick embryo lysyl oxidase by various lathyrogens and the antagonistic effect of pyridoxal." Int J Exp Pathol 73(5): 613-624.

Levental, K. R., et al. (2009). "Matrix crosslinking forces tumor progression by enhancing integrin signaling." Cell 139(5): 891-906.

Li, R.-k., et al. (2015). "Lysyl oxidase-like 4 (LOXL4) promotes proliferation and metastasis of gastric cancer via FAK/Src pathway." Journal of Cancer Research and Clinical Oncology 141(2): 269-281.

Li, W., et al. (2003). "Lysyl oxidase oxidizes basic fibroblast growth factor and inactivates its mitogenic potential." Journal of cellular biochemistry 88(1): 152-164.

Liu, G., et al. (1997). "Irreversible inhibition of lysyl oxidase by homocysteine thiolactone and its selenium and oxygen analogues. Implications for homocystinuria." J Biol Chem 272(51): 32370-32377.

Liu, J., et al. (2014). "Correlations of lysyl oxidase with MMP2/MMP9 expression and its prognostic value in non-small cell lung cancer." Int J Clin Exp Pathol 7(9): 6040-6047.

Lopez, B., et al. (2010). "Role of lysyl oxidase in myocardial fibrosis: from basic science to clinical aspects." Am. J. Physiol. 299(1, Pt. 2): H1-H9.

Lopez, B., et al. (2013). "Osteopontin-mediated myocardial fibrosis in heart failure: a role for lysyl oxidase?" Cardiovasc. Res. 99(1): 111-120.

Lopez, B., et al. (2012). "Collagen Cross-Linking But Not Collagen Amount Associates With Elevated Filling Pressures in Hypertensive Patients With Stage C Heart Failure: Potential Role of Lysyl Oxidase." Hypertension 60(3): 677-683.

Lucero, H. A. and H. M. Kagan (2006). "Lysyl oxidase: an oxidative enzyme and effector of cell function." Cellular and molecular life sciences: CMLS 63(19-20): 2304-2316.

Lucero, H. A., et al. (2008). "Lysyl oxidase oxidizes cell membrane proteins and enhances the chemotactic response of vascular smooth muscle cells." J Biol Chem 283(35): 24103-24117.

Ma, W. (2013). "Methods for treating alzheimer's disease by administering certain synthetic compounds". WO2013111013A2

Maki, J. M., et al. (2002). "Inactivation of the lysyl oxidase gene Lox leads to aortic aneurysms, cardiovascular dysfunction, and perinatal death in mice." Circulation 106 (19): 2503-2509.

Mambetsariev, I., et al. (2014). "Stiffness-activated GEF-H1 expression exacerbates LPS-induced lung inflammation." PLoS One 9(4): e92670/92671-e92670/92612, 92612 pp.

Mammoto, A., et al. (2013). "Control of lung vascular permeability and endotoxin-induced pulmonary oedema by changes in extracellular matrix mechanics." Nature communications 4: 1759.

Mammoto, T., et al. (2013). "Role of Collagen Matrix in Tumor Angiogenesis and Glioblastoma Multiforme Progression." The American Journal of Pathology 183(4): 1293-1305.

Marshall, D. and V. Smith (2011). "In vivo screening assays for identifying inhibitors of LOXL2 activity". WO 2011022670

Marshall, D., et al. (2012). "Anti-LOXL2 antibody, siRNA, shRNA, ribozyme and triplex oligonucleotide to increase efficacy of antitumor agent and treat cancer". WO2012139045A1

Martinez-Martinez, E et al. (2016). The lysyl oxidase inhibitor (β-aminopropionitrile) reduces leptin profibrotic effects and ameliorates cardiovascular remodeling in diet-induced obesity in rats. Journal of Molecular and Cellular Cardiology, 92, 96-104

Miana, M., et al. (2015). "The lysyl oxidase inhibitor β-aminopropionitrile reduces body weight gain and improves the metabolic profile in diet-induced obesity in rats." Dis. Models Mech. 8(6): 543-551.

Millanes-Romero, A., et al. (2013). "Regulation of Heterochromatin Transcription by Snail1/LOXL2 during Epithelial-to-Mesenchymal Transition." Molecular Cell 52(5): 746-757.

Miller, B. W., et al. (2015). "Targeting the LOX/hypoxia axis reverses many of the features that make pancreatic cancer deadly: inhibition of LOX abrogates metastasis and enhances drug efficacy." EMBO Mol Med 7(8): 1063-1076.

Moreno-Bueno, G., et al. (2011). "Lysyl oxidase-like 2 (LOXL2), a new regulator of cell polarity required for metastatic dissemination of basal-like breast carcinomas." EMBO Mol Med 3(9): 528-544.

Murawaki, Y., et al. (1991). "Serum lysyl oxidase activity in chronic liver disease in comparison with serum levels of prolyl hydroxylase and laminin." Hepatology 14(6): 1167-1173.

Nave, A. H., et al. (2014). "Lysyl Oxidases Play a Causal Role in Vascular Remodeling in Clinical and Experimental Pulmonary Arterial Hypertension." Arterioscler., Thromb., Vasc. Biol. 34(7): 1446-1458.

Neufeld, G. and V. Brekhman (2009). "Use of shRNA targeting LOXL2 gene in modulating angiogenesis and treating tumors, metastasis, fibrosis, and pulmonary alveolar proteinosis". WO2009010974A2

Nicholson, R. I., et al. (2001). "EGFR and cancer prognosis." European Journal of Cancer 37, Supplement 4: 9-15.

Nishikawa, R., et al. (2015). "Tumour-suppressive microRNA-29s directly regulate LOXL2 expression and inhibit cancer cell migration and invasion in renal cell carcinoma." FEBS letters 589(16): 2136-2145.

Nuthakki, V. K., et al. (2004). "Lysyl oxidase expression in a rat model of arterial balloon injury." J Vasc Surg 40(1): 123-129.

Offenberg, H., et al. (2008). "TIMP-1 expression in human colorectal cancer is associated with TGF-B1, LOXL2, INHBA1, TNF-AIP6 and TIMP-2 transcript profiles." Mol Oncol 2(3): 233-240.

Ohmura, H., et al. (2012). "Cardiomyocyte-specific transgenic expression of lysyl oxidase-like protein-1 induces cardiac hypertrophy in mice." Hypertens. Res. 35(11): 1063-1068.

Osawa, T., et al. (2013). "Lysyl oxidase secreted by tumour endothelial cells promotes angiogenesis and metastasis." Br J Cancer 109(8): 2237-2247.

Palfreyman, M. G., et al. (1989). "Preparation of allylamines, inhibitors of lysyl oxidase". EP330218A2

Papadantonakis, N., et al. (2012). "Megakaryocyte pathology and bone marrow fibrosis: the lysyl oxidase connection." Blood 120(9): 1774-1781.

Park, H.-Y. L., et al. (2014). "Lysyl oxidase-like 2 level and glaucoma surgical outcomes." Invest. Ophthalmol. Visual Sci. 55(5): 3337-3343.

Peinado, H., et al. (2005). "A molecular role for lysyl oxidase-like 2 enzyme in snail regulation and tumor progression." EMBO J 24(19): 3446-3458.

Peinado, H., et al. (2008). "Lysyl Oxidase-Like 2 as a New Poor Prognosis Marker of Squamous Cell Carcinomas." Cancer research 68(12): 4541-4550.

Peng, L., et al. (2009). "Secreted LOXL2 is a novel therapeutic target that promotes gastric cancer metastasis via the Src/FAK pathway." Carcinogenesis 30(10): 1660-1669.

Pickup, M. W., et al. (2013). "Stromally Derived Lysyl Oxidase Promotes Metastasis of Transforming Growth Factor-p-Deficient Mouse Mammary Carcinomas." Cancer Res. 73(17): 5336-5346.

Pinnell, S. R. and G. R. Martin (1968). "The cross-linking of collagen and elastin: enzymatic conversion of lysine in peptide linkage to alpha-aminoadipic-delta-semialdehyde (allysine) by an extract from bone." Proceedings of the National Academy of Sciences 61(2): 708-716.

Priyanka, T. et al. (2016) "Lysyl oxidase (LOX) inhibitors as anti-scarring agents" Abstracts of Papers, 252nd ACS National Meeting & Exposition, Philadelphia, PA, United States, Aug. 21-25, 2016, BIOL-98

Ree, A. H., et al. (2008). "Treatment and diagnosis of metastatic prostate cancer with inhibitors of epidermal growth factor receptor (EGFR)". WO2008125633A2

Reynault, O. et al. (1997). "A convenient synthesis of new halothienyl β-aminoacids as versatile building block." Org. Prep. Proc. Int. 29(4): 488-494.

Ricard-Blum, S., et al. (1996). "Mechanism of collagen network stabilization in human irreversible granulomatous liver fibrosis." Gastroenterology 111(1): 172-182.

Rimar, D., et al. (2014). "Brief report: lysyl oxidase is a potential biomarker of fibrosis in systemic sclerosis." Arthritis Rheumatol 66(3): 726-730.

Roehrig, F et al. (2017) "VEGF-ablation therapy reduces drug delivery and therapeutic response in ECM-dense tumors" Oncogene 36(1), 1-12.

Romero, F. et al. (2016). "4,5,6,7-Tetrahydro-1-H-pyrazolo [4,3-C]pyrimidine-3-amine compounds as CBP and/or EP300 inhibitors." WO2016/086200A1

Rosin, N. L., et al. (2015). "Disruption of Collagen Homeostasis Can Reverse Established Age-Related Myocardial Fibrosis." Am. J. Pathol. 185(3): 631-642.

Rowbottom, M. W. et al. (2016a). "Preparation of substituted pyridinylmethylamine compounds as lysyl oxidase-like 2 inhibitors". WO2016144702

Rowbottom, M. W. et al. (2016b). "Preparation of fluorinated pyridine derivatives as lysyl oxidase-like 2 inhibitors and uses thereof." WO2016144703

Rowbottom, M. W.; Hutchinson, J. H. (2017a). "Preparation of pyrimidine derivatives as Lysyl oxidase-like 2 inhibitors useful for the treatment of fibrosis." WO2017003862

Rowbottom, M. W.; Hutchinson, J. H. (2017b). "Lysyl oxidase-like 2 inhibitors and uses thereof." WO2017015221

Ruiz, L. A., et al. (2011). "Single-nucleotide polymorphisms in the lysyl oxidase-like protein 4 and complement component 3 genes are associated with increased risk for endometriosis and endometriosis-associated infertility." Fertil Steril 96(2): 512-515.

Sansom, O. (2012). Targeting the tumour microenvironment in pancreatic cancer. EACR-IACR Joint Conference: Tumour Microenvironment, Dublin, Ireland.

Sayre, L. M. (2007). "Amine compounds for amine oxidase inhibitors, and therapeutic use". WO2007005737A2

Schietke, R., et al. (2010). "The lysyl oxidases LOX and LOXL2 are necessary and sufficient to repress E-cadherin in hypoxia: insights into cellular transformation processes mediated by HIF-1." J Biol Chem 285(9): 6658-6669.

Schlotzer-Schrehardt, U., et al. (2008). "Genotype-correlated expression of lysyl oxidase-like 1 in ocular tissues of patients with pseudoexfoliation syndrome/glaucoma and normal patients." American Journal of Pathology 173(6): 1724-1735.

Schohe-Loop, R., et al. (2003). "Preparation of 2-phenyl-3 (2H)-pyridazinones as lysyl oxidase inhibitors for preventing and treating fibrosis". DE10216144A1

Schuetze, F., et al. (2015). "Inhibition of Lysyl Oxidases Improves Drug Diffusion and Increases Efficacy of Cytotoxic Treatment in 3D Tumor Models." Sci. Rep. 5: 17576.

Schweighauser, L., et al. (2015). "Attraction or Repulsion? London Dispersion Forces Control Azobenzene Switches." Angew. Chem. Int ed 54(45): 13436-13439.

Scola, N. and T. Gorogh (2010). "LOXL4 as a selective molecular marker in primary and metastatic head/neck carcinoma." Anticancer Res 30(11): 4567-4571.

Se, L Y et al. (2017) "Expression of Lysyl Oxidase Predictive of Distant Metastasis of Laryngeal Cancer". Otolaryngology—head and neck surgery; 156(3), 489-497

Shen, C. J., et al. (2014). "Ionizing radiation induces tumor cell lysyl oxidase secretion." BMC Cancer 14: 532/531-532/510.

Shinobu, M et al. (2016) "Lysyl oxidase is associated with increased thrombosis and platelet reactivity". Blood; 127 (11), 1493-1501

Siegel, R. C., et al. (1978). "Biochemical and immunochemical study of lysyl oxidase in experimental hepatic fibrosis in the rat." Proceedings of the National Academy of Sciences 75(6): 2945-2949.

Smith, V. and A. K. Holzer (2010). "Chemotherapeutic methods and compositions for treating cancer by inhibiting activity of lysyl oxidase-type enzyme". WO2010080769A2

Smith, V. and P. Van Vlasselaer (2011). "Tumor therapy by inhibiting the activity or expression of lysyl oxidase-like 2 with antibodies or inhibitory nucleic acids". WO2011022710A1

Stalmans, I., et al. (2010). "Use of lysyl oxidase related protein inhibitors for treatment of ocular neovascularization and fibrotic damage". WO2010091279A1

Stalmans, I., et al. (2011). "Methods of treatmenting ocular fibrosis by modulating the activity of lysyl oxidase-type enzymes". US20110076285A1

Stewart, G. D., et al. (2008). "Analysis of hypoxia-associated gene expression in prostate cancer: lysyl oxidase and glucose transporter-1 expression correlate with Gleason score." Oncol Rep 20(6): 1561-1567.

Tadmor, T., et al. (2013). "The expression of lysyl-oxidase gene family members in myeloproliferative neoplasms." American Journal of Hematology 88(5): 355-358.

Tang, H et al. "Lysyl oxidase drives tumour progression by trapping EGF receptors at the cell surface." Nat Commun. 8:14909

Tang, S. S., et al. (1984). "Beta-substituted ethylamine derivatives as suicide inhibitors of lysyl oxidase." J Biol Chem 259(2): 975-979.

Threadgill, D. and C. J. Barrick (2007). "Use of EGFR inhibitors to prevent or treat obesity". WO2007011702A2

Toustrup, K., et al. (2011). "Development of a hypoxia gene expression classifier with predictive impact for hypoxic modification of radiotherapy in head and neck cancer." Cancer research 71(17): 5923-5931.

Tsang, A. W. and C. M. Furdui (2015). "Methods and compositions comprising epidermal growth factor receptor (EGFR) inhibitors for the treatment of *Chlamydia* infection and related diseases and disorders". WO2015038755A1

Uzel, M. I., et al. (2001). "Multiple bone morphogenetic protein 1-related mammalian metalloproteinases process pro-lysyl oxidase at the correct physiological site and control lysyl oxidase activation in mouse embryo fibroblast cultures." J Biol Chem 276(25): 22537-22543.

Vadasz, Z., et al. (2005). "Abnormal deposition of collagen around hepatocytes in Wilson's disease is associated with hepatocyte specific expression of lysyl oxidase and lysyl oxidase like protein-2." J Hepatol 43(3): 499-507.

Van Bergen, T., et al. (2013). "The role of LOX and LOXL2 in scar formation after glaucoma surgery." Invest. Ophthalmol. Visual Sci. 54(8): 5788-5796.

Van Bierbeek, A and Gingras, M. (1998) "Polysulfurated branched molecules containing functionalized m-phenylene sulfides." Tetrahedron Lett, 39(35): 6283-6286.

van Nimwegen, M. J. and B. van de Water (2007). "Focal adhesion kinase: a potential target in cancer therapy." Biochem Pharmacol 73(5): 597-609.

Vitalba, D S et al. (2016). "Major Action of Endogenous Lysyl Oxidase in Clear Cell Renal Cell Carcinoma Progression and Collagen Stiffness Revealed by Primary Cell Cultures" Am. J. Pathol.; 186(9), 2473-2485

Weihua, Z., et al. (2008). "Survival of Cancer Cells Is Maintained by EGFR Independent of Its Kinase Activity." Cancer Cell 13(5): 385-393.

Wiel, C., et al. (2013). "Lysyl oxidase activity regulates oncogenic stress response and tumorigenesis." Cell Death Dis 4: e855.

Wilgus, M.-L., et al. (2011). "Lysyl oxidase: A lung adenocarcinoma biomarker of invasion and survival." Cancer 117(10): 2186-2191.

Wilhelmus, M. M. M., et al. (2013). "Extracellular matrix modulator lysyl oxidase colocalizes with amyloid-beta pathology in Alzheimer's disease and hereditary cerebral hemorrhage with amyloidosis-Dutch type." Exp. Gerontol. 48(2): 109-114.

Williamson, P. R. and H. M. Kagan (1987). "Electronegativity of aromatic amines as a basis for the development of ground state inhibitors of lysyl oxidase." J Biol Chem 262(30): 14520-14524.

Wong, C. C.-L., et al. (2011). "Hypoxia-inducible factor 1 is a master regulator of breast cancer metastatic niche formation." Proceedings of the National Academy of Sciences 108(39): 16369-16374.

Wong, C. C.-L., et al. (2014). "Lysyl oxidase-like 2 is critical to tumor microenvironment and metastatic niche formation in hepatocellular carcinoma." Hepatology (Hoboken, NJ, U. S.) 60(5): 1645-1658.

Xiao Q and Ge G. (2012) "Lysyl Oxidase, Extracellular Matrix Remodeling and Cancer Metastasis" Cancer Microenviron. 5(3): 261-273

Xu, J., et al. (2014). "67 laminin receptor promotes the malignant potential of tumour cells up-regulating lysyl oxidase-like 2 expression in cholangiocarcinoma." Digestive and Liver Disease 46(8): 750-757.

Yang, X., et al. (2013). "Inactivation of lysyl oxidase by β-aminopropionitrile inhibits hypoxia-induced invasion and migration of cervical cancer cells." Oncol Rep 29(2): 542-548.

Yang, Z., et al. (2010). "Uric acid increases fibronectin synthesis through upregulation of lysyl oxidase expression in rat renal tubular epithelial cells." Am. J. Physiol. 299(2, Pt. 2): F336-F346.

Zaffryar-Eilot, S., et al. (2013). "Lysyl oxidase-like-2 promotes tumour angiogenesis and is a potential therapeutic target in angiogenic tumours." Carcinogenesis 34(10): 2370-2379.

Zenkel, M., et al. (2011). "Regulation of lysyl oxidase-like 1 (LOXL1) and elastin-related genes by pathogenic factors associated with pseudoexfoliation syndrome." Invest Ophthalmol Vis Sci 52(11): 8488-8495.

Zhao X and Subramaian S. (2017). "Intrinsic Resistance of Solid Tumors to Immune Checkpoint Blockade Therapy" Cancer Res; 77(4), 817-822

Zhi, C et al. (2017) "Elevated ischaemia-associated lysyl oxidase activity in delayed graft failure 6-12 months after renal transplantation" Experimental Physiology 102(2), 282-287

Zhu, J., et al. (2015). "Lysyl Oxidase Is Predictive of Unfavorable Outcomes and Essential for Regulation of Vascular Endothelial Growth Factor in Hepatocellular Carcinoma." Digestive Diseases and Sciences: 1-13.

Zibadi, S., et al. (2010). "T lymphocyte regulation of lysyl oxidase in diet-induced cardiac fibrosis." Cardiovasc Toxicol 10(3): 190-198.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

The present disclosure relates embodiments as disclosed in clauses 1 to 56:

1. A compound having the structure of Formula (I):

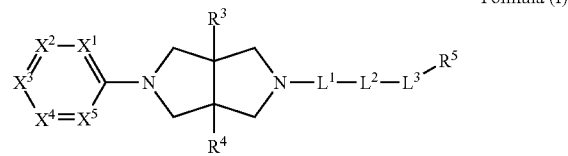

Formula (I)

or a pharmaceutically acceptable salt thereof, wherein
$X^1$ and $X^5$ is each selected from $CR^1$ or N;
$X^2$, $X^3$ and $X^4$ is each selected from $CR^1$, $CR^2$ or N, provided at least one of $X^2$, $X^3$ and $X^4$ is $CR^2$ and provided only one of $X^1$, $X^2$, $X^3$, $X^4$ and $X^5$ can be N;
$R^1$ is at each occurrence independently selected from hydrogen, halo, cyano, hydroxy, $C_1$-$C_6$ alkyl, $C_2$-$C_6$ alkenyl, $C_2$-$C_6$ alkynyl, $C_1$-$C_6$ alkoxy, $C_1$-$C_6$ alkylcarbonyl, $C_1$-$C_6$ alkoxy-carbonyl, —C(O)NR$^7$R$^8$, —SO$_2$R$^7$, or —SO$_2$NR$^7$R$^8$, where
any alkyl, alkenyl, alkynyl or alkoxy in $R^1$ may be optionally substituted by one, two or three substituents independently selected from halo, cyano, oxo, hydroxy, carboxy, $R^7$, —OR', —C(O)R$^7$, —OC(O)R$^7$ or —C(O)OR$^7$;
$R^2$ is at each occurrence independently selected from —O—Y$^1$—R$^{2a}$,   —O—Y$^2$—C(O)—Y$^1$—R$^{2a}$, —O—Y$^2$—C(O)—Y$^1$—NR$^{2b}$R$^{2c}$,  —S—Y$^1$—R$^{2a}$, —S—Y$^2$—C(O)—Y$^1$—NR$^{2b}$R$^{2c}$,   —SO$_2$—Y$^1$—R$^{2a}$, —NR$^{2b}$R$^{2c}$ or —NR$^{2a}$—Y$^2$—C(O)—Y$^1$—NR$^{2b}$R$^{2c}$;
$Y^1$ is selected from a bond, $C_1$-$C_4$ alkylene, $C_2$-$C_4$ alkenylene or $C_2$-$C_4$ alkynylene, where
any alkylene, alkenylene or alkynylene in $Y^1$ may be optionally substituted by one or two substituents independently selected from halo, cyano, hydroxy, carboxy, $R^6$, —OR$^6$, —C(O)R$^6$ or —C(O)OR$^6$;
$Y^2$ is selected from $C_1$-$C_4$ alkylene, $C_2$-$C_4$ alkenylene or $C_2$-$C_4$ alkynylene, where
any alkylene, alkenylene or alkynylene in $Y^2$ may be optionally substituted by one or two substituents independently selected from halo, cyano, hydroxy, carboxy, $R^6$, —OR$^6$, —C(O)R$^6$ or —C(O)OR$^6$;
$R^{2a}$ is selected from $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkenyl, 3- to 6-membered monocyclic heterocyclyl, phenyl, or 5- or 6-membered heteroaryl, where
any alkyl, alkenyl, alkynyl, cycloalkyl, cycloalkenyl or heterocyclyl in $R^{2a}$ may be optionally substituted by one, two or three substituents independently selected from halo, cyano, oxo, hydroxy, carboxy, $R^6$, —$OR^6$, —$C(O)R^6$, —$C(O)OR^6$, —$OC(O)R^6$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$;
- any phenyl or heteroaryl in $R^{2a}$ may be optionally substituted by one, two or three substituents independently selected from halo, cyano, carboxy, $R^6$, —$OR^6$, —$C(O)R^6$, —$C(O)OR^6$, —$OC(O)R^6$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$; and
- any heterocyclyl or heteroaryl in $R^{2a}$ includes 1, 2 or 3 heteroatoms selected from N, O or S in the ring;

$R^{2b}$ and $R^{2c}$ is each independently selected from $C_1$-$C_6$ alkyl, $C_3$-$C_6$ alkenyl or $C_3$-$C_6$ alkynyl, where
- any alkyl, alkenyl or alkynyl in $R^{2b}$ and $R^{2c}$ may be optionally substituted by one, two or three substituents independently selected from halo, cyano, oxo, hydroxy, carboxy, $R^6$, —$OR^6$, —$C(O)R^6$, —$C(O)OR^6$, —$OC(O)R^6$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$; or $R^{2b}$ and $R^{2c}$ together with the nitrogen atom to which they are attached form a 3- to 7-membered heterocycloalkyl, optionally including one or two additional heteroatoms selected from O, N or S in the ring,
- said heterocycloalkyl formed by $R^{2b}$ and $R^{2c}$ may be optionally substituted by one, two or three substituents independently selected from halo, cyano, hydroxy, carboxy, $R^6$, —$OR^6$, —$C(O)R^6$, —$C(O)OR^6$, —$OC(O)R^6$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$;
- any S in the ring of said heterocycloalkyl formed by $R^{2b}$ and $R^{2c}$ may be optionally oxidized;

optionally when (i) $CR^1$ and $CR^2$ are adjacent, (ii) $R^1$ is $C_1$-$C_6$ alkyl, (iii) $R^2$ is —O—$Y^1$—$R^{2a}$, —O—$Y^2$—C(O)—$Y^1$—$R^{2a}$, —S—$Y^1$—$R^{2a}$ or —$SO_2$—$Y^1$—$R^{2a}$ and (iv) $R^{2a}$ is $C_1$-$C_6$ alkyl, then $R^1$ and $R^2$ together with the carbon atom to which they are attached may form a 4- to 7-membered heterocycloalkyl including one heteroatom selected from O or S in the ring;

optionally when (i) $CR^2$ and $CR^2$ are adjacent, (ii) each $R^2$ is independently selected from —O—$Y^1$—$R^{2a}$, —O—$Y^2$—C(O)—$Y^1$—$R^{2a}$, —S—$Y^1$—$R^{2a}$ or —$SO_2$—$Y^1R^{2a}$, and (iii) each $R^{2a}$ is $C_1$-$C_6$ alkyl, then the first $R^2$ and the second $R^2$ together with the carbon atom to which they are attached may form a 4- to 7-membered heterocycloalkyl including two heteroatoms selected from O or S in the ring;

$R^3$ and $R^4$ is each independently selected from hydrogen, hydroxy, carboxy, $C_1$-$C_6$ alkyl, $C_1$-$C_6$ alkoxy, $C_1$-$C_6$ alkyl-carbonyl or $C_1$-$C_6$ alkoxy-carbonyl,
- any alkyl or alkoxy in $R^3$ and $R^4$ may be optionally substituted by one, two or three substituents independently selected from halo, cyano, or hydroxy; or $R^3$ and $R^4$ together with the carbon atom to which they are attached form a 3- to 7-membered cycloalkyl,
- said cycloalkyl formed by $R^3$ and $R^4$ may be optionally substituted by one, two or three substituents independently selected from halo, cyano, hydroxy, carboxy, $R^6$, —$OR^6$, —$C(O)R^6$ or —$C(O)OR^6$;

$L^1$ and $L^3$ is each independently selected from a bond, $C_1$-$C_4$ alkylene, $C_2$-$C_4$ alkenylene or $C_2$-$C_4$ alkynylene, where
- any alkylene, alkenylene or alkynylene in $L^3$ and $L^1$ may be optionally substituted by one or two substituents independently selected from halo, cyano, oxo, hydroxy, carboxy, $R^6$, —$OR^6$, —$C(O)R^6$ or —$C(O)OR^6$;

$L^2$ is selected from a bond, —O—, —C(O)—, —C(O)O—, —OC(O)—, —$C(O)NR^7$—, —$NR^7C(O)$—, —$NR^7$—, —$SO_2NR^7$—, —$NR^7SO_2$—, —S—, —$SO_2$—, —$SO_2O$—, —$OSO_2$—, —$NR^7SO_2NR^8$—, —$NR^7C(O)NR^8$—, —$C(O)NR^7NR^8$—, —$NR^7NR^8C(O)$—, —$NR^7C(O)O$— or —$OC(O)NR^7$—;

$R^5$ is selected from hydrogen, $C_1$-$C_6$ alkyl, $C_2$-$C_6$ alkenyl, $C_2$-$C_6$ alkynyl, $C_3$-$C_{12}$ cycloalkyl, $C_3$-$C_{12}$ cycloalkenyl, 3- to 12-membered heterocyclyl, phenyl or 5- or 6-membered heteroaryl, where
- any heterocyclyl or heteroaryl in $R^5$ includes 1, 2 or 3 heteroatoms selected from N, O or S in the ring;
- any alkyl, alkenyl or alkynyl in $R^5$ may be optionally substituted by one, two or three substituents independently selected from halo, cyano, oxo, hydroxy, carboxy, nitro, $R^6$, —$OR^6$, —$C(O)R^6$, —$C(O)OR^6$, —$OC(O)R^6$, —$C(O)NR^6R^7$, —$NR^7C(O)R^8$, —$NR^6R^7$, —$SO_2NR^6R^7$, —$NR^7SO_2R^8$, —$SR^7$, —$SO_2R^7$, —$SO_2OR^7$, —$OSO_2R^7$, —$NR^8SO_2NR^6R^7$, —$NR^8C(O)NR^6R^7$, —$NR^7C(O)OR^8$ or —$OC(O)NR^6R^7$;
- any cycloalkyl, cycloalkenyl, heterocyclyl, phenyl or heteroaryl in $R^5$ may be optionally substituted by one, two or three substituents independently selected from halo, cyano, oxo, nitro, $R^7$, —$OR'$, —$C(O)R^7$, —$OC(O)R^7$, —$C(O)OR^7$, —$C(O)NR^7R^8$, —$NR^7C(O)R^8$, —$NR^7R^8$, —$SO_2NR^7R^8$, —$NR^7SO_2R^8$, —$SR^7$, —$SO_2R^7$, —$SO_2OR^7$, —$OSO_2R^7$, —$NR^7SO_2NR^8R^9$, —$NR^7C(O)NR^8R^9$, —$NR^7C(O)OR^8$ or —$OC(O)NR^7R^8$;

$R^6$ is at each occurrence independently selected from $C_1$-$C_4$ alkyl, $C_1$-$C_4$ haloalkyl, $C_1$-$C_4$ hydroxyalkyl, $C_1$-$C_4$ cyanoalkyl, $R^7$, $R^8$ and $R^9$ is at each occurrence independently selected from hydrogen or $C_1$-$C_4$ alkyl, where
- any $C_1$-$C_4$ alkyl in $R^7$, $R^8$ and $R^9$ may be optionally substituted by one, two or three substituents independently selected from halo, cyano, oxo, hydroxy, carboxy, $R^6$, —$OR^6$, —$C(O)R^6$ or —$C(O)OR^6$;

provided when $L^2$ is linked to $L^1$ by a nitrogen atom, then $L^1$ is not a bond;

provided when $R^5$ is $C_3$-$C_{12}$ cycloalkyl, $C_3$-$C_{12}$ cycloalkenyl, 3- to 12-membered heterocyclyl, phenyl or 5- or 6-membered heteroaryl, then at least one of $L^1$, $L^2$ and $L^3$ is nota bond;

provided -$L^1$-$L^2$-$L^3$-$R^5$ is not benzyl, benzyloxycarbonyl or tert-butyloxycarbonyl;

provided when $X^3$ is N and each of $X^5$ and $X^1$ is $CR^1$, then $R^1$ is not cyano;

provided when one of $X^2$ or $X^4$ is N, one of $X^2$ or $X^4$ is $CR^2$ and $L^1$-$L^2$-$L^3$-$R^5$ is 2-pyridylmethyl or 3-pyridylmethyl, then $R^2$ is not —O-benzyl;

provided when one of $X^2$ or $X^4$ is $CR^2$ and $X^3$ is $CR^1$, then $R^1$ is not chloro.

2. A compound in accordance with clause 1 having the structure of Formula (I-a):

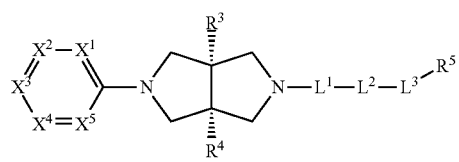

Formula (I-a)

or a pharmaceutically acceptable salt thereof.

3. A compound in accordance with clause 1 or clause 2, or a pharmaceutically acceptable salt thereof, wherein $X^3$ is $CR^2$.

4. A compound in accordance with clause 3, or a pharmaceutically acceptable salt thereof, wherein each of $X^1$, $X^2$, $X^4$ and $X^5$ is selected from $CR^1$ or N; provided only one of $X^1$, $X^2$, $X^4$ and $X^5$ can be N.

5. A compound in accordance with clause 4, or a pharmaceutically acceptable salt thereof, wherein each of $X^1$, $X^2$, $X^4$ and $X^5$ is $CR^1$.

6. A compound in accordance with any one of the preceding clauses having the structure of Formula (II-a):

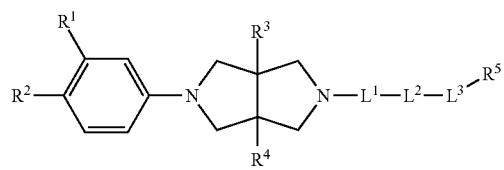

Formula (II-a)

or a pharmaceutically acceptable salt thereof.

7. A compound in accordance with any one of the preceding clauses, or a pharmaceutically acceptable salt thereof, wherein $L^1$ is selected from a bond or unsubstituted $C_1$-$C_4$ alkylene, in particular $L^1$ is a bond.

8. A compound in accordance with any one of the preceding clauses, or a pharmaceutically acceptable salt thereof, wherein $L^3$ is selected from a bond or unsubstituted $C_1$-$C_4$ alkylene, in particular $L^3$ is a bond.

9. A compound in accordance with any one of the preceding clauses having the structure of Formula (IV-a):

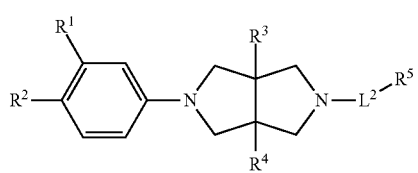

Formula (IV-a)

or a pharmaceutically acceptable salt thereof.

10. A compound in accordance with any one of the preceding clauses, or a pharmaceutically acceptable salt thereof, wherein $L^2$ is selected from a bond, —C(O)—, —C(O)O—, —C(O)NR$^7$—, —SO$_2$NR$^7$—, —SO$_2$— or —C(O)NR$^7$NR$^8$—, in particular $L^2$ is selected from a bond, —C(O)—, —C(O)O—, —C(O)NH—, —C(O)N(CH$_3$)—, —C(O)N(CH$_2$CH$_3$OH)—, —SO$_2$NH—, —SO$_2$— or —C(O)NHNH—.

11. A compound in accordance with any one of the preceding clauses, or a pharmaceutically acceptable salt thereof, wherein $L^2$ is selected from a bond, —C(O)—, —C(O)O— or —C(O)NR$^7$—, in particular $L^2$ is selected from a bond, —C(O)— or —C(O)NR$^7$—.

12. A compound in accordance with any one of the preceding clauses having the structure of Formula (V):

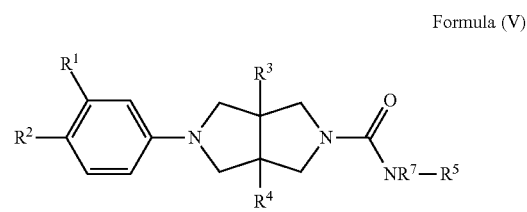

Formula (V)

or a pharmaceutically acceptable salt thereof.

13. A compound in accordance with any one of the preceding clauses, or a pharmaceutically acceptable salt thereof, wherein $R^2$ is selected from —O—$Y^1$—$R^{2a}$, —S—$Y^1$—$R^{2a}$, —SO$_2$—$Y^1$—$R^{2a}$ or —NR$^{2b}$R$^{2c}$.

14. A compound in accordance with any one of the preceding clauses, or a pharmaceutically acceptable salt thereof, wherein $Y^1$ is a bond.

15. A compound in accordance with any one of the preceding clauses, having the structure of Formula (VIII-c):

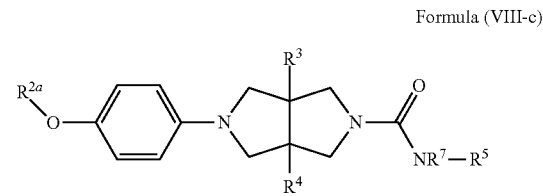

Formula (VIII-c)

or a pharmaceutically acceptable salt thereof.

16. A compound in accordance with any one of the preceding clauses, having the structure of Formula (VIII-d):

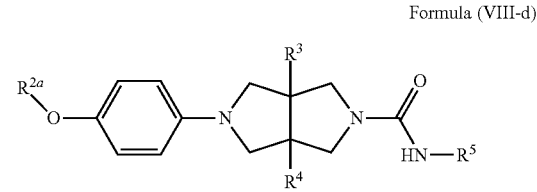

Formula (VIII-d)

or a pharmaceutically acceptable salt thereof.

17. A compound in accordance with any one of the preceding clauses, or a pharmaceutically acceptable salt thereof, wherein $R^{2a}$ is selected from unsubstituted $C_1$-$C_4$ alkyl, $C_1$-$C_4$ alkyl substituted by $C_1$-$C_4$ alkoxy, unsubstituted $C_3$-$C_6$ cycloalkyl, unsubstituted 3- to 6-membered monocyclic heterocycloalkyl, or unsubstituted phenyl, in particular $R^{2a}$ is unsubstituted $C_1$-$C_4$ alkyl.

18. A compound in accordance with any one of the preceding clauses, or a pharmaceutically acceptable salt thereof, wherein $R^{2a}$ is unsubstituted $C_1$-$C_4$ alkyl, in particular methyl or ethyl.

19. A compound in accordance with in accordance with any one of clauses 1 to 14, having the structure of Formula (XII-c):

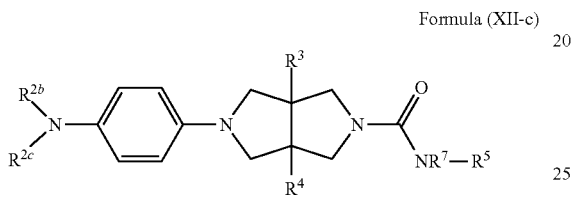

Formula (XII-c)

or a pharmaceutically acceptable salt thereof.

20. A compound in accordance with in accordance with any one of clauses 1 to 14, having the structure of Formula (XII-d):

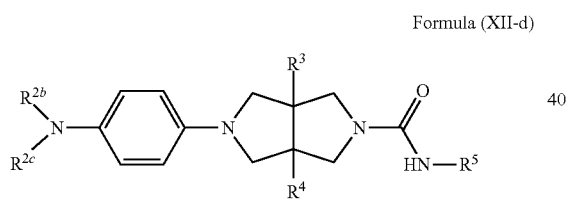

Formula (XII-d)

or a pharmaceutically acceptable salt thereof.

21. A compound in accordance with any one clauses 1 to 14, 19 or 20, or a pharmaceutically acceptable salt thereof, wherein $R^{2b}$ and $R^{2c}$ is each independently selected from $C_1$-$C_6$ alkyl optionally substituted by —$NR^7R^8$, where $R^7$ and $R^8$ is each independently selected from unsubstituted $C_1$-$C_4$ alkyl, in particular $R^{2b}$ is unsubstituted $C_1$-$C_4$ alkyl and $R^{2c}$ is $C_1$-$C_4$ alkyl substituted by —$N(CH_3)_2$.

22. A compound in accordance with any one of clauses 1 to 14 or 19 to 21, or a pharmaceutically acceptable salt thereof, wherein $R^{2b}$ and $R^{2c}$ together with the nitrogen atom to which they are attached form a 3- to 7-membered heterocycloalkyl, optionally including one additional heteroatom selected from N or S in the ring, said heterocycloalkyl formed by $R^{2b}$ and $R^{2c}$ may be optionally substituted by one substituent independently selected from hydroxy or —$SO_2R^7$;

any S in the ring of said heterocycloalkyl formed by $R^{2b}$ and $R^{2c}$ may be optionally oxidized;

in particular $R^{2b}$ and $R^{2c}$ together with the nitrogen atom to which they are attached form:

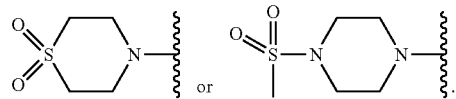

23. A compound in accordance with any one of the preceding clauses, or a pharmaceutically acceptable salt thereof, wherein $R^3$ and $R^4$ is each independently selected from hydrogen, hydroxy, carboxy, unsubstituted $C_1$-$C_6$ alkyl (e.g. methyl), unsubstituted $C_1$-$C_6$ alkoxy (e.g. methoxy), or unsubstituted $C_1$-$C_6$ alkoxycarbonyl (e.g. methoxycarbonyl), in particular $R^3$ and $R^4$ is each independently selected from hydrogen or unsubstituted $C_1$-$C_4$ alkyl (e.g. methyl).

24. A compound in accordance with any one of the preceding clauses, or a pharmaceutically acceptable salt thereof, wherein $R^3$ and $R^4$ is each hydrogen.

25. A compound in accordance with any one of clauses 1 to 22, or a pharmaceutically acceptable salt thereof, wherein $R^3$ and $R^4$ together with the carbon atom to which they are attached form an unsubstituted 3- to 7-membered cycloalkyl.

26. A compound in accordance with any one of the preceding clauses, or a pharmaceutically acceptable salt thereof, wherein $R^1$ is selected from hydrogen, halo, cyano, $C_1$-$C_6$ alkyl or $C_2$-$C_6$ alkenyl, where
  any alkyl and alkenyl in $R^1$ may be optionally substituted by one substituent selected from cyano, hydroxy, carboxy, —$C(O)R^6$ or $C(O)OR^6$, where $R^6$ is $C_1$-$C_4$ alkyl.

27. A compound in accordance with any one of the preceding clauses, or a pharmaceutically acceptable salt thereof, wherein $R^1$ is hydrogen.

28. A compound in accordance with any one of the preceding clauses, or a pharmaceutically acceptable salt thereof, wherein $R^5$ is selected from $C_1$-$C_6$ alkyl, $C_2$-$C_6$ alkenyl, $C_2$-$C_6$ alkynyl, $C_3$-$C_{12}$ cycloalkyl, 3- to 12-membered heterocycloalkyl, phenyl or 5- or 6-membered heteroaryl, where
  any heterocycloalkyl or heteroaryl in $R^5$ includes 1, 2 or 3 heteroatoms selected from N, O or S in the ring;
  any alkyl, alkenyl or alkynyl in $R^5$ may be optionally substituted by one, two or three substituents independently selected from halo, cyano, oxo, hydroxy, carboxy, nitro, $R^6$, —$OR^6$, $SO_2R^7$;
  any cycloalkyl, heterocycloalkyl, phenyl or heteroaryl in $R^5$ may be optionally substituted by one, two or three substituents independently selected from halo, cyano, oxo, nitro, $R^7$, —$OR^7$, —$SO_2R^7$.

29. A compound in accordance with any one of the preceding clauses, or a pharmaceutically acceptable salt thereof, wherein $R^5$ is selected from $C_1$-$C_6$ alkyl, $C_3$-$C_{12}$ cycloalkyl, 3- to 12-membered heterocycloalkyl, phenyl or 5- or 6-membered heteroaryl, where
  any heterocycloalkyl or heteroaryl in $R^5$ includes 1, 2 or 3 heteroatoms selected from N, O or S in the ring;
  any alkyl in $R^5$ may be optionally substituted by cyano or hydroxy;
  any cycloalkyl, heterocycloalkyl, phenyl or heteroaryl in $R^5$ may be optionally substituted by oxo, nitro or hydroxy.

30. A compound in accordance with clause 15 or clause 16, or a pharmaceutically acceptable salt thereof, wherein
  $R^{2a}$ is unsubstituted $C_1$-$C_4$ alkyl;

R³ and R⁴ is each independently selected from hydrogen or unsubstituted $C_1$-$C_4$ alkyl (e.g. methyl);

R⁵ is selected from $C_1$-$C_6$ alkyl, $C_3$-$C_6$ cycloalkyl, 3- to 6-membered heterocycloalkyl, phenyl or 5- or 6-membered heteroaryl, where
  any heterocycloalkyl or heteroaryl in R⁵ includes 1, 2 or 3 heteroatoms selected from N, O or S in the ring;
  any alkyl in R⁵ may be optionally substituted by cyano or hydroxy;
  any cycloalkyl, heterocycloalkyl, phenyl or heteroaryl in R⁵ may be optionally substituted by oxo, nitro or hydroxy; and R⁷, when present, is $C_1$-$C_4$ alkyl optionally substituted by hydroxy.

31. A compound in accordance with clause 19 or clause 20, or a pharmaceutically acceptable salt thereof, wherein
  $R^{2b}$ is unsubstituted $C_1$-$C_4$ alkyl,
  $R^{2c}$ is $C_1$-$C_4$ alkyl substituted by —N(CH₃)₂;
  R³ and R⁴ is each independently selected from hydrogen or unsubstituted $C_1$-$C_4$ alkyl (e.g. methyl);
  R⁵ is selected from $C_1$-$C_6$ alkyl, $C_3$-$C_6$ cycloalkyl, 3- to 6-membered heterocycloalkyl, phenyl or 5- or 6-membered heteroaryl, where
    any heterocycloalkyl or heteroaryl in R⁵ includes 1, 2 or 3 heteroatoms selected from N, O or S in the ring;
    any alkyl in R⁵ may be optionally substituted by cyano or hydroxy;
    any cycloalkyl, heterocycloalkyl, phenyl or heteroaryl in R⁵ may be optionally substituted by oxo, nitro or hydroxy; and
  R⁷, when present, is $C_1$-$C_4$ alkyl optionally substituted by hydroxy.

32. A compound in accordance with clause 19 or clause 20, or a pharmaceutically acceptable salt thereof, wherein
  $R^{2b}$ and $R^{2c}$ together with the nitrogen atom to which they are attached form:

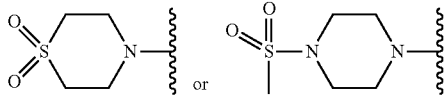 [SMILES: *N1CCS(=O)(=O)CC1 ; *N1CCN(S(C)(=O)=O)CC1]

R³ and R⁴ is each independently selected from hydrogen or unsubstituted $C_1$-$C_4$ alkyl (e.g. methyl);
  R⁵ is selected from $C_1$-$C_6$ alkyl, $C_3$-$C_6$ cycloalkyl, 3- to 6-membered heterocycloalkyl, phenyl or 5- or 6-membered heteroaryl, where
    any heterocycloalkyl or heteroaryl in R⁵ includes 1, 2 or 3 heteroatoms selected from N, O or S in the ring;
    any alkyl in R⁵ may be optionally substituted by cyano or hydroxy;
    any cycloalkyl, heterocycloalkyl, phenyl or heteroaryl in R⁵ may be optionally substituted by oxo, nitro or hydroxy;
  R⁷, when present, is $C_1$-$C_4$ alkyl optionally substituted by hydroxy.

33. A compound in accordance with clause 1, wherein the compound is selected from any of the compounds in Table 1, or Table 1a, or a pharmaceutically acceptable salt of any of the foregoing compounds.

34. A compound in accordance with of any one of clauses 1 to 33 for use as a medicament.

35. A compound in accordance with of any one of clauses 1 to 33, wherein the compound is for use in the treatment of a disease or medical condition mediated by LOX.

36. A compound in accordance with of any one of clauses 1 to 33, wherein the compound is for use in the manufacture of a medicament for the treatment of a disease or medical condition mediated by LOX.

37. A method of treating a disease or medical condition mediated by LOX in a subject in need thereof, the method comprising administering to the subject an effective amount of a compound in accordance with any one of clauses 1 to 33, or a pharmaceutically acceptable salt thereof.

38. A compound of any one of clauses 1 to 33, wherein the compound is for use in the treatment of a proliferative disease.

39. A compound of clause 38, wherein the proliferative disease is cancer.

40. A compound of any one of clauses 1 to 33 for use in the treatment or prevention of cancer associated with overexpression of EGFR.

41. A compound for use in accordance with clause 40, wherein the cancer is selected from the group consisting of: NSCLC, pancreatic cancer, squamous cells carcinoma, skin cancer, thyroid, colorectal, prostate, renal, breast, head and neck cancers, glioma, mesothelioma, epidermal carcinomas ovarian, cervical, bladder and oesophageal cancers and a biliary cancer such as cholangiocarcinoma.

42. A compound for use in accordance with clause 40 or clause 41, wherein the compound is a lysyl oxidase inhibitor and downregulates expression of MATN2 and/or activation of SMAD2 as measured by upregulation of pSMAD2.

43. A compound for use in accordance with clause 40 or clause 41, wherein the compound is a lysyl inhibitor and inhibits maturation of lysyl oxidase.

44. A compound for use in accordance with clause 40 or clause 41, wherein the compound is a lysyl inhibitor and inhibits the catalytic activity of lysyl oxidase.

45. A compound for use in accordance with clause 40 or clause 41, wherein the compound is a lysyl oxidase inhibitor does not inhibit MAO-A and/or MAO-B.

46. A compound of any one of clauses 1 to 33, wherein the compound is for use in the treatment a fibrotic disease, such as liver fibrosis, lung fibrosis, kidney fibrosis, cardiac fibrosis, myelofibrosis or schleroderma.

47. A method of treating or preventing cancer in a subject, said method comprising administering a therapeutically effective amount of a lysyl oxidase inhibitor to said subject, wherein said subject has a cancer associated with overexpression of EGFR and the lysyl oxidase inhibitor is a compound in accordance with any one of clauses 1 to 33.

48. A method in accordance with clause 47, wherein said method comprises determining the level EGFR in a biological sample of said subject, and administering a lysyl oxidase inhibitor to said subject when the presence of EGFR is determined to be overexpressed in the biological sample.

49. A method in accordance with clause 47 or clause 48, wherein the method further comprises the steps of determining the level of one or more of MATN2, pSMAD2 or HTRA1 in a biological sample of said subject, and administering a lysyl oxidase inhibitor to said subject in response to one or more of the following:
a) the level of MATN2 is greater than a reference sample;
b) the level of pSMAD2 is lower than a reference sample; or
c) the level of HTRA1 is greater than a reference sample and the level of pSMAD2 is lower than a reference sample.
50. A method in accordance with any of clauses 47 to 49, wherein said subject has a cancer selected from the group consisting of: NSCLC, pancreatic cancer, squamous cells carcinoma, skin cancer, thyroid, colorectal, prostate, renal, breast, head and neck cancers, glioma, mesothelioma, epidermal carcinomas ovarian, cervical, bladder and oesophageal cancers and a biliary cancer such as cholangiocarcinoma.
51. A method in accordance with any of clauses 47 to 50, wherein the lysyl oxidase inhibitor downregulates expression of MATN2 and/or upregulates pSMAD2.
52. A method in accordance with any of clauses 47 to 51, wherein the lysyl inhibitor inhibits: maturation of lysyl oxidase, catalytic activity of lysyl oxidase or both maturation and catalytic activity.
53. A method in accordance with any of clauses 47 to 52, wherein the lysyl oxidase inhibitor does not inhibit MAO-A and/or MAO-B.
54. A method of determining a treatment regimen for a subject with cancer, comprising:
a) determining the level of one or more of EGFR, MATN2 and HTRA1 in a biological sample; and
b) administering a treatment regimen comprising a therapeutically effective amount of a compound of any one of clauses 1 to 33, when levels of one or more of EGFR, MATN2 and HTRA1 are elevated compared to a reference sample.
55. The method in accordance with clause 54, wherein the HTRA1 is homotrimeric HTRA1.
56. A pharmaceutical composition comprising a compound according to any one of clauses 1 to 33 and a pharmaceutically acceptable carrier.
57. A pharmaceutical composition according to clause 56, further comprising an additional therapeutically active ingredient.

SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Forward primer used for cloning of LOX cDNA
      into pEGFP-N1/proGFP2-N1

<400> SEQUENCE: 1
gagagagcta gcatgcgttt cgcctggg                                28

<210> SEQ ID NO 2
<211> LENGTH: 33
<212> TYPE: DNA
<213> ORGANISM: Artificial Sequence
<220> FEATURE:
<223> OTHER INFORMATION: Reverse primer used for cloning of LOX cDNA
      into pEGFP-N1/proGFP2-N1

<400> SEQUENCE: 2
tctctcctcg agatacggtg aaattgtgca gcc                          33

-continued
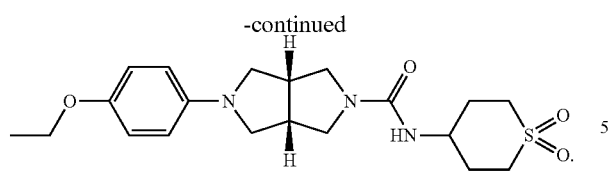

The invention claimed is:
1. A compound having the structure of Formula (II-a):

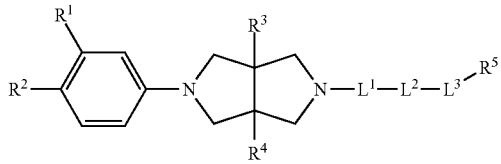

Formula (II-a)

or a pharmaceutically acceptable salt thereof, wherein
$R^1$ is selected from hydrogen, halo, cyano, hydroxy, $C_1$-$C_6$ alkyl, $C_2$-$C_6$ alkenyl, $C_2$-$C_6$ alkynyl, $C_1$-$C_6$ alkoxy, $C_1$-$C_6$ alkyl-carbonyl, $C_1$-$C_6$ alkoxy-carbonyl, —C(O)NR$^7$R$^8$, —SO$_2$R$^7$, or —SO$_2$NR$^7$R$^8$, where
any alkyl, alkenyl, alkynyl or alkoxy in $R^1$ may be optionally substituted by one, two or three substituents independently selected from halo, cyano, oxo, hydroxy, carboxy, $R^7$, —OR$^7$, —C(O)R$^7$, —OC(O)R$^7$ or —C(O)OR$^7$;
$R^2$ is selected from —O—Y$^1$—R$^{2a}$, —O—Y$^2$—C(O)—Y$^1$-R$^{2a}$, —O—Y$^2$—C(O)—Y$^1$—NR$^{2b}$R$^{2c}$, —S—Y$^1$—R$^{2a}$, —S—Y$^2$—C(O)—Y$^1$—NR$^{2b}$R$^{2c}$, —SO$_2$—Y$^1$—R$^{2a}$, —NR$^{2b}$R$^{2c}$ or —NR$^{2a}$—Y$^2$—C(O)—Y$^1$—NR$^{2b}$R$^{2c}$;
$Y^1$ is selected from a bond, $C_1$-$C_4$ alkylene, $C_2$-$C_4$ alkenylene or $C_2$-$C_4$ alkynylene, where
any alkylene, alkenylene or alkynylene in $Y^1$ may be optionally substituted by one or two substituents independently selected from halo, cyano, hydroxy, carboxy, $R^6$, —OR$^6$, —C(O)R$^6$ or —C(O)OR$^6$;
$Y^2$ is selected from $C_1$-$C_4$ alkylene, $C_2$-$C_4$ alkenylene or $C_2$-$C_4$ alkynylene, where
any alkylene, alkenylene or alkynylene in Y 2 may be optionally substituted by one or two substituents independently selected from halo, cyano, hydroxy, carboxy, $R^6$, —OR$^6$, —C(O)R$^6$ or —C(O)OR$^6$;
$R^{2a}$ is selected from $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkenyl, 3- to 6-membered monocyclic heterocyclyl, phenyl, or 5- or 6-membered heteroaryl, where
any alkyl, alkenyl, alkynyl, cycloalkyl, cycloalkenyl or heterocyclyl in $R^{2a}$ may be optionally substituted by one, two or three substituents independently selected from halo, cyano, oxo, hydroxy, carboxy, $R^6$, —OR$^6$, —C(O)R$^6$, —C(O)OR$^6$, —OC(O)R$^6$, —C(O)NR$^7$R$^8$, —NR$^7$C(O)R$^8$, —NR$^7$R$^8$, —SO$_2$NR$^7$R$^8$, —NR$^7$SO$_2$R$^8$, —SR$^7$, —SO$_2$R$^7$, —SO$_2$OR$^7$, —OSO$_2$R$^7$, —NR$^7$SO$_2$NR$^8$R$^9$, —NR$^7$C(O)NR$^8$R$^9$, —NR$^7$C(O)OR$^8$ or —OC(O)NR$^7$R$^8$;
any phenyl or heteroaryl in $R^{2a}$ may be optionally substituted by one, two or three substituents independently selected from halo, cyano, carboxy, $R^6$, —OR$^6$, —C(O)R$^6$, —C(O)OR$^6$, —OC(O)R$^6$, —C(O)NR$^7$R$^8$, —NR$^7$C(O)R$^8$, —NR$^7$R$^8$, —SO$_2$NR$^7$R$^8$, —NR$^7$SO$_2$R$^8$, —SR$^7$, —SO$_2$R$^7$, —SO$_2$OR$^7$, —OSO$_2$R$^7$, —NR$^7$SO$_2$NR$^8$R$^9$, —NR$^7$C(O)NR$^8$R$^9$, —NR$^7$C(O)OR$^8$ or —OC(O)NR$^7$R$^8$; and
any heterocyclyl or heteroaryl in $R^{2a}$ includes 1, 2 or 3 heteroatoms selected from N, O or S in the ring;
$R^{2b}$ and $R^{2c}$ is each independently selected from $C_1$-$C_6$ alkyl, $C_3$-$C_6$ alkenyl or $C_3$-$C_6$ alkynyl, where any alkyl, alkenyl or alkynyl in $R^{2b}$ and $R^{2c}$ may be optionally substituted by one, two or three substituents independently selected from halo, cyano, oxo, hydroxy, carboxy, $R^6$, —OR$^6$, —C(O)R$^6$, —C(O)OR$^6$, —OC(O)R$^6$, —C(O)NR$^7$R$^8$, —NR$^7$C(O)R$^8$, —NR$^7$R$^8$, —SO$_2$NR$^7$R$^8$, —NR$^7$SO$_2$R$^8$, —SR$^7$, —SO$_2$R$^7$, —SO$_2$OR$^7$, —OSO$_2$R$^7$, —NR$^7$SO$_2$NR$^8$R$^9$, —NR$^7$C(O)NR$^8$R$^9$, —NR$^7$C(O)OR$^8$ or —OC(O)NR$^7$R$^8$;
or
$R^{2b}$ and $R^{2c}$ together with the nitrogen atom to which they are attached form a 3- to 7-membered heterocycloalkyl, optionally including one or two additional heteroatoms selected from O, N or S in the ring,
said heterocycloalkyl formed by $R^{2b}$ and $R^{2c}$ may be optionally substituted by one, two or three substituents independently selected from halo, cyano, hydroxy, carboxy, $R^6$, —OR$^6$, —C(O)R$^6$, —C(O)OR$^6$, —OC(O)R$^6$, —C(O)NR$^7$R$^8$, —NR$^7$C(O)R$^8$, —NR$^7$R$^8$, —SO$_2$NR$^7$R$^8$, —NR$^7$SO$_2$R$^8$, —SR$^7$, —SO$_2$R$^7$, —SO$_2$OR$^7$, —OSO$_2$R$^7$, —NR$^7$SO$_2$NR$^8$R$^9$, —NR$^7$C(O)NR$^8$R$^9$, —NR$^7$C(O)OR$^8$ or —OC(O)NR$^7$R$^8$;
any S in the ring of said heterocycloalkyl formed by $R^{2b}$ and $R^{2c}$ may be optionally oxidized;
optionally when (i) $R^1$ is $C_1$-$C_6$ alkyl, (ii) $R^2$ is —O—Y$^1$—R$^{2a}$, —O—Y$^2$—C(O)—Y$^1$—R$^{2a}$, —S—Y$^1$—R$^{2a}$ or —SO$_2$—Y$^1$—R$^{2a}$ and (iii) $R^{2a}$ is $C_1$-$C_6$ alkyl, then $R^1$ and $R^2$ together with the carbon atom to which they are attached may form a 4- to 7-membered heterocycloalkyl including one heteroatom selected from O or S in the ring;
$R^3$ and $R^4$ is each independently selected from hydrogen, hydroxy, carboxy, $C_1$-$C_6$ alkyl, $C_1$-$C_6$ alkoxy, $C_1$-$C_6$ alkyl-carbonyl or $C_1$-$C_6$ alkoxy-carbonyl,
any alkyl or alkoxy in $R^3$ and $R^4$ may be optionally substituted by one, two or three substituents independently selected from halo, cyano, or hydroxy; or
$R^3$ and $R^4$ together with the carbon atom to which they are attached form a 3- to 7-membered cycloalkyl,
said cycloalkyl formed by $R^3$ and $R^4$ may be optionally substituted by one, two or three substituents independently selected from halo, cyano, hydroxy, carboxy, $R^6$, —OR$^6$, —C(O)R$^6$ or —C(O)OR$^6$;
$L^1$ and $L^3$ is each independently selected from a bond, $C_1$-$C_4$ alkylene, $C_2$-$C_4$ alkenylene or $C_2$-$C_4$ alkynylene, where
any alkylene, alkenylene or alkynylene in $L^3$ and $L^1$ may be optionally substituted by one or two substituents independently selected from halo, cyano, oxo, hydroxy, carboxy, $R^6$, —OR$^6$, —C(O)R$^6$ or —C(O)OR$^6$;
$L^2$ is selected from a bond, —O—, —C(O)—, —C(O)O—, —OC(O)—, —C(O)NR$^7$—, —NR$^7$C(O)—, —NR$^7$—, —SO$_2$NR$^7$—, —NR$^7$SO$_2$—, —S—, —SO$_2$—, —SO$_2$O—, —OSO$_2$—, —NR$^7$SO$_2$NR$^8$—, —NR$^7$C(O)NR$^8$—, —C(O)NR$^7$NR$^8$—, —NR$^7$NR$^8$C(O)—, —NR$^7$C(O)O— or —OC(O)NR$^7$—;
$R^5$ is selected from $C_1$-$C_6$ alkyl, $C_2$-$C_6$ alkenyl, $C_2$-$C_6$ alkynyl, $C_3$-$C_{12}$ cycloalkyl, $C_3$-$C_{12}$ cycloalkenyl, 3- to 12-membered heterocyclyl, phenyl or 5- or 6-membered heteroaryl, where
any heterocyclyl or heteroaryl in $R^5$ includes 1, 2 or 3 heteroatoms selected from N, O or S in the ring;
any alkyl, alkenyl or alkynyl in $R^5$ may be optionally substituted by one, two or three substituents independently selected from halo, cyano, oxo, hydroxy, carboxy, nitro, R⁶, —OR⁶, —C(O)R⁶, —C(O)OR⁶, —OC(O)R⁶, —C(O)NR⁶R⁷, —NR⁷C(O)R⁸, —NR⁶R⁷, —SO₂NR⁶R⁷, —NR⁷SO₂R⁸, —SR⁷, —SO₂R⁷, —SO₂OR⁷, —OSO₂R⁷, —NR⁸SO₂NR⁶R⁷, —NR⁸C(O)NR⁶R⁷, —NR⁷C(O)OR⁸ or —OC(O)NR⁶R⁷;

any cycloalkyl, cycloalkenyl, heterocyclyl, phenyl or heteroaryl in R⁵ may be optionally substituted by one, two or three substituents independently selected from halo, cyano, oxo, nitro, R⁷, —OR⁷, —C(O)R⁷, —OC(O)R⁷, —C(O)OR⁷, —C(O)NR⁷R⁸, —NR⁷C(O)R⁸, —NR⁷R⁸, —SO₂NR⁷R⁸, —NR⁷SO₂R⁸, —SR⁷, —SO₂R⁷, —SO₂OR⁷, —OSO₂R⁷, —NR⁷SO₂NR⁸R⁹, —NR⁷C(O)NR⁸R⁹, —NR⁷C(O)OR⁸ or —OC(O)NR⁷R⁸;

R⁶ is at each occurrence independently selected from C₁-C₄ alkyl, C₁-C₄ haloalkyl, C₁-C₄ hydroxyalkyl, C₁-C₄ cyanoalkyl, R⁷, R⁸ and R⁹ is at each occurrence independently selected from hydrogen or C₁-C₄ alkyl, where
any C₁-C₄ alkyl in R⁷, R⁸ and R⁹ may be optionally substituted by one, two or three substituents independently selected from halo, cyano, oxo, hydroxy, carboxy, R⁶, —OR⁶, —C(O)R⁶ or —C(O)OR⁶;

provided when L² is linked to L¹ by a nitrogen atom, then L¹ is not a bond;

provided when R⁵ is C₃-C₁₂ cycloalkyl, C₃-C₁₂ cycloalkenyl, 3- to 12-membered heterocyclyl, phenyl or 5- or 6-membered heteroaryl, then at least one of L¹, L² and L³ is not a bond; and provided -L¹-L²-L³-R⁵ is not benzyl, benzyloxycarbonyl or tert-butyloxycarbonyl.

2. The compound of claim 1, or a pharmaceutically acceptable salt thereof, wherein L¹ is selected from a bond or unsubstituted C₁-C₄ alkylene.

3. The compound of claim 1, or a pharmaceutically acceptable salt thereof, wherein L³ is selected from a bond or unsubstituted C₁-C₄ alkylene.

4. The compound of claim 1, having the structure of Formula (IV-a):

Formula (IV-a)

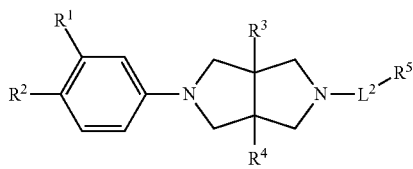

or a pharmaceutically acceptable salt thereof.

5. The compound of claim 1, or a pharmaceutically acceptable salt thereof, wherein
L² is selected from a bond, —C(O)— or —C(O)NR⁷—.

6. The compound of claim 1, having the structure of Formula (V):

Formula (V)

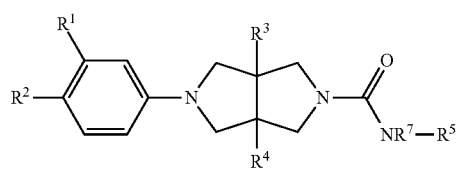

or a pharmaceutically acceptable salt thereof.

7. The compound of claim 1, or a pharmaceutically acceptable salt thereof, wherein R² is selected from —O—Y¹—R²ᵃ, —S—Y¹—R²ᵃ, —SO₂—Y¹—R²ᵃ or —NR²ᵇR²ᶜ, optionally Y¹ is a bond.

8. The compound of claim 1, having the structure of Formula (VIII-c) or (VIII-d):

Formula (VIII-c)

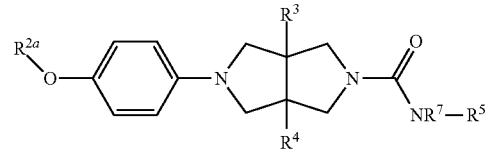

Formula (VIII-d)

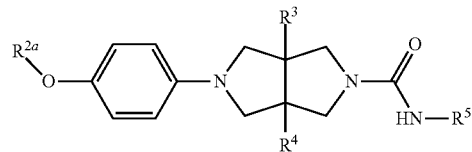

or a pharmaceutically acceptable salt thereof.

9. The compound of claim 1, or a pharmaceutically acceptable salt thereof, wherein
R²ᵃ is selected from unsubstituted C₁-C₄ alkyl, C₁-C₄ alkyl substituted by C₁-C₄ alkoxy, unsubstituted C₃-C₆ cycloalkyl, unsubstituted 3- to 6-membered monocyclic heterocycloalkyl, or unsubstituted phenyl.

10. The compound of claim 1, having the structure of Formula (XII-c) or (XII-d):

Formula (XII-c)

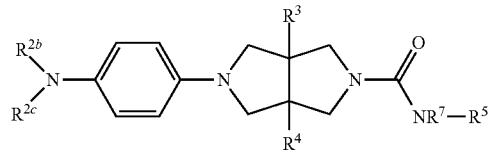

Formula (XII-d)

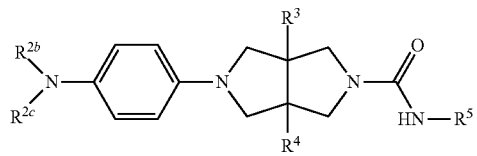

or a pharmaceutically acceptable salt thereof.

11. The compound of claim 1, or a pharmaceutically acceptable salt thereof, wherein
R²ᵇ and R²ᶜ together with the nitrogen atom to which they are attached form a 3- to 7-membered heterocycloalkyl, optionally including one additional heteroatom selected from N or S in the ring,
said heterocycloalkyl formed by R²ᵇ and R²ᶜ may be optionally substituted by one substituent independently selected from hydroxy or —SO₂R⁷;
any S in the ring of said heterocycloalkyl formed by R²ᵇ and R²ᶜ may be optionally oxidized.

12. The compound claim 1, or a pharmaceutically acceptable salt thereof, wherein R³ and R⁴ is each independently selected from hydrogen or unsubstituted C₁-C₄ alkyl.

13. The compound claim 1, or a pharmaceutically acceptable salt thereof, wherein $R^3$ and $R^4$ together with the carbon atom to which they are attached form an unsubstituted 3- to 7-membered cycloalkyl.

14. The compound claim 1, or a pharmaceutically acceptable salt thereof, wherein
$R^1$ is hydrogen.

15. The compound claim 1, or a pharmaceutically acceptable salt thereof, wherein
$R^5$ is selected from $C_1$-$C_6$ alkyl, $C_2$-$C_6$ alkenyl, $C_2$-$C_6$ alkynyl, $C_3$-$C_{12}$ cycloalkyl, 3- to 12-membered heterocycloalkyl, phenyl or 5- or 6-membered heteroaryl, where
any heterocycloalkyl or heteroaryl in $R^5$ includes 1, 2 or 3 heteroatoms selected from N, O or S in the ring;
any alkyl, alkenyl or alkynyl in $R^5$ may be optionally substituted by one, two or three substituents independently selected from halo, cyano, oxo, hydroxy, carboxy, nitro, $R^6$, —$OR^6$, $SO_2R^7$;
any cycloalkyl, heterocycloalkyl, phenyl or heteroaryl in $R^5$ may be optionally substituted by one, two or three substituents independently selected from halo, cyano, nitro, $R^7$, —$OR^7$, —$SO_2R^7$.

16. The compound of claim 1, wherein the compound is selected from:

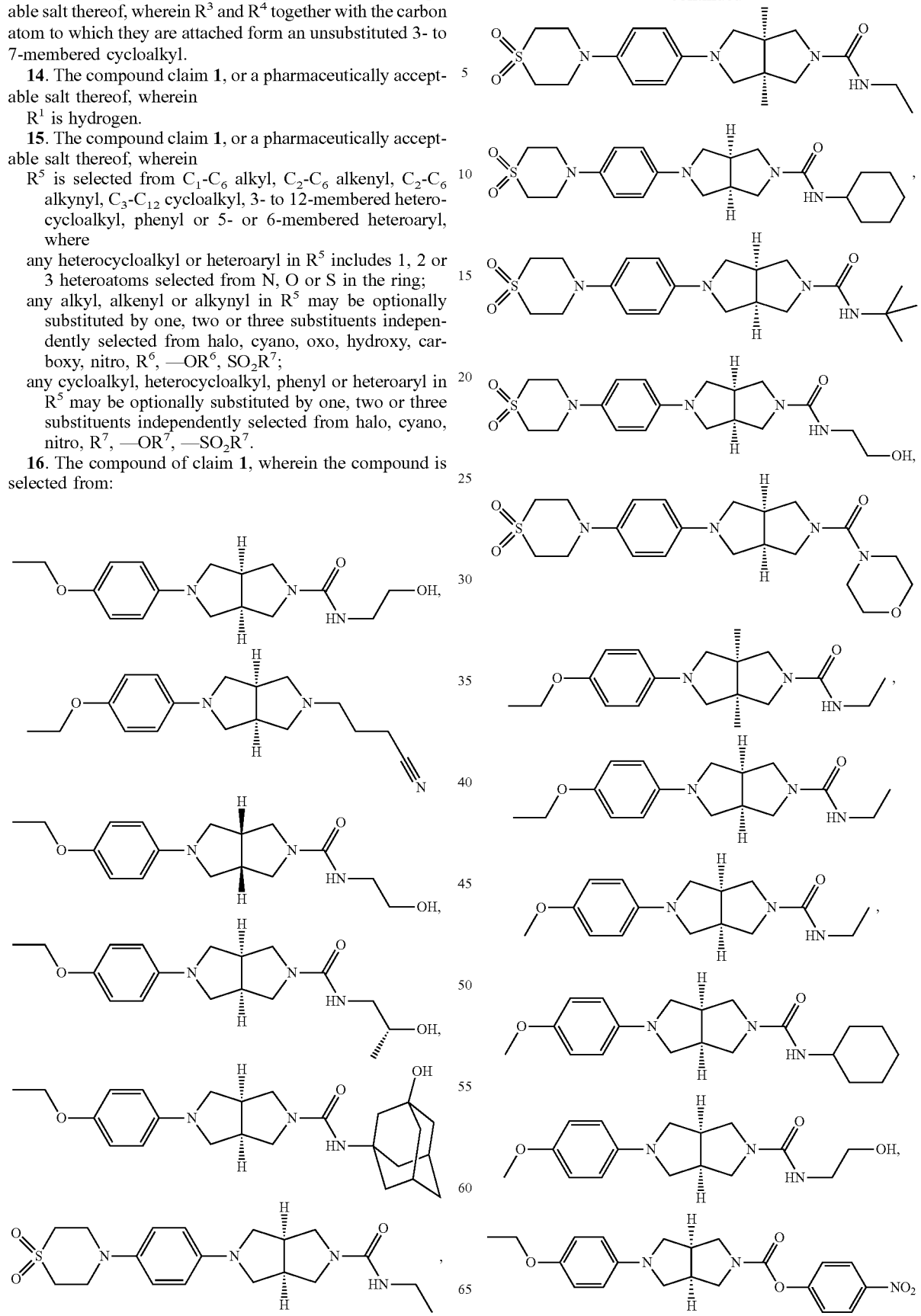

-continued

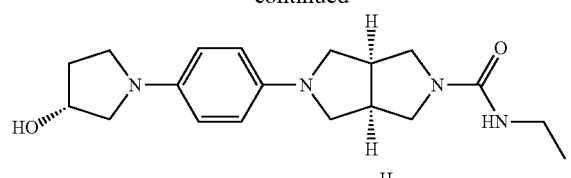,

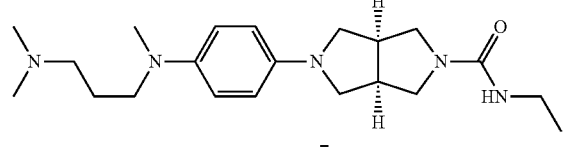,

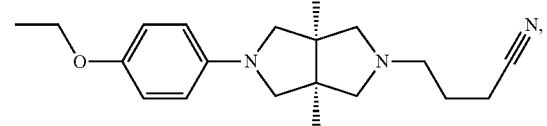,

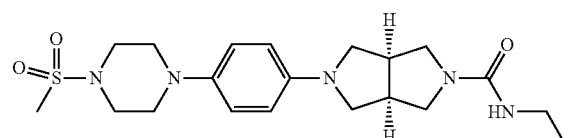,

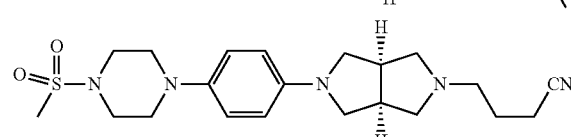,

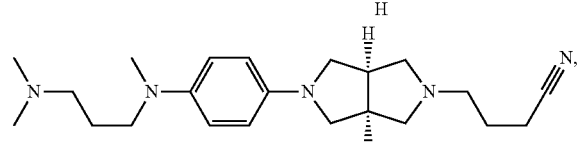,

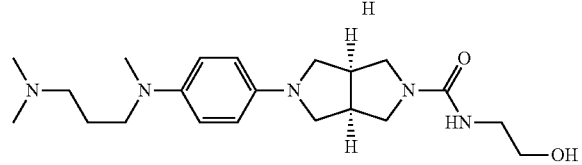,

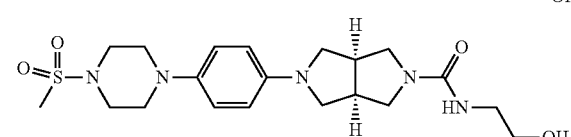,

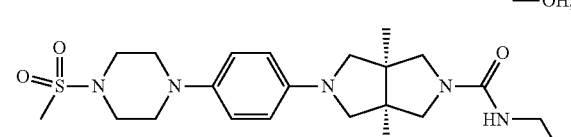,

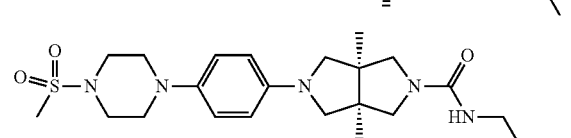,

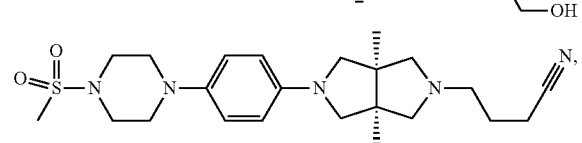,

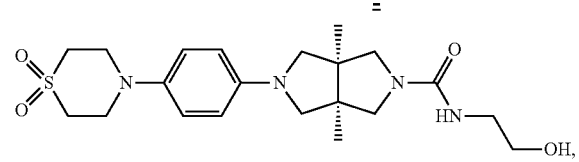,

-continued

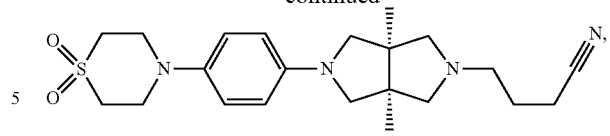,

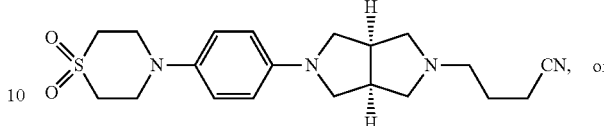, or

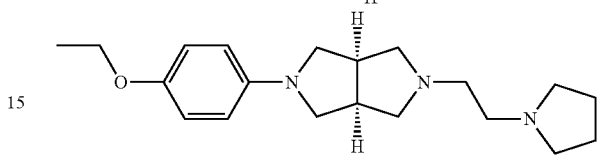

or a pharmaceutically acceptable salt of any of the foregoing compounds.

17. A method of treating a disease or medical condition mediated by LOX in a subject in need thereof, the method comprising administering to the subject an effective amount of the compound according to claim 1, or a pharmaceutically acceptable salt thereof.

18. The method according to claim 17, wherein the disease or medical condition mediated by LOX is selected from cancer or a fibrotic disease.

19. A compound, or a pharmaceutically acceptable salt thereof, selected from:

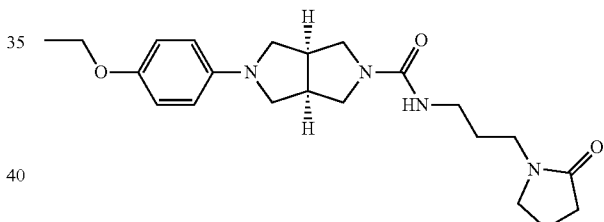,

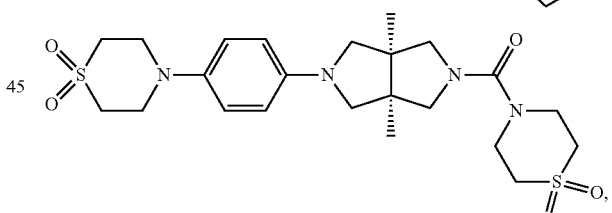,

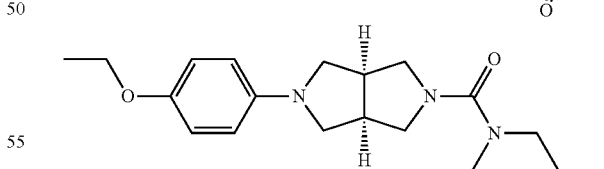,

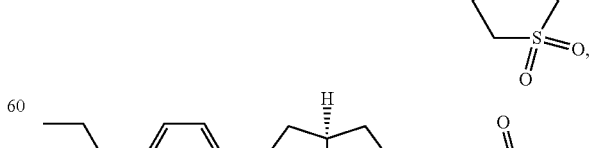,

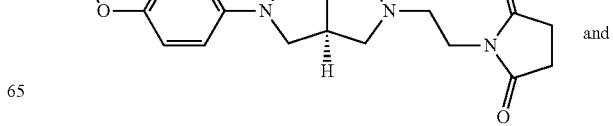 and